US011325957B2

(12) United States Patent
Gilbert et al.

(10) Patent No.: US 11,325,957 B2
(45) Date of Patent: May 10, 2022

(54) METHODS AND COMPOSITIONS FOR REDUCING THE IMMUNOGENICITY OF CHIMERIC NOTCH RECEPTORS

(71) Applicant: Cell Design Labs, Inc., Emeryville, CA (US)

(72) Inventors: Amy Gilbert, San Francisco, CA (US); Vladimir Slepushkin, Vallejo, CA (US); Peter Emtage, Lafayette, CA (US); Anselm Levskaya, Oakland, CA (US); Spencer Scott, San Francisco, CA (US)

(73) Assignee: Cell Design Labs, Inc., Emeryville, CA (US)

( * ) Notice: Subject to any disclaimer, the term of this patent is extended or adjusted under 35 U.S.C. 154(b) by 68 days.

(21) Appl. No.: 16/010,805

(22) Filed: Jun. 18, 2018

(65) Prior Publication Data

US 2018/0362603 A1 Dec. 20, 2018

Related U.S. Application Data

(60) Provisional application No. 62/603,993, filed on Jun. 19, 2017, provisional application No. 62/556,765, filed on Sep. 11, 2017.

(51) Int. Cl.
| | | |
|---|---|---|
| *C07K 14/47* | (2006.01) | |
| *C07K 14/71* | (2006.01) | |
| *C07K 16/18* | (2006.01) | |
| *C07K 19/00* | (2006.01) | |
| *C12N 5/10* | (2006.01) | |
| *C12N 15/63* | (2006.01) | |
| *C12N 15/85* | (2006.01) | |
| *A61K 48/00* | (2006.01) | |
| *C07K 16/28* | (2006.01) | |
| *C07K 14/705* | (2006.01) | |
| *C07K 16/46* | (2006.01) | |
| *A61P 35/04* | (2006.01) | |
| *A61K 39/00* | (2006.01) | |

(52) U.S. Cl.
CPC .......... *C07K 14/4702* (2013.01); *A61K 48/00* (2013.01); *C07K 14/4705* (2013.01); *C07K 14/705* (2013.01); *C07K 14/70517* (2013.01); *C07K 14/71* (2013.01); *C07K 16/28* (2013.01); *C07K 16/2803* (2013.01); *C07K 19/00* (2013.01); *C12N 5/10* (2013.01); *C12N 15/63* (2013.01); *C12N 15/85* (2013.01); *A61K 2039/5156* (2013.01); *A61P 35/04* (2018.01); *C07K 16/462* (2013.01); *C07K 2317/569* (2013.01); *C07K 2317/622* (2013.01); *C07K 2317/626* (2013.01); *C07K 2317/70* (2013.01); *C07K 2319/00* (2013.01); *C07K 2319/02* (2013.01); *C07K 2319/03* (2013.01); *C07K 2319/09* (2013.01); *C07K 2319/33* (2013.01); *C07K 2319/41* (2013.01); *C07K 2319/50* (2013.01); *C07K 2319/70* (2013.01); *C07K 2319/71* (2013.01); *C07K 2319/80* (2013.01); *C07K 2319/95* (2013.01); *C12N 2740/16043* (2013.01); *C12N 2830/15* (2013.01); *C12N 2830/85* (2013.01)

(58) Field of Classification Search
CPC .. A61K 39/3955; A61K 48/00; A61K 38/177; C07K 2317/622; C07K 2319/03; C07K 2319/33; C07K 14/705; C07K 2319/00; C07K 16/28; C07K 2319/50; C07K 14/70596; C07K 2319/80
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,946,778 | A | 8/1990 | Ladner et al. |
| 5,225,539 | A | 7/1993 | Winter |
| 5,476,786 | A | 12/1995 | Huston et al. |
| 9,670,281 | B2 | 6/2017 | Lim et al. |
| 9,834,608 | B2 | 12/2017 | Lim et al. |
| 2003/0109678 | A1 | 6/2003 | Cortese et al. |
| 2016/0264665 | A1* | 9/2016 | Lim ........................ C07K 14/71 |

FOREIGN PATENT DOCUMENTS

| | | |
|---|---|---|
| EP | 0404097 | 12/1990 |
| WO | WO 1986/01533 | 3/1986 |
| WO | WO 1993/11161 | 6/1993 |
| WO | WO 2014/127261 | 8/2014 |
| WO | 16138034 A1 | 9/2016 |
| WO | 17123559 A2 | 7/2017 |
| WO | 19164979 A1 | 8/2019 |

OTHER PUBLICATIONS

Beatty et al. Chimeric antigen receptor-modified T cells for the treatment of solid tumors: Defining the challenges and next steps. Pharmacol Therapeutics 166: 30-39, 2016.*
Bork, A. Powers and pitfalls in sequence analysis: the 70% hurdle. Genome Res 10: 398-400, 2000.*
Bork et al. Go hunting in sequence databases but watch out for the traps. Trends in Genetics. 12(10): 425-427, 1996.*
Brenner, S.E. Errors in genome function. Trends in Genetics 15(4): 132-133, 1999.*

(Continued)

*Primary Examiner* — Bridget E Bunner
(74) *Attorney, Agent, or Firm* — Barnes & Thornburg LLP

(57) ABSTRACT

The present invention relates to methods and compositions for reducing the immunogenicity of chimeric Notch receptors, and specifically to transcription factors useful for controlling gene expression delivered to tissues by such chimeric Notch receptors.

15 Claims, 7 Drawing Sheets

Specification includes a Sequence Listing.

(56) References Cited

OTHER PUBLICATIONS

Doerks et al. Protein annotation: detective work for function prediction. Trends in Genetics 14(6): 248-250, 1998.*

Kojika et al. Notch receptors and hematopoiesis. Exp Hematol 29: 1041-1052, 2001.*

Liu et al. Comparative analysis of Notch 1 and Notch2 binding sites in the genome of BxPC3 pancreatic cancer cells. J Cancer 8: 65-73, 2017.*

Ngo et al. Computational complexity, protein structure prediction, and the Levinthal paradox. The Protein Folding Problem and Tertiary Structure Prediction, pp. 492-495, 1994.*

Roybal et al. Engineering T cells with customized therapeutic response programs using synthetic Notch receptors. Cell 167: 419-432, 2016.*

Skolnick et al. From genes to protein structure and function: novel applications of computational approaches in the genomic era. Trends in Biotech 18(1): 34-39, 2000.*

Smith et al. The challenges of genome sequence annotation or "The devil is in the details". Nature Biotech 15: 1222-1223, 1997.*

Tokuriki et al. Stability effects of mutations and protein evolvability. Curr Opin Structural Biol 19: 596-604, 2009.*

Wells. J.A. Additivity of mutational effects in proteins. Biochemistry 29 (37): 8509-8517, 1990.*

Yong et al. CAR T-cell therapy of solid tumors. Immunol Cell Biol 95: 356-363, 2017.*

Gordon et al. The molecular logic of Notch signaling—a structural and biochemical perspective. J Cell Sci 121: 3109-3119, 2008.*

Mizutani et al. Conservation of the biochemical mechanisms of signal transduction among mammalian Notch family members. Proc Natl Acad Sci USA 98(16): 9026-9031, 2001.*

Barrett et al., "Chimeric antigen receptor therapy for cancer," Ann. Rev. Med. 65:333-347, Jan. 2014.

Bird et al., "Single-chain antigen-binding proteins," Science 242:423-426, Oct. 1988.

Cartellieri et al., "Chimeric antigen receptor-engineered T cells for immunotherapy of cancer," J. Biomed. Biotechnol. vol. 2010, Article ID 956304, May 2010.

Cheadle et al., "CAR T cells: driving the road from the laboratory to the clinic," Immunol. Rev. 257(1):91-106, Jan. 2014.

Chen et al., "Fusion protein linkers: property, design and functionality," Adv. Drug Deliv. Rev. 65:1357-1369, Oct. 2013.

Fedorov et al., "PD-1- and CTLA-4-based inhibitory chimeric antigen receptors (iCARs) divert off-target immunotherapy responses," Sci. Transl. Med. 5(215):215ra172, Dec. 2013.

Frain, "The liver-specific transcription factor LF-B1 contains a highly diverged homeobox DNA binding domain," Cell 59:145-157, Oct. 1990.

Furukawa et al., "Crx, a novel otx-like homeobox gene, shows photoreceptor-specific expression and regulates photoreceptor differentiation," Cell 91(4):531-541, Nov. 1997.

Galfre and Milstein, "Preparation of Monoclonal Antibodies: Strategies and Procedures," Methods Enzymol. 73(B):3-46, 1981.

Glienke et al., "Advantages and applications of CAR-expressing natural killer cells," Front. Pharmacol. 6:21, Feb. 2015.

Graham et al., "Characteristics of a human cell line transformed by DNA from human adenovirus type 5," J. Gen. Virol. 36:59-74, Jul. 1977.

Hollinger et al., "'Diabodies': small bivalent and bispecific antibody fragments," Proc. Natl. Acad. Sci. U.S.A. 90: 6444-6448, Jul. 1993.

Holt et al., "Domain antibodies: proteins for therapy," Trends Biotechnol. 21:484-490, Nov. 2003.

Hong et al., "TAZ, a transcriptional modulator of mesechymal stem cell differentiation," Science 309(5737):4074-1078, Aug. 2005.

Hrecka et al., "Vpx relieves the inhibition of HIV-1 infection of macrophages mediated by the SAMHD1 protein," Nature 474(7353):658-661, Jun. 2011.

Jacobson et al., "Structure of Pit-1 POU domain bound to DNA as a dimer: unexpected arrangement and flexibility," Genes Develop. 11(2):198-212, Jan. 1997.

Kakarla and Gottschalk, "CAR T cells for solid tumors: armed and ready to go?" Cancer J. 20(2):151-155, Mar.-Apr. 2014.

Klebanoff et al., "Customizing Functionalitiy and Payload Delivery for Receptor-Engineered T Cells," Cell 167(2):304-306, Oct. 2016.

Klein et al., "Design and characterization of structured protein linkers with differing flexibilities," Protein Eng. Design Select. 27(10): 325-330, Oct. 2014.

Lian et al., "The role of YAP transcription coactivator in regulating stem cell self-renewal and differentiation," Genes Develop. 24(11):1106-1118, Jun. 2010.

Long et al., "Harnessing the antitumor potential of macrophages for cancer immunotherapy," Oncoimmunology 2:e26860, Dec. 2013.

Morsut et al., "Engineering Customized Cell Sensing and Response Behaviors Using Synthetic Notch Receptors," Cell 164(4):780-791, Feb. 2016.

Moyes et al., "Genetically Engineered Macrophages: A Potential Platform for Cancer Immunotherapy," Human Gene Therapy 28(2):200-215, Feb. 2017.

Najafabadi et al., "C2H2 zinc finger proteins greatly expand the human regulatory lexicon," Nature Biotechnol. 33(5):555-562, May 2015.

Omori et al., "CREB-H: a novel mammalian transcription factor belonging to the CREB/ATF family and functioning via the box-B element with a liver-specific expression," Nucleic Acids Res. 29(10):2154-2162, May 2001.

Pancewicz and Nicot, "Current views on the role of Notch signaling and the pathogenesis of human leukemia," BMC Cancer 11(1):502, Dec. 2011.

PCT International Search Report and Written Opinion in International Appln. No. PCT/US2018/038218, dated Sep. 14, 2018, 16 pages.

Pegram et al., "CD28z CARs and Armored CARs," Cancer J. 20(2):127-133, Mar. 2014.

Pluckthun, "Antibodies from Escherichia coli," Pharmacol. Monoclonal Antibodies 113:269-315, 1994.

Priyanka et al., "Linkers in the structural biology of protein-protein interactions," Protein Sci. 22(2):453-167, Feb. 2013.

Riddell et al., "Adoptive Therapy with Chimeric Antigen Receptor Modified T Cells of Defined Subset Composition," Cancer J. 20(2):141-144, Mar. 2014.

Roybal et al., "Precision Tumor Recognition by T Cells With Combinatorial Antigen-Sensing Circuits," Cell 164(4):770-779, Feb. 2016.

Sadelain et al., "The basic principles of chimeric antigen receptor (CAR) design," Cancer Discov. 3(4):388-398, Apr. 2013.

Thiel et al., "Regulation of life and death by the zinc finger transcription factor Egr-1," J. Cell. Physiol. 193(3):287-282, Dec. 2002.

Urlaub and Chasin, "Isolation of Chinese hamster cell mutants deficient in dihydrofolate reductase activity," Proc. Natl. Acad. Sci. U.S.A. 77:4216-4220, Jul. 1980.

Wang et al., "The nuclear facto-kB RelA transcription factor is constitutively activated in human pancreatic adenocarcinoma cells," Clin. Cancer Res. 5(1):119-127, 1999.

Weintraub and Davis, "The myoD gene family: nodal point during specification of the muscle cell lineage," Science 251(4995):761, Feb. 1991.

Zapata et al., "Engineering linear F(ab')$_2$ fragments for efficient production in Escherichia coli and enhanced antiproliferative activity," Protein Eng. 8(10):1057-1062, Oct. 1995.

International Search Report, issued in PCT/US2019/018813, dated Jun. 11, 2019.

International Preliminary Report on Patentability, issued in PCT/US2019/0018813, dated Aug. 27, 2020.

Kipniss et al., "Engineering Cell Sensing and Responses using a GPCR-Coupled CRISPR-Cas System," Nature Communications, vol. 8, No. 1, (2017), pp. 1-10.

Examination Report issued in related Australian Application No. 2018289383, dated Oct. 22, 2020.

Examination Report issued in related Canadian Application No. 3065549, dated Oct. 23, 2020.

Office Action, issued in related Japanese Application No. 2019-569872, dated Mar. 9, 2021.

(56) References Cited

OTHER PUBLICATIONS

Notice of Preliminary Rejection issued in related Korean Application No. 10-2020-7001681, dated Dec. 2, 2020.
Final Rejection, issued in related Korean Application No. 10-2020-7001681, dated Aug. 11, 2021.
Examination Report, issued in related European Application No. 18745721.3, dated Aug. 5, 2021.
Office Action issued in CA Application No. 3065549, dated Sep. 8, 2021.
Final Rejection issued in KR Application No. 10-2020-7001681, dated Aug. 10, 2021.
Communication issued in EP Application No. 18745721.3, dated Aug. 5, 2021.
Substantive Examination Report issued in SA Application No. 519410835, dated Aug. 31, 2021.

\* cited by examiner

Domain Architecture of Natural Human Notch Proteins and Engineered Synthetic Notch Proteins (SynNotch)

```
                        SEQUENCE LISTING

<160> NUMBER OF SEQ ID NOS: 35

<210> SEQ ID NO 1
<211> LENGTH: 22
<212> TYPE: PRT
<213> ORGANISM: Homo sapiens

<400> SEQUENCE: 1

Met Ala Leu Pro Val Thr Ala Leu Leu Leu Pro Leu Ala Leu Leu Leu
1               5                   10                  15

His Ala Ala Arg Pro Ser
            20

<210> SEQ ID NO 2
<211> LENGTH: 10
<212> TYPE: PRT
<213> ORGANISM: Artificial Sequence
<220> FEATURE:
<223> OTHER INFORMATION: Myc tag

<400> SEQUENCE: 2

Glu Gln Lys Leu Ile Ser Glu Glu Asp Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: GS linker

<400> SEQUENCE: 3

Gly Ser Ala Ala Ala Gly Gly Ser Gly Gly Ser Gly Gly Ser
1               5                   10

<210> SEQ ID NO 4
<211> LENGTH: 8
<212> TYPE: PRT
<213> ORGANISM: Artificial Sequence
<220> FEATURE:
<223> OTHER INFORMATION: GS linker

<400> SEQUENCE: 4

Gly Gly Gly Ser Gly Gly Gly Ser
1               5

<210> SEQ ID NO 5
<211> LENGTH: 638
<212> TYPE: PRT
<213> ORGANISM: Homo sapiens

<400> SEQUENCE: 5

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
```

```
                50                  55                  60
Gly Glu Thr Arg Gly Ser Glu Asp Glu Thr Asp Asp Gly Glu Asp
 65                  70                  75                  80

Phe Thr Pro Pro Ile Leu Lys Glu Leu Glu Asn Leu Ser Pro Glu Glu
                 85                  90                  95

Ala Ala His Gln Lys Ala Val Val Glu Thr Leu Leu Gln Glu Asp Pro
                100                 105                 110

Trp Arg Val Ala Lys Met Val Lys Ser Tyr Leu Gln Gln His Asn Ile
                115                 120                 125

Pro Gln Arg Glu Val Val Asp Thr Thr Gly Leu Asn Gln Ser His Leu
                130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
                180                 185                 190

Glu Leu Pro Thr Lys Lys Gly Arg Arg Asn Arg Phe Lys Trp Gly Pro
                195                 200                 205

Ala Ser Gln Gln Ile Leu Phe Gln Ala Tyr Glu Arg Gln Lys Asn Pro
210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
                260                 265                 270

Lys Glu Glu Ala Phe Arg His Lys Leu Ala Met Asp Thr Tyr Ser Gly
                275                 280                 285

Pro Pro Pro Gly Pro Gly Pro Gly Pro Ala Leu Pro Ala His Ser Ser
                290                 295                 300

Pro Gly Leu Pro Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
                340                 345                 350

Pro Thr Gly Leu Glu Pro Ser His Ser Leu Leu Ser Thr Glu Ala Lys
                355                 360                 365

Leu Val Ser Ala Ala Gly Gly Pro Leu Pro Pro Val Ser Thr Leu Thr
370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
                420                 425                 430

Thr Leu Val Ile Gly Leu Ala Ser Thr Gln Ala Gln Ser Val Pro Val
                435                 440                 445

Ile Asn Ser Met Gly Ser Ser Leu Thr Thr Leu Gln Pro Val Gln Phe
                450                 455                 460

Ser Gln Pro Leu His Pro Ser Tyr Gln Gln Pro Leu Met Pro Pro Val
465                 470                 475                 480
```

```
Gln Ser His Val Thr Gln Ser Pro Phe Met Ala Thr Met Ala Gln Leu
            485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
            515                 520                 525

Asn Leu Ser Ala Leu Ala Ser Leu Thr Pro Thr Lys Gln Glu Ala Ala
            530                 535                 540

Leu Leu Pro Gln Val Phe Thr Ser Asp Thr Glu Ala Ser Ser Glu Ser
545                 550                 555                 560

Gly Leu His Thr Pro Ala Ser Gln Ala Thr Thr Leu His Val Pro Ser
            565                 570                 575

Gln Asp Pro Ala Gly Ile Gln His Leu Gln Pro Ala His Arg Leu Ser
            580                 585                 590

Ala Ser Pro Thr Val Ser Ser Ser Leu Val Leu Tyr Gln Ser Ser
            595                 600                 605

Asp Ser Ser Asn Gly Gln Ser His Leu Leu Pro Ser Asn His Ser Val
            610                 615                 620

Ile Glu Thr Phe Ile Ser Thr Gln Met Ala Ser Ser Ser Gln
625                 630                 635

<210> SEQ ID NO 6
<211> LENGTH: 631
<212> TYPE: PRT
<213> ORGANISM: Homo sapiens

<400> SEQUENCE: 6

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
            35                  40                  45

Ser Cys Gly Gly Gly Arg Gly Glu Leu Ala Glu Leu Pro Asn Gly Leu
        50                  55                  60

Gly Glu Thr Arg Gly Ser Glu Asp Glu Thr Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
            115                 120                 125

Pro Gln Arg Glu Val Val Asp Thr Thr Gly Leu Asn Gln Ser His Leu
            130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
            165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
            195                 200                 205

Ala Ser Gln Gln Ile Leu Phe Gln Ala Tyr Glu Arg Gln Lys Asn Pro
```

```
                210                 215                 220
Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
                260                 265                 270

Lys Glu Glu Ala Phe Arg His Lys Leu Ala Met Asp Thr Tyr Ser Gly
                275                 280                 285

Pro Pro Pro Gly Pro Gly Pro Gly Pro Ala Leu Pro Ala His Ser Ser
290                 295                 300

Pro Gly Leu Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
                340                 345                 350

Pro Thr Gly Leu Glu Pro Ser His Ser Leu Leu Ser Thr Glu Ala Lys
                355                 360                 365

Leu Val Ser Ala Ala Gly Gly Pro Leu Pro Pro Val Ser Thr Leu Thr
                370                 375                 380

Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
                420                 425                 430

Thr Leu Val Ile Gly Leu Ala Ser Thr Gln Ala Gln Ser Val Pro Val
                435                 440                 445

Ile Asn Ser Met Gly Ser Ser Leu Thr Thr Leu Gln Pro Val Gln Phe
                450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
                500                 505                 510

Thr His Thr Gly Leu Leu Pro Gln Thr Met Leu Ile Thr Asp Thr Thr
                515                 520                 525

Asn Leu Ser Ala Leu Ala Ser Leu Thr Pro Thr Lys Gln Val Phe Thr
530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
                565                 570                 575

His Leu Gln Pro Ala His Arg Leu Ser Ala Ser Pro Thr Val Ser Ser
                580                 585                 590

Ser Ser Leu Val Leu Tyr Gln Ser Ser Asp Ser Ser Asn Gly Gln Ser
                595                 600                 605

His Leu Leu Pro Ser Asn His Ser Val Ile Glu Thr Phe Ile Ser Thr
                610                 615                 620

Gln Met Ala Ser Ser Ser Gln
625                 630
```

```
<210> SEQ ID NO 7
<211> LENGTH: 662
<212> TYPE: PRT
<213> ORGANISM: Homo sapiens

<400> SEQUENCE: 7

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Ser Gly
        275                 280                 285

Pro Pro Pro Gly Pro Gly Pro Gly Pro Ala Leu Pro Ala His Ser Ser
    290                 295                 300

Pro Gly Leu Pro Pro Ala Leu Ser Pro Ser Lys Val His Gly Val
305                 310                 315                 320

Arg Tyr Gly Gln Pro Ala Thr Ser Glu Thr Ala Glu Val Pro Ser Ser
                325                 330                 335

Ser Gly Gly Pro Leu Val Thr Val Ser Thr Pro Leu His Gln Val Ser
            340                 345                 350

Pro Thr Gly Leu Glu Pro Ser His Ser Leu Leu Ser Thr Glu Ala Lys
        355                 360                 365

Leu Val Ser Ala Ala Gly Gly Pro Leu Pro Pro Val Ser Thr Leu Thr
```

```
                 370                 375                 380
Ala Leu His Ser Leu Glu Gln Thr Ser Pro Gly Leu Asn Gln Gln Pro
385                 390                 395                 400

Gln Asn Leu Ile Met Ala Ser Leu Pro Gly Val Met Thr Ile Gly Pro
                405                 410                 415

Gly Glu Pro Ala Ser Leu Gly Pro Thr Phe Thr Asn Thr Gly Ala Ser
            420                 425                 430

Thr Leu Val Ile Gly Leu Ala Ser Thr Gln Ala Gln Ser Val Pro Val
        435                 440                 445

Ile Asn Ser Met Gly Ser Ser Leu Thr Thr Leu Gln Pro Val Gln Phe
    450                 455                 460

Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
                485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
        515                 520                 525

Asn Leu Ser Ala Leu Ala Ser Leu Thr Pro Thr Lys Gln Val Arg Ser
    530                 535                 540

Arg Pro Ala Gly Pro Pro Leu Ala Cys Asp Arg Ala Pro His Pro His
545                 550                 555                 560

Ile Pro Arg Ala Gln Glu Ala Ala Leu Leu Pro Gln Val Phe Thr Ser
                565                 570                 575

Asp Thr Glu Ala Ser Ser Glu Ser Gly Leu His Thr Pro Ala Ser Gln
            580                 585                 590

Ala Thr Thr Leu His Val Pro Ser Gln Asp Pro Ala Ser Ile Gln His
        595                 600                 605

Leu Gln Pro Ala His Arg Leu Ser Ala Ser Pro Thr Val Ser Ser Ser
    610                 615                 620

Ser Leu Val Leu Tyr Gln Ser Ser Asp Ser Ser Asn Gly Gln Ser His
625                 630                 635                 640

Leu Leu Pro Ser Asn His Ser Val Ile Glu Thr Phe Ile Ser Thr Gln
                645                 650                 655

Met Ala Ser Ser Ser Gln
            660

<210> SEQ ID NO 8
<211> LENGTH: 3438
<212> TYPE: DNA
<213> ORGANISM: Homo sapiens

<400> SEQUENCE: 8
ggggccctga ttcacgggcc gctggggcca gggttggggg ttgggggtgc ccacagggct      60
tggctagtgg ggttttgggg gggcagtggg tgcaaggagt ttggtttgtg tctgccggcc     120
ggcaggcaaa cgcaacccac gcggtggggg aggcggctag cgtggtggac ccgggccgcg     180
tggccctgtg gcagccgagc catggttttct aaactgagcc agctgcagac ggagctcctg     240
gcggccctgc tcgagtcagg gctgagcaaa gaggcactga tccaggcact gggtgagccg     300 ggccctacc tcctggctgg agaaggcccc ctggacaagg gggagtcctg cggcggcgt     360 cgaggggagc tggctgagct gcccaatggg ctggggagaa ctcggggctc cgaggacgag     420
acggacgacg atggggaaga cttcacgcca cccatcctca aagagctgga gaacctcagc     480
```

```
cctgaggagg cggcccacca gaaagccgtg gtggagaccc ttctgcagga ggacccgtgg    540
cgtgtggcga agatggtcaa gtcctacctg cagcagcaca acatcccaca gcgggaggtg    600
gtcgatacca ctggcctcaa ccagtcccac ctgtcccaac acctcaacaa gggcactccc    660
atgaagacgc agaagcgggc cgccctgtac acctggtacg tccgcaagca gcgagaggtg    720
gcgcagcagt tcacccatgc agggcaggga gggctgattg aagagcccac aggtgatgag    780
ctaccaacca agaaggggcg gaggaaccgt ttcaagtggg gcccagcatc ccagcagatc    840
ctgttccagg cctatgagag gcagaagaac cctagcaagg aggagcgaga gacgctagtg    900
gaggagtgca ataggggcgga atgcatccag agagggtgt ccccatcaca ggcacagggg    960
ctgggctcca acctcgtcac ggaggtgcgt gtctacaact ggtttgccaa ccggcgcaaa   1020
gaagaagcct tccggcacaa gctggccatg gacacgtaca gcgggccccc cccagggcca   1080
ggcccgggac ctgcgctgcc cgctcacagc tcccctggcc tgcctccacc tgccctctcc   1140
cccagtaagg tccacggtgt gcgctatgga cagcctgcga ccagtgagac tgcagaagta   1200
ccctcaagca gcggcggtcc cttagtgaca gtgtctacac ccctccacca agtgtccccc   1260
acgggcctgg agcccagcca cagcctgctg agtacagaag ccaagctggt ctcagcagct   1320
gggggccccc tccccctgt cagcaccctg acagcactgc acagcttgga gcagacatcc   1380
ccaggcctca accagcagcc ccagaacctc atcatggcct cacttcctgg ggtcatgacc   1440
atcgggcctg gtgagcctgc ctccctgggt cctacgttca ccaacacagg tgcctccacc   1500
ctggtcatcg gcctggcctc cacgcaggca cagagtgtgc cggtcatcaa cagcatgggc   1560
agcagcctga ccaccctgca gcccgtccag ttctcccagc cgctgcaccc ctcctaccag   1620
cagccgctca tgccacctgt gcagagccat gtgacccaga gccccttcat ggccaccatg   1680
gctcagctgc agagccccca cgccctctac agccacaagc ccgaggtggc ccagtacacc   1740
cacacgggcc tgctcccgca gactatgctc atcaccgaca ccaccaacct gagcgccctg   1800
gccagcctca cgcccaccaa gcaggaggct gctctgctcc cccaggtctt cacctcagac   1860
actgaggcct ccagtgagtc cgggcttcac acgccggcat ctcaggccac caccctccac   1920
gtccccagcc aggaccctgc cggcatccag cacctgcagc cggcccaccg gctcagcgcc   1980
agccccacag tgtcctccag cagcctggtg ctgtaccaga gctcagactc cagcaatggc   2040
cagagccacc tgctgccatc caaccacagc gtcatcgaga ccttcatctc cacccagatg   2100
gcctcttcct cccagtaacc acggcacctg ggccctgggg cctgtactgc ctgcttgggg   2160
ggtgatgagg gcagcagcca gccctgcctg gaggacctga gctgccgag caaccgtggc   2220 ccttcctgga cagctgtgcc tcgctcccca ctctgctctg atgcatcaga aagggagggc   2280
tctgaggcgc cccaacccgt ggaggctgct cggggtgcac aggaggggt cgtggagagc   2340 taggagcaaa gcctgttcat ggcagatgta ggagggactg tcgctgcttc gtgggataca   2400
gtcttcttac ttggaactga aggggcggc ctatgacttg gcaccccca gcctgggcct   2460 atggagagcc ctgggaccgc tacaccactc tggcagccac acttctcagg acacaggcct   2520
gtgtagctgt gacctgctga gctctgagag gccctggatc agcgtggcct tgttctgtca   2580
ccaatgtacc caccgggcca ctccttcctg ccccaactcc ttccagctag tgacccacat   2640
gccatttgta ctgaccccat cacctactca cacaggcatt tcctgggtgg ctactctgtg   2700
ccagagcctg gggctctaac gcctgagccc agggaggccg aagctaacag ggaaggcagg   2760
cagggctctc ctggcttccc atccccagcg attccctctc ccaggcccca tgacctccag   2820
```

-continued

```
ctttcctgta tttgttccca agagcatcat gcctctgagg ccagcctggc ctcctgcctc    2880
tactgggaag gctacttcgg ggctgggaag tcgtccttac tcctgtggga gcctcgcaac    2940
ccgtgccaag tccaggtcct ggtggggcag ctcctctgtc tcgagcgccc tgcagaccct    3000
gcccttgttt ggggcaggag tagctgagct cacaaggcag caaggcccga gcagctgagc    3060
agggccgggg aactggccaa gctgaggtgc ccaggagaag aaagaggtga ccccagggca    3120
caggagctac ctgtgtggac aggactaaca ctcagaagcc tggggcctg gctggctgag     3180
ggcagttcgc agccaccctg aggagtctga ggtcctgagc actgccagga gggacaaagg    3240
agcctgtgaa cccaggacaa gcatggtccc acatccctgg gcctgctgct gagaacctgg    3300
ccttcagtgt accgcgtcta ccctgggatt caggaaaagg cctggggtga cccggcaccc    3360
cctgcagctt gtagccagcc ggggcgagtg gcacgtttat ttaactttta gtaaagtcaa    3420
ggagaaatgc ggtggaaa                                                  3438
```

<210> SEQ ID NO 9
<211> LENGTH: 3417
<212> TYPE: DNA
<213> ORGANISM: Homo sapiens

<400> SEQUENCE: 9

```
ggggccctga ttcacgggcc gctggggcca gggttggggg ttgggggtgc ccacagggct      60
tggctagtgg ggttttgggg gggcagtggg tgcaaggagt ttggtttgtg tctgccggcc    120
ggcaggcaaa cgcaacccac gcggtggggg aggcggctag cgtggtggac ccgggccgcg    180
tggcccctgtg gcagccgagc catggtttct aaactgagcc agctgcagac ggagctcctg    240
gcggccctgc tcgagtcagg gctgagcaaa gaggcactga tccaggcact gggtgagccg    300
gggccctacc tcctggctgg agaaggcccc tggacaaggg ggagtcctg cggcggcggt     360
cgaggggagc tggctgagct gcccaatggg ctggggaga ctcggggctc cgaggacgag      420
acggacgacg atggggaaga cttcacgcca cccatcctca aagagctgga gaacctcagc    480
cctgaggagg cggcccacca gaaagccgtg gtggagaccc ttctgcagga ggacccgtgg    540
cgtgtggcga agatggtcaa gtcctacctg cagcagcaca catccccaca gcgggaggtg    600
gtcgatacca ctggcctcaa ccagtcccac ctgtcccaac acctcaacaa gggcactccc    660
atgaagacgc agaagcgggc cgccctgtac acctggtacg tccgcaagca gcgagaggtg    720
gcgcagcagt tcacccatgc agggcaggga gggctgattg aagagcccac aggtgatgag    780
ctaccaacca agaaggggcg gaggaaccgt ttcaagtggg gcccagcatc ccagcagatc    840
ctgttccagg cctatgagag gcagaagaac cctagcaagg aggagcgaga gacgctagtg    900
gaggagtgca ataggcgga atgcatccag agagggtgt ccccatcaca ggcacagggg     960
ctgggctcca acctcgtcac ggaggtgcgt gtctacaact ggtttgccaa ccggcgcaaa   1020
gaagaagcct tccggcacaa gctggccatg gacacgtaca cggggccccc ccagggcca   1080
ggcccgggac ctgcgctgcc cgctcacagc tcccctggcc tgcctccacc tgccctctcc   1140
cccagtaagg tccacggtgt gcgctatgga cagcctgcga ccagtgagac tgcagaagta   1200
ccctcaagca gcgcggtcc cttagtgaca gtgtctacac ccctccacca agtgtccccc   1260
acgggcctgg agcccagcca cagcctgctg agtacagaag ccaagctggt ctcagcagct   1320
gggggcccc tcccccctgt cagcaccctg acagcactgc acagcttgga gcagacatcc   1380
ccaggcctca accagcagcc ccagaacctc atcatggcct cacttcctgg ggtcatgacc   1440
atcgggcctg gtgagcctgc ctccctgggt cctacgttca ccaacacagg tgcctccacc   1500
```

-continued

| | |
|---|---|
| ctggtcatcg gcctggcctc cacgcaggca cagagtgtgc cggtcatcaa cagcatgggc | 1560 |
| agcagcctga ccaccctgca gcccgtccag ttctcccagc cgctgcaccc ctcctaccag | 1620 |
| cagccgctca tgccacctgt gcagagccat gtgacccaga gccccttcat ggccaccatg | 1680 |
| gctcagctgc agagccccca cgccctctac agccacaagc ccgaggtggc ccagtacacc | 1740 |
| cacacgggcc tgctcccgca gactatgctc atcaccgaca ccaccaacct gagcgccctg | 1800 |
| gccagcctca cgcccaccaa gcaggtcttc acctcagaca ctgaggcctc cagtgagtcc | 1860 |
| gggcttcaca cgccggcatc tcaggccacc accctccacg tccccagcca ggaccctgcc | 1920 |
| ggcatccagc acctgcagcc ggccaccgg tcagcgccca gccccacagt gtcctccagc | 1980 |
| agcctggtgc tgtaccagag ctcagactcc agcaatggcc agagccacct gctgccatcc | 2040 |
| aaccacagcg tcatcgagac cttcatctcc acccagatgg cctcttcctc ccagtaacca | 2100 |
| cggcacctgg gccctggggc ctgtactgcc tgcttggggg gtgatgaggg cagcagccag | 2160 |
| ccctgcctgg aggacctgag cctgccgagc aaccgtggcc cttcctggac agctgtgcct | 2220 |
| cgctccccac tctgctctga tgcatcagaa agggagggct ctgaggcgcc caacccgtg | 2280 |
| gaggctgctc ggggtgcaca ggaggggtc gtggagagct aggagcaaag cctgttcatg | 2340 |
| gcagatgtag gagggactgt cgctgcttcg tgggatacag tcttcttact tggaactgaa | 2400 |
| gggggcggcc tatgacttgg gcaccccag cctgggccta tggagagccc tgggaccgct | 2460 |
| acaccactct ggcagccaca cttctcagga cacaggcctg tgtagctgtg acctgctgag | 2520 |
| ctctgagagg ccctggatca gcgtggcctt gttctgtcac caatgtaccc accgggccac | 2580 |
| tccttcctgc cccaactcct tccagctagt gacccacatg ccatttgtac tgaccccatc | 2640 |
| acctactcac acaggcattt cctgggtggc tactctgtgc cagagcctgg ggctctaacg | 2700 |
| cctgagccca gggaggccga agctaacagg gaaggcaggc agggctctcc tggcttccca | 2760 |
| tccccagcga ttccctctcc caggcccat gacctcagc tttcctgtat tgttcccaa | 2820 |
| gagcatcatg cctctgaggc cagcctggcc tcctgcctct actgggaagg ctacttcggg | 2880 |
| gctgggaagt cgtccttact cctgtgggag cctcgcaacc cgtgccaagt ccaggtcctg | 2940 |
| gtggggcagc tcctctgtct cgagcgccct gcagaccctg cccttgtttg gggcaggagt | 3000 |
| agctgagctc acaaggcagc aaggcccgag cagctgagca gggccgggga actggccaag | 3060 |
| ctgaggtgcc caggagaaga aagaggtgac cccaggcac aggagctacc tgtgtggaca | 3120 |
| ggactaacac tcagaagcct gggggcctgg ctggctgagg cagttcgca gccaccctga | 3180 |
| ggagtctgag gtcctgagca ctgccaggag ggacaaagga gcctgtgaac ccaggacaag | 3240 |
| catggtccca catccctggg cctgctgctg agaacctggc cttcagtgta ccgcgtctac | 3300 |
| cctgggattc aggaaaaggc ctgggtgac ccggcacccc ctgcagcttg tagccagccg | 3360 |
| gggcgagtgg cacgttttat taactttag taaagtcaag gagaaatgcg gtggaaa | 3417 |

<210> SEQ ID NO 10
<211> LENGTH: 3563
<212> TYPE: DNA
<213> ORGANISM: Homo sapiens

<400> SEQUENCE: 10

| | |
|---|---|
| ataaatatga accttggaga atttccccag ctccaatgta aacagaacag gcaggggccc | 60 |
| tgattcacgg gccgctgggg ccaggggttgg gggttggggg tgcccacagg gcttggctag | 120 |
| tggggttttg gggggcagt gggtgcaagg agtttggttt gtgtctgccg gccggcaggc | 180 |

```
aaacgcaacc cacgcggtgg gggaggcggc tagcgtggtg gacccgggcc gcgtggccct    240
gtggcagccg agccatggtt tctaaactga gccagctgca gacggagctc ctggcggccc    300
tgctcgagtc agggctgagc aaagaggcac tgatccaggc actgggtgag ccggggccct    360
acctcctggc tggagaaggc cccctggaca agggggagtc ctgcggcggc ggtcgagggg    420
agctggctga gctgcccaat gggctggggg agactcgggg ctccgaggac gagacggacg    480
acgatgggga agacttcacg ccacccatcc tcaaagagct ggagaacctc agccctgagg    540
aggcggccca ccagaaagcc gtggtggaga cccttctgca ggaggacccg tggcgtgtgg    600
cgaagatggt caagtcctac ctgcagcagc acaacatccc acagcgggag gtggtcgata    660
ccactggcct caaccagtcc cacctgtccc aacacctcaa caagggcact cccatgaaga    720
cgcagaagcg ggccgccctg tacacctggt acgtccgcaa gcagcgagag gtggcgcagc    780
agttcaccca tgcagggcag ggagggctga ttgaagagcc cacaggtgat gagctaccaa    840
ccaagaaggg gcggaggaac cgtttcaagt ggggcccagc atcccagcag atcctgttcc    900
aggcctatga gaggcagaag aaccctagca aggaggagcc agagacgcta gtggaggagt    960
gcaatagggc ggaatgcatc cagagagggg tgtccccatc acaggcacag gggctgggct   1020
ccaacctcgt cacggaggtg cgtgtctaca actggtttgc caaccggcgc aaagaagaag   1080
ccttccggca caagctggcc atggacacgt acagcgggcc cccccagggg ccaggcccgg   1140
gacctgcgct gcccgctcac agctcccctg gcctgcctcc acctgccctc tcccccagta   1200
aggtccacgg tgtgcgctat ggacagcctg cgaccagtga gactgcagaa gtaccctcaa   1260
gcagcggcgg tcccttagtg acagtgtcta caccccctcca ccaagtgtcc cccacgggcc   1320
tggagcccag ccacagcctg ctgagtacag aagccaagct ggtctcagca gctggggcc    1380 ccctcccccc tgtcagcacc ctgacagcac tgcacagctt ggagcagaca tccccaggcc   1440
tcaaccagca gccccagaac ctcatcatgg cctcacttcc tggggtcatg accatcgggc   1500 ctggtgagc tgcctccctg gtcctacgt tcaccaacac aggtgcctcc accctggtca    1560
tcggcctggc ctccacgcag gcacagagtg tgccggtcat caacagcatg ggcagcagcc   1620
tgaccaccct gcagccgtc cagttctccc agccgctgca cccctcctac cagcagccgc    1680
tcatgccacc tgtgcagagc catgtgaccc agagccccctt catggccacc atggctcagc   1740
tgcagagccc ccacgccctc tacagccaca gcccgaggt ggcccagtac acccacacgg    1800
gcctgctccc gcagactatg ctcatcaccg acaccaccaa cctgagcgcc ctggccagcc   1860
tcacgcccac caagcaggta aggtccaggc ctgctggccc tcccttggcc tgtgacagag   1920 ccccctcaccc ccacatcccc cgggctcagg aggctgctct gctcccccag gtcttcacct   1980
cagacactga ggcctccagt gagtccgggc ttcacacgcc ggcatctcag gccaccaccc   2040
tccacgtccc cagccaggac cctgccagca tccagcacct gcagcggcc caccggctca    2100 gcgccagccc cacagtgtcc tccagcagcc tggtgctgta ccagagctca gactccagca    2160
atggccagag ccacctgctg ccatccaacc acagcgtcat cgagaccttc atctccaccc    2220
agatggcctc ttcctcccag taaccacggc acctgggccc tggggcctgt actgcctgct    2280 tgggggggtga tgagggcagc agccagccct gcctggagga cctgagcctg ccagcaacc    2340 gtggccttc ctggacagct gtgcctcgct ccccactctg ctctgatgca tcagaaaggg   2400
agggctctga ggcgcccaa cccgtggagg ctgctcgggg tgcacaggag ggggtcgtgg    2460
agagctagga gcaaagcctg ttcatggcag atgtaggagg gactgtcgct gcttcgtggg   2520
atacagtctt cttacttgga actgaagggg gcggcctatg acttgggcac ccccagcctg   2580
```

```
ggcctatgga gagccctggg accgctacac cactctggca gccacacttc tcaggacaca    2640
ggcctgtgta gctgtgacct gctgagtctc gagaggccct ggatcagcgt ggccttgttc    2700
tgtcaccaat gtacccaccg ggccactcct tcctgcccca actccttcca gctagtgacc    2760
cacatgccat ttgtactgac cccatcacct actcacacag gcatttcctg ggtggctact    2820
ctgtgccaga gcctggggct ctaacgcctg agcccaggga ggccgaagct aacagggaag    2880
gcaggcaggg ctctcctggc ttcccatccc cagcgattcc ctctcccagg ccccatgacc    2940
tccagctttc ctgtatttgt tcccaagagc atcatgcctc tgaggccagc ctggcctcct    3000
gcctctactg ggaaggctac ttcggggctg ggaagtcgtc cttactcctg tgggagcctc    3060
gcaacccgtg ccaagtccag gtcctggtgg ggcagctcct ctgtctcgag cgccctgcag    3120
accctgccct tgtttggggc aggagtagct gagctcacaa ggcagcaagg cccgagcagc    3180
tgagcagggc cggggaactg gccaagctga ggtgcccagg agaagaaaga ggtgaccccca   3240 gggcacagga gctacctgtg tggacaggac taacactcag aagcctgggg gcctggctgg    3300
ctgagggcag ttcgcagcca ccctgaggag tctgaggtcc tgagcactgc caggagggac    3360
aaaggagcct gtgaacccag acaagcatg gtcccacatc cctgggcctg ctgctgagaa     3420
cctggccttc agtgtaccgc gtctaccctg ggattcagga aaaggcctgg ggtgacccgg    3480
caccccctgc agcttgtagc cagccggggc gagtggcacg tttatttaac ttttagtaaa    3540
gtcaaggaga aatgcggtgg aaa                                           3563
```

<210> SEQ ID NO 11
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(7)
<223> OTHER INFORMATION: HNF1-alpha binding sequence

<400> SEQUENCE: 11

```
gttaatnatt aac                                                         13
```

<210> SEQ ID NO 12
<211> LENGTH: 551
<212> TYPE: PRT
<213> ORGANISM: Homo sapiens

<400> SEQUENCE: 12

```
Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
                100                 105                 110
```

```
Phe Gln Asn Leu Gly Ile Gln Cys Val Lys Lys Arg Asp Leu Glu Gln
            115                 120                 125

Ala Ile Ser Gln Arg Ile Gln Thr Asn Asn Asn Pro Phe Gln Val Pro
        130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
                180                 185                 190

Glu Leu Lys Ile Cys Arg Val Asn Arg Asn Ser Gly Ser Cys Leu Gly
            195                 200                 205

Gly Asp Glu Ile Phe Leu Leu Cys Asp Lys Val Gln Lys Glu Asp Ile
        210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
                260                 265                 270

Arg Arg Pro Ser Asp Arg Glu Leu Ser Glu Pro Met Glu Phe Gln Tyr
            275                 280                 285

Leu Pro Asp Thr Asp Asp Arg His Arg Ile Glu Glu Lys Arg Lys Arg
        290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Arg Arg Ile Ala Val Pro Ser Arg
                325                 330                 335

Ser Ser Ala Ser Val Pro Lys Pro Ala Pro Gln Pro Tyr Pro Phe Thr
                340                 345                 350

Ser Ser Leu Ser Thr Ile Asn Tyr Asp Glu Phe Pro Thr Met Val Phe
            355                 360                 365

Pro Ser Gly Gln Ile Ser Gln Ala Ser Ala Leu Ala Pro Ala Pro Pro
        370                 375                 380

Gln Val Leu Pro Gln Ala Pro Ala Pro Ala Pro Ala Pro Ala Met Val
385                 390                 395                 400

Ser Ala Leu Ala Gln Ala Pro Ala Pro Val Pro Val Leu Ala Pro Gly
                405                 410                 415

Pro Pro Gln Ala Val Ala Pro Pro Ala Pro Lys Pro Thr Gln Ala Gly
                420                 425                 430

Glu Gly Thr Leu Ser Glu Ala Leu Leu Gln Leu Gln Phe Asp Asp Glu
            435                 440                 445

Asp Leu Gly Ala Leu Leu Gly Asn Ser Thr Asp Pro Ala Val Phe Thr
        450                 455                 460

Asp Leu Ala Ser Val Asp Asn Ser Glu Phe Gln Gln Leu Leu Asn Gln
465                 470                 475                 480

Gly Ile Pro Val Ala Pro His Thr Thr Glu Pro Met Leu Met Glu Tyr
                485                 490                 495

Pro Glu Ala Ile Thr Arg Leu Val Thr Gly Ala Gln Arg Pro Pro Asp
                500                 505                 510

Pro Ala Pro Ala Pro Leu Gly Ala Pro Gly Leu Pro Asn Gly Leu Leu
            515                 520                 525
```

```
Ser Gly Asp Glu Asp Phe Ser Ser Ile Ala Asp Met Asp Phe Ser Ala
    530                 535                 540
Leu Leu Ser Gln Ile Ser Ser
545                 550

<210> SEQ ID NO 13
<211> LENGTH: 548
<212> TYPE: PRT
<213> ORGANISM: Homo sapiens

<400> SEQUENCE: 13

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Glu Glu
    130                 135                 140

Gln Arg Gly Asp Tyr Asp Leu Asn Ala Val Arg Leu Cys Phe Gln Val
145                 150                 155                 160

Thr Val Arg Asp Pro Ser Gly Arg Pro Leu Arg Leu Pro Pro Val Leu
                165                 170                 175

Ser His Pro Ile Phe Asp Asn Arg Ala Pro Asn Thr Ala Glu Leu Lys
            180                 185                 190

Ile Cys Arg Val Asn Arg Asn Ser Gly Ser Cys Leu Gly Gly Asp Glu
        195                 200                 205

Ile Phe Leu Leu Cys Asp Lys Val Gln Lys Glu Asp Ile Glu Val Tyr
    210                 215                 220

Phe Thr Gly Pro Gly Trp Glu Ala Arg Gly Ser Phe Ser Gln Ala Asp
225                 230                 235                 240

Val His Arg Gln Val Ala Ile Val Phe Arg Thr Pro Pro Tyr Ala Asp
                245                 250                 255

Pro Ser Leu Gln Ala Pro Val Arg Val Ser Met Gln Leu Arg Arg Pro
            260                 265                 270

Ser Asp Arg Glu Leu Ser Glu Pro Met Glu Phe Gln Tyr Leu Pro Asp
        275                 280                 285

Thr Asp Asp Arg His Arg Ile Glu Glu Lys Arg Lys Arg Thr Tyr Glu
    290                 295                 300

Thr Phe Lys Ser Ile Met Lys Lys Ser Pro Phe Ser Gly Pro Thr Asp
305                 310                 315                 320

Pro Arg Pro Pro Arg Arg Ile Ala Val Pro Ser Arg Ser Ser Ala
                325                 330                 335

Ser Val Pro Lys Pro Ala Pro Gln Pro Tyr Pro Phe Thr Ser Ser Leu
            340                 345                 350
```

Ser Thr Ile Asn Tyr Asp Glu Phe Pro Thr Met Val Phe Pro Ser Gly
            355                 360                 365

Gln Ile Ser Gln Ala Ser Ala Leu Ala Pro Ala Pro Pro Gln Val Leu
        370                 375                 380

Pro Gln Ala Pro Ala Pro Ala Pro Ala Met Val Ser Ala Leu
385                 390                 395                 400

Ala Gln Ala Pro Ala Pro Val Pro Val Leu Ala Pro Gly Pro Pro Gln
                405                 410                 415

Ala Val Ala Pro Pro Ala Pro Lys Pro Thr Gln Ala Gly Glu Gly Thr
                420                 425                 430

Leu Ser Glu Ala Leu Leu Gln Leu Gln Phe Asp Asp Glu Asp Leu Gly
            435                 440                 445

Ala Leu Leu Gly Asn Ser Thr Asp Pro Ala Val Phe Thr Asp Leu Ala
            450                 455                 460

Ser Val Asp Asn Ser Glu Phe Gln Gln Leu Leu Asn Gln Gly Ile Pro
465                 470                 475                 480

Val Ala Pro His Thr Thr Glu Pro Met Leu Met Glu Tyr Pro Glu Ala
                485                 490                 495

Ile Thr Arg Leu Val Thr Gly Ala Gln Arg Pro Pro Asp Pro Ala Pro
            500                 505                 510

Ala Pro Leu Gly Ala Pro Gly Leu Pro Asn Gly Leu Leu Ser Gly Asp
            515                 520                 525

Glu Asp Phe Ser Ser Ile Ala Asp Met Asp Phe Ser Ala Leu Leu Ser
530                 535                 540

Gln Ile Ser Ser
545

<210> SEQ ID NO 14
<211> LENGTH: 482
<212> TYPE: PRT
<213> ORGANISM: Homo sapiens

<400> SEQUENCE: 14

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
                20                  25                  30

Arg Phe Arg Tyr Lys Cys Glu Gly Arg Ser Ala Gly Ser Ile Pro Gly
            35                  40                  45

Glu Arg Ser Thr Asp Thr Thr Lys Thr His Pro Thr Ile Lys Ile Asn
        50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
                100                 105                 110

Phe Gln Asn Leu Gly Ile Gln Cys Val Lys Lys Arg Asp Leu Glu Gln
            115                 120                 125

Ala Ile Ser Gln Arg Ile Gln Thr Asn Asn Asn Pro Phe Gln Val Pro
        130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro

```
                        165                 170                 175
Pro Val Leu Ser His Pro Ile Phe Asp Asn Arg Ala Pro Asn Thr Ala
                180                 185                 190
Glu Leu Lys Ile Cys Arg Val Asn Arg Asn Ser Gly Ser Cys Leu Gly
            195                 200                 205
Gly Asp Glu Ile Phe Leu Leu Cys Asp Lys Val Gln Lys Glu Asp Ile
        210                 215                 220
Glu Val Tyr Phe Thr Gly Pro Gly Trp Glu Ala Arg Gly Ser Phe Ser
225                 230                 235                 240
Gln Ala Asp Val His Arg Gln Val Ala Ile Val Phe Arg Thr Pro Pro
                245                 250                 255
Tyr Ala Asp Pro Ser Leu Gln Ala Pro Val Arg Val Ser Met Gln Leu
                260                 265                 270
Arg Arg Pro Ser Asp Arg Glu Leu Ser Glu Pro Met Glu Phe Gln Tyr
            275                 280                 285
Leu Pro Asp Thr Asp Asp Arg His Arg Ile Glu Glu Lys Arg Lys Arg
        290                 295                 300
Thr Tyr Glu Thr Phe Lys Ser Ile Met Lys Lys Ser Pro Phe Ser Gly
305                 310                 315                 320
Pro Thr Asp Pro Arg Pro Pro Arg Arg Ile Ala Val Pro Ser Arg
                325                 330                 335
Ser Ser Ala Ser Val Pro Lys Pro Ala Pro Gly Pro Gln Ala Val
                340                 345                 350
Ala Pro Pro Ala Pro Lys Pro Thr Gln Ala Gly Glu Gly Thr Leu Ser
            355                 360                 365
Glu Ala Leu Leu Gln Leu Gln Phe Asp Asp Glu Asp Leu Gly Ala Leu
        370                 375                 380
Leu Gly Asn Ser Thr Asp Pro Ala Val Phe Thr Asp Leu Ala Ser Val
385                 390                 395                 400
Asp Asn Ser Glu Phe Gln Gln Leu Leu Asn Gln Gly Ile Pro Val Ala
                405                 410                 415
Pro His Thr Thr Glu Pro Met Leu Met Glu Tyr Pro Glu Ala Ile Thr
                420                 425                 430
Arg Leu Val Thr Gly Ala Gln Arg Pro Pro Asp Pro Ala Pro Ala Pro
            435                 440                 445
Leu Gly Ala Pro Gly Leu Pro Asn Gly Leu Leu Ser Gly Asp Glu Asp
        450                 455                 460
Phe Ser Ser Ile Ala Asp Met Asp Phe Ser Ala Leu Leu Ser Gln Ile
465                 470                 475                 480
Ser Ser

<210> SEQ ID NO 15
<211> LENGTH: 448
<212> TYPE: PRT
<213> ORGANISM: Homo sapiens

<400> SEQUENCE: 15

Met Asp Glu Leu Phe Pro Leu Ile Phe Pro Ala Glu Pro Ala Gln Ala
1               5                   10                  15
Ser Gly Pro Tyr Val Glu Ile Ile Glu Gln Pro Lys Gln Arg Gly Met
                20                  25                  30
Arg Phe Arg Tyr Lys Cys Glu Gly Arg Ser Ala Gly Ser Ile Pro Gly
            35                  40                  45
Glu Arg Ser Thr Asp Thr Thr Lys Thr His Pro Thr Ile Lys Ile Asn
```

```
            50                  55                  60
Gly Tyr Thr Gly Pro Gly Thr Val Arg Ile Ser Leu Val Thr Lys Asp
 65                  70                  75                  80

Pro Pro His Arg Pro His Pro His Glu Leu Val Gly Lys Asp Cys Arg
                 85                  90                  95

Asp Gly Phe Tyr Glu Ala Glu Leu Cys Pro Asp Arg Cys Ile His Ser
                100                 105                 110

Phe Gln Asn Leu Gly Ile Gln Cys Val Lys Lys Arg Asp Leu Glu Gln
                115                 120                 125

Ala Ile Ser Gln Arg Ile Gln Thr Asn Asn Pro Phe Gln Val Pro
130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
                180                 185                 190

Glu Leu Lys Ile Cys Arg Val Asn Arg Asn Ser Gly Ser Cys Leu Gly
                195                 200                 205

Gly Asp Glu Ile Phe Leu Leu Cys Asp Lys Val Gln Lys Glu Asp Ile
210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
                260                 265                 270

Arg Arg Pro Ser Asp Arg Glu Leu Ser Glu Pro Met Glu Phe Gln Tyr
                275                 280                 285

Leu Pro Asp Thr Asp Asp Arg His Arg Ile Glu Glu Lys Arg Lys Arg
                290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Arg Arg Ile Ala Val Pro Ser Arg
                325                 330                 335

Ser Ser Ala Ser Val Pro Lys Pro Ala Pro Gln Pro Tyr Pro Phe Thr
                340                 345                 350

Ser Ser Leu Ser Thr Ile Asn Tyr Asp Glu Phe Pro Thr Met Val Phe
                355                 360                 365

Pro Ser Gly Gln Ile Ser Gln Ala Ser Ala Leu Ala Pro Ala Pro Pro
370                 375                 380

Gln Val Leu Pro Gln Ala Pro Ala Pro Ala Pro Ala Pro Ala Met Val
385                 390                 395                 400

Ser Ala Leu Ala Gln Arg Pro Pro Asp Pro Ala Pro Ala Pro Leu Gly
                405                 410                 415

Ala Pro Gly Leu Pro Asn Gly Leu Leu Ser Gly Asp Glu Asp Phe Ser
                420                 425                 430

Ser Ile Ala Asp Met Asp Phe Ser Ala Leu Leu Ser Gln Ile Ser Ser
                435                 440                 445

<210> SEQ ID NO 16
<211> LENGTH: 480
<212> TYPE: PRT
<213> ORGANISM: Homo sapiens
```

<400> SEQUENCE: 16

```
Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Asp Asp Arg
210                 215                 220

His Arg Ile Glu Glu Lys Arg Lys Arg Thr Tyr Glu Thr Phe Lys Ser
225                 230                 235                 240

Ile Met Lys Lys Ser Pro Phe Ser Gly Pro Thr Asp Pro Arg Pro Pro
                245                 250                 255

Pro Arg Arg Ile Ala Val Pro Ser Arg Ser Ser Ala Ser Val Pro Lys
            260                 265                 270

Pro Ala Pro Gln Pro Tyr Pro Phe Thr Ser Ser Leu Ser Thr Ile Asn
        275                 280                 285

Tyr Asp Glu Phe Pro Thr Met Val Phe Pro Ser Gly Gln Ile Ser Gln
290                 295                 300

Ala Ser Ala Leu Ala Pro Ala Pro Gln Val Leu Pro Gln Ala Pro
305                 310                 315                 320

Ala Pro Ala Pro Ala Pro Ala Met Val Ser Ala Leu Ala Gln Ala Pro
                325                 330                 335

Ala Pro Val Pro Val Leu Ala Pro Gly Pro Pro Gln Ala Val Ala Pro
            340                 345                 350

Pro Ala Pro Lys Pro Thr Gln Ala Gly Glu Gly Thr Leu Ser Glu Ala
        355                 360                 365

Leu Leu Gln Leu Gln Phe Asp Asp Glu Asp Leu Gly Ala Leu Leu Gly
370                 375                 380

Asn Ser Thr Asp Pro Ala Val Phe Thr Asp Leu Ala Ser Val Asp Asn
385                 390                 395                 400

Ser Glu Phe Gln Gln Leu Leu Asn Gln Gly Ile Pro Val Ala Pro His
```

Thr Thr Glu Pro Met Leu Met Glu Tyr Pro Glu Ala Ile Thr Arg Leu
                405                 410                 415

Val Thr Gly Ala Gln Arg Pro Pro Asp Pro Ala Pro Ala Pro Leu Gly
            420                 425                 430

Ala Pro Gly Leu Pro Asn Gly Leu Leu Ser Gly Asp Glu Asp Phe Ser
        435                 440                 445

Ser Ile Ala Asp Met Asp Phe Ser Ala Leu Leu Ser Gln Ile Ser Ser
    450                 455                 460

465                 470                 475                 480

<210> SEQ ID NO 17
<211> LENGTH: 445
<212> TYPE: PRT
<213> ORGANISM: Homo sapiens

<400> SEQUENCE: 17

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn His Asp Arg His Arg Ile
            180                 185                 190

Glu Glu Lys Arg Lys Arg Thr Tyr Glu Thr Phe Lys Ser Ile Met Lys
        195                 200                 205

Lys Ser Pro Phe Ser Gly Pro Thr Asp Pro Arg Pro Pro Pro Arg Arg
    210                 215                 220

Ile Ala Val Pro Ser Arg Ser Ser Ala Ser Val Pro Lys Pro Ala Pro
225                 230                 235                 240

Gln Pro Tyr Pro Phe Thr Ser Ser Leu Ser Thr Ile Asn Tyr Asp Glu
                245                 250                 255

Phe Pro Thr Met Val Phe Pro Ser Gly Gln Ile Ser Gln Ala Ser Ala
            260                 265                 270

Leu Ala Pro Ala Pro Pro Gln Val Leu Pro Gln Ala Pro Ala Pro Ala
        275                 280                 285

Pro Ala Pro Ala Met Val Ser Ala Leu Ala Gln Ala Pro Ala Pro Val
    290                 295                 300

```
Pro Val Leu Ala Pro Gly Pro Pro Gln Ala Val Ala Pro Pro Ala Pro
305                 310                 315                 320

Lys Pro Thr Gln Ala Gly Glu Gly Thr Leu Ser Glu Ala Leu Leu Gln
            325                 330                 335

Leu Gln Phe Asp Asp Glu Asp Leu Gly Ala Leu Leu Gly Asn Ser Thr
            340                 345                 350

Asp Pro Ala Val Phe Thr Asp Leu Ala Ser Val Asp Asn Ser Glu Phe
            355                 360                 365

Gln Gln Leu Leu Asn Gln Gly Ile Pro Val Ala Pro His Thr Thr Glu
370                 375                 380

Pro Met Leu Met Glu Tyr Pro Glu Ala Ile Thr Arg Leu Val Thr Gly
385                 390                 395                 400

Ala Gln Arg Pro Pro Asp Pro Ala Pro Ala Pro Leu Gly Ala Pro Gly
            405                 410                 415

Leu Pro Asn Gly Leu Leu Ser Gly Asp Glu Asp Phe Ser Ser Ile Ala
            420                 425                 430

Asp Met Asp Phe Ser Ala Leu Leu Ser Gln Ile Ser Ser
            435                 440                 445

<210> SEQ ID NO 18
<211> LENGTH: 2595
<212> TYPE: DNA
<213> ORGANISM: Homo sapiens

<400> SEQUENCE: 18
agcgcgcagg cgcggccgga ttccgggcag tgacgcgacg gcgggccgcg cggcgcattt      60
ccgcctctgg cgaatggctc gtctgtagtg cacgccgcgg gcccagctgc gaccccggcc     120
ccgcccccgg gaccccggcc atggacgaac tgttccccct catcttcccg gcagagccag     180
cccaggcctc tggcccctat gtggagatca ttgagcagcc aagcagcggg gcatgcgct      240 tccgctacaa gtgcgagggg cgctccgcgg gcagcatccc aggcgagagg agcacagata     300
ccaccaagac ccaccccacc atcaagatca atggctacac aggaccaggg acagtgcgca     360
tctccctggt caccaaggac cctcctcacc ggcctcaccc cacgagctt gtaggaaagg      420 actgccggga tggcttctat gaggctgagc tctgcccgga ccgctgcatc cacagtttcc     480
agaacctggg aatccagtgt gtgaagaagc gggacctgga gcaggctatc agtcagcgca     540
tccagaccaa caacaacccc ttccaagttc ctatagaaga gcagcgtggg gactacgacc     600
tgaatgctgt gcggctctgc ttccaggtga cagtgcggga cccatcaggc aggccctcc     660 gcctgccgcc tgtcctttct catcccatct ttgacaatcg tgcccccaac actgccgagc     720
tcaagatctg ccgagtgaac cgaaactctg gcagctgcct cggtgggat gagatcttcc      780 tactgtgtga caaggtgcag aaagaggaca ttgaggtgta tttcacggga ccaggctggg     840
aggcccgagg ctccttttcg caagctgatg tgcaccgaca agtggccatt gtgttccgga     900
cccctcccta cgcagacccc agcctgcagg tcctgtgcg tgtctccatg cagctgcggc      960
ggccttccga ccgggagctc agtgagccca tggaattcca gtacctgcca gatacagacg    1020
atcgtcaccg gattgaggag aaacgtaaaa ggacatatga ccttcaag agcatcatga      1080 agaagagtcc tttcagcgga cccaccgacc ccggcctcc acctcgacgc attgctgtgc     1140
cttcccgcag ctcagcttct gtccccaagc cagcacccca gccctatccc tttacgtcat    1200
ccctgagcac catcaactat gatgagtttc ccaccatggt gtttccttct gggcagatca    1260
gccaggcctc ggccttggcc ccggcccctc ccaagtcct gccccaggct ccagcccctg    1320
```

| | |
|---|---:|
| cccctgctcc agccatggta tcagctctgg cccaggcccc agcccctgtc ccagtcctag | 1380 |
| ccccaggccc tcctcaggct gtggcccac ctgcccccaa gcccaccag gctggggaag | 1440 |
| gaacgctgtc agaggccctg ctgcagctgc agtttgatga tgaagacctg ggggccttgc | 1500 |
| ttggcaacag cacagaccca gctgtgttca cagacctggc atccgtcgac aactccgagt | 1560 |
| ttcagcagct gctgaaccag ggcatacctg tggccccca cacaactgag cccatgctga | 1620 |
| tggagtaccc tgaggctata actcgcctag tgacaggggc ccagaggccc ccgacccag | 1680 |
| ctcctgctcc actgggggcc ccggggctcc ccaatggcct cctttcagga gatgaagact | 1740 |
| tctcctccat tgcggacatg gacttctcag ccctgctgag tcagatcagc tcctaagggg | 1800 |
| gtgacgcctg ccctccccag agcactgggt tgcagggat tgaagccctc caaaagcact | 1860 |
| tacggattct ggtggggtgt gttccaactg cccccaactt tgtggatgtc ttccttggag | 1920 |
| gggggagcca tattttattc ttttattgtc agtatctgta tctctctctc tttttggagg | 1980 |
| tgcttaagca gaagcattaa cttctctgga aaggggggag ctgggaaac tcaaactttt | 2040 |
| cccctgtcct gatggtcagc tcccttctct gtagggaact ctggggtccc ccatcccat | 2100 |
| cctccagctt ctggtactct cctagagaca gaagcaggct ggaggtaagg cctttgagcc | 2160 |
| cacaaagcct tatcaagtgt cttccatcat ggattcatta cagcttaatc aaaataacgc | 2220 |
| cccagatacc agcccctgta tggcactggc attgtccctg tgcctaacac cagcgtttga | 2280 |
| ggggctggcc ttcctgccct acagaggtct ctgccggctc tttccttgct caaccatggc | 2340 |
| tgaaggaaac cagtgcaaca gcactggctc tctccaggat ccagaagggg tttggtctgg | 2400 |
| gacttccttg ctctccctct tctcaagtgc cttaatagta gggtaagttg ttaagagtgg | 2460 |
| gggagagcag gctggcagct ctccagtcag gaggcatagt ttttactgaa caatcaaagc | 2520 |
| acttggactc ttgctctttc tactctgaac taataaatct gttgccaagc tggctagaaa | 2580 |
| aaaaaaaaaa aaaaa | 2595 |

<210> SEQ ID NO 19
<211> LENGTH: 2586
<212> TYPE: DNA
<213> ORGANISM: Homo sapiens

<400> SEQUENCE: 19

| | |
|---|---:|
| agcgcgcagg cgcggccgga ttccgggcag tgacgcgacg gcgggccgcg cggcgcattt | 60 |
| ccgcctctgg cgaatggctc gtctgtagtg cacgccgcgg gcccagctgc gaccccggcc | 120 |
| ccgcccccgg gacccggcc atggacgaac tgttcccct catcttcccg gcagagccag | 180 |
| cccaggcctc tggcccctat gtggagatca ttgagcagcc caagcagcgg ggcatgcgct | 240 |
| tccgctacaa gtgcgagggg cgctccgcgg gcagcatccc aggcgagagg agcacagata | 300 |
| ccaccaagac ccacccacc atcaagatca atggctacac aggaccaggg acagtgcgca | 360 |
| tctccctggt caccaaggac cctcctcacc ggcctcaccc cacgagctt gtaggaaagg | 420 |
| actgccgga tggcttctat gaggctgagc tctgcccgga ccgctgcatc cacagtttcc | 480 |
| agaacctggg aatccagtgt gtgaagaagc gggacctgga gcaggctatc agtcagcgca | 540 |
| tccagaccaa caacaacccc ttccaagaag agcagcgtgg ggactacgac ctgaatgctg | 600 |
| tgcggctctg cttccaggtg acagtgcggg acccatcagg caggcccctc gcctgccgc | 660 |
| ctgtcctttc tcatcccatc tttgacaatc gtgcccccaa cactgccgag ctcaagatct | 720 |
| gccgagtgaa ccgaaactct ggcagctgcc tcggtgggga tgagatcttc ctactgtgtg | 780 |
| acaaggtgca gaaagaggac attgaggtgt atttcacggg accaggctgg gaggcccgag | 840 |

```
gctcctttc  gcaagctgat  gtgcaccgac  aagtggccat  tgtgttccgg  accctccct      900 acgcagaccc  cagcctgcag  gctcctgtgc  gtgtctccat  gcagctgcgg  cggccttccg     960
accgggagct  cagtgagccc  atggaattcc  agtacctgcc  agatacagac  gatcgtcacc    1020
ggattgagga  gaaacgtaaa  aggacatatg  agaccttcaa  gagcatcatg  aagaagagtc    1080
ctttcagcgg  acccaccgac  ccccggcctc  cacctcgacg  cattgctgtg  ccttcccgca    1140
gctcagcttc  tgtccccaag  ccagcacccc  agccctatcc  ctttacgtca  tccctgagca    1200
ccatcaacta  tgatgagttt  cccaccatgg  tgtttccttc  tgggcagatc  agccaggcct    1260
cggccttggc  cccggcccct  ccccaagtcc  tgccccaggc  tccagcccct  gcccctgctc    1320
cagccatggt  atcagctctg  gcccaggccc  agcccctgt   cccagtccta  gccccaggcc    1380
ctcctcaggc  tgtggcccca  cctgccccca  agcccaccca  ggctggggaa  ggaacgctgt    1440
cagaggccct  gctgcagctg  cagtttgatg  atgaagacct  gggggccttg  cttggcaaca    1500
gcacagaccc  agctgtgttc  acagacctgg  catccgtcga  caactccgag  tttcagcagc    1560
tgctgaacca  gggcatacct  gtggccccc   acacaactga  gcccatgctg  atggagtacc    1620
ctgaggctat  aactcgccta  gtgacagggg  cccagaggcc  ccccgaccca  gctcctgctc    1680 cactggggc   cccggggctc  cccaatggcc  tcctttcagg  agatgaagac  ttctcctcca    1740
ttgcggacat  ggacttctca  gccctgctga  gtcagatcag  ctcctaaggg  ggtgacgcct    1800 gccctccca   gagcactggg  ttgcagggga  ttgaagccct  ccaaaagcac  ttacggattc    1860 tggtgggtg   tgttccaact  gccccaact   ttgtggatgt  cttccttgga  gggggagcc    1920 atatttatt   cttttattgt  cagtatctgt  atctctctct  cttttggag   gtgcttaagc    1980 agaagcatta  acttctctgg  aaaggggga   gctgggaaa   ctcaaacttt  tcccctgtcc    2040
tgatggtcag  ctcccttctc  tgtagggaac  tctgggtcc   cccatcccca  tcctccagct    2100
tctggtactc  tcctagagac  agaagcaggc  tggaggtaag  gcctttgagc  cacaaagcc    2160 ttatcaagtg  tcttccatca  tggattcatt  acagcttaat  caaaataacg  ccccagatac    2220
cagcccctgt  atggcactgg  cattgtccct  gtgcctaaca  ccagcgtttg  aggggctggc    2280
cttcctgccc  tacagaggtc  tctgccggct  cttttccttgc  tcaaccatgg  ctgaaggaaa    2340
ccagtgcaac  agcactggct  ctctccagga  tccagaaggg  gtttggtctg  gacttccttt    2400 gctctcctc   ttctcaagtg  ccttaatagt  agggtaagtt  gttaagagtg  ggggagagca    2460
ggctggcagc  tctccagtca  ggaggcatag  ttttactga   acaatcaaag  cacttggact    2520
cttgctcttt  ctactctgaa  ctaataaatc  tgttgccaag  ctggctagaa  aaaaaaaaa    2580 aaaaaa                                                                    2586
```

<210> SEQ ID NO 20
<211> LENGTH: 2388
<212> TYPE: DNA
<213> ORGANISM: Homo sapiens

<400> SEQUENCE: 20

```
agcgcgcagg  cgcggccgga  ttccgggcag  tgacgcgacg  gcgggccgcg  cggcgcattt      60
ccgcctctgg  cgaatggctc  gtctgtagtg  cacgccgcgg  gcccagctgc  gaccccggcc     120
ccgcccccgg  gaccccggcc  atggacgaac  tgttcccct   catcttcccg  gcagagccag     180
cccaggcctc  tggccctat   gtggagatca  ttgagcagcc  caagcagcgg  ggcatgcgct     240
tccgctacaa  gtgcgagggg  cgctccgcgg  gcagcatccc  aggcgagagg  agcacagata     300
```

| | |
|---|---|
| ccaccaagac ccaccccacc atcaagatca atggctacac aggaccaggg acagtgcgca | 360 |
| tctccctggt caccaaggac cctcctcacc ggcctcaccc ccacgagctt gtaggaaagg | 420 |
| actgccggga tggcttctat gaggctgagc tctgcccgga ccgctgcatc cacagtttcc | 480 |
| agaacctggg aatccagtgt gtgaagaagc gggacctgga gcaggctatc agtcagcgca | 540 |
| tccagaccaa caacaacccc ttccaagttc ctatagaaga gcagcgtggg gactacgacc | 600 |
| tgaatgctgt gcggctctgc ttccaggtga cagtgcggga cccatcaggc aggcccctcc | 660 |
| gcctgccgcc tgtcctttct catcccatct ttgacaatcg tgcccccaac actgccgagc | 720 |
| tcaagatctg ccgagtgaac cgaaactctg cagctgcct cggtggggat gagatcttcc | 780 |
| tactgtgtga caaggtgcag aaagaggaca ttgaggtgta tttcacggga ccaggctggg | 840 |
| aggcccgagg ctccttttcg caagctgatg tgcaccgaca agtggccatt gtgttccgga | 900 |
| cccctcccta cgcagacccc agcctgcagg ctcctgtgcg tgtctccatg cagctgcggc | 960 |
| ggccttccga ccgggagctc agtgagccca tggaattcca gtacctgcca gatacagacg | 1020 |
| atcgtcaccg gattgaggag aaacgtaaaa ggacatatga gaccttcaag agcatcatga | 1080 |
| agaagagtcc tttcagcgga cccaccgacc cccggcctcc acctcgacgc attgctgtgc | 1140 |
| cttcccgcag ctcagcttct gtccccaagc cagccccagg ccctcctcag gctgtggccc | 1200 |
| cacctgcccc caagcccacc caggctgggg aaggaacgct gtcagaggcc ctgctgcagc | 1260 |
| tgcagtttga tgatgaagac ctgggggcct tgcttggcaa cagcacagac ccagctgtgt | 1320 |
| tcacagacct ggcatccgtc gacaactccg agtttcagca gctgctgaac cagggcatac | 1380 |
| ctgtggcccc ccacacaact gagcccatgc tgatggagta ccctgaggct ataactcgcc | 1440 |
| tagtgacagg ggcccagagg cccccccgacc cagctcctgc tccactgggg gccccggggc | 1500 |
| tccccaatgg cctcctttca ggagatgaag acttctcctc cattgcggac atggacttct | 1560 |
| cagccctgct gagtcagatc agctcctaag ggggtgacgc ctgccctccc cagagcactg | 1620 |
| ggttgcaggg gattgaagcc ctccaaaagc acttacggat tctggtgggg tgtgttccaa | 1680 |
| ctgcccccaa ctttgtggat gtcttccttg gaggggggag ccatattta ttcttttatt | 1740 |
| gtcagtatct gtatctctct ctcttttttgg aggtgcttaa gcagaagcat taacttctct | 1800 |
| ggaaaggggg gagctgggga aactcaaact tttcccctgt cctgatggtc agctcccttc | 1860 |
| tctgtaggga actctggggt cccccatccc catcctccag cttctggtac tctcctagag | 1920 |
| acagaagcag gctggaggta aggcctttga gcccacaaag ccttatcaag tgtcttccat | 1980 |
| catggattca ttacagctta atcaaaataa cgccccagat accagcccct gtatggcact | 2040 |
| ggcattgtcc ctgtgcctaa caccagcgtt tgaggggctg gccttcctgc cctacagagg | 2100 |
| tctctgccgg ctcttttcctt gctcaaccat ggctgaagga accagtgca acagcactgg | 2160 |
| ctctctccag gatccagaag gggtttggtc tgggacttcc ttgctctccc tcttctcaag | 2220 |
| tgccttaata gtagggtaag ttgttaagag tgggggagag caggctggca gctctccagt | 2280 |
| caggaggcat agtttttact gaacaatcaa agcacttgga ctcttgctct ttctactctg | 2340 |
| aactaataaa tctgttgcca agctggctag aaaaaaaaaa aaaaaaaa | 2388 |

<210> SEQ ID NO 21
<211> LENGTH: 2286
<212> TYPE: DNA
<213> ORGANISM: Homo sapiens

<400> SEQUENCE: 21

| | |
|---|---|
| agcgcgcagg cgcggccgga ttccgggcag tgacgcgacg gcgggccgcg cggcgcattt | 60 |

```
ccgcctctgg cgaatggctc gtctgtagtg cacgccgcgg gcccagctgc gaccccggcc      120
ccgcccccgg gaccccggcc atggacgaac tgttccccct catcttcccg gcagagccag      180
cccaggcctc tggcccctat gtggagatca ttgagcagcc caagcagcgg ggcatgcgct      240
tccgctacaa gtgcgagggg cgctccgcgg gcagcatccc aggcgagagg agcacagata      300
ccaccaagac ccaccccacc atcaagatca atggctacac aggaccaggg acagtgcgca      360
tctccctggt caccaaggac cctcctcacc ggcctcaccc ccacgagctt gtaggaaagg      420
actgccggga tggcttctat gaggctgagc tctgcccgga ccgctgcatc cacagtttcc      480
agaacctggg aatccagtgt gtgaagaagc gggacctgga gcaggctatc agtcagcgca      540
tccagaccaa caacaacccc ttccaagttc ctatagaaga gcagcgtggg gactacgacc      600
tgaatgctgt gcggctctgc ttccaggtga cagtgcggga cccatcaggc aggcccctcc      660
gcctgccgcc tgtcctttct catcccatct ttgacaatcg tgccccccaac actgccgagc      720 tcaagatctg ccgagtgaac cgaaactctg gcagctgcct cggtggggat gagatcttcc      780
tactgtgtga caaggtgcag aaagaggaca ttgaggtgta tttcacggga ccaggctggg      840
aggcccgagg ctccttttcg caagctgatg tgcaccgaca agtggccatt gtgttccgga      900
cccctcccta cgcagacccc agcctgcagg ctcctgtgcg tgtctccatg cagctgcggc      960
ggccttccga ccgggagctc agtgagccca tggaattcca gtacctgcca gatacagacg     1020
atcgtcaccg gattgaggag aaacgtaaaa ggacatatga gaccttcaag agcatcatga     1080
agaagagtcc tttcagcgga cccaccgacc ccggcctcc acctcgacgc attgctgtgc      1140
cttcccgcag ctcagcttct gtccccaagc cagcacccca gccctatccc tttacgtcat     1200
ccctgagcac catcaactat gatgagtttc ccaccatggt gtttccttct gggcagatca     1260
gccaggcctc ggccttggcc ccggcccctc cccaagtcct gccccaggct ccagcccctg     1320
cccctgctcc agccatggta tcagctctgg cccagaggcc ccccgaccca gctcctgctc     1380 cactggggc cccggggctc cccaatggcc tcctttcagg agatgaagac ttctcctcca     1440
ttgcggacat ggacttctca gccctgctga gtcagatcag ctcctaaggg ggtgacgcct     1500
gccctcccca gagcactggg ttgcaggga ttgaagccct ccaaaagcac ttacggattc      1560
tggtggggtg tgttccaact gcccccaact ttgtggatgt cttccttgga ggggggagcc     1620 atatttatt cttttattgt cagtatctgt atctctctct cttttggag gtgcttaagc      1680 agaagcatta acttctctgg aaagggggga gctgggaaa ctcaaacttt tccctgtcc      1740 tgatggtcag ctcccttctc tgtagggaac tctggggtcc cccatcccca tcctccagct     1800
tctggtactc tcctagagac agaagcaggc tggaggtaag gcctttgagc ccacaaagcc     1860
ttatcaagtg tcttccatca tggattcatt acagcttaat caaaataacg ccccagatac     1920
cagcccctgt atggcactgg cattgtccct gtgcctaaca ccagcgtttg agggctggc     1980 cttcctgccc tacagaggtc tctgccggct ctttccttgc tcaaccatgg ctgaaggaaa     2040
ccagtgcaac agcactggct ctctccagga tccagaaggg gtttggtctg ggacttcctt    2100
gctctccctc ttctcaagtg ccttaatagt agggtaagtt gttaagagtg ggggagagca     2160
ggctggcagc tctccagtca ggaggcatag tttttactga acaatcaaag cacttggact    2220
cttgctcttt ctactctgaa ctaataaatc tgttgccaag ctggctagaa aaaaaaaaa      2280 aaaaaa                                                                2286
```

<210> SEQ ID NO 22

```
<211> LENGTH: 2341
<212> TYPE: DNA
<213> ORGANISM: Homo sapiens

<400> SEQUENCE: 22
attccgggca gtgacgcgac ggcgggccgc gcggcgcatt tccgcctctg gcgaatggct      60
cgtctgtagt gcacgccgcg ggcccagctg cgaccccggc cccgccccg ggaccccggc      120 catggacgaa ctgttccccc tcatcttccc ggcagagcca gcccaggcct ctggccccta     180
tgtggagatc attgagcagc ccaagcagcg gggcatgcgc ttccgctaca agtgcgaggg     240
gcgctccgcg ggcagcatcc caggcgagag gagcacagat accaccaaga cccacccca    300 catcaagatc aatggctaca caggaccagg gacagtgcgc atctccctgg tcaccaagga    360
ccctcctcac cggcctcacc cccacgagct tgtaggaaag gactgccggg atggcttcta    420
tgaggctgag ctctgcccgg accgctgcat ccacagtttc cagaacctgg aatccagtg    480 tgtgaagaag cgggacctgg agcaggctat cagtcagcgc atccagacca acaacaaccc    540
cttccaagtt cctatagaag agcagcgtgg ggactacgac ctgaatgctg tgcggctctg    600
cttccaggtg acagtgcggg acccatcagg caggcccctc cgcctgccgc ctgtcctttc    660
tcatcccatc tttgacaatc gtgccccaa cactgccgag ctcaagatct gccgagtgaa    720
ccgaaactct ggcagctgcc tcggtgggga tgagatcttc ctactgtgtg acaaggtgca    780
gaaagacgat cgtcaccgga ttgaggagaa acgtaaaagg acatatgaga ccttcaagag    840
catcatgaag aagagtcctt tcagcggacc caccgacccc cggcctccac ctcgacgcat    900
tgctgtgcct tcccgcagct cagcttctgt ccccaagcca gcacccagc cctatcccctt    960 tacgtcatcc ctgagcacca tcaactatga tgagtttccc accatggtgt tccttctgg    1020 gcagatcagc caggcctcgg ccttggcccc ggccccctccc caagtcctgc cccaggctcc    1080
agcccctgcc cctgctccag ccatggtatc agctctggcc caggcccag ccctgtccc    1140 agtcctagcc ccaggccctc ctcaggctgt ggccccacct gccccaagc cacccaggc    1200 tgggaagga acgctgtcag aggccctgct gcagctgcag tttgatgatg aagacctggg    1260
ggccttgctt ggcaacagca cagacccagc tgtgttcaca gacctggcat ccgtcgacaa    1320
ctccgagttt cagcagctgc tgaaccaggg catacctgtg gcccccaca caactgagcc    1380 catgctgatg gagtaccctg aggctataac tcgcctagtg acaggggccc agaggccccc    1440
cgacccagct cctgctccac tgggggcccc ggggctcccc aatggcctcc tttcaggaga    1500
tgaagacttc tcctccattg cggacatgga cttctcagcc ctgctgagtc agatcagctc    1560 ctaaggggt gacgcctgcc ctcccagag cactgggttg caggggattg aagccctcca    1620
aaagcactta cggattctgg tggggtgtgt tccaactgcc cccaactttg tggatgtctt    1680
ccttggaggg gggagccata ttttattctt ttattgtcag tatctgtatc tctctctctt    1740 tttgaggtg cttaagcaga agcattaact tctctggaaa gggggagct ggggaaactc    1800 aaactttttcc cctgtcctga tggtcagctc ccttctctgt agggaactct ggggtccccc    1860
atccccatcc tccagcttct ggtactctcc tagagacaga agcaggctgg aggtaaggcc    1920
tttgagccca caaagcctta tcaagtgtct tccatcatgg attcattaca gcttaatcaa    1980
aataacgccc cagataccag cccctgtatg gcactggcat tgtccctgtg cctaacacca    2040
gcgtttgagg ggctggcctt cctgccctac agaggtctct gccggctctt tccttgctca    2100
accatggctg aaggaaacca gtgcaacagc actggctctc tccaggatcc agaaggggtt    2160
tggtctggga cttccttgct ctccctcttc tcaagtgcct taatagtagg gtaagttgtt    2220
```

-continued

| | |
|---|---|
| aagagtgggg gagagcaggc tggcagctct ccagtcagga ggcatagttt ttactgaaca | 2280 |
| atcaaagcac ttggactctt gctctttcta ctctgaacta taaatctgt tgccaagctg | 2340 |
| g | 2341 |

<210> SEQ ID NO 23
<211> LENGTH: 2236
<212> TYPE: DNA
<213> ORGANISM: Homo sapiens

<400> SEQUENCE: 23

| | |
|---|---|
| attccgggca gtgacgcgac ggcgggccgc gcggcgcatt tccgcctctg gcgaatggct | 60 |
| cgtctgtagt gcacgccgcg ggcccagctg cgaccccggc cccgccccg ggaccccggc | 120 |
| catggacgaa ctgttccccc tcatcttccc ggcagagcca gcccaggcct ctggcccta | 180 |
| tgtggagatc attgagcagc ccaagcagcg gggcatgcgc ttccgctaca agtgcgaggg | 240 |
| gcgctccgcg ggcagcatcc caggcgagag gagcacagat accaccaaga cccaccccac | 300 |
| catcaagatc aatggctaca caggaccagg gacagtgcgc atctccctgg tcaccaagga | 360 |
| ccctcctcac cggcctcacc cccacgagct tgtaggaaag gactgccggg atggcttcta | 420 |
| tgaggctgag ctctgcccgg accgctgcat ccacagtttc cagaacctgg gaatccagtg | 480 |
| tgtgaagaag cgggacctgg agcaggctat cagtcagcgc atccagacca acaacaaccc | 540 |
| cttccaagtt cctatagaag agcagcgtgg ggactacgac ctgaatgctg tgcggctctg | 600 |
| cttccaggtg acagtgcggg acccatcagg caggcccctc cgcctgccgc ctgtcctttc | 660 |
| tcatcccatc tttgacaatc acgatcgtca ccggattgag gagaaacgta aaggacata | 720 |
| tgagaccttc aagagcatca tgaagaagag tcctttcagc ggacccaccg accccggcc | 780 |
| tccacctcga cgcattgctg tgccttcccg cagctcagct tctgtcccca gccagcacc | 840 |
| ccagccctat ccctttacgt catccctgag caccatcaac tatgatgagt ttcccaccat | 900 |
| ggtgttttcct tctgggcaga tcagccaggc ctcggccttg gccccggccc ctccccaagt | 960 |
| cctgccccag gctccagccc ctgccccctgc tccagccatg gtatcagctc tggcccaggc | 1020 |
| cccagcccct gtcccagtcc tagccccagg ccctcctcag gctgtggccc cacctgcccc | 1080 |
| caagcccacc caggctgggg aaggaacgct gtcagaggcc ctgctgcagc tgcagtttga | 1140 |
| tgatgaagac ctgggggcct tgcttggcaa cagcacagac ccagctgtgt tcacagacct | 1200 |
| ggcatccgtc gacaactccg agtttcagca gctgctgaac cagggcatac ctgtggcccc | 1260 |
| ccacacaact gagcccatgc tgatggagta ccctgaggct ataactcgcc tagtgacagg | 1320 |
| ggcccagagg ccccccgacc cagctcctgc tccactgggg gccccggggc tccccaatgg | 1380 |
| cctcctttca ggagatgaag acttctcctc cattgcggac atggacttct cagccctgct | 1440 |
| gagtcagatc agctcctaag ggggtgacgc ctgccctccc cagagcactg ggttgcaggg | 1500 |
| gattgaagcc ctccaaaagc acttacggat tctggtgggg tgtgttccaa ctgccccaa | 1560 |
| ctttgtggat gtcttccttg gagggggag ccatatttta ttcttttatt gtcagtatct | 1620 |
| gtatctctct ctctttttgg aggtgcttaa gcagaagcat taacttctct ggaaagggg | 1680 |
| gagctgggga aactcaaact tttcccctgt cctgatggtc agctcccttc tctgtaggga | 1740 |
| actctggggt cccccatccc catcctccag cttctggtac tctcctagag acagaagcag | 1800 |
| gctgaggta aggcctttga gcccacaaag cctatcaag tgtcttccat catggattca | 1860 |
| ttacagctta atcaaaataa cgccccagat accagccct gtatggcact ggcattgtcc | 1920 |

```
ctgtgcctaa caccagcgtt tgaggggctg gccttcctgc cctacagagg tctctgccgg      1980
ctctttcctt gctcaaccat ggctgaagga aaccagtgca acagcactgg ctctctccag      2040
gatccagaag gggtttggtc tgggacttcc ttgctctccc tcttctcaag tgccttaata      2100
gtagggtaag ttgttaagag tgggggagag caggctggca gctctccagt caggaggcat      2160 agttttact gaacaatcaa agcacttgga ctcttgctct ttctactctg aactaataaa       2220
tctgttgcca agctgg                                                      2236

<210> SEQ ID NO 24
<211> LENGTH: 2555
<212> TYPE: PRT
<213> ORGANISM: Homo sapiens

<400> SEQUENCE: 24

Met Pro Pro Leu Leu Ala Pro Leu Leu Cys Leu Ala Leu Leu Pro Ala
1               5                   10                  15

Leu Ala Ala Arg Gly Pro Arg Cys Ser Gln Pro Gly Glu Thr Cys Leu
                20                  25                  30

Asn Gly Gly Lys Cys Glu Ala Ala Asn Gly Thr Glu Ala Cys Val Cys
            35                  40                  45

Gly Gly Ala Phe Val Gly Pro Arg Cys Gln Asp Pro Asn Pro Cys Leu
        50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
                100                 105                 110

Asn Gly Gly Thr Cys Asp Leu Leu Thr Leu Thr Glu Tyr Lys Cys Arg
            115                 120                 125

Cys Pro Pro Gly Trp Ser Gly Lys Ser Cys Gln Gln Ala Asp Pro Cys
        130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
                180                 185                 190

Gly Thr Cys His Asn Glu Val Gly Ser Tyr Arg Cys Val Cys Arg Ala
            195                 200                 205

Thr His Thr Gly Pro Asn Cys Glu Arg Pro Tyr Val Pro Cys Ser Pro
        210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
                260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
        290                 295                 300

Ala Cys Gln Asn Gly Gly Thr Cys His Asn Thr His Gly Gly Tyr Asn
305                 310                 315                 320
```

-continued

```
Cys Val Cys Val Asn Gly Trp Thr Gly Glu Asp Cys Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
        370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
        450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
            565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
            595                 600                 605

Ser Gln Pro Cys Arg His Gly Gly Thr Cys Gln Asp Arg Asp Asn Ala
            610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
            645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735
```

Tyr Lys Cys Asp Cys Asp Pro Gly Trp Ser Gly Thr Asn Cys Asp Ile
                740                 745                 750

Asn Asn Asn Glu Cys Glu Ser Asn Pro Cys Val Asn Gly Gly Thr Cys
                755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Val Ala Gly Tyr Lys Cys Asn
                805                 810                 815

Cys Leu Leu Pro Tyr Thr Gly Ala Thr Cys Glu Val Val Leu Ala Pro
                820                 825                 830

Cys Ala Pro Ser Pro Cys Arg Asn Gly Gly Glu Cys Arg Gln Ser Glu
                835                 840                 845

Asp Tyr Glu Ser Phe Ser Cys Val Cys Pro Thr Gly Trp Gln Gly Gln
                850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
                900                 905                 910

Pro Asn Pro Cys His Asn Gly Gly Ser Cys Thr Asp Gly Ile Asn Thr
                915                 920                 925

Ala Phe Cys Asp Cys Leu Pro Gly Phe Arg Gly Thr Phe Cys Glu Glu
                930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
                980                 985                 990

Phe Asn Gly Gly Thr Cys Val Asp Gly Ile Asn Ser Phe Thr Cys Leu
                995                 1000                1005

Cys Pro Pro Gly Phe Thr Gly Ser Tyr Cys Gln His Asp Val Asn
                1010                1015                1020

Glu Cys Asp Ser Gln Pro Cys Leu His Gly Gly Thr Cys Gln Asp
                1025                1030                1035

Gly Cys Gly Ser Tyr Arg Cys Thr Cys Pro Gln Gly Tyr Thr Gly
                1040                1045                1050

Pro Asn Cys Gln Asn Leu Val His Trp Cys Asp Ser Ser Pro Cys
                1055                1060                1065

Lys Asn Gly Gly Lys Cys Trp Gln Thr His Thr Gln Tyr Arg Cys
                1070                1075                1080

Glu Cys Pro Ser Gly Trp Thr Gly Leu Tyr Cys Asp Val Pro Ser
                1085                1090                1095

Val Ser Cys Glu Val Ala Ala Gln Arg Gln Gly Val Asp Val Ala
                1100                1105                1110

Arg Leu Cys Gln His Gly Gly Leu Cys Val Asp Ala Gly Asn Thr
                1115                1120                1125

His His Cys Arg Cys Gln Ala Gly Tyr Thr Gly Ser Tyr Cys Glu
                1130                1135                1140

Asp Leu Val Asp Glu Cys Ser Pro Ser Pro Cys Gln Asn Gly Ala

-continued

```
            1145                1150                1155
Thr Cys Thr Asp Tyr Leu Gly Gly Tyr Ser Cys Lys Cys Val Ala
        1160                1165                1170
Gly Tyr His Gly Val Asn Cys Ser Glu Glu Ile Asp Glu Cys Leu
        1175                1180                1185
Ser His Pro Cys Gln Asn Gly Gly Thr Cys Leu Asp Leu Pro Asn
        1190                1195                1200
Thr Tyr Lys Cys Ser Cys Pro Arg Gly Thr Gln Gly Val His Cys
        1205                1210                1215
Glu Ile Asn Val Asp Asp Cys Asn Pro Pro Val Asp Pro Val Ser
        1220                1225                1230
Arg Ser Pro Lys Cys Phe Asn Asn Gly Thr Cys Val Asp Gln Val
        1235                1240                1245
Gly Gly Tyr Ser Cys Thr Cys Pro Pro Gly Phe Val Gly Glu Arg
        1250                1255                1260
Cys Glu Gly Asp Val Asn Glu Cys Leu Ser Asn Pro Cys Asp Ala
        1265                1270                1275
Arg Gly Thr Gln Asn Cys Val Gln Arg Val Asn Asp Phe His Cys
        1280                1285                1290
Glu Cys Arg Ala Gly His Thr Gly Arg Arg Cys Glu Ser Val Ile
        1295                1300                1305
Asn Gly Cys Lys Gly Lys Pro Cys Lys Asn Gly Gly Thr Cys Ala
        1310                1315                1320
Val Ala Ser Asn Thr Ala Arg Gly Phe Ile Cys Lys Cys Pro Ala
        1325                1330                1335
Gly Phe Glu Gly Ala Thr Cys Glu Asn Asp Ala Arg Thr Cys Gly
        1340                1345                1350
Ser Leu Arg Cys Leu Asn Gly Gly Thr Cys Ile Ser Gly Pro Arg
        1355                1360                1365
Ser Pro Thr Cys Leu Cys Leu Gly Pro Phe Thr Gly Pro Glu Cys
        1370                1375                1380
Gln Phe Pro Ala Ser Ser Pro Cys Leu Gly Gly Asn Pro Cys Tyr
        1385                1390                1395
Asn Gln Gly Thr Cys Glu Pro Thr Ser Glu Ser Pro Phe Tyr Arg
        1400                1405                1410
Cys Leu Cys Pro Ala Lys Phe Asn Gly Leu Leu Cys His Ile Leu
        1415                1420                1425
Asp Tyr Ser Phe Gly Gly Gly Ala Gly Arg Asp Ile Pro Pro Pro
        1430                1435                1440
Leu Ile Glu Glu Ala Cys Glu Leu Pro Glu Cys Gln Glu Asp Ala
        1445                1450                1455
Gly Asn Lys Val Cys Ser Leu Gln Cys Asn Asn His Ala Cys Gly
        1460                1465                1470
Trp Asp Gly Gly Asp Cys Ser Leu Asn Phe Asn Asp Pro Trp Lys
        1475                1480                1485
Asn Cys Thr Gln Ser Leu Gln Cys Trp Lys Tyr Phe Ser Asp Gly
        1490                1495                1500
His Cys Asp Ser Gln Cys Asn Ser Ala Gly Cys Leu Phe Asp Gly
        1505                1510                1515
Phe Asp Cys Gln Arg Ala Glu Gly Gln Cys Asn Pro Leu Tyr Asp
        1520                1525                1530
Gln Tyr Cys Lys Asp His Phe Ser Asp Gly His Cys Asp Gln Gly
        1535                1540                1545
```

```
Cys Asn Ser Ala Glu Cys Glu Trp Asp Gly Leu Asp Cys Ala Glu
1550                1555                1560

His Val Pro Glu Arg Leu Ala Ala Gly Thr Leu Val Val Val Val
1565                1570                1575

Leu Met Pro Pro Glu Gln Leu Arg Asn Ser Ser Phe His Phe Leu
1580                1585                1590

Arg Glu Leu Ser Arg Val Leu His Thr Asn Val Val Phe Lys Arg
1595                1600                1605

Asp Ala His Gly Gln Gln Met Ile Phe Pro Tyr Tyr Gly Arg Glu
1610                1615                1620

Glu Glu Leu Arg Lys His Pro Ile Lys Arg Ala Ala Glu Gly Trp
1625                1630                1635

Ala Ala Pro Asp Ala Leu Leu Gly Gln Val Lys Ala Ser Leu Leu
1640                1645                1650

Pro Gly Gly Ser Glu Gly Gly Arg Arg Arg Glu Leu Asp Pro
1655                1660                1665

Met Asp Val Arg Gly Ser Ile Val Tyr Leu Glu Ile Asp Asn Arg
1670                1675                1680

Gln Cys Val Gln Ala Ser Ser Gln Cys Phe Gln Ser Ala Thr Asp
1685                1690                1695

Val Ala Ala Phe Leu Gly Ala Leu Ala Ser Leu Gly Ser Leu Asn
1700                1705                1710

Ile Pro Tyr Lys Ile Glu Ala Val Gln Ser Glu Thr Val Glu Pro
1715                1720                1725

Pro Pro Pro Ala Gln Leu His Phe Met Tyr Val Ala Ala Ala Ala
1730                1735                1740

Phe Val Leu Leu Phe Phe Val Gly Cys Gly Val Leu Leu Ser Arg
1745                1750                1755

Lys Arg Arg Arg Gln His Gly Gln Leu Trp Phe Pro Glu Gly Phe
1760                1765                1770

Lys Val Ser Glu Ala Ser Lys Lys Lys Arg Arg Glu Pro Leu Gly
1775                1780                1785

Glu Asp Ser Val Gly Leu Lys Pro Leu Lys Asn Ala Ser Asp Gly
1790                1795                1800

Ala Leu Met Asp Asp Asn Gln Asn Glu Trp Gly Asp Glu Asp Leu
1805                1810                1815

Glu Thr Lys Lys Phe Arg Phe Glu Glu Pro Val Val Leu Pro Asp
1820                1825                1830

Leu Asp Asp Gln Thr Asp His Arg Gln Trp Thr Gln Gln His Leu
1835                1840                1845

Asp Ala Ala Asp Leu Arg Met Ser Ala Met Ala Pro Thr Pro Pro
1850                1855                1860

Gln Gly Glu Val Asp Ala Asp Cys Met Asp Val Asn Val Arg Gly
1865                1870                1875

Pro Asp Gly Phe Thr Pro Leu Met Ile Ala Ser Cys Ser Gly Gly
1880                1885                1890

Gly Leu Glu Thr Gly Asn Ser Glu Glu Glu Glu Asp Ala Pro Ala
1895                1900                1905

Val Ile Ser Asp Phe Ile Tyr Gln Gly Ala Ser Leu His Asn Gln
1910                1915                1920

Thr Asp Arg Thr Gly Glu Thr Ala Leu His Leu Ala Ala Arg Tyr
1925                1930                1935
```

```
Ser Arg Ser Asp Ala Ala Lys Arg Leu Leu Glu Ala Ser Ala Asp
    1940            1945            1950

Ala Asn Ile Gln Asp Asn Met Gly Arg Thr Pro Leu His Ala Ala
    1955            1960            1965

Val Ser Ala Asp Ala Gln Gly Val Phe Gln Ile Leu Ile Arg Asn
    1970            1975            1980

Arg Ala Thr Asp Leu Asp Ala Arg Met His Asp Gly Thr Thr Pro
    1985            1990            1995

Leu Ile Leu Ala Ala Arg Leu Ala Val Glu Gly Met Leu Glu Asp
    2000            2005            2010

Leu Ile Asn Ser His Ala Asp Val Asn Ala Val Asp Asp Leu Gly
    2015            2020            2025

Lys Ser Ala Leu His Trp Ala Ala Val Asn Asn Val Asp Ala
    2030            2035            2040

Ala Val Val Leu Leu Lys Asn Gly Ala Asn Lys Asp Met Gln Asn
    2045            2050            2055

Asn Arg Glu Glu Thr Pro Leu Phe Leu Ala Ala Arg Glu Gly Ser
    2060            2065            2070

Tyr Glu Thr Ala Lys Val Leu Leu Asp His Phe Ala Asn Arg Asp
    2075            2080            2085

Ile Thr Asp His Met Asp Arg Leu Pro Arg Asp Ile Ala Gln Glu
    2090            2095            2100

Arg Met His His Asp Ile Val Arg Leu Leu Asp Glu Tyr Asn Leu
    2105            2110            2115

Val Arg Ser Pro Gln Leu His Gly Ala Pro Leu Gly Gly Thr Pro
    2120            2125            2130

Thr Leu Ser Pro Pro Leu Cys Ser Pro Asn Gly Tyr Leu Gly Ser
    2135            2140            2145

Leu Lys Pro Gly Val Gln Gly Lys Lys Val Arg Lys Pro Ser Ser
    2150            2155            2160

Lys Gly Leu Ala Cys Gly Ser Lys Glu Ala Lys Asp Leu Lys Ala
    2165            2170            2175

Arg Arg Lys Lys Ser Gln Asp Gly Lys Gly Cys Leu Leu Asp Ser
    2180            2185            2190

Ser Gly Met Leu Ser Pro Val Asp Ser Leu Glu Ser Pro His Gly
    2195            2200            2205

Tyr Leu Ser Asp Val Ala Ser Pro Pro Leu Leu Pro Ser Pro Phe
    2210            2215            2220

Gln Gln Ser Pro Ser Val Pro Leu Asn His Leu Pro Gly Met Pro
    2225            2230            2235

Asp Thr His Leu Gly Ile Gly His Leu Asn Val Ala Ala Lys Pro
    2240            2245            2250

Glu Met Ala Ala Leu Gly Gly Gly Gly Arg Leu Ala Phe Glu Thr
    2255            2260            2265

Gly Pro Pro Arg Leu Ser His Leu Pro Val Ala Ser Gly Thr Ser
    2270            2275            2280

Thr Val Leu Gly Ser Ser Ser Gly Gly Ala Leu Asn Phe Thr Val
    2285            2290            2295

Gly Gly Ser Thr Ser Leu Asn Gly Gln Cys Glu Trp Leu Ser Arg
    2300            2305            2310

Leu Gln Ser Gly Met Val Pro Asn Gln Tyr Asn Pro Leu Arg Gly
    2315            2320            2325

Ser Val Ala Pro Gly Pro Leu Ser Thr Gln Ala Pro Ser Leu Gln
```

```
                2330                2335                2340

His Gly Met Val Gly Pro Leu His Ser Ser Leu Ala Ala Ser Ala
            2345                2350                2355

Leu Ser Gln Met Met Ser Tyr Gln Gly Leu Pro Ser Thr Arg Leu
            2360                2365                2370

Ala Thr Gln Pro His Leu Val Gln Thr Gln Gln Val Gln Pro Gln
            2375                2380                2385

Asn Leu Gln Met Gln Gln Gln Asn Leu Gln Pro Ala Asn Ile Gln
            2390                2395                2400

Gln Gln Gln Ser Leu Gln Pro Pro Pro Pro Pro Gln Pro His
            2405                2410                2415

Leu Gly Val Ser Ser Ala Ala Ser Gly His Leu Gly Arg Ser Phe
            2420                2425                2430

Leu Ser Gly Glu Pro Ser Gln Ala Asp Val Gln Pro Leu Gly Pro
            2435                2440                2445

Ser Ser Leu Ala Val His Thr Ile Leu Pro Gln Glu Ser Pro Ala
            2450                2455                2460

Leu Pro Thr Ser Leu Pro Ser Ser Leu Val Pro Pro Val Thr Ala
            2465                2470                2475

Ala Gln Phe Leu Thr Pro Pro Ser Gln His Ser Tyr Ser Ser Pro
            2480                2485                2490

Val Asp Asn Thr Pro Ser His Gln Leu Gln Val Pro Glu His Pro
            2495                2500                2505

Phe Leu Thr Pro Ser Pro Glu Ser Pro Asp Gln Trp Ser Ser Ser
            2510                2515                2520

Ser Pro His Ser Asn Val Ser Asp Trp Ser Glu Gly Val Ser Ser
            2525                2530                2535

Pro Pro Thr Ser Met Gln Ser Gln Ile Ala Arg Ile Pro Glu Ala
            2540                2545                2550

Phe Lys
    2555

<210> SEQ ID NO 25
<211> LENGTH: 2471
<212> TYPE: PRT
<213> ORGANISM: Homo sapiens

<400> SEQUENCE: 25

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
            35                  40                  45

Gly Tyr Cys Lys Cys Pro Glu Gly Phe Leu Gly Glu Tyr Cys Gln His
        50                  55                  60

Arg Asp Pro Cys Glu Lys Asn Arg Cys Gln Asn Gly Gly Thr Cys Val
65                  70                  75                  80

Ala Gln Ala Met Leu Gly Lys Ala Thr Cys Arg Cys Ala Ser Gly Phe
                85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125
```

```
Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
            340                 345                 350

Cys Ile Asp Arg Val Ala Ser Phe Ser Cys Met Cys Pro Glu Gly Lys
        355                 360                 365

Ala Gly Leu Leu Cys His Leu Asp Asp Ala Cys Ile Ser Asn Pro Cys
370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
            420                 425                 430

Cys Val Asn Thr Asp Gly Ala Phe His Cys Glu Cys Leu Lys Gly Tyr
        435                 440                 445

Ala Gly Pro Arg Cys Glu Met Asp Ile Asn Glu Cys His Ser Asp Pro
450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
            500                 505                 510

Val Asn Arg Phe Gln Cys Leu Cys Pro Pro Gly Phe Thr Gly Pro Val
        515                 520                 525

Cys Gln Ile Asp Ile Asp Asp Cys Ser Ser Thr Pro Cys Leu Asn Gly
530                 535                 540

Ala Lys Cys Ile Asp His Pro Asn Gly Tyr Glu Cys Gln Cys Ala Thr
```

-continued

```
545                 550                 555                 560
Gly Phe Thr Gly Val Leu Cys Glu Glu Asn Ile Asp Asn Cys Asp Pro
                565                 570                 575
Asp Pro Cys His His Gly Gln Cys Gln Asp Gly Ile Asp Ser Tyr Thr
                580                 585                 590
Cys Ile Cys Asn Pro Gly Tyr Met Gly Ala Ile Cys Ser Asp Gln Ile
                595                 600                 605
Asp Glu Cys Tyr Ser Ser Pro Cys Leu Asn Asp Gly Arg Cys Ile Asp
            610                 615                 620
Leu Val Asn Gly Tyr Gln Cys Asn Cys Gln Pro Gly Thr Ser Gly Val
625                 630                 635                 640
Asn Cys Glu Ile Asn Phe Asp Asp Cys Ala Ser Asn Pro Cys Ile His
                645                 650                 655
Gly Ile Cys Met Asp Gly Ile Asn Arg Tyr Ser Cys Val Cys Ser Pro
                660                 665                 670
Gly Phe Thr Gly Gln Arg Cys Asn Ile Asp Ile Asp Glu Cys Ala Ser
                675                 680                 685
Asn Pro Cys Arg Lys Gly Ala Thr Cys Ile Asn Gly Val Asn Gly Phe
                690                 695                 700
Arg Cys Ile Cys Pro Glu Gly Pro His His Pro Ser Cys Tyr Ser Gln
705                 710                 715                 720
Val Asn Glu Cys Leu Ser Asn Pro Cys Ile His Gly Asn Cys Thr Gly
                725                 730                 735
Gly Leu Ser Gly Tyr Lys Cys Leu Cys Asp Ala Gly Trp Val Gly Ile
                740                 745                 750
Asn Cys Glu Val Asp Lys Asn Glu Cys Leu Ser Asn Pro Cys Gln Asn
                755                 760                 765
Gly Gly Thr Cys Asp Asn Leu Val Asn Gly Tyr Arg Cys Thr Cys Lys
                770                 775                 780
Lys Gly Phe Lys Gly Tyr Asn Cys Gln Val Asn Ile Asp Glu Cys Ala
785                 790                 795                 800
Ser Asn Pro Cys Leu Asn Gln Gly Thr Cys Phe Asp Asp Ile Ser Gly
                805                 810                 815
Tyr Thr Cys His Cys Val Leu Pro Tyr Thr Gly Lys Asn Cys Gln Thr
                820                 825                 830
Val Leu Ala Pro Cys Ser Pro Asn Pro Cys Glu Asn Ala Ala Val Cys
                835                 840                 845
Lys Glu Ser Pro Asn Phe Glu Ser Tyr Thr Cys Leu Cys Ala Pro Gly
850                 855                 860
Trp Gln Gly Gln Arg Cys Thr Ile Asp Ile Asp Glu Cys Ile Ser Lys
865                 870                 875                 880
Pro Cys Met Asn His Gly Leu Cys His Asn Thr Gln Gly Ser Tyr Met
                885                 890                 895
Cys Glu Cys Pro Pro Gly Phe Ser Gly Met Asp Cys Glu Glu Asp Ile
                900                 905                 910
Asp Asp Cys Leu Ala Asn Pro Cys Gln Asn Gly Gly Ser Cys Met Asp
            915                 920                 925
Gly Val Asn Thr Phe Ser Cys Leu Cys Leu Pro Gly Phe Thr Gly Asp
930                 935                 940
Lys Cys Gln Thr Asp Met Asn Glu Cys Leu Ser Glu Pro Cys Lys Asn
945                 950                 955                 960
Gly Gly Thr Cys Ser Asp Tyr Val Asn Ser Tyr Thr Cys Lys Cys Gln
                965                 970                 975
```

```
Ala Gly Phe Asp Gly Val His Cys Glu Asn Asn Ile Asn Glu Cys Thr
            980                 985                 990

Glu Ser Ser Cys Phe Asn Gly Gly Thr Cys Val Asp Gly Ile Asn Ser
            995                1000                1005

Phe Ser Cys Leu Cys Pro Val Gly Phe Thr Gly Ser Phe Cys Leu
        1010                1015                1020

His Glu Ile Asn Glu Cys Ser Ser His Pro Cys Leu Asn Glu Gly
        1025                1030                1035

Thr Cys Val Asp Gly Leu Gly Thr Tyr Arg Cys Ser Cys Pro Leu
        1040                1045                1050

Gly Tyr Thr Gly Lys Asn Cys Gln Thr Leu Val Asn Leu Cys Ser
        1055                1060                1065

Arg Ser Pro Cys Lys Asn Lys Gly Thr Cys Val Gln Lys Lys Ala
        1070                1075                1080

Glu Ser Gln Cys Leu Cys Pro Ser Gly Trp Ala Gly Ala Tyr Cys
        1085                1090                1095

Asp Val Pro Asn Val Ser Cys Asp Ile Ala Ala Ser Arg Arg Gly
        1100                1105                1110

Val Leu Val Glu His Leu Cys Gln His Ser Gly Val Cys Ile Asn
        1115                1120                1125

Ala Gly Asn Thr His Tyr Cys Gln Cys Pro Leu Gly Tyr Thr Gly
        1130                1135                1140

Ser Tyr Cys Glu Glu Gln Leu Asp Glu Cys Ala Ser Asn Pro Cys
        1145                1150                1155

Gln His Gly Ala Thr Cys Ser Asp Phe Ile Gly Gly Tyr Arg Cys
        1160                1165                1170

Glu Cys Val Pro Gly Tyr Gln Gly Val Asn Cys Glu Tyr Glu Val
        1175                1180                1185

Asp Glu Cys Gln Asn Gln Pro Cys Gln Asn Gly Gly Thr Cys Ile
        1190                1195                1200

Asp Leu Val Asn His Phe Lys Cys Ser Cys Pro Pro Gly Thr Arg
        1205                1210                1215

Gly Leu Leu Cys Glu Glu Asn Ile Asp Asp Cys Ala Arg Gly Pro
        1220                1225                1230

His Cys Leu Asn Gly Gly Gln Cys Met Asp Arg Ile Gly Gly Tyr
        1235                1240                1245

Ser Cys Arg Cys Leu Pro Gly Phe Ala Gly Glu Arg Cys Glu Gly
        1250                1255                1260

Asp Ile Asn Glu Cys Leu Ser Asn Pro Cys Ser Ser Glu Gly Ser
        1265                1270                1275

Leu Asp Cys Ile Gln Leu Thr Asn Asp Tyr Leu Cys Val Cys Arg
        1280                1285                1290

Ser Ala Phe Thr Gly Arg His Cys Glu Thr Phe Val Asp Val Cys
        1295                1300                1305

Pro Gln Met Pro Cys Leu Asn Gly Gly Thr Cys Ala Val Ala Ser
        1310                1315                1320

Asn Met Pro Asp Gly Phe Ile Cys Arg Cys Pro Pro Gly Phe Ser
        1325                1330                1335

Gly Ala Arg Cys Gln Ser Ser Cys Gly Gln Val Lys Cys Arg Lys
        1340                1345                1350

Gly Glu Gln Cys Val His Thr Ala Ser Gly Pro Arg Cys Phe Cys
        1355                1360                1365
```

```
Pro Ser Pro Arg Asp Cys Glu Ser Gly Cys Ala Ser Ser Pro Cys
    1370                1375                1380

Gln His Gly Gly Ser Cys His Pro Gln Arg Gln Pro Pro Tyr Tyr
    1385                1390                1395

Ser Cys Gln Cys Ala Pro Pro Phe Ser Gly Ser Arg Cys Glu Leu
    1400                1405                1410

Tyr Thr Ala Pro Pro Ser Thr Pro Pro Ala Thr Cys Leu Ser Gln
    1415                1420                1425

Tyr Cys Ala Asp Lys Ala Arg Asp Gly Val Cys Asp Glu Ala Cys
    1430                1435                1440

Asn Ser His Ala Cys Gln Trp Asp Gly Gly Asp Cys Ser Leu Thr
    1445                1450                1455

Met Glu Asn Pro Trp Ala Asn Cys Ser Ser Pro Leu Pro Cys Trp
    1460                1465                1470

Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys
    1490                1495                1500

Lys Tyr Asp Lys Tyr Cys Ala Asp His Phe Lys Asp Asn His Cys
    1505                1510                1515

Asp Gln Gly Cys Asn Ser Glu Glu Cys Gly Trp Asp Gly Leu Asp
    1520                1525                1530

Cys Ala Ala Asp Gln Pro Glu Asn Leu Ala Glu Gly Thr Leu Val
    1535                1540                1545

Ile Val Val Leu Met Pro Pro Glu Gln Leu Leu Gln Asp Ala Arg
    1550                1555                1560

Ser Phe Leu Arg Ala Leu Gly Thr Leu Leu His Thr Asn Leu Arg
    1565                1570                1575

Ile Lys Arg Asp Ser Gln Gly Glu Leu Met Val Tyr Pro Tyr Tyr
    1580                1585                1590

Gly Glu Lys Ser Ala Ala Met Lys Lys Gln Arg Met Thr Arg Arg
    1595                1600                1605

Ser Leu Pro Gly Glu Gln Glu Gln Glu Val Ala Gly Ser Lys Val
    1610                1615                1620

Phe Leu Glu Ile Asp Asn Arg Gln Cys Val Gln Asp Ser Asp His
    1625                1630                1635

Cys Phe Lys Asn Thr Asp Ala Ala Ala Leu Leu Ala Ser His
    1640                1645                1650

Ala Ile Gln Gly Thr Leu Ser Tyr Pro Leu Val Ser Val Val Ser
    1655                1660                1665

Glu Ser Leu Thr Pro Glu Arg Thr Gln Leu Leu Tyr Leu Leu Ala
    1670                1675                1680

Val Ala Val Val Ile Ile Leu Phe Ile Ile Leu Leu Gly Val Ile
    1685                1690                1695

Met Ala Lys Arg Lys Arg Lys His Gly Ser Leu Trp Leu Pro Glu
    1700                1705                1710

Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln
    1730                1735                1740

Val Ser Glu Ala Asn Leu Ile Gly Thr Gly Thr Ser Glu His Trp
    1745                1750                1755

Val Asp Asp Glu Gly Pro Gln Pro Lys Lys Val Lys Ala Glu Asp
```

```
                    1760                1765                1770

Glu Ala Leu Leu Ser Glu Glu Asp Asp Pro Ile Asp Arg Arg Pro
            1775                1780                1785

Trp Thr Gln Gln His Leu Glu Ala Ala Asp Ile Arg Arg Thr Pro
            1790                1795                1800

Ser Leu Ala Leu Thr Pro Pro Gln Ala Glu Gln Glu Val Asp Val
            1805                1810                1815

Leu Asp Val Asn Val Arg Gly Pro Asp Gly Cys Thr Pro Leu Met
            1820                1825                1830

Leu Ala Ser Leu Arg Gly Gly Ser Ser Asp Leu Ser Asp Glu Asp
            1835                1840                1845

Glu Asp Ala Glu Asp Ser Ser Ala Asn Ile Ile Thr Asp Leu Val
            1850                1855                1860

Tyr Gln Gly Ala Ser Leu Gln Ala Gln Thr Asp Arg Thr Gly Glu
            1865                1870                1875

Met Ala Leu His Leu Ala Ala Arg Tyr Ser Arg Ala Asp Ala Ala
            1880                1885                1890

Lys Arg Leu Leu Asp Ala Gly Ala Asp Ala Asn Ala Gln Asp Asn
            1895                1900                1905

Met Gly Arg Cys Pro Leu His Ala Ala Val Ala Ala Asp Ala Gln
            1910                1915                1920

Gly Val Phe Gln Ile Leu Ile Arg Asn Arg Val Thr Asp Leu Asp
            1925                1930                1935

Ala Arg Met Asn Asp Gly Thr Thr Pro Leu Ile Leu Ala Ala Arg
            1940                1945                1950

Leu Ala Val Glu Gly Met Val Ala Glu Leu Ile Asn Cys Gln Ala
            1955                1960                1965

Asp Val Asn Ala Val Asp Asp His Gly Lys Ser Ala Leu His Trp
            1970                1975                1980

Ala Ala Ala Val Asn Asn Val Glu Ala Thr Leu Leu Leu Leu Lys
            1985                1990                1995

Asn Gly Ala Asn Arg Asp Met Gln Asp Asn Lys Glu Glu Thr Pro
            2000                2005                2010

Leu Phe Leu Ala Ala Arg Glu Gly Ser Tyr Glu Ala Ala Lys Ile
            2015                2020                2025

Leu Leu Asp His Phe Ala Asn Arg Asp Ile Thr Asp His Met Asp
            2030                2035                2040

Arg Leu Pro Arg Asp Val Ala Arg Asp Arg Met His His Asp Ile
            2045                2050                2055

Val Arg Leu Leu Asp Glu Tyr Asn Val Thr Pro Ser Pro Pro Gly
            2060                2065                2070

Thr Val Leu Thr Ser Ala Leu Ser Pro Val Ile Cys Gly Pro Asn
            2075                2080                2085

Arg Ser Phe Leu Ser Leu Lys His Thr Pro Met Gly Lys Lys Ser
            2090                2095                2100

Arg Arg Pro Ser Ala Lys Ser Thr Met Pro Thr Ser Leu Pro Asn
            2105                2110                2115

Leu Ala Lys Glu Ala Lys Asp Ala Lys Gly Ser Arg Arg Lys Lys
            2120                2125                2130

Ser Leu Ser Glu Lys Val Gln Leu Ser Glu Ser Ser Val Thr Leu
            2135                2140                2145

Ser Pro Val Asp Ser Leu Glu Ser Pro His Thr Tyr Val Ser Asp
            2150                2155                2160
```

```
Thr Thr Ser Ser Pro Met Ile Thr Ser Pro Gly Ile Leu Gln Ala
    2165            2170            2175

Ser Pro Asn Pro Met Leu Ala Thr Ala Ala Pro Ala Pro Val
    2180            2185            2190

His Ala Gln His Ala Leu Ser Phe Ser Asn Leu His Glu Met Gln
    2195            2200            2205

Pro Leu Ala His Gly Ala Ser Thr Val Leu Pro Ser Val Ser Gln
    2210            2215            2220

Leu Leu Ser His His His Ile Val Ser Pro Gly Ser Gly Ser Ala
    2225            2230            2235

Gly Ser Leu Ser Arg Leu His Pro Val Pro Val Pro Ala Asp Trp
    2240            2245            2250

Met Asn Arg Met Glu Val Asn Glu Thr Gln Tyr Asn Glu Met Phe
    2255            2260            2265

Gly Met Val Leu Ala Pro Ala Glu Gly Thr His Pro Gly Ile Ala
    2270            2275            2280

Pro Gln Ser Arg Pro Pro Glu Gly Lys His Ile Thr Thr Pro Arg
    2285            2290            2295

Glu Pro Leu Pro Pro Ile Val Thr Phe Gln Leu Ile Pro Lys Gly
    2300            2305            2310

Ser Ile Ala Gln Pro Ala Gly Ala Pro Gln Pro Gln Ser Thr Cys
    2315            2320            2325

Pro Pro Ala Val Ala Gly Pro Leu Pro Thr Met Tyr Gln Ile Pro
    2330            2335            2340

Glu Met Ala Arg Leu Pro Ser Val Ala Phe Pro Thr Ala Met Met
    2345            2350            2355

Pro Gln Gln Asp Gly Gln Val Ala Gln Thr Ile Leu Pro Ala Tyr
    2360            2365            2370

His Pro Phe Pro Ala Ser Val Gly Lys Tyr Pro Thr Pro Pro Ser
    2375            2380            2385

Gln His Ser Tyr Ala Ser Ser Asn Ala Ala Glu Arg Thr Pro Ser
    2390            2395            2400

His Ser Gly His Leu Gln Gly Glu His Pro Tyr Leu Thr Pro Ser
    2405            2410            2415

Pro Glu Ser Pro Asp Gln Trp Ser Ser Ser Ser Pro His Ser Ala
    2420            2425            2430

Ser Asp Trp Ser Asp Val Thr Thr Ser Pro Thr Pro Gly Gly Ala
    2435            2440            2445

Gly Gly Gly Gln Arg Gly Pro Gly Thr His Met Ser Glu Pro Pro
    2450            2455            2460

His Asn Asn Met Gln Val Tyr Ala
    2465            2470

<210> SEQ ID NO 26
<211> LENGTH: 1235
<212> TYPE: PRT
<213> ORGANISM: Homo sapiens

<400> SEQUENCE: 26

Met Pro Ala Leu Arg Pro Ala Leu Leu Trp Ala Leu Leu Ala Leu Trp
1               5                   10                  15

Leu Cys Cys Ala Ala Pro Ala His Ala Leu Gln Cys Arg Asp Gly Tyr
                20                  25                  30

Glu Pro Cys Val Asn Glu Gly Met Cys Val Thr Tyr His Asn Gly Thr
```

```
            35                  40                  45
Gly Tyr Cys Lys Cys Pro Glu Gly Phe Leu Gly Glu Tyr Cys Gln His
 50                  55                  60

Arg Asp Pro Cys Glu Lys Asn Arg Cys Gln Asn Gly Gly Thr Cys Val
 65                  70                  75                  80

Ala Gln Ala Met Leu Gly Lys Ala Thr Cys Arg Cys Ala Ser Gly Phe
                 85                  90                  95

Thr Gly Glu Asp Cys Gln Tyr Ser Thr Ser His Pro Cys Phe Val Ser
                100                 105                 110

Arg Pro Cys Leu Asn Gly Gly Thr Cys His Met Leu Ser Arg Asp Thr
                115                 120                 125

Tyr Glu Cys Thr Cys Gln Val Gly Phe Thr Gly Lys Glu Cys Gln Trp
                130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
                180                 185                 190

Gln His Gly Gly Thr Cys Leu Asn Leu Pro Gly Ser Tyr Gln Cys Gln
                195                 200                 205

Cys Pro Gln Gly Phe Thr Gly Gln Tyr Cys Asp Ser Leu Tyr Val Pro
                210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
                260                 265                 270

Gly Val Cys Val Asp Gly Val Asn Thr Tyr Asn Cys Arg Cys Pro Pro
                275                 280                 285

Gln Trp Thr Gly Gln Phe Cys Thr Glu Asp Val Asp Glu Cys Leu Leu
                290                 295                 300

Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
                340                 345                 350

Cys Ile Asp Arg Val Ala Ser Phe Ser Cys Met Cys Pro Glu Gly Lys
                355                 360                 365

Ala Gly Leu Leu Cys His Leu Asp Asp Ala Cys Ile Ser Asn Pro Cys
                370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
                420                 425                 430

Cys Val Asn Thr Asp Gly Ala Phe His Cys Glu Cys Leu Lys Gly Tyr
                435                 440                 445

Ala Gly Pro Arg Cys Glu Met Asp Ile Asn Glu Cys His Ser Asp Pro
                450                 455                 460
```

```
Cys Gln Asn Asp Ala Thr Cys Leu Asp Lys Ile Gly Phe Thr Cys
465                 470                 475                 480

Leu Cys Met Pro Gly Phe Lys Gly Val His Cys Glu Leu Glu Ile Asn
            485                 490                 495

Glu Cys Gln Ser Asn Pro Cys Val Asn Gly Gln Cys Val Asp Lys
            500                 505                 510

Val Asn Arg Phe Gln Cys Leu Cys Pro Pro Gly Phe Thr Gly Pro Val
            515                 520                 525

Cys Gln Ile Asp Ile Asp Asp Cys Ser Ser Thr Pro Cys Leu Asn Gly
530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
            565                 570                 575

Asp Pro Cys His His Gly Gln Cys Gln Asp Gly Ile Asp Ser Tyr Thr
            580                 585                 590

Cys Ile Cys Asn Pro Gly Tyr Met Gly Ala Ile Cys Ser Asp Gln Ile
            595                 600                 605

Asp Glu Cys Tyr Ser Ser Pro Cys Leu Asn Asp Gly Arg Cys Ile Asp
            610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
            645                 650                 655

Gly Ile Cys Met Asp Gly Ile Asn Arg Tyr Ser Cys Val Cys Ser Pro
            660                 665                 670

Gly Phe Thr Gly Gln Arg Cys Asn Ile Asp Ile Asp Glu Cys Ala Ser
            675                 680                 685

Asn Pro Cys Arg Lys Gly Ala Thr Cys Ile Asn Gly Val Asn Gly Phe
            690                 695                 700

Arg Cys Ile Cys Pro Glu Gly Pro His His Pro Ser Cys Tyr Ser Gln
705                 710                 715                 720

Val Asn Glu Cys Leu Ser Asn Pro Cys Ile His Gly Asn Cys Thr Gly
            725                 730                 735

Gly Leu Ser Gly Tyr Lys Cys Leu Cys Asp Ala Gly Trp Val Gly Ile
            740                 745                 750

Asn Cys Glu Val Asp Lys Asn Glu Cys Leu Ser Asn Pro Cys Gln Asn
            755                 760                 765

Gly Gly Thr Cys Asp Asn Leu Val Asn Gly Tyr Arg Cys Thr Cys Lys
            770                 775                 780

Lys Gly Phe Lys Gly Tyr Asn Cys Gln Val Asn Ile Asp Glu Cys Ala
785                 790                 795                 800

Ser Asn Pro Cys Leu Asn Gln Gly Thr Cys Phe Asp Asp Ile Ser Gly
            805                 810                 815

Tyr Thr Cys His Cys Val Leu Pro Tyr Thr Gly Lys Asn Cys Gln Thr
            820                 825                 830

Val Leu Ala Pro Cys Ser Pro Asn Pro Cys Glu Asn Ala Ala Val Cys
            835                 840                 845

Lys Glu Ser Pro Asn Phe Glu Ser Tyr Thr Cys Leu Cys Ala Pro Gly
            850                 855                 860

Trp Gln Gly Gln Arg Cys Thr Ile Asp Ile Asp Glu Cys Ile Ser Lys
865                 870                 875                 880
```

Pro Cys Met Asn His Gly Leu Cys His Asn Thr Gln Gly Ser Tyr Met
            885                 890                 895

Cys Glu Cys Pro Pro Gly Phe Ser Gly Met Asp Cys Glu Glu Asp Ile
        900                 905                 910

Asp Asp Cys Leu Ala Asn Pro Cys Gln Asn Gly Gly Ser Cys Met Asp
            915                 920                 925

Gly Val Asn Thr Phe Ser Cys Leu Cys Leu Pro Gly Phe Thr Gly Asp
        930                 935                 940

Lys Cys Gln Thr Asp Met Asn Glu Cys Leu Ser Glu Pro Cys Lys Asn
945                 950                 955                 960

Gly Gly Thr Cys Ser Asp Tyr Val Asn Ser Tyr Thr Cys Lys Cys Gln
            965                 970                 975

Ala Gly Phe Asp Gly Val His Cys Glu Asn Asn Ile Asn Glu Cys Thr
        980                 985                 990

Glu Ser Ser Cys Phe Asn Gly Gly Thr Cys Val Asp Gly Ile Asn Ser
            995                 1000                1005

Phe Ser Cys Leu Cys Pro Val Gly Phe Thr Gly Ser Phe Cys Leu
        1010                1015                1020

His Glu Ile Asn Glu Cys Ser Ser His Pro Cys Leu Asn Glu Gly
        1025                1030                1035

Thr Cys Val Asp Gly Leu Gly Thr Tyr Arg Cys Ser Cys Pro Leu
        1040                1045                1050

Gly Tyr Thr Gly Lys Asn Cys Gln Thr Leu Val Asn Leu Cys Ser
        1055                1060                1065

Arg Ser Pro Cys Lys Asn Lys Gly Thr Cys Val Gln Lys Lys Ala
        1070                1075                1080

Glu Ser Gln Cys Leu Cys Pro Ser Gly Trp Ala Gly Ala Tyr Cys
        1085                1090                1095

Asp Val Pro Asn Val Ser Cys Asp Ile Ala Ala Ser Arg Arg Gly
        1100                1105                1110

Val Leu Val Glu His Leu Cys Gln His Ser Gly Val Cys Ile Asn
        1115                1120                1125

Ala Gly Asn Thr His Tyr Cys Gln Cys Pro Leu Gly Tyr Thr Gly
        1130                1135                1140

Ser Tyr Cys Glu Glu Gln Leu Asp Glu Cys Ala Ser Asn Pro Cys
        1145                1150                1155

Gln His Gly Ala Thr Cys Ser Asp Phe Ile Gly Gly Tyr Arg Cys
        1160                1165                1170

Glu Cys Val Pro Gly Tyr Gln Gly Val Asn Cys Glu Tyr Glu Val
        1175                1180                1185

Asp Glu Cys Gln Asn Gln Pro Cys Gln Asn Gly Gly Thr Cys Ile
        1190                1195                1200

Asp Leu Val Asn His Phe Lys Cys Ser Cys Pro Pro Gly Thr Arg
        1205                1210                1215

Gly Met Lys Ser Ser Leu Ser Ile Phe Pro Gly His Cys Leu
        1220                1225                1230

Lys Leu
1235

<210> SEQ ID NO 27
<211> LENGTH: 2321
<212> TYPE: PRT
<213> ORGANISM: Homo sapiens

<400> SEQUENCE: 27

```
Met Gly Pro Gly Ala Arg Gly Arg Arg Arg Arg Pro Met Ser
1               5                   10                  15

Pro Pro Pro Pro Pro Pro Val Arg Ala Leu Pro Leu Leu Leu Leu
                20                  25              30

Leu Ala Gly Pro Gly Ala Ala Ala Pro Pro Cys Leu Asp Gly Ser Pro
        35              40                  45

Cys Ala Asn Gly Gly Arg Cys Thr Gln Leu Pro Ser Arg Glu Ala Ala
        50              55                  60

Cys Leu Cys Pro Pro Gly Trp Val Gly Glu Arg Cys Gln Leu Glu Asp
65              70                  75                  80

Pro Cys His Ser Gly Pro Cys Ala Gly Arg Gly Val Cys Gln Ser Ser
            85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
            165                 170                 175

Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
        195                 200                 205

Gly Gly Thr Cys Arg Gln Ser Gly Asp Leu Thr Tyr Asp Cys Ala Cys
    210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
            245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
        275                 280                 285

Gly Thr Cys Phe Asn Thr Leu Gly Gly His Ser Cys Val Cys Val Asn
    290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
            325                 330                 335

Tyr Cys Ala Cys Pro Met Gly Lys Thr Gly Leu Leu Cys His Leu Asp
        340                 345                 350

Asp Ala Cys Val Ser Asn Pro Cys His Glu Asp Ala Ile Cys Asp Thr
    355                 360                 365

Asn Pro Val Asn Gly Arg Ala Ile Cys Thr Cys Pro Pro Gly Phe Thr
370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
            405                 410                 415
```

-continued

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Ile Gly Gln Phe Thr Cys Ile Cys Met Ala Gly Phe Thr Gly Thr
            450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
                485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
                565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605

Pro Ser Gly Thr Thr Gly Val Asn Cys Glu Val Asn Ile Asp Asp Cys
610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                645                 650                 655

Glu Ile Asn Glu Cys Ala Ser Ser Pro Cys Gly Glu Gly Gly Ser Cys
            660                 665                 670

Val Asp Gly Glu Asn Gly Phe Arg Cys Leu Cys Pro Pro Gly Ser Leu
            675                 680                 685

Pro Pro Leu Cys Leu Pro Ser His Pro Cys Ala His Glu Pro Cys
690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
            740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
            770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln

-continued

```
                835                 840                 845
Asp Ile Asn Asp Cys Asp Pro Asn Pro Cys Leu Asn Gly Gly Ser Cys
        850                 855                 860
Gln Asp Gly Val Gly Ser Phe Ser Cys Ser Cys Leu Pro Gly Phe Ala
865                 870                 875                 880
Gly Pro Arg Cys Ala Arg Asp Val Asp Glu Cys Leu Ser Asn Pro Cys
                885                 890                 895
Gly Pro Gly Thr Cys Thr Asp His Val Ala Ser Phe Thr Cys Thr Cys
        900                 905                 910
Pro Pro Gly Tyr Gly Gly Phe His Cys Glu Gln Asp Leu Pro Asp Cys
        915                 920                 925
Ser Pro Ser Ser Cys Phe Asn Gly Gly Thr Cys Val Asp Gly Val Asn
930                 935                 940
Ser Phe Ser Cys Leu Cys Arg Pro Gly Tyr Thr Gly Ala His Cys Gln
945                 950                 955                 960
His Glu Ala Asp Pro Cys Leu Ser Arg Pro Cys Leu His Gly Gly Val
                965                 970                 975
Cys Ser Ala Ala His Pro Gly Phe Arg Cys Thr Cys Leu Glu Ser Phe
        980                 985                 990
Thr Gly Pro Gln Cys Gln Thr Leu Val Asp Trp Cys Ser Arg Gln Pro
        995                1000                1005
Cys Gln Asn Gly Gly Arg Cys Val Gln Thr Gly Ala Tyr Cys Leu
    1010                1015                1020
Cys Pro Pro Gly Trp Ser Gly Arg Leu Cys Asp Ile Arg Ser Leu
    1025                1030                1035
Pro Cys Arg Glu Ala Ala Ala Gln Ile Gly Val Arg Leu Glu Gln
    1040                1045                1050
Leu Cys Gln Ala Gly Gly Gln Cys Val Asp Glu Asp Ser Ser His
    1055                1060                1065
Tyr Cys Val Cys Pro Glu Gly Arg Thr Gly Ser His Cys Glu Gln
    1070                1075                1080
Glu Val Asp Pro Cys Leu Ala Gln Pro Cys Gln His Gly Gly Thr
    1085                1090                1095
Cys Arg Gly Tyr Met Gly Gly Tyr Met Cys Glu Cys Leu Pro Gly
    1100                1105                1110
Tyr Asn Gly Asp Asn Cys Glu Asp Asp Val Asp Glu Cys Ala Ser
    1115                1120                1125
Gln Pro Cys Gln His Gly Gly Ser Cys Ile Asp Leu Val Ala Arg
    1130                1135                1140
Tyr Leu Cys Ser Cys Pro Pro Gly Thr Leu Gly Val Leu Cys Glu
    1145                1150                1155
Ile Asn Glu Asp Asp Cys Gly Pro Gly Pro Pro Leu Asp Ser Gly
    1160                1165                1170
Pro Arg Cys Leu His Asn Gly Thr Cys Val Asp Leu Val Gly Gly
    1175                1180                1185
Phe Arg Cys Thr Cys Pro Pro Gly Tyr Thr Gly Leu Arg Cys Glu
    1190                1195                1200
Ala Asp Ile Asn Glu Cys Arg Ser Gly Ala Cys His Ala Ala His
    1205                1210                1215
Thr Arg Asp Cys Leu Gln Asp Pro Gly Gly Gly Phe Arg Cys Leu
    1220                1225                1230
Cys His Ala Gly Phe Ser Gly Pro Arg Cys Gln Thr Val Leu Ser
    1235                1240                1245
```

```
Pro  Cys  Glu  Ser  Gln  Pro  Cys  Gln  His  Gly  Gly  Gln  Cys  Arg  Pro
     1250                1255                1260

Ser  Pro  Gly  Pro  Gly  Gly  Gly  Leu  Thr  Phe  Thr  Cys  His  Cys  Ala
     1265                1270                1275

Gln  Pro  Phe  Trp  Gly  Pro  Arg  Cys  Glu  Arg  Val  Ala  Arg  Ser  Cys
     1280                1285                1290

Arg  Glu  Leu  Gln  Cys  Pro  Val  Gly  Val  Pro  Cys  Gln  Gln  Thr  Pro
     1295                1300                1305

Arg  Gly  Pro  Arg  Cys  Ala  Cys  Pro  Pro  Gly  Leu  Ser  Gly  Pro  Ser
     1310                1315                1320

Cys  Arg  Ser  Phe  Pro  Gly  Ser  Pro  Pro  Gly  Ala  Ser  Asn  Ala  Ser
     1325                1330                1335

Cys  Ala  Ala  Ala  Pro  Cys  Leu  His  Gly  Gly  Ser  Cys  Arg  Pro  Ala
     1340                1345                1350

Pro  Leu  Ala  Pro  Phe  Phe  Arg  Cys  Ala  Cys  Ala  Gln  Gly  Trp  Thr
     1355                1360                1365

Gly  Pro  Arg  Cys  Glu  Ala  Pro  Ala  Ala  Ala  Pro  Glu  Val  Ser  Glu
     1370                1375                1380

Glu  Pro  Arg  Cys  Pro  Arg  Ala  Ala  Cys  Gln  Ala  Lys  Arg  Gly  Asp
     1385                1390                1395

Gln  Arg  Cys  Asp  Arg  Glu  Cys  Asn  Ser  Pro  Gly  Cys  Gly  Trp  Asp
     1400                1405                1410

Gly  Gly  Asp  Cys  Ser  Leu  Ser  Val  Gly  Asp  Pro  Trp  Arg  Gln  Cys
     1415                1420                1425

Glu  Ala  Leu  Gln  Cys  Trp  Arg  Leu  Phe  Asn  Asn  Ser  Arg  Cys  Asp
     1430                1435                1440

Pro  Ala  Cys  Ser  Ser  Pro  Ala  Cys  Leu  Tyr  Asp  Asn  Phe  Asp  Cys
     1445                1450                1455

His  Ala  Gly  Gly  Arg  Glu  Arg  Thr  Cys  Asn  Pro  Val  Tyr  Glu  Lys
     1460                1465                1470

Tyr  Cys  Ala  Asp  His  Phe  Ala  Asp  Gly  Arg  Cys  Asp  Gln  Gly  Cys
     1475                1480                1485

Asn  Thr  Glu  Glu  Cys  Gly  Trp  Asp  Gly  Leu  Asp  Cys  Ala  Ser  Glu
     1490                1495                1500

Val  Pro  Ala  Leu  Leu  Ala  Arg  Gly  Val  Leu  Val  Leu  Thr  Val  Leu
     1505                1510                1515

Leu  Pro  Pro  Glu  Glu  Leu  Leu  Arg  Ser  Ser  Ala  Asp  Phe  Leu  Gln
     1520                1525                1530

Arg  Leu  Ser  Ala  Ile  Leu  Arg  Thr  Ser  Leu  Arg  Phe  Arg  Leu  Asp
     1535                1540                1545

Ala  His  Gly  Gln  Ala  Met  Val  Phe  Pro  Tyr  His  Arg  Pro  Ser  Pro
     1550                1555                1560

Gly  Ser  Glu  Pro  Arg  Ala  Arg  Arg  Glu  Leu  Ala  Pro  Glu  Val  Ile
     1565                1570                1575

Gly  Ser  Val  Val  Met  Leu  Glu  Ile  Asp  Asn  Arg  Leu  Cys  Leu  Gln
     1580                1585                1590

Ser  Pro  Glu  Asn  Asp  His  Cys  Phe  Pro  Asp  Ala  Gln  Ser  Ala  Ala
     1595                1600                1605

Asp  Tyr  Leu  Gly  Ala  Leu  Ser  Ala  Val  Glu  Arg  Leu  Asp  Phe  Pro
     1610                1615                1620

Tyr  Pro  Leu  Arg  Asp  Val  Arg  Gly  Glu  Pro  Leu  Glu  Pro  Pro  Glu
     1625                1630                1635
```

```
Pro Ser Val Pro Leu Leu Pro Leu Leu Val Ala Gly Ala Val Leu
    1640                1645                1650

Leu Leu Val Ile Leu Val Leu Gly Val Met Val Ala Arg Arg Lys
    1655                1660                1665

Arg Glu His Ser Thr Leu Trp Phe Pro Glu Gly Phe Ser Leu His
    1670                1675                1680

Lys Asp Val Ala Ser Gly His Lys Gly Arg Arg Glu Pro Val Gly
    1685                1690                1695

Gln Asp Ala Leu Gly Met Lys Asn Met Ala Lys Gly Glu Ser Leu
    1700                1705                1710

Met Gly Glu Val Ala Thr Asp Trp Met Asp Thr Glu Cys Pro Glu
    1715                1720                1725

Ala Lys Arg Leu Lys Val Glu Glu Pro Gly Met Gly Ala Glu Glu
    1730                1735                1740

Ala Val Asp Cys Arg Gln Trp Thr Gln His His Leu Val Ala Ala
    1745                1750                1755

Asp Ile Arg Val Ala Pro Ala Met Ala Leu Thr Pro Pro Gln Gly
    1760                1765                1770

Asp Ala Asp Ala Asp Gly Met Asp Val Asn Val Arg Gly Pro Asp
    1775                1780                1785

Gly Phe Thr Pro Leu Met Leu Ala Ser Phe Cys Gly Gly Ala Leu
    1790                1795                1800

Glu Pro Met Pro Thr Glu Glu Asp Glu Ala Asp Asp Thr Ser Ala
    1805                1810                1815

Ser Ile Ile Ser Asp Leu Ile Cys Gln Gly Ala Gln Leu Gly Ala
    1820                1825                1830

Arg Thr Asp Arg Thr Gly Glu Thr Ala Leu His Leu Ala Ala Arg
    1835                1840                1845

Tyr Ala Arg Ala Asp Ala Ala Lys Arg Leu Leu Asp Ala Gly Ala
    1850                1855                1860

Asp Thr Asn Ala Gln Asp His Ser Gly Arg Thr Pro Leu His Thr
    1865                1870                1875

Ala Val Thr Ala Asp Ala Gln Gly Val Phe Gln Ile Leu Ile Arg
    1880                1885                1890

Asn Arg Ser Thr Asp Leu Asp Ala Arg Met Ala Asp Gly Ser Thr
    1895                1900                1905

Ala Leu Ile Leu Ala Ala Arg Leu Ala Val Glu Gly Met Val Glu
    1910                1915                1920

Glu Leu Ile Ala Ser His Ala Asp Val Asn Ala Val Asp Glu Leu
    1925                1930                1935

Gly Lys Ser Ala Leu His Trp Ala Ala Ala Val Asn Asn Val Glu
    1940                1945                1950

Ala Thr Leu Ala Leu Leu Lys Asn Gly Ala Asn Lys Asp Met Gln
    1955                1960                1965

Asp Ser Lys Glu Glu Thr Pro Leu Phe Leu Ala Ala Arg Glu Gly
    1970                1975                1980

Ser Tyr Glu Ala Ala Lys Leu Leu Leu Asp His Phe Ala Asn Arg
    1985                1990                1995

Glu Ile Thr Asp His Leu Asp Arg Leu Pro Arg Asp Val Ala Gln
    2000                2005                2010

Glu Arg Leu His Gln Asp Ile Val Arg Leu Leu Asp Gln Pro Ser
    2015                2020                2025

Gly Pro Arg Ser Pro Pro Gly Pro His Gly Leu Gly Pro Leu Leu
```

| | | 2030 | | | 2035 | | | 2040 | | |

Cys Pro Pro Gly Ala Phe Leu Pro Gly Leu Lys Ala Ala Gln Ser
     2045                      2050                    2055

Gly Ser Lys Lys Ser Arg Arg Pro Pro Gly Lys Ala Gly Leu Gly
     2060                      2065                    2070

Pro Gln Gly Pro Arg Gly Arg Gly Lys Lys Leu Thr Leu Ala Cys
     2075                      2080                    2085

Pro Gly Pro Leu Ala Asp Ser Ser Val Thr Leu Ser Pro Val Asp
     2090                      2095                    2100

Ser Leu Asp Ser Pro Arg Pro Phe Gly Gly Pro Pro Ala Ser Pro
     2105                      2110                    2115

Gly Gly Phe Pro Leu Glu Gly Pro Tyr Ala Ala Thr Ala Thr
     2120                      2125                    2130

Ala Val Ser Leu Ala Gln Leu Gly Gly Pro Gly Arg Ala Gly Leu
     2135                      2140                    2145

Gly Arg Gln Pro Pro Gly Gly Cys Val Leu Ser Leu Gly Leu Leu
     2150                      2155                    2160

Asn Pro Val Ala Val Pro Leu Asp Trp Ala Arg Leu Pro Pro Pro
     2165                      2170                    2175

Ala Pro Pro Gly Pro Ser Phe Leu Leu Pro Leu Ala Pro Gly Pro
     2180                      2185                    2190

Gln Leu Leu Asn Pro Gly Thr Pro Val Ser Pro Gln Glu Arg Pro
     2195                      2200                    2205

Pro Pro Tyr Leu Ala Val Pro Gly His Gly Glu Glu Tyr Pro Ala
     2210                      2215                    2220

Ala Gly Ala His Ser Ser Pro Pro Lys Ala Arg Phe Leu Arg Val
     2225                      2230                    2235

Pro Ser Glu His Pro Tyr Leu Thr Pro Ser Pro Glu Ser Pro Glu
     2240                      2245                    2250

His Trp Ala Ser Pro Ser Pro Pro Ser Leu Ser Asp Trp Ser Glu
     2255                      2260                    2265

Ser Thr Pro Ser Pro Ala Thr Ala Thr Gly Ala Met Ala Thr Thr
     2270                      2275                    2280

Thr Gly Ala Leu Pro Ala Gln Pro Leu Pro Leu Ser Val Pro Ser
     2285                      2290                    2295

Ser Leu Ala Gln Ala Gln Thr Gln Leu Gly Pro Gln Pro Glu Val
     2300                      2305                    2310

Thr Pro Lys Arg Gln Val Leu Ala
     2315                      2320

<210> SEQ ID NO 28
<211> LENGTH: 2003
<212> TYPE: PRT
<213> ORGANISM: Homo sapiens

<400> SEQUENCE: 28

Met Gln Pro Pro Ser Leu Leu Leu Leu Leu Leu Leu Leu Leu
1               5                    10                   15

Cys Val Ser Val Val Arg Pro Arg Gly Leu Leu Cys Gly Ser Phe Pro
            20                    25                    30

Glu Pro Cys Ala Asn Gly Gly Thr Cys Leu Ser Leu Ser Leu Gly Gln
               35                   40                    45

Gly Thr Cys Gln Cys Ala Pro Gly Phe Leu Gly Glu Thr Cys Gln Phe
     50                      55                    60

-continued

```
Pro Asp Pro Cys Gln Asn Ala Gln Leu Cys Gln Asn Gly Gly Ser Cys
 65                  70                  75                  80

Gln Ala Leu Leu Pro Ala Pro Leu Gly Leu Pro Ser Ser Pro Ser Pro
                 85                  90                  95

Leu Thr Pro Ser Phe Leu Cys Thr Cys Leu Pro Gly Phe Thr Gly Glu
            100                 105                 110

Arg Cys Gln Ala Lys Leu Glu Asp Pro Cys Pro Pro Ser Phe Cys Ser
        115                 120                 125

Lys Arg Gly Arg Cys His Ile Gln Ala Ser Gly Arg Pro Gln Cys Ser
    130                 135                 140

Cys Met Pro Gly Trp Thr Gly Glu Gln Cys Gln Leu Arg Asp Phe Cys
145                 150                 155                 160

Ser Ala Asn Pro Cys Val Asn Gly Gly Val Cys Leu Ala Thr Tyr Pro
                165                 170                 175

Gln Ile Gln Cys His Cys Pro Pro Gly Phe Glu Gly His Ala Cys Glu
            180                 185                 190

Arg Asp Val Asn Glu Cys Phe Gln Asp Pro Gly Pro Cys Pro Lys Gly
        195                 200                 205

Thr Ser Cys His Asn Thr Leu Gly Ser Phe Gln Cys Leu Cys Pro Val
    210                 215                 220

Gly Gln Glu Gly Pro Arg Cys Glu Leu Arg Ala Gly Pro Cys Pro Pro
225                 230                 235                 240

Arg Gly Cys Ser Asn Gly Gly Thr Cys Gln Leu Met Pro Glu Lys Asp
                245                 250                 255

Ser Thr Phe His Leu Cys Leu Cys Pro Pro Gly Phe Ile Gly Pro Asp
            260                 265                 270

Cys Glu Val Asn Pro Asp Asn Cys Val Ser His Gln Cys Gln Asn Gly
        275                 280                 285

Gly Thr Cys Gln Asp Gly Leu Asp Thr Tyr Thr Cys Leu Cys Pro Glu
    290                 295                 300

Thr Trp Thr Gly Trp Asp Cys Ser Glu Asp Val Asp Glu Cys Glu Thr
305                 310                 315                 320

Gln Gly Pro Pro His Cys Arg Asn Gly Gly Thr Cys Gln Asn Ser Ala
                325                 330                 335

Gly Ser Phe His Cys Val Cys Val Ser Gly Trp Gly Gly Thr Ser Cys
            340                 345                 350

Glu Glu Asn Leu Asp Asp Cys Ile Ala Ala Thr Cys Ala Pro Gly Ser
        355                 360                 365

Thr Cys Ile Asp Arg Val Gly Ser Phe Ser Cys Leu Cys Pro Pro Gly
    370                 375                 380

Arg Thr Gly Leu Leu Cys His Leu Glu Asp Met Cys Leu Ser Gln Pro
385                 390                 395                 400

Cys His Gly Asp Ala Gln Cys Ser Thr Asn Pro Leu Thr Gly Ser Thr
                405                 410                 415

Leu Cys Leu Cys Gln Pro Gly Tyr Ser Gly Pro Thr Cys His Gln Asp
            420                 425                 430

Leu Asp Glu Cys Leu Met Ala Gln Gln Gly Pro Ser Pro Cys Glu His
        435                 440                 445

Gly Gly Ser Cys Leu Asn Thr Pro Gly Ser Phe Asn Cys Leu Cys Pro
    450                 455                 460

Pro Gly Tyr Thr Gly Ser Arg Cys Glu Ala Asp His Asn Glu Cys Leu
465                 470                 475                 480

Ser Gln Pro Cys His Pro Gly Ser Thr Cys Leu Asp Leu Leu Ala Thr
```

```
                485                 490                 495
Phe His Cys Leu Cys Pro Pro Gly Leu Glu Gly Gln Leu Cys Glu Val
                500                 505                 510

Glu Thr Asn Glu Cys Ala Ser Ala Pro Cys Leu Asn His Ala Asp Cys
                515                 520                 525

His Asp Leu Leu Asn Gly Phe Gln Cys Ile Cys Leu Pro Gly Phe Ser
                530                 535                 540

Gly Thr Arg Cys Glu Glu Asp Ile Asp Glu Cys Arg Ser Ser Pro Cys
545                 550                 555                 560

Ala Asn Gly Gly Gln Cys Gln Asp Gln Pro Gly Ala Phe His Cys Lys
                565                 570                 575

Cys Leu Pro Gly Phe Glu Gly Pro Arg Cys Gln Thr Glu Val Asp Glu
                580                 585                 590

Cys Leu Ser Asp Pro Cys Pro Val Gly Ala Ser Cys Leu Asp Leu Pro
                595                 600                 605

Gly Ala Phe Phe Cys Leu Cys Pro Ser Gly Phe Thr Gly Gln Leu Cys
                610                 615                 620

Glu Val Pro Leu Cys Ala Pro Asn Leu Cys Gln Pro Lys Gln Ile Cys
625                 630                 635                 640

Lys Asp Gln Lys Asp Lys Ala Asn Cys Leu Cys Pro Asp Gly Ser Pro
                645                 650                 655

Gly Cys Ala Pro Pro Glu Asp Asn Cys Thr Cys His His Gly His Cys
                660                 665                 670

Gln Arg Ser Ser Cys Val Cys Asp Val Gly Trp Thr Gly Pro Glu Cys
                675                 680                 685

Glu Ala Glu Leu Gly Gly Cys Ile Ser Ala Pro Cys Ala His Gly Gly
                690                 695                 700

Thr Cys Tyr Pro Gln Pro Ser Gly Tyr Asn Cys Thr Cys Pro Thr Gly
705                 710                 715                 720

Tyr Thr Gly Pro Thr Cys Ser Glu Glu Met Thr Ala Cys His Ser Gly
                725                 730                 735

Pro Cys Leu Asn Gly Gly Ser Cys Asn Pro Ser Pro Gly Gly Tyr Tyr
                740                 745                 750

Cys Thr Cys Pro Pro Ser His Thr Gly Pro Gln Cys Gln Thr Ser Thr
                755                 760                 765

Asp Tyr Cys Val Ser Ala Pro Cys Phe Asn Gly Gly Thr Cys Val Asn
                770                 775                 780

Arg Pro Gly Thr Phe Ser Cys Leu Cys Ala Met Gly Phe Gln Gly Pro
785                 790                 795                 800

Arg Cys Glu Gly Lys Leu Arg Pro Ser Cys Ala Asp Ser Pro Cys Arg
                805                 810                 815

Asn Arg Ala Thr Cys Gln Asp Ser Pro Gln Gly Pro Arg Cys Leu Cys
                820                 825                 830

Pro Thr Gly Tyr Thr Gly Gly Ser Cys Gln Thr Leu Met Asp Leu Cys
                835                 840                 845

Ala Gln Lys Pro Cys Pro Arg Asn Ser His Cys Leu Gln Thr Gly Pro
                850                 855                 860

Ser Phe His Cys Leu Cys Leu Gln Gly Trp Thr Gly Pro Leu Cys Asn
865                 870                 875                 880

Leu Pro Leu Ser Ser Cys Gln Lys Ala Ala Leu Ser Gln Gly Ile Asp
                885                 890                 895

Val Ser Ser Leu Cys His Asn Gly Gly Leu Cys Val Asp Ser Gly Pro
                900                 905                 910
```

-continued

```
Ser Tyr Phe Cys His Cys Pro Pro Gly Phe Gln Gly Ser Leu Cys Gln
    915                 920                 925

Asp His Val Asn Pro Cys Glu Ser Arg Pro Cys Gln Asn Gly Ala Thr
    930                 935                 940

Cys Met Ala Gln Pro Ser Gly Tyr Leu Cys Cys Ala Pro Gly Tyr
945                 950                 955                 960

Asp Gly Gln Asn Cys Ser Lys Glu Leu Asp Ala Cys Gln Ser Gln Pro
                965                 970                 975

Cys His Asn His Gly Thr Cys Thr Pro Lys Pro Gly Gly Phe His Cys
                980                 985                 990

Ala Cys Pro Pro Gly Phe Val Gly Leu Arg Cys Glu Gly Asp Val Asp
            995                 1000                1005

Glu Cys Leu Asp Gln Pro Cys His Pro Thr Gly Thr Ala Ala Cys
    1010                1015                1020

His Ser Leu Ala Asn Ala Phe Tyr Cys Gln Cys Leu Pro Gly His
    1025                1030                1035

Thr Gly Gln Trp Cys Glu Val Glu Ile Asp Pro Cys His Ser Gln
    1040                1045                1050

Pro Cys Phe His Gly Gly Thr Cys Glu Ala Thr Ala Gly Ser Pro
    1055                1060                1065

Leu Gly Phe Ile Cys His Cys Pro Lys Gly Phe Glu Gly Pro Thr
    1070                1075                1080

Cys Ser His Arg Ala Pro Ser Cys Gly Phe His His Cys His His
    1085                1090                1095

Gly Gly Leu Cys Leu Pro Ser Pro Lys Pro Gly Phe Pro Pro Arg
    1100                1105                1110

Cys Ala Cys Leu Ser Gly Tyr Gly Gly Pro Asp Cys Leu Thr Pro
    1115                1120                1125

Pro Ala Pro Lys Gly Cys Gly Pro Pro Ser Pro Cys Leu Tyr Asn
    1130                1135                1140

Gly Ser Cys Ser Glu Thr Thr Gly Leu Gly Gly Pro Gly Phe Arg
    1145                1150                1155

Cys Ser Cys Pro His Ser Ser Pro Gly Pro Arg Cys Gln Lys Pro
    1160                1165                1170

Gly Ala Lys Gly Cys Glu Gly Arg Ser Gly Asp Gly Ala Cys Asp
    1175                1180                1185

Ala Gly Cys Ser Gly Pro Gly Gly Asn Trp Asp Gly Gly Asp Cys
    1190                1195                1200

Ser Leu Gly Val Pro Asp Pro Trp Lys Gly Cys Pro Ser His Ser
    1205                1210                1215

Arg Cys Trp Leu Leu Phe Arg Asp Gly Gln Cys His Pro Gln Cys
    1220                1225                1230

Asp Ser Glu Glu Cys Leu Phe Asp Gly Tyr Asp Cys Glu Thr Pro
    1235                1240                1245

Pro Ala Cys Thr Pro Ala Tyr Asp Gln Tyr Cys His Asp His Phe
    1250                1255                1260

His Asn Gly His Cys Glu Lys Gly Cys Asn Thr Ala Glu Cys Gly
    1265                1270                1275

Trp Asp Gly Gly Asp Cys Arg Pro Glu Asp Gly Asp Pro Glu Trp
    1280                1285                1290

Gly Pro Ser Leu Ala Leu Leu Val Val Leu Ser Pro Pro Ala Leu
    1295                1300                1305
```

-continued

| | | | | | | | | | | | |
|---|---|---|---|---|---|---|---|---|---|---|---|
|Asp|Gln|Gln|Leu|Phe|Ala|Leu|Ala|Arg|Val|Leu|Ser|Leu|Thr|Leu|
|1310| | | | |1315| | | | |1320| | | | |

Arg Val Gly Leu Trp Val Arg Lys Asp Arg Asp Gly Arg Asp Met
1325                1330                1335

Val Tyr Pro Tyr Pro Gly Ala Arg Ala Glu Glu Lys Leu Gly Gly
1340                1345                1350

Thr Arg Asp Pro Thr Tyr Gln Glu Arg Ala Ala Pro Gln Thr Gln
1355                1360                1365

Pro Leu Gly Lys Glu Thr Asp Ser Leu Ser Ala Gly Phe Val Val
1370                1375                1380

Val Met Gly Val Asp Leu Ser Arg Cys Gly Pro Asp His Pro Ala
1385                1390                1395

Ser Arg Cys Pro Trp Asp Pro Gly Leu Leu Arg Phe Leu Ala
1400                1405                1410

Ala Met Ala Ala Val Gly Ala Leu Glu Pro Leu Leu Pro Gly Pro
1415                1420                1425

Leu Leu Ala Val His Pro His Ala Gly Thr Ala Pro Pro Ala Asn
1430                1435                1440

Gln Leu Pro Trp Pro Val Leu Cys Ser Pro Val Ala Gly Val Ile
1445                1450                1455

Leu Leu Ala Leu Gly Ala Leu Leu Val Leu Gln Leu Ile Arg Arg
1460                1465                1470

Arg Arg Arg Glu His Gly Ala Leu Trp Leu Pro Pro Gly Phe Thr
1475                1480                1485

Arg Arg Pro Arg Thr Gln Ser Ala Pro His Arg Arg Pro Pro
1490                1495                1500

Leu Gly Glu Asp Ser Ile Gly Leu Lys Ala Leu Lys Pro Lys Ala
1505                1510                1515

Glu Val Asp Glu Asp Gly Val Val Met Cys Ser Gly Pro Glu Glu
1520                1525                1530

Gly Glu Glu Val Gly Gln Ala Glu Glu Thr Gly Pro Pro Ser Thr
1535                1540                1545

Cys Gln Leu Trp Ser Leu Ser Gly Gly Cys Gly Ala Leu Pro Gln
1550                1555                1560

Ala Ala Met Leu Thr Pro Pro Gln Glu Ser Glu Met Glu Ala Pro
1565                1570                1575

Asp Leu Asp Thr Arg Gly Pro Asp Gly Val Thr Pro Leu Met Ser
1580                1585                1590

Ala Val Cys Cys Gly Glu Val Gln Ser Gly Thr Phe Gln Gly Ala
1595                1600                1605

Trp Leu Gly Cys Pro Glu Pro Trp Glu Pro Leu Leu Asp Gly Gly
1610                1615                1620

Ala Cys Pro Gln Ala His Thr Val Gly Thr Gly Glu Thr Pro Leu
1625                1630                1635

His Leu Ala Ala Arg Phe Ser Arg Pro Thr Ala Ala Arg Arg Leu
1640                1645                1650

Leu Glu Ala Gly Ala Asn Pro Asn Gln Pro Asp Arg Ala Gly Arg
1655                1660                1665

Thr Pro Leu His Ala Ala Val Ala Ala Asp Ala Arg Glu Val Cys
1670                1675                1680

Gln Leu Leu Leu Arg Ser Arg Gln Thr Ala Val Asp Ala Arg Thr
1685                1690                1695

Glu Asp Gly Thr Thr Pro Leu Met Leu Ala Ala Arg Leu Ala Val

| | | | | | | | | | | |
|---|---|---|---|---|---|---|---|---|---|---|
| | | 1700 | | | 1705 | | | 1710 | | |

Glu Asp Leu Val Glu Glu Leu Ile Ala Ala Gln Ala Asp Val Gly
    1715                1720                1725

Ala Arg Asp Lys Trp Gly Lys Thr Ala Leu His Trp Ala Ala Ala
1730                1735                1740

Val Asn Asn Ala Arg Ala Ala Arg Ser Leu Leu Gln Ala Gly Ala
1745                1750                1755

Asp Lys Asp Ala Gln Asp Asn Arg Glu Gln Thr Pro Leu Phe Leu
1760                1765                1770

Ala Ala Arg Glu Gly Ala Val Glu Val Ala Gln Leu Leu Leu Gly
    1775                1780                1785

Leu Gly Ala Ala Arg Glu Leu Arg Asp Gln Ala Gly Leu Ala Pro
1790                1795                1800

Ala Asp Val Ala His Gln Arg Asn His Trp Asp Leu Leu Thr Leu
1805                1810                1815

Leu Glu Gly Ala Gly Pro Pro Glu Ala Arg His Lys Ala Thr Pro
    1820                1825                1830

Gly Arg Glu Ala Gly Pro Phe Pro Arg Ala Arg Thr Val Ser Val
1835                1840                1845

Ser Val Pro Pro His Gly Gly Gly Ala Leu Pro Arg Cys Arg Thr
1850                1855                1860

Leu Ser Ala Gly Ala Gly Pro Arg Gly Gly Gly Ala Cys Leu Gln
    1865                1870                1875

Ala Arg Thr Trp Ser Val Asp Leu Ala Ala Arg Gly Gly Gly Ala
1880                1885                1890

Tyr Ser His Cys Arg Ser Leu Ser Gly Val Gly Ala Gly Gly Gly
1895                1900                1905

Pro Thr Pro Arg Gly Arg Arg Phe Ser Ala Gly Met Arg Gly Pro
    1910                1915                1920

Arg Pro Asn Pro Ala Ile Met Arg Gly Arg Tyr Gly Val Ala Ala
1925                1930                1935

Gly Arg Gly Gly Arg Val Ser Thr Asp Asp Trp Pro Cys Asp Trp
1940                1945                1950

Val Ala Leu Gly Ala Cys Gly Ser Ala Ser Asn Ile Pro Ile Pro
    1955                1960                1965

Pro Pro Cys Leu Thr Pro Ser Pro Glu Arg Gly Ser Pro Gln Leu
1970                1975                1980

Asp Cys Gly Pro Pro Ala Leu Gln Glu Met Pro Ile Asn Gln Gly
1985                1990                1995

Gly Glu Gly Lys Lys
    2000

```
<210> SEQ ID NO 29
<211> LENGTH: 9322
<212> TYPE: DNA
<213> ORGANISM: Homo sapiens

<400> SEQUENCE: 29
atgccgccgc tcctggcgcc cctgctctgc ctggcgctgc tgcccgcgct cgccgcacga      60
ggcccgcgat gctcccagcc cggtgagacc tgcctgaatg gcgggaagtg tgaagcggcc     120
aatggcacgg aggcctgcgt ctgtggcggg gccttcgtgg gccgcgatgc caggaccccc     180
aacccgtgcc tcagcacccc ctgcaagaac gccgggacat gccacgtggt ggaccgcaga     240
ggcgtggcag actatgcctg cagctgtgcc ctgggcttct ctgggcccct ctgcctgaca     300
```

```
cccctggaca atgcctgcct caccaacccc tgccgcaacg ggggcacctg cgacctgctc      360
acgctgacgg agtacaagtg ccgctgcccg cccggctggt cagggaaatc gtgccagcag      420
gctgacccgt gcgcctccaa cccctgcgcc aacggtggcc agtgcctgcc cttcgaggcc      480
tcctacatct gccactgccc acccagcttc catggcccca cctgccggca ggatgtcaac      540
gagtgtggcc agaagcccgg gctttgccgc cacggaggca cctgccacaa cgaggtcggc      600
tcctaccgct gcgtctgccg cgccacccac actggcccca actgcgagcg ccctacgtg       660 ccctgcagcc cctcgccctg ccagaacggg ggcacctgcc gccccacggg cgacgtcacc      720
cacgagtgtg cctgcctgcc aggcttcacc ggccagaact gtgaggaaaa tatcgacgat      780
tgtccaggaa acaactgcaa gaacgggggt gcctgtgtgg acgcgtgaa cacctacaac       840 tgccgctgcc cgccagagtg gacaggtcag tactgtaccg aggatgtgga cgagtgccag      900
ctgatgccaa atgcctgcca gaacggcggg acctgccaca cacccacgg tggctacaac       960 tgcgtgtgtg tcaacggctg gactggtgag gactgcagcg agaacattga tgactgtgcc     1020
agcgccgcct gcttccacgg cgccacctgc catgaccgtg tggcctcctt ctactgcgag     1080
tgtccccatg gccgcacagg tctgctgtgc cacctcaacg acgcatgcat cagcaacccc     1140
tgtaacgagg ctccaactg cgacaccaac cctgtcaatg gcaaggccat ctgcacctgc      1200
ccctcggggt acacgggccc ggcctgcagc caggacgtgg atgagtgctc gctgggtgcc     1260 aaccctgcg agcatgcggg caagtgcatc aacacgctgg gctccttcga gtgccagtgt     1320
ctgcagggct acacgggccc ccgatgcgag atcgacgtca acgagtgcgt ctcgaacccg     1380
tgccagaacg acgccacctg cctggaccag attggggagt ccagtgcat ctgcatgccc      1440 ggctacgagg tgtgcactg cgaggtcaac acagacgagt gtgccagcag cccctgcctg      1500
cacaatggcc gctgcctgga caagatcaat gagttccagt gcgagtgccc cacgggcttc     1560
actgggcatc tgtgccagta cgatgtggac gagtgtgcca gcaccccctg caagaatggt     1620
gccaagtgcc tggacggacc caacacttac acctgtgtgt gcacggaagg gtacacgggg     1680
acgcactgcg aggtggacat cgatgagtgc gaccccgacc cctgccacta cggctcctgc     1740
aaggacggcg tcgccaccct cacctgcctc tgccgcccag gctacacggg ccaccactgc     1800
gagaccaaca tcaacgagtg ctccagccag ccctgccgcc acggggcac ctgccaggac      1860 cgcgacaacg cctacctctg cttctgcctg aaggggacca caggaccaa ctgcgagatc      1920 aacctggatg actgtgccag cagccctgc gactcgggca cctgtctgga caagatcgat     1980
ggctacgagt gtgcctgtga gccgggctac acagggagca tgtgtaacat caacatcgat     2040
gagtgtgcgg caaccctg ccacaacggg ggcacctgcg aggacggcat caatggcttc       2100
acctgccgct gccccgaggg ctaccacgac cccacctgcc tgtctgaggt caatgagtgc     2160
aacagcaacc cctgcgtcca cggggcctgc cgggacagcc tcaacgggta caagtgcgac     2220
tgtgaccctg gtggagtgg accaactgt gacatcaaca caatgagtg tgaatccaac        2280 ccttgtgtca acggcggcac ctgcaaagac atgaccagtg gctacgtgtg cacctgccgg     2340
gagggcttca gcgtccaa ctgccagacc aacatcaacg agtgtgcgtc caacccatgt      2400
ctgaaccagg gcacgtgtat tgacgacgtt gccgggtaca agtgcaactg cctgctgccc     2460
tacacaggtg ccacgtgtga ggtggtgctg gccccgtgtg cccccagccc ctgcagaaac     2520 ggcgggagt gcaggcaatc cgaggactat gagagcttct cctgtgtctg ccccacgggc     2580
tggcaagggc agacctgtga ggtcgacatc aacgagtgcg ttctgagccc gtgccggcac     2640
```

```
ggcgcatcct gccagaacac ccacggcggc taccgctgcc actgccaggc cggctacagt    2700
gggcgcaact gcgagaccga catcgacgac tgccggccca acccgtgtca acgggggc      2760 tcctgcacag acggcatcaa cacggccttc tgcgactgcc tgcccggctt ccggggcact    2820
ttctgtgagg aggacatcaa cgagtgtgcc agtgacccct gccgcaacgg ggccaactgc    2880
acggactgcg tggacagcta cacgtgcacc tgccccgcag gcttcagcgg gatccactgt    2940
gagaacaaca cgcctgactg cacagagagc tcctgcttca cggtggcac ctgcgtggac     3000 ggcatcaact cgttcaccctg cctgtgtcca cccggcttca cgggcagcta ctgccagcac   3060
gatgtcaatg agtgcgactc acagccctgc ctgcatggcg gcacctgtca ggacggctgc   3120
ggctcctaca ggtgcacctg cccccagggc tacactggcc ccaactgcca gaaccttgtg    3180
cactggtgtg actcctcgcc ctgcaagaac ggcggcaaat gctggcagac ccacacccag   3240
taccgctgcg agtgccccag cggctggacc ggcctttact gcgacgtgcc cagcgtgtcc   3300
tgtgaggtgg ctgcgcagcg acaaggtgtt gacgttgccc gcctgtgcca gcatggaggg    3360
ctctgtgtgg acgcgggcaa cacgcaccac tgccgctgcc aggcgggcta cacaggcagc   3420
tactgtgagg acctggtgga cgagtgctca cccagcccct gccagaacgg ggccacctgc    3480
acggactacc tgggcggcta ctcctgcaag tgcgtggccg gctaccacgg ggtgaactgc    3540
tctgaggaga tcgacgagtg cctctcccac ccctgccaga acggggccac ctgcctcgac    3600
ctccccaaca cctacaagtg ctcctgccca cggggcactc agggtgtgca ctgtgagatc    3660
aacgtggacg actgcaatcc ccccgttgac cccgtgtccc ggagccccaa gtgctttaac    3720
aacggcacct gcgtggacca ggtgggcggc tacagctgca cctgcccgcc gggcttcgtg    3780
ggtgagcgct gtgaggggga tgtcaacgag tgcctgtcca atccctgcga cgcccgtggc    3840
acccagaact gcgtgcagcg cgtcaatgac ttccactgcg agtgccgtgc tggtcacacc    3900
gggcgccgct gcgagtccgt catcaatggc tgcaaaggca gccctgcaa gaatgggggc     3960 acctgcgccg tggcctccaa caccgcccgc gggttcatct gcaagtgccc tgcgggcttc    4020
gagggcgcca cgtgtgagaa tgacgctcgt acctgcggca gcctgcgctg cctcaacggc    4080
ggcacatgca tctccggccc gcgcagcccc acctgcctgt gcctgggccc cttcacgggc    4140
cccgaatgcc agttcccggc cagcagcccc tgcctgggcg gcaacccctg ctacaaccag    4200
gggacctgtg agcccacatc cgagagcccc ttctaccgtt gcctgtgccc cgccaaattc    4260
aacgggctct tgtgccacat cctggactac agcttcgggg gtggggccgg gcgcgacatc    4320 ccccccgccgc tgatcgagga ggcgtgcgag ctgcccgagt gccaggagga cgcgggcaac   4380
aaggtctgca gcctgcagtg caacaaccac gcgtgcggct gggacggcgg tgactgctcc    4440
ctcaacttca tgacccctg gaagaactgc acgcagtctc tgcagtgctg gaagtacttc     4500
agtgacggcc actgtgacag ccagtgcaac tcagccggct gcctcttcga cggctttgac    4560
tgccagcgtg cggaaggcca gtgcaacccc ctgtacgacc agtactgcaa ggaccacttc    4620
agcgacgggc actgcgacca gggctgcaac agcgcgcgagt gcgagtggga cgggctggac    4680
tgtgcggagc atgtacccga gaggctggcg gccggcacgc tggtggtggt ggtgctgatg    4740
ccgccggagc agctgcgcaa cagctccttc cacttcctgc gggagctcag ccgcgtgctg    4800
cacaccaacg tggtcttcaa gcgtgacgca cacgccagc agatgatctt ccctactac      4860 ggccgcgagg aggagctgcg caagcacccc atcaagcgtg ccgccgaggg ctgggccgca    4920
cctgacgccc tgctgggcca ggtgaaggcc tcgctgctcc ctggtggcag cgagggtggg    4980
cggcggcgga gggagctgga ccccatggac gtccgcggct ccatcgtcta cctggagatt    5040
```

```
gacaaccggc agtgtgtgca ggcctcctcg cagtgcttcc agagtgccac cgacgtggcc   5100
gcattcctgg gagcgctcgc ctcgctgggc agcctcaaca tccctacaa gatcgaggcc    5160
gtgcagagtg agaccgtgga gccgcccccg ccggcgcagc tgcacttcat gtacgtggcg   5220
gcggccgcct ttgtgcttct gttcttcgtg ggctgcgggg tgctgctgtc ccgcaagcgc   5280
cggcggcagc atggccagct ctggttccct gagggcttca aagtgtctga ggccagcaag   5340
aagaagcggc gggagcccct cggcgaggac tccgtgggcc tcaagcccct gaagaacgct   5400
tcagacggtg ccctcatgga cgacaaccag aatgagtggg gggacgagga cctggagacc   5460
aagaagttcc ggttcgagga gcccgtggtt ctgcctgacc tggacgacca gacagaccac   5520
cggcagtgga ctcagcagca cctggatgcc gctgacctgc gcatgtctgc catggccccc   5580
acaccgcccc agggtgaggt tgacgccgac tgcatggacg tcaatgtccg cgggcctgat   5640
ggcttcaccc cgctcatgat cgcctcctgc agcgggggcg gcctggagac gggcaacagc   5700
gaggaagagg aggacgcgcc ggccgtcatc tccgacttca tctaccaggg cgccagcctg   5760
cacaaccaga cagaccgcac gggcgagacc gccttgcacc tggccgcccg ctactcacgc   5820
tctgatgccg ccaagcgcct gctggaggcc agcgcagatg ccaacatcca ggacaacatg   5880
ggccgcaccc cgctgcatgc ggctgtgtct gccgacgcac aaggtgtctt ccagatcctg   5940
atccggaacc gagccacaga cctggatgcc cgcatgcatg atggcacgac gccactgatc   6000
ctggctgccc gcctggccgt ggagggcatg ctggaggacc tcatcaactc acacgccgac   6060
gtcaacgccg tagatgacct gggcaagtcc gccctgcact gggccgccgc cgtgaacaat   6120
gtggatgccg cagttgtgct cctgaagaac ggggctaaca agatatgca gaacaacagg    6180
gaggagacac ccctgtttct ggccgcccgg gagggcagct acgagaccgc caaggtgctg   6240
ctggaccact ttgccaaccg ggacatcacg gatcatatgg accgcctgcc gcgcgacatc   6300
gcacaggagc gcatgcatca cgacatcgtg aggctgctgg acgagtacaa cctggtgcgc   6360
agcccgcagc tgcacggagc cccgctgggg ggcacgccca cctgtcgcc ccgctctgc    6420
tcgcccaacg gctacctggg cagcctcaag cccggcgtgc agggcaagaa ggtccgcaag   6480
cccagcagca aaggcctggc ctgtggaagc aaggaggcca aggacctcaa ggcacggagg   6540
aagaagtccc aggacggcaa gggctgcctg ctggacagct ccggcatgct ctcgcccgtg   6600
gactccctgg agtcacccca tggctacctg tcagacgtgg cctcgccgcc actgctgccc   6660
tccccgttcc agcagtctcc gtccgtgccc ctcaaccacc tgcctgggat gcccgacacc   6720
cacctgggca tcgggcacct gaacgtgcg gccaagcccg agatggcggc gctggtgggg   6780
ggcggccggc tggcctttga gactggccca cctcgtctct cccacctgcc tgtggcctct   6840
ggcaccagca ccgtcctggg ctccagcagc ggaggggccc tgaatttcac tgtgggcggg   6900
tccaccagtt tgaatggtca atgcgagtgg ctgtcccggc tgcagagcgg catggtgccg   6960
aaccaataca ccctctgcg ggggagtgtg gcaccaggcc cctgagcac acaggcccc     7020
tccctgcagc atggcatggt aggcccgctg cacagtagcc ttgctgccag cgccctgtcc   7080
cagatgatga gctaccaggg cctgcccagc acccggctgg ccacccagcc tcacctggtg   7140
cagacccagc aggtgcagcc acaaaactta cagatgcagc agcagaacct gcagccagca   7200
aacatccagc agcagcaaag cctgcagccg ccaccaccac caccacagcc gcaccttggc   7260
gtgagctcag cagccagcgg ccacctgggc cggagcttcc tgagtggaga gccgagccag   7320
gcagacgtgc agccactggg ccccagcagc ctggcggtgc acactattct gccccaggag   7380
```

```
agccccgccc tgcccacgtc gctgccatcc tcgctggtcc cacccgtgac cgcagcccag    7440
ttcctgacgc cccctcgca gcacagctac tcctcgcctg tggacaacac ccccagccac    7500
cagctacagg tgcctgagca ccccttcctc acccgtccc ctgagtcccc tgaccagtgg    7560
tccagctcgt ccccgcattc caacgtctcc gactggtccg agggcgtctc cagccctccc    7620
accagcatgc agtcccagat cgcccgcatt ccggaggcct tcaagtaaac ggcgcgcccc    7680
acgagacccc ggcttccttt cccaagcctt cgggcgtctg tgtgcgctct gtggatgcca    7740
gggccgacca gaggagcctt tttaaaacac atgttttat acaaataag aacgaggatt    7800 ttaattttt ttagtattta tttatgtact tttattttac acagaaacac tgcctttta    7860 tttatatgta ctgttttatc tggccccagg tagaaacttt tatctattct gagaaaacaa    7920
gcaagttctg agagccaggg ttttcctacg taggatgaaa agattcttct gtgtttataa    7980
aatataaaca aagattcatg atttataaat gccatttatt tattgattcc tttttcaaa    8040 atccaaaaag aaatgatgtt ggagaaggga agttgaacga gcatagtcca aaaagctcct    8100
ggggcgtcca ggccgcgccc ttttccccgac gcccacccaa ccccaagcca gcccggccgc    8160
tccaccagca tcacctgcct gttaggagaa gctgcatcca gaggcaaacg gaggcaaagc    8220
tggctcacct tccgcacgcg gattaatttg catctgaaat aggaaacaag tgaaagcata    8280
tgggttagat gttgccatgt gttttagatg gtttcttgca agcatgcttg tgaaaatgtg    8340
ttctcggagt gtgtatgcca agagtgcacc catggtacca atcatgaatc tttgtttcag    8400
gttcagtatt atgtagttgt tcgttggtta tacaagttct tggtccctcc agaaccaccc    8460 cggcccctg cccgttcttg aaatgtaggc atcatgcatg tcaaacatga gatgtgtgga    8520
ctgtggcact tgcctgggtc acacacggag gcatcctacc cttttctggg gaaagacact    8580
gcctgggctg accccggtgg cggccccagc acctcagcct gcacagtgtc ccccaggttc    8640
cgaagaagat gctccagcaa cacagcctgg gccccagctc gcgggacccg acccccgtg    8700 ggctcccgtg ttttgtagga gacttgccag agccgggcac attgagctgt gcaacgccgt    8760
gggctgcgtc ctttggtcct gtccccgcag ccctggcagg gggcatgcgg tcgggcaggg    8820
gctggaggga ggcgggggct gcccttggc caccctcct agtttgggag gagcagattt    8880
ttgcaatacc aagtatagcc tatggcagaa aaaatgtctg taaatatgtt tttaaaggtg    8940 gatttttgttt aaaaaatctt aatgaatgag tctgttgtgt gtcatgccag tgagggacgt    9000
cagacttggc tcagctcggg gagccttagc cgcccatgca ctggggacgc tccgctgccg    9060
tgccgcctgc actcctcagg gcagcctccc ccggctctac gggggccgcg tggtgccatc    9120 cccaggggc atgaccagat gcgtcccaag atgttgattt ttactgtgtt ttataaaata    9180
gagtgtagtt tacagaaaaa gactttaaaa gtgatctaca tgaggaactg tagatgatgt    9240
atttttttca tcttttttgt taactgattt gcaataaaaa tgatactgat ggtgatctgg    9300
cttccaaaaa aaaaaaaaa aa    9322
```

<210> SEQ ID NO 30
<211> LENGTH: 11474
<212> TYPE: DNA
<213> ORGANISM: Homo sapiens

<400> SEQUENCE: 30

```
gcttgcggtg ggaggaggcg gctgaggcgg aaggacacac gaggctgctt cgttgcacac      60
ccgagaaagt ttcagccaaa cttcgggcgg cggctgaggc ggcggccgag gagcggcgga     120
ctcggggcgc ggggagtcga ggcatttgcg cctgggcttc ggagcgtagc gccagggcct     180
```

```
gagcctttga agcaggagga ggggaggaga gagtggggct cctctatcgg gacccctcc      240 ccatgtggat ctgcccaggc ggcggcggcg gcggcggagg aggaggcgac cgagaagatg      300
cccgccctgc gccccgctct gctgtgggcg ctgctggcgc tctggctgtg ctgcgcggcc      360
cccgcgcatg cattgcagtg tcgagatggc tatgaaccct gtgtaaatga aggaatgtgt      420
gttacctacc acaatggcac aggatactgc aaatgtccag aaggcttctt gggggaatat      480
tgtcaacatc gagaccctg tgagaagaac cgctgccaga atggtgggac ttgtgtggcc       540
caggccatgc tggggaaagc cacgtgccga tgtgcctcag ggtttacagg agaggactgc      600
cagtactcaa catctcatcc atgctttgtg tctcgaccct gcctgaatgg cggcacatgc      660
catatgctca gccgggatac ctatgagtgc acctgtcaag tcgggtttac aggtaaggag      720
tgccaatgga cggatgcctg cctgtctcat ccctgtgcaa atggaagtac ctgtaccact      780
gtggccaacc agttctcctg caaatgcctc acaggcttca cagggcagaa atgtgagact      840
gatgtcaatg agtgtgacat tccaggacac tgccagcatg gtggcacctg cctcaacctg      900
cctggttcct accagtgcca gtgccctcag ggcttcacag ccagtactg tgacagcctg      960 tatgtgccct gtgcaccctc accttgtgtc aatggaggca cctgtcggca gactggtgac      1020 ttcactttg agtgcaactg ccttccaggt tttgaaggga gcacctgtga ggaatatt       1080 gatgactgcc ctaaccacag gtgtcagaat ggaggggttt gtgtggatgg ggtcaacact      1140
tacaactgcc gctgtcccc acaatggaca ggacagttct gcacagagga tgtggatgaa      1200
tgcctgctgc agcccaatgc ctgtcaaaat gggggcacct gtgccaaccg caatggaggc      1260
tatggctgtg tatgtgtcaa cggctggagt ggagatgact gcagtgagaa cattgatgat      1320
tgtgccttcg cctcctgtac tccaggctcc acctgcatcg accgtgtggc ctccttctct      1380
tgcatgtgcc cagaggggaa ggcaggtctc ctgtgtcatc tggatgatgc atgcatcagc      1440
aatccttgcc acaagggggc actgtgtgac accaaccccc taaatgggca atatatttgc      1500
acctgcccac aaggctacaa aggggctgac tgcacagaag atgtggatga atgtgccatg      1560
gccaatagca atccttgtga gcatgcagga aaatgtgtga acacggatgg cgccttccac      1620
tgtgagtgtc tgaagggtta tgcaggacct cgttgtgaga tggacatcaa tgagtgccat      1680
tcagacccct gccagaatga tgctacctgt ctggataaga ttggaggctt cacatgtctg      1740
tgcatgccag gtttcaaagg tgtgcattgt gaattagaaa taaatgaatg tcagagcaac      1800
ccttgtgtga acaatgggca gtgtgtggat aaagtcaatc gtttccagtg cctgtgtcct      1860
cctggtttca ctgggccagt ttgccagatt gatattgatg actgttccag tactccgtgt      1920
ctgaatgggg caaagtgtat cgatcacccg aatggctatg aatgccagtg tgccacaggt      1980
ttcactggtg tgttgtgtga ggagaacatt gacaactgtg accccgatcc ttgccaccat      2040
ggtcagtgtc aggatggtat tgattcctac acctgcatct gcaatcccgg gtacatgggc      2100
gccatctgca gtgaccagat tgatgaatgt acagcagcc cttgcctgaa cgatggtcgc      2160
tgcattgacc tggtcaatgg ctaccagtgc aactgccagc caggcacgtc agggggttaat     2220 tgtgaaatta atttttgatga ctgtgcaagt aacccttgta tccatggaat ctgtatggat      2280
ggcattaatc gctacagttg tgtctgctca ccaggattca cagggcagag atgtaacatt      2340
gacattgatg agtgtgcctc caatccctgt cgcaagggtg caacatgtat caacggtgtg      2400 aatggttttcc gctgtatatg cccgaggga ccccatcacc ccagctgcta ctcacaggtg      2460
aacgaatgcc tgagcaatcc ctgcatccat ggaaactgta ctggaggtct cagtggatat      2520
```

```
aagtgtctct gtgatgcagg ctgggttggc atcaactgtg aagtggacaa aaatgaatgc    2580
ctttcgaatc catgccagaa tggaggaact tgtgacaatc tggtgaatgg atacaggtgt    2640
acttgcaaga agggctttaa aggctataac tgccaggtga atattgatga atgtgcctca    2700
aatccatgcc tgaaccaagg aacctgcttt gatgacataa gtggctacac ttgccactgt    2760
gtgctgccat acacaggcaa gaattgtcag acagtattgg ctccctgttc cccaaaccct    2820
tgtgagaatg ctgctgtttg caaagagtca ccaaattttg agagttatac ttgcttgtgt    2880
gctcctggct ggcaaggtca gcggtgtacc attgacattg acgagtgtat ctccaagccc    2940
tgcatgaacc atggtctctg ccataacacc cagggcagct acatgtgtga atgtccacca    3000
ggcttcagtg gtatggactg tgaggaggac attgatgact gccttgccaa tccttgccag    3060
aatggaggtt cctgtatgga tggagtgaat actttctcct gcctctgcct tccgggtttc    3120
actggggata agtgccagac agacatgaat gagtgtctga gtgaaccctg taagaatgga    3180
gggacctgct ctgactacgt caacagttac acttgcaagt gccaggcagg atttgatgga    3240
gtccattgtg agaacaacat caatgagtgc actgagagct cctgtttcaa tggtggcaca    3300
tgtgttgatg ggattaactc cttctcttgc ttgtgccctg tgggtttcac tggatccttc    3360
tgcctccatg agatcaatga atgcagctct catccatgcc tgaatgaggg aacgtgtgtt    3420
gatggcctgg gtacctaccg ctgcagctgc ccctgggct acactgggaa aaactgtcag    3480
accctggtga atctctgcag tcggtctcca tgtaaaaaca aaggtacttg cgttcagaaa    3540
aaagcagagt cccagtgcct atgtccatct ggatgggctg gtgcctattg tgacgtgccc    3600
aatgtctctt gtgacatagc agcctccagg agaggtgtgc ttgttgaaca cttgtgccag    3660
cactcaggtg tctgcatcaa tgctggcaac acgcattact gtcagtgccc cctgggctat    3720
actgggagct actgtgagga gcaactcgat gagtgtgcgt ccaaccctg ccagcacggg    3780 gcaacatgca gtgacttcat tggtggatac agatgcgagt gtgtcccagg ctatcagggt    3840
gtcaactgtg agtatgaagt ggatgagtgc cagaatcagc cctgccagaa tggaggcacc    3900
tgtattgacc ttgtgaacca tttcaagtgc tcttgcccac caggcactcg gggcctactc    3960
tgtgaagaga acattgatga ctgtgcccgg ggtccccatt gccttaatgg tggtcagtgc    4020
atggatagga ttggaggcta cagttgtcgc tgcttgcctg gctttgctgg ggagcgttgt    4080
gagggagaca tcaacgagtg cctctccaac ccctgcagct ctgagggcag cctggactgt    4140
atacagctca ccaatgacta cctgtgtgtt tgccgtagtg cctttactgg ccggcactgt    4200
gaaaccttcg tcgatgtgtg tccccagatg ccctgcctga atggagggac ttgtgctgtg    4260
gccagtaaca tgcctgatgg tttcattgc cgttgtcccc cgggattttc cggggcaagg    4320
tgccagagca gctgtggaca agtgaaatgt aggaaggggg agcagtgtgt gcacaccgcc    4380
tctggacccc gctgcttctg ccccagtccc cgggactgcg agtcaggctg tgccagtagc    4440
ccctgccagc acggggcag ctgccaccct cagcgccagc ctccttatta ctcctgccag    4500 tgtgcccac cattctcggg tagccgctgt gaactctaca cggcacccc cagcacccct    4560 cctgccacct gtctgagcca gtattgtgcc gacaaagctc gggatggcgt ctgtgatgag    4620
gcctgcaaca gccatgcctg ccagtgggat ggggtgact gttctctcac catggagaac    4680
ccctgggcca actgctcctc cccacttccc tgctgggatt atatcaacaa ccagtgtgat    4740
gagctgtgca acacggtcga gtgcctgttt gacaactttg aatgccaggg gaacagcaag    4800
acatgcaagt atgacaaata ctgtgcagac cacttcaaag acaaccactg tgaccagggg    4860
tgcaacagtg aggagtgtgg ttgggatggg ctggactgtg ctgctgacca acctgagaac    4920
```

```
ctggcagaag gtaccctggt tattgtggta ttgatgccac ctgaacaact gctccaggat    4980
gctcgcagct tcttgcgggc actgggtacc ctgctccaca ccaacctgcg cattaagcgg    5040
gactcccagg gggaactcat ggtgtacccc tattatggtg agaagtcagc tgctatgaag    5100
aaacagagga tgacacgcag atcccttcct ggtgaacaag aacaggaggt ggctggctct    5160
aaagtctttc tggaaattga caaccgccag tgtgttcaag actcagacca ctgcttcaag    5220
aacacggatg cagcagcagc tctcctggcc tctcacgcca tacaggggac cctgtcatac    5280
cctcttgtgt ctgtcgtcag tgaatccctg actccagaac gcactcagct cctctatctc    5340
cttgctgttg ctgttgtcat cattctgttt attattctgc tgggggtaat catggcaaaa    5400
cgaaagcgta agcatggctc tctctggctg cctgaaggtt tcactcttcg ccgagatgca    5460
agcaatcaca agcgtcgtga gccagtggga caggatgctg tggggctgaa aaatctctca    5520
gtgcaagtct cagaagctaa cctaattggt actggaacaa gtgaacactg ggtcgatgat    5580
gaagggcccc agccaaagaa agtaaaggct gaagatgagg ccttactctc agaagaagat    5640
gaccccattg atcgacggcc atggacacag cagcaccttg aagctgcaga catccgtagg    5700
acaccatcgc tggctctcac ccctcctcag gcagagcagg aggtggatgt gttagatgtg    5760
aatgtccgtg gcccagatgg ctgcacccca ttgatgttgg cttctctccg aggaggcagc    5820
tcagatttga gtgatgaaga tgaagatgca gaggactctt ctgctaacat catcacagac    5880
ttggtctacc agggtgccag cctccaggcc cagacagacc ggactggtga gatggccctg    5940 cacctttgcag cccgctactc acgggctgat gctgccaagc gtctcctgga tgcaggtgca    6000
gatgccaatg cccaggacaa catgggccgc tgtccactcc atgctgcagt ggcagctgat    6060
gcccaaggtg tcttccagat tctgattcgc aaccgagtaa ctgatctaga tgccaggatg    6120
aatgatggta ctacacccct gatcctggct gcccgcctgg ctgtggaggg aatggtggca    6180
gaactgatca actgccaagc ggatgtgaat gcagtggatg accatggaaa atctgctctt    6240
cactgggcag ctgctgtcaa taatgtggag gcaactcttt tgttgttgaa aaatgggggcc    6300 aaccgagaca tgcaggacaa caaggaagag acacctctgt ttcttgctgc ccgggagggg    6360
agctatgaag cagccaagat cctgttagac cattttgcca atcgagacat cacagaccat    6420
atggatcgtc ttccccggga tgtggctcgg atcgcatgc accatgacat tgtgcgcctt    6480
ctggatgaat acaatgtgac cccaagccct ccaggcaccg tgttgacttc tgctctctca    6540
cctgtcatct gtgggcccaa cagatctttc ctcagcctga gcacacccc aatgggcaag    6600 aagtctagac ggcccagtgc caagagtacc atgcctacta gcctccctaa ccttgccaag    6660
gaggcaaagg atgccaaggg tagtaggagg aagaagtctc tgagtgagaa ggtccaactg    6720
tctgagagtt cagtaacttt atcccctgtt gattccctag aatctcctca cacgtatgtt    6780
tccgacacca catcctctcc aatgattaca tcccctggga tcttacaggc ctcacccaac    6840
cctatgttgg ccactgccgc ccctcctgcc ccagtccatg cccagcatgc actatctttt    6900
tctaaccttc atgaaatgca gcctttggca catggggcca gcactgtgct tccctcagtg    6960
agccagttgc tatcccacca ccacattgtg tctccaggca gtggcagtgc tggaagcttg    7020
agtaggctcc atcagtccc agtcccagca gattggatga accgcatgga ggtgaatgag    7080
acccagtaca atgagatgtt tggtatggtc ctggctccag ctgagggcac ccatcctggc    7140
atagctcccc agagcaggcc acctgaaggg aagcacataa ccacccctcg ggagcccttg    7200 cccccccattg tgactttcca gctcatccct aaaggcagta ttgcccaacc agcggggggct    7260
```

-continued

| | |
|---|---|
| ccccagcctc agtccacctg ccctccagct gttgcgggcc ccctgcccac catgtaccag | 7320 |
| attccagaaa tggcccgttt gcccagtgtg gctttcccca ctgccatgat gccccagcag | 7380 |
| gacgggcagg tagctcagac cattctccca gcctatcatc ctttcccagc ctctgtgggc | 7440 |
| aagtacccca cacccccttc acagcacagt tatgcttcct caaatgctgc tgagcgaaca | 7500 |
| cccagtcaca gtggtcacct ccagggtgag catccctacc tgacaccatc cccagagtct | 7560 |
| cctgaccagt ggtcaagttc atcaccccac tctgcttctg actggtcaga tgtgaccacc | 7620 |
| agccctaccc ctgggggtgc tggaggaggt cagcgggac ctgggacaca catgtctgag | 7680 |
| ccaccacaca acaacatgca ggtttatgcg tgagagagtc cacctccagt gtagagacat | 7740 |
| aactgacttt tgtaaatgct gctgaggaac aaatgaaggt catccgggag agaaatgaag | 7800 |
| aaatctctgg agccagcttc tagaggtagg aaagagaaga tgttcttatt cagataatgc | 7860 |
| aagagaagca attcgtcagt ttcactgggt atctgcaagg cttattgatt attctaatct | 7920 |
| aataagacaa gtttgtggaa atgcaagatg aatacaagcc ttgggtccat gtttactctc | 7980 |
| ttctatttgg agaataagat ggatgcttat tgaagcccag acattcttgc agcttggact | 8040 |
| gcattttaag ccctgcaggc ttctgccata tccatgagaa gattctacac tagcgtcctg | 8100 |
| ttgggaatta tgccctggaa ttctgcctga attgacctac gcatctcctc ctccttggac | 8160 |
| attcttttgt cttcatttgg tgcttttggt tttgcacctc tccgtgattg tagccctacc | 8220 |
| agcatgttat agggcaagac ctttgtgctt ttgatcattc tggcccatga aagcaacttt | 8280 |
| ggtctccttt cccctcctgt cttcccggta tcccttggag tctcacaagg tttactttgg | 8340 |
| tatggttctc agcacaaacc tttcaagtat gttgtttctt tggaaaatgg acatactgta | 8400 |
| ttgtgttctc ctgcatatat cattcctgga gagagaaggg gagaagaata cttttcttca | 8460 |
| acaaattttg ggggcaggag atcccttcaa gaggctgcac cttaatttt cttgtctgtg | 8520 |
| tgcaggtctt catataaact ttaccaggaa gaagggtgtg agtttgttgt ttttctgtgt | 8580 |
| atgggcctgg tcagtgtaaa gttttatcct tgatagtcta gttactatga ccctccccac | 8640 |
| tttttttaaaa ccagaaaaag gtttggaatg ttggaatgac caagagacaa gttaactcgt | 8700 |
| gcaagagcca gttacccacc cacaggtccc cctacttcct gccaagcatt ccattgactg | 8760 |
| cctgtatgga acacatttgt cccagatctg agcattctag gcctgtttca ctcactcacc | 8820 |
| cagcatatga aactagtctt aactgttgag ccttttcctt catatccaca gaagacactg | 8880 |
| tctcaaatgt tgtaccctgg ccatttagga ctgaactttc cttagcccaa gggacccagt | 8940 |
| gacagttgtc ttccgtttgt cagatgatca gtctctactg attatcttgc tgcttaaagg | 9000 |
| cctgctcacc aatctttctt tcacaccgtg tggtccgtgt tactggtata cccagtatgt | 9060 |
| tctcactgaa gacatggact ttatatgttc aagtgcagga attggaaagt tggacttgtt | 9120 |
| ttctatgatc caaaacagcc ctataagaag gttggaaaag gaggaactat atagcagcct | 9180 |
| ttgctatttt ctgctaccat ttcttttcct ctgaagcggc catgacattc cctttggcaa | 9240 |
| ctaacgtaga aactcaacag aacatttttcc tttcctagag tcacctttta gatgataatg | 9300 |
| gacaactata gacttgctca ttgttcagac tgattgcccc tcacctgaat ccactctctg | 9360 |
| tattcatgct cttggcaatt tctttgactt tcttttaagg gcagaagcat tttagttaat | 9420 |
| tgtagataaa gaatagtttt cttcctcttc tccttgggcc agttaataat tggtccatgg | 9480 |
| ctacactgca acttccgtcc agtgctgtga tgcccatgac acctgcaaaa taagttctgc | 9540 |
| ctgggcattt tgtagatatt aacaggtgaa ttcccgactc ttttggtttg aatgacagtt | 9600 |
| ctcattcctt ctatggctgc aagtatgcat cagtgcttcc cacttacctg atttgtctgt | 9660 |

```
cggtggcccc atatggaaac cctgcgtgtc tgttggcata atagtttaca aatggttttt    9720
tcagtcctat ccaaatttat tgaaccaaca aaaataatta cttctgccct gagataagca    9780
gattaagttt gttcattctc tgctttattc tctccatgtg gcaacattct gtcagcctct    9840
ttcatagtgt gcaaacattt tatcattcta aatggtgact ctctgccctt ggacccattt    9900
attattcaca gatggggaga acctatctgc atggacctct gtggaccaca gcgtacctgc    9960 cccttctgc cctcctgctc cagccccact tctgaaagta tcagctactg atccagccac     10020
tggatatttt atatcctccc ttttccttaa gcacaatgtc agaccaaatt gcttgtttct    10080
ttttcttgga ctactttaat ttggatcctt gggtttgga gaaagggaat gtgaaagctg     10140
tcattacaga caacaggttt cagtgatgag gaggacaaca ctgcctttca aacttttttac   10200 tgatctctta gattttaaga actcttgaat tgtgtggtat ctaataaaag ggaaggtaag    10260
atggataatc actttctcat ttgggttctg aattggagac tcagttttta tgagacacat    10320
cttttatgcc atgtatagat cctcccctgc tattttggt ttatttttat tgttataaat     10380
gctttctttc tttgactcct cttctgcctg cctttgggga taggtttttt tgtttgttta    10440
tttgcttcct ctgttttgtt ttaagcatca ttttcttatg tgaggtgggg aagggaaagg    10500
tatgagggaa agagagtctg agaattaaaa tattttagta taagcaattg gctgtgatgc    10560
tcaaatccat tgcatcctct tattgaattt gccaatttgt aattttttgca taataaagaa   10620 ccaaaggtgt aatgttttgt tgagaggtgg tttagggatt ttggccctaa ccaatacatt    10680
gaatgtatga tgactatttg ggaggacaca tttatgtacc cagaggcccc cactaataag    10740
tggtactatg gttacttcct tgtgtacatt tctcttaaaa gtgatattat atctgtttgt    10800
atgagaaacc cagtaaccaa taaaatgacc gcatattcct gactaaacgt agtaaggaaa    10860
atgcacactt tgttttact tttccgtttc attctaaagg tagttaagat gaaatttata     10920
tgaaagcatt tttatcacaa aataaaaaag gtttgccaag ctcagtggtg ttgtattttt    10980
tattttccaa tactgcatcc atggcctggc agtgttacct catgatgtca aatttgctg     11040 agagagcaaa ttttcttttc tttctgaatc ccacaaagcc tagcaccaaa cttctttttt    11100 tcttcctta attagatcat aaataaatga tcctggggaa aaagcatctg tcaaatagga     11160
aacatcacaa aactgagcac tcttctgtgc actagccata gctggtgaca aacagatggt    11220
tgctcaggga caaggtgcct tccaatgaa atgcgaagta gttgctatag caagaattgg     11280
gaactgggat ataagtcata atattaatta tgctgttatg taaatgattg gtttgtaaca    11340
ttccttaagt gaaatttgtg tagaacttaa tatacaggat tataaaataa tattttgtgt    11400
ataaatttgt tataagttca cattcataca tttatttata aagtcagtga gatatttgaa    11460
catgaaaaaa aaaa                                                      11474
```

<210> SEQ ID NO 31
<211> LENGTH: 4326
<212> TYPE: DNA
<213> ORGANISM: Homo sapiens

<400> SEQUENCE: 31

```
gcttgcggtg ggaggaggcg gctgaggcgg aaggacacac gaggctgctt cgttgcacac      60
ccgagaaagt ttcagccaaa cttcgggcgg cggctgaggc ggcggccgag gagcggcgga     120
ctcggggcgc ggggagtcga ggcatttgcg cctgggcttc ggagcgtagc gccagggcct     180
gagcctttga agcaggagga ggggaggaga gagtgggggct cctctatcgg gacccctcc    240
```

-continued

```
ccatgtggat ctgcccaggc ggcggcggcg gcggcggagg aggaggcgac cgagaagatg    300
cccgccctgc gccccgctct gctgtgggcg ctgctggcgc tctggctgtg ctgcgcggcc    360
cccgcgcatg cattgcagtg tcgagatggc tatgaaccct gtgtaaatga aggaatgtgt    420
gttacctacc acaatggcac aggatactgc aaatgtccag aaggcttctt ggggaatat    480 tgtcaacatc gagacccctg tgagaagaac cgctgccaga atggtgggac ttgtgtggcc    540
caggccatgt gggaaagc cacgtgccga tgtgcctcag ggtttacagg agaggactgc    600
cagtactcaa catctcatcc atgctttgtg tctcgaccct gcctgaatgg cggcacatgc    660
catatgctca gccgggatac ctatgagtgc acctgtcaag tcgggtttac aggtaaggag    720
tgccaatgga cggatgcctg cctgtctcat ccctgtgcaa atggaagtac ctgtaccact    780
gtggccaacc agttctcctg caaatgcctc acaggcttca cagggcagaa atgtgagact    840
gatgtcaatg agtgtgacat tccaggacac tgccagcatg tggcacctg cctcaacctg    900 cctggttcct accagtgcca gtgccctcag ggcttcacag gccagtactg tgacagcctg    960 tatgtgcct gtgcaccctc accttgtgtc aatggaggca cctgtcggca gactggtgac   1020
ttcacttttg agtgcaactg ccttccaggt tttgaaggga gcacctgtga gaggaatatt   1080
gatgactgcc ctaaccacag gtgtcagaat ggagggttt gtgtggatgg ggtcaacact   1140
tacaactgcc gctgtccccc acaatggaca ggacagttct gcacagagga tgtggatgaa   1200
tgcctgctgc agcccaatgc ctgtcaaaat gggggcacct gtgccaaccg caatggaggc   1260
tatggctgtg tatgtgtcaa cggctggagt ggagatgact gcagtgagaa cattgatgat   1320
tgtgccttcg cctcctgtac tccaggctcc acctgcatcg accgtgtggc ctccttctct   1380
tgcatgtgcc cagaggggaa ggcaggtctc ctgtgtcatc tggatgatgc atgcatcagc   1440
aatccttgcc acaaggggc actgtgtgac accaaccccc taaatgggca atatatttgc   1500
acctgcccac aaggctacaa aggggctgac tgcacagaag atgtggatga atgtgccatg   1560
gccaatagca atccttgtga gcatgcagga aaatgtgtga acacggatgg cgccttccac   1620
tgtgagtgtc tgaagggtta tgcaggacct cgttgtgaga tggacatcaa tgagtgccat   1680
tcagacccct gccagaatga tgctaccgt ctggataaga ttggaggctt cacatgtctg   1740
tgcatgccag gtttcaaagg tgtgcattgt gaattagaaa taaatgaatg tcagagcaac   1800
ccttgtgtga acaatgggca gtgtgtggat aaagtcaatc gtttccagtg cctgtgtcct   1860
cctggtttca ctgggccagt ttgccagatt gatattgatg actgttccag tactccgtgt   1920
ctgaatgggg caaagtgtat cgatcacccg aatggctatg aatgccagtg tgccacaggt   1980
ttcactggtg tgttgtgtga ggagaacatt gacaactgtg accccgatcc ttgccaccat   2040
ggtcagtgtc aggatggtat tgattcctac acctgcatct gcaatcccgg gtacatgggc   2100
gccatctgca gtgaccagat tgatgaatgt acagcagcc cttgcctgaa cgatggtcgc   2160
tgcattgacc tggtcaatgg ctaccagtgc aactgccagc caggcacgtc agggttaat   2220 tgtgaaatta attttgatga ctgtgcaagt aacccttgta tccatggaat ctgtatggat   2280
ggcattaatc gctacagttg tgtctgctca ccaggattca gggcagag atgtaacatt   2340 gacattgatg agtgtgcctc aatccctgt cgcaagggtg caacatgtat caacggtgtg   2400
aatggtttcc gctgtatatg ccccgaggga ccccatcacc ccagctgcta ctcacaggtg   2460
aacgaatgcc tgagcaatcc ctgcatccat ggaaactgta ctggaggtct cagtggatat   2520
aagtgtctct gtgatgcagg ctgggttggc atcaactgtg aagtggacaa aaatgaatgc   2580
ctttcgaatc catgccagaa tggaggaact tgtgacaatc tggtgaatgg atacaggtgt   2640
```

```
acttgcaaga agggctttaa aggctataac tgccaggtga atattgatga atgtgcctca    2700
aatccatgcc tgaaccaagg aacctgcttt gatgacataa gtggctacac ttgccactgt    2760
gtgctgccat acacaggcaa gaattgtcag acagtattgg ctccctgttc cccaaaccct    2820
tgtgagaatg ctgctgtttg caaagagtca ccaaattttg agagttatac ttgcttgtgt    2880
gctcctggct ggcaaggtca gcggtgtacc attgacattg acgagtgtat ctccaagccc    2940
tgcatgaacc atggtctctg ccataacacc cagggcagct acatgtgtga atgtccacca    3000
ggcttcagtg gtatggactg tgaggaggac attgatgact gccttgccaa tccttgccag    3060
aatggaggtt cctgtatgga tggagtgaat actttctcct gcctctgcct tccgggtttc    3120
actggggata agtgccagac agacatgaat gagtgtctga gtgaaccctg taagaatgga    3180
gggacctgct ctgactacgt caacagttac acttgcaagt gccaggcagg atttgatgga    3240
gtccattgtg agaacaacat caatgagtgc actgagagct cctgtttcaa tggtggcaca    3300
tgtgttgatg ggattaactc cttctcttgc ttgtgccctg tgggtttcac tggatccttc    3360
tgcctccatg agatcaatga atgcagctct catccatgcc tgaatgaggg aacgtgtgtt    3420
gatggcctgg gtacctaccg ctgcagctgc cccctgggct acactgggaa aaactgtcag    3480
accctggtga atctctgcag tcggtctcca tgtaaaaaca aaggtacttg cgttcagaaa    3540
aaagcagagt cccagtgcct atgtccatct ggatgggctg gtgcctattg tgacgtgccc    3600
aatgtctctt gtgacatagc agcctccagg agaggtgtgc ttgttgaaca cttgtgccag    3660
cactcaggtg tctgcatcaa tgctggcaac acgcattact gtcagtgccc cctgggctat    3720
actgggagct actgtgagga gcaactcgat gagtgtgcgt ccaacccctg ccagcacggg    3780
gcaacatgca gtgacttcat tggtggatac agatgcgagt gtgtcccagg ctatcagggt    3840
gtcaactgtg agtatgaagt ggatgagtgc cagaatcagc cctgccagaa tggaggcacc    3900
tgtattgacc ttgtgaacca tttcaagtgc tcttgcccac caggcactcg gggtatgaaa    3960
tcatccttat ccattttcca tccagggcat tgtcttaagt tataaatcca ttcttagtgt    4020 tcagggatt ttataaaatt aaagatagga agactagctt cattccaagc atttagttct    4080
acatcctagt aattcaagcc atttattct cccatctctt gctagctctg atgttgtggt    4140
ttatgttgtc agttttatct ggttgtttgg catcttgata ttccatgaaa cacagaatat    4200
ggaagggata caacattagc ataacattaa aaaattagcc tggtcagtaa gatttcttgt    4260
tgcttcacag aaaagcaact aatggcctct aaaataaaca atttacattt aaaaaaaaa    4320 aaaaaa                                                                4326

<210> SEQ ID NO 32
<211> LENGTH: 8089
<212> TYPE: DNA
<213> ORGANISM: Homo sapiens

<400> SEQUENCE: 32
gcggcgcgga ggctggcccg ggacgcgccc ggagcccagg gaaggaggga ggaggggagg      60
gtcgcggccg gccgccatgg ggccggggc ccgtggccgc cgccgccgcc gtcgcccgat     120
gtcgccgcca ccgccaccgc cacccgtgcg ggcgctgccc ctgctgctgc tgctagcggg    180
gccgggggct gcagcccccc cttgcctgga cggaagcccg tgtgcaaatg gaggtcgttg    240
cacccagctg ccctcccggg aggctgcctg cctgtgcccg cctggctggg tgggtgagcg    300
gtgtcagctg gaggacccct gtcactcagg cccctgtgct ggccgtggtg tctgccagag    360
```

-continued

```
ttcagtggtg gctggcaccg cccgattctc atgccggtgc ccccgtggct tccgaggccc    420
tgactgctcc ctgccagatc cctgcctcag cagcccttgt gcccacggtg cccgctgctc    480
agtggggccc gatggacgct tcctctgctc ctgcccacct ggctaccagg ccgcagctg    540
ccgaagcgac gtggatgagt gccgggtggg tgagccctgc cgccatggtg gcacctgcct    600
caacacacct ggctccttcc gctgccagtg tccagctggc tacacagggc cactatgtga    660
gaaccccgcg gtgccctgtg caccctcacc atgccgtaac gggggcacct gcaggcagag    720
tggcgacctc acttacgact gtgcctgtct tcctgggttt gagggtcaga attgtgaagt    780
gaacgtggac gactgtccag acaccgatg tctcaatggg gggacatgcg tggatggcgt    840
caacacctat aactgccagt gccctcctga gtggacaggc cagttctgca cggaggacgt    900
ggatgagtgt cagctgcagc ccaacgcctg ccacaatggg ggtacctgct tcaacacgct    960
gggtggccac agctgcgtgt gtgtcaatgg ctggacaggc gagagctgca gtcagaatat   1020
cgatgactgt gccacagccg tgtgcttcca tggggccacc tgccatgacc gcgtggcttc   1080
tttctactgt gcctgcccca tgggcaagac tggcctcctg tgtcacctgg atgacgcctg   1140
tgtcagcaac ccctgccacg aggatgctat ctgtgacaca aatccggtga acggccgggc   1200
catttgcacc tgtcctcccg gcttcacggg tgggcatgt gaccaggatg tggacgagtg   1260
ctctatcggc gccaacccct gcgagcactt gggcaggtgc gtgaacacgc agggctcctt   1320
cctgtgccag tgcggtcgtg gctacactgg acctcgctgt gagaccgatg tcaacgagtg   1380
tctgtcgggg ccctgccgaa accaggccac gtgcctcgac cgcataggcc agttcacctg   1440
tatctgtatg gcaggcttca caggaaccta ttgcgaggtg gacattgacg agtgtcagag   1500
tagcccctgt gtcaacggtg gggtctgcaa ggaccgagtc aatggcttca gctgcacctg   1560
cccctcgggc ttcagcggct ccacgtgtca gctggacgtg gacgaatgcg ccagcacgcc   1620
ctgcaggaat ggcgccaaat gcgtggacca gcccgatggc tacgagtgcc gctgtgccga   1680
gggctttgag gcacgctgt gtgatcgcaa cgtggacgac tgctccccctg acccatgcca   1740
ccatggtcgc tgcgtggatg gcatcgccag cttctcatgt gcctgtgctc ctggctacac   1800
gggcacacgc tgcgagagcc aggtggacga atgccgcagc cagccctgcc gccatggcgg   1860
caaatgccta gacctggtgg acaagtacct ctgccgctgc cttctgggg ccacaggtgt   1920
gaactgcgaa gtgaacattg acgactgtgc agcaacccc tgcaccttg gagtctgccg   1980
tgatggcatc aaccgctacg actgtgtctg ccaacctggc ttcacagggc cccttgtaa    2040
cgtggagatc aatgagtgtg cttccagccc atgcggcgag ggaggttcct gtgtggatgg   2100
ggaaaatggc ttccgctgcc tctgcccgcc tggctccttg cccccactct gcctcccccc   2160
gagccatccc tgtgcccatg agccctgcag tcacggcatc tgctatgatg cacctggcgg   2220
gttccgctgt gtgtgtgagc ctggctggag tggccccgc tgcagccaga gcctggcccg   2280
agacgcctgt gagtcccagc cgtgcagggc cggtgggaca tgcagcagcg atggaatggg   2340
tttccactgc acctgcccgc ctggtgtcca gggacgtcag tgtgaactcc tctccccctg   2400
cacccgaac ccctgtgagc atggggggccg ctgcgagtct gcccctggcc agctgcctgt   2460
ctgctcctgc cccagggct ggcaaggcc acgatgccag caggatgtgg acagtgtgc    2520
tggccccgca ccctgtggcc ctcatggtat ctgcaccaac ctggcaggga gtttcagctg   2580
cacctgccat ggaggtgcaca ctggcccctt ctgcgatcag acatcaatg actgtgaccc   2640
caacccatgc ctgaacggtg gctcgtgcca agacggcgtg ggctcctttt cctgctcctg   2700
cctccctggt ttcgccggcc cacgatgcgc ccgcgatgtg gatgagtgcc tgagcaaccc   2760
```

```
ctgcggcccg ggcacctgta ccgaccacgt ggcctccttc acctgcacct gcccgccagg    2820
ctacggaggc ttccactgcg aacaggacct gcccgactgc agcccagct cctgcttcaa     2880 tggcgggacc tgtgtggacg gcgtgaactc gttcagctgc ctgtgccgtc ccggctacac    2940
aggagcccac tgccaacatg aggcagaccc ctgcctctcg cggccctgcc tacacggggg    3000
cgtctgcagc gccgcccacc ctggcttccg ctgcacctgc ctcgagagct tcacgggccc    3060
gcagtgccaa cgctggtgg attggtgcag ccgccagcct tgtcaaaacg ggggtcgctg     3120
cgtccagact ggggcctatt gcctttgtcc ccctggatgg agcggacgcc tctgtgacat    3180
ccgaagcttg ccctgcaggg aggccgcagc ccagatcggg gtgcggctgg agcagctgtg    3240
tcaggcgggt gggcagtgtg tggatgaaga cagctcccac tactgcgtgt gcccagaggg    3300
ccgtactggt agccactgtg agcaggaggt ggaccctgc ttggcccagc cctgccagca     3360 tgggggggacc tgccgtggct atatggggg ctacatgtgt gagtgtcttc ctggctacaa    3420
tggtgataac tgtgaggacg acgtggacga gtgtgcctcc cagccctgcc agcacggggg    3480
ttcatgcatt gacctcgtgg cccgctatct ctgctcctgt ccccaggaa cgctgggggt     3540 gctctgcgag attaatgagg atgactgcg cccaggccca ccgctggact cagggccccg     3600
gtgcctacac aatggcacct cgtggacct ggtgggtggt ttccgctgca cctgtccccc     3660
aggatacact ggtttgcgct gcgaggcaga catcaatgag tgtcgctcag gtgcctgcca    3720
cgcggcacac acccgggact gcctgcagga cccaggcgga ggtttccgtt gcctttgtca    3780
tgctggcttc tcaggtcctc gctgtcagac tgtcctgtct ccctgcgagt cccagccatg    3840
ccagcatgga ggccagtgcc gtcctagccc gggtcctggg ggtgggctga ccttcacctg    3900
tcactgtgcc cagccgttct ggggtccgcg ttgcgagcgg gtggcgcgct cctgccggga    3960
gctgcagtgc ccggtgggcg tcccatgcca gcagacgccc cgcgggccgc gctgcgcctg    4020
ccccccaggg ttgtcgggac cctcctgccg cagcttcccg gggtcgccgc cggggggccag   4080 caacgccagc tgcgcggccg cccccctgtct ccacgggggc tcctgccgcc ccgcgccgct   4140
cgcgcccttc ttccgctgcg cttgcgcgca gggctggacc gggccgcgct gcgaggcgcc    4200
cgccgcggca cccgaggtct cggaggagcc gcggtgcccg cgccgcgcct gcaggccaa     4260 gcgcggggac cagcgctgcg accgcgagtg caacagccca ggctgcggct gggacggcgg    4320
cgactgctcg ctgagcgtgg gcgaccctg gcggcaatgc gaggcgctgc agtgctggcg    4380
cctcttcaac aacagccgct gcgaccccgc ctgcagctcg cccgcctgcc tctacgacaa    4440
cttcgactgc cacgccggtg gccgagcg cacttgcaac ccggtgtacg agaagtactg      4500
cgccgaccac tttgccgacg gccgctgcga ccagggctgc aacacggagg agtgcggctg    4560
ggatgggctg gattgtgcca gcgaggtgcc ggccctgctg gcccgcggcg tgctggtgct    4620
cacagtgctg ctgccgccag aggagctact gcgttccagc gccgactttc tgcagcggct    4680
cagcgccatc ctgcgcacct cgctgcgctt ccgcctggac gcgcacggcc aggccatggt    4740
cttcccttac accggccta gtcctggctc gaacccccgg gccgtcgggg agctggcccc    4800
cgaggtgatc ggctcggtag taatgctgga gattgacaac cggctctgcc tgcagtcgcc    4860
tgagaatgat cactgcttcc ccgatgccca gagcgccgct gactacctgg gagcgttgtc    4920
agcggtggag cgcctggact tcccgtaccc actgcgggac gtgcgggggg agccgctgga    4980
gcctccagaa cccagcgtcc cgctgctgcc actgctagtg gcgggcgctg tcttgctgct    5040
ggtcattctc gtcctggggtg tcatggtggc ccggcgcaag cgcgagcaca gcaccctctg    5100
```

```
gttccctgag ggcttctcac tgcacaagga cgtggcctct ggtcacaagg gccggcggga   5160
acccgtgggc caggacgcgc tgggcatgaa aacatggcc aagggtgaga gcctgatggg    5220
ggaggtggcc acagactgga tggacacaga gtgcccagag gccaagcggc taaaggtaga   5280
ggagccaggc atgggggctg aggaggctgt ggattgccgt cagtggactc aacaccatct   5340
ggttgctgct gacatccgcg tggcaccagc catggcactg acaccaccac agggcgacgc   5400
agatgctgat ggcatggatg tcaatgtgcg tggcccagat ggcttcaccc cgctaatgct   5460
ggcttccttc tgtgggggg ctctggagcc aatgccaact gaagaggatg aggcagatga    5520
cacatcagct agcatcatct ccgacctgat ctgccagggg gctcagcttg ggcacggac    5580 tgaccgtact ggcgagactg ctttgcacct ggctgcccgt tatgcccgtg ctgatgcagc   5640
caagcggctg ctggatgctg gggcagacac caatgcccag gaccactcag gccgcactcc   5700
cctgcacaca gctgtcacag ccgatgccca gggtgtcttc cagattctca tccgaaaccg   5760
ctctacagac ttggatgccc gcatggcaga tggctcaacg gcactgatcc tggcggcccg   5820
cctggcagta gagggcatgg tggaagagct catcgccagc catgctgatg tcaatgctgt   5880
ggatgagctt gggaaatcag ccttacactg gctgcggct gtgaacaacg tggaagccac    5940
tttggccctg ctcaaaaatg gagccaataa ggacatgcag gatagcaagg aggagacccc   6000
cctattcctg gccgcccgcg agggcagcta tgaggctgcc aagctgctgt tggaccactt   6060
tgccaaccgt gagatcaccg accacctgga caggctgccg cgggacgtag cccaggagag   6120
actgcaccag gacatcgtgc gcttgctgga tcaacccagt gggcccccgca gcccccccgg   6180 tccccacggc ctggggcctc tgctctgtcc tccagggggcc ttcctcctg gcctcaaagc   6240 ggcacagtcg gggtccaaga agagcaggag gcccccgggg aaggcggggc tggggccgca   6300
ggggccccgg gggcggggca agaagctgac gctggcctgc ccgggccccc tggctgacag   6360
ctcggtcacg ctgtcgcccg tggactcgct ggactccccg cggccttcg gtgggccccc     6420 tgcttcccct ggtggcttcc cccttgaggg gccctatgca gctgccactg ccactgcagt   6480
gtctctggca cagcttggtg gcccaggccg ggcgggtcta gggcgccagc cccctggagg   6540
atgtgtactc agcctgggcc tgctgaaccc tgtggctgtg ccctcgatt gggcccggct     6600 gccccacct gccccctccag gcccctcgtt cctgctgcca ctggcgccgg accccagct     6660 gctcaaccca gggaccccg tctccccgca ggagcggccc ccgccttacc tggcagtccc   6720
aggacatggc gaggagtacc cggcggctgg ggcacacagc agcccccaa aggcccgctt    6780 cctgcgggtt cccagtgagc acccttacct gaccccatcc cccgaatccc ctgagcactg   6840
ggccagcccc tcacctccct ccctctcaga ctggtccgaa tccacgccta gcccagccac   6900
tgccactggg gccatggcca ccaccactgg ggcactgcct gccagcccac ttcccttgtc   6960
tgttcccagc tcccttgctc aggcccagac ccagctgggg ccccagccgg aagttacccc   7020
caagaggcaa gtgttggcct gagacgctcg tcagttctta gatcttgggg gcctaaagag   7080 accccgtcc tgcctccttt ctttctctgt ctcttccttc cttttagtct ttttcatcct    7140 cttctcttc caccaaccct cctgcatcct tgccttgcag cgtgaccgag ataggtcatc    7200
agcccagggc ttcagtcttc ctttatttat aatgggtggg ggctaccacc caccctctca   7260
gtcttgtgaa gagtctggga cctccttctt ccccacttct ctcttccctc attccttct     7320 ctctccttct ggcctctcat ttccttacac tctgacatga atgaattatt attattttta   7380
ttttcttttt ttttttaca ttttgtatag aaacaaattc atttaaacaa acttattatt     7440
attatttttt acaaaatata tatatggaga tgctccctcc ccctgtgaac ccccagtgc    7500
```

```
cccgtgggg ctgagtctgt gggcccattc ggccaagctg gattctgtgt acctagtaca    7560
caggcatgac tgggatcccg tgtaccgagt acacgaccca ggtatgtacc aagtaggcac    7620
ccttgggcgc acccactggg gccaggggtc ggggagtgt  tgggagcctc ctccccaccc    7680
cacctccctc acttcactgc attccagatg gacatgttc  catagccttg ctggggaagg    7740
gcccactgcc aactccctct gccccagccc cacccttggc catctccctt tgggaactag    7800
ggggctgctg gtgggaaatg ggagccaggg cagatgtatg cattcctttg tgtccctgta    7860
aatgtgggac tacaagaaga ggagctgcct gagtggtact ttctcttcct ggtaatcctc    7920
tggcccagcc tcatggcaga atagaggtat ttttaggcta ttttttgtaat atggcttctg    7980 gtcaaaatcc ctgtgtagct gaattcccaa gccctgcatt gtacagcccc ccactcccct    8040
caccacctaa taaaggaata gttaacactc aaaaaaaaaa aaaaaaaaa               8089
```

<210> SEQ ID NO 33
<211> LENGTH: 6762
<212> TYPE: DNA
<213> ORGANISM: Homo sapiens

<400> SEQUENCE: 33

```
agacgtgagg cttgcagcag gccgaggagg aagaagaggg gcagtgggag cagaggaggt      60
ggctcctgcc ccagtgagag ctctgagggt ccctgcctga agagggacag ggaccggggc     120
ttggagaagg ggctgtggaa tgcagccccc ttcactgctg ctgctgctgc tgctgctgct     180
gctgctatgt gtctcagtgg tcagacccag agggctgctg tgtgggagtt cccagaacc     240 ctgtgccaat ggaggcacct gcctgagcct gtctctggga caagggacct gccagtgtgc     300
ccctggcttc ctgggtgaga cgtgccagtt cctgaccccc tgccagaacg cccagctctg     360
ccaaaatgga ggcagctgcc aagccctgct tcccgctccc ctagggctcc ccagctctcc     420
ctctccattg acacccagct tcttgtgcac ttgcctccct ggcttcactg gtgagagatg     480
ccaggccaag cttgaagacc cttgtcctcc ctccttctgt tccaaagggg ccgctgcca      540 catccaggcc tcgggccgcc acagtgctc  ctgcatgcct ggatggacag gtgagcagtg     600
ccagcttcgg gacttctgtt cagccaaccc atgtgttaat ggagggtgt  gtctggccac     660 ataccccag  atccagtgcc actgccacc  gggcttcgag ggccatgcct gtgaacgtga     720
tgtcaacgag tgcttccagg acccaggacc ctgccccaaa ggcacctcct gcataacac      780 cctgggctcc ttccagtgcc tctgccctgt ggggcaggag ggtccacgtt gtgagctgcg     840
ggcaggaccc tgccctccta ggggctgttc gaatgggggc acctgccagc tgatgccaga     900
gaaagactcc acctttcacc tctgcctctg tcccccaggt ttcataggcc cagactgtga     960
ggtgaatcca gacaactgtg tcagccacca gtgtcagaat gggggcactt gccaggatgg    1020
gctggacacc tacacctgcc tctgcccaga aacctggaca ggctgggact gctccgaaga    1080
tgtggatgag tgtgagaccc agggtcccc  tcactgcaga aacggggca  cctgccagaa    1140 ctctgctggt agctttcact gcgtgtgtgt gagtggctgg ggcggcacaa gctgtgagga    1200
gaacctggat gactgtattg ctgccacctg tgccccggga tccacctgca ttgaccgggt    1260
gggctctttc tcctgcctct gcccacctgg acgcacagga ctcctgtgcc acttggaaga    1320
catgtgtctg agccagccgt gccatgggga tgcccaatgc agcaccaacc ccctcacagg    1380
ctccacactc tgcctgtgtc agcctggcta ttcggggccc acctgccacc aggacctgga    1440
cgagtgtctg atggcccagc aaggcccaag tccctgtgaa catggcggtt cctgcctcaa    1500
```

```
cactcctggc tccttcaact gcctctgtcc acctggctac acaggctccc gttgtgaggc   1560
tgatcacaat gagtgcctct cccagccctg ccacccagga agcacctgtc tggacctact   1620
tgccaccttc cactgcctct gcccgccagg cttagaaggg cagctctgtg aggtggagac   1680
caacgagtgt gcctcagctc cctgcctgaa ccacgcggat tgccatgacc tgctcaacgg   1740
cttccagtgc atctgcctgc ctggattctc cggcacccga tgtgaggagg atatcgatga   1800
gtgcagaagc tctccctgtg ccaatggtgg gcagtgccag gaccagcctg gagccttcca   1860
ctgcaagtgt ctcccaggct ttgaagggcc acgctgtcaa acagaggtgg atgagtgcct   1920
gagtgaccca tgtcccgttg gagccagctg ccttgatctt ccaggagcct tcttttgcct   1980
ctgcccctct ggtttcacag gccagctctg tgaggttccc ctgtgtgctc ccaacctgtg   2040
ccagcccaag cagatatgta aggaccagaa agacaaggcc aactgcctct gtcctgatgg   2100
aagccctggc tgtgccccac ctgaggacaa ctgcacctgc caccacgggc actgccagag   2160
atcctcatgt gtgtgtgacg tgggttggac ggggccagag tgtgaggcag agctagggg   2220 ctgcatctct gcccctgtg cccatggggg gacctgctac cccagccct ctggctacaa   2280 ctgcacctgc cctacaggct acacaggacc cacctgtagt gaggagatga cagcttgtca   2340
ctcagggcca tgtctcaatg gcggctcctg caaccctagc cctggaggct actactgcac   2400
ctgccctcca agccacacag ggccccagtg ccaaaccagc actgactact gtgtgtctgc   2460
cccgtgcttc aatgggggta cctgtgtgaa caggcctggc accttctcct gcctctgtgc   2520
catgggcttc cagggcccgc gctgtgaggg aaagctccgc cccagctgtg cagacagccc   2580
ctgtaggaat agggcaacct gccaggacag ccctcagggt ccccgctgcc tctgccccac   2640
tggctacacc ggaggcagct gccagactct gatggactta tgtgcccaga gccctgccc   2700 acgcaattcc cactgcctcc agactgggcc ctccttccac tgcttgtgcc tccaggatg   2760 gaccgggcct ctctgcaacc ttccactgtc tcctgccag aaggctgcac tgagccaagg   2820
catagacgtc tcttcccttt gccacaatgg aggcctctgt gtcgacagcg gcccctccta   2880
tttctgccac tgcccccctg gattccaagg cagcctgtgc caggatcacg tgaacccatg   2940
tgagtccagg ccttgccaga acggggccac ctgcatggcc cagcccagtg ggtatctctg   3000
ccagtgtgcc ccaggctacg atggacagaa ctgctcaaag gaactcgatg cttgtcagtc   3060
ccaaccctgt cacaaccatg gaacctgtac tcccaaacct ggaggattcc actgtgcctg   3120
ccctccaggc tttgtggggc tacgctgtga gggagacgtg gacgagtgtc tggaccagcc   3180
ctgccacccc acaggcactg cagcctgcca ctctctggcc aatgccttct actgccagtg   3240
tctgcctgga cacacaggcc agtggtgtga ggtggagata gaccctgcc acagccaacc   3300 ctgctttcat ggagggacct gtgaggccac agcaggatca ccctgggtt tcatctgcca   3360 ctgccccaag ggttttgaag ccccacctg cagccacagg gcccttcct gcggcttcca   3420 tcactgccac cacggaggcc tgtgtctgcc ctcccctaag ccaggcttcc caccacgctg   3480
tgcctgcctc agtggctatg ggggtcctga ctgcctgacc ccaccagctc ctaaaggctg   3540
tggccctccc tccccatgcc tatacaatgg cagctgctca gagaccacgg gcttgggggg   3600
cccaggcttt cgatgctcct gccctcacag ctctccaggg ccccggtgtc agaaacccgg   3660
agccaagggg tgtgagggca aagtggaga tggggcctgc gatgctggct gcagtggccc   3720
gggaggaaac tgggatggag gggactgctc tctgggagtc ccagacccct ggaagggctg   3780
cccctcccac tctcggtgct ggcttctctt ccggacgggc agtgccacc cacagtgtga   3840 ctctgaagag tgtctgtttg atggctacga ctgtgagacc cctccagcct gcactccagc   3900
```

```
ctatgaccag tactgccatg atcacttcca caacgggcac tgtgagaaag gctgcaacac    3960
tgcagagtgt ggctgggatg gaggtgactg caggcctgaa gatggggacc cagagtgggg    4020
gccctccctg gccctgctgg tggtactgag ccccccagcc ctagaccagc agctgtttgc    4080
cctggcccgg gtgctgtccc tgactctgag ggtaggactc tgggtaagga aggatcgtga    4140
tggcagggac atggtgtacc cctatcctgg ggcccgggct gaagaaaagc taggaggaac    4200
tcgggacccc acctatcagg agagagcagc ccctcaaacg cagcccctgg gcaaggagac    4260
cgactccctc agtgctgggt tgtggtggt catgggtgtg gatttgtccc gctgtggccc    4320
tgaccacccg gcatcccgct gtccctggga ccctgggctt ctactccgct tccttgctgc    4380
gatggctgca gtgggagccc tggagcccct gctgctggga ccactgctgg ctgtccaccc    4440
tcatgcaggg accgcacccc ctgccaacca gcttccctgg cctgtgctgt gctccccagt    4500
ggccggggtg attctcctgg ccctaggggc tcttctcgtc ctccagctca tccggcgtcg    4560
acgccgagag catggagctc tctgctgccc cctggtttc actcgacggc ctcggactca    4620
gtcagctccc caccgacgcc ggcccccact aggcgaggac agcattggtc tcaaggcact    4680
gaagccaaag gcagaagttg atgaggatgg agttgtgatg tgctcaggcc tgaggaggg    4740 agaggaggtg ggccaggctg aagaaacagg cccaccctcc acgtgccagc tctggtctct    4800
gagtggtggc tgtgggggcgc tccctcaggc agccatgcta actcctcccc aggaatctga    4860
gatggaagcc cctgacctgg acaccgtgg acctgatggg gtgacacccc tgatgtcagc    4920
agtttgctgt ggggaagtac agtccggac cttccaaggg gcatggttgg gatgtcctga    4980
gccctgggaa cctctgctgg atggaggggc ctgtccccag gctcacaccg tgggcactgg    5040
ggagaccccc ctgcacctgg ctgcccgatt ctcccggcca accgctgccc gccgcctcct    5100
tgaggctgga gccaaccca accagccaga ccgggcaggg cgcacacccc ttcatgctgc    5160
tgtggctgct gatgctcggg aggtctgcca gcttctgctc cgtagcagac aaactgcagt    5220
ggacgctcgc acagaggacg ggaccacacc cttgatgctg gctgccaggc tggcggtgga    5280
agacctggtt gaagaactga ttgcagccca agcagacgtg ggggccagag ataaatgggg    5340
gaaaactgcg ctgcactggg ctgctgccgt gaacaacgcc cgagccgccc gctcgcttct    5400
ccaggccgga gccgataaag atgcccagga caacagggag cagacgccgc tattcctggc    5460
ggcgcgggaa ggagcggtgg aagtagccca gctactgctg gggctggggg cagcccgaga    5520
gctgcgggac caggctgggc tagcgccggc ggacgtcgct caccaacgta accactggga    5580
tctgctgacg ctgctggaag gggctgggcc accagaggcc cgtcacaaag ccacgccggg    5640
ccgcgaggct gggcccttcc cgcgcgcacg gacggtgtca gtaagcgtgc cccgcatgg    5700 gggcggggct ctgccgcgct gccggacgct gtcagccgga gcaggccctc gtggggcgg    5760 agcttgtctg caggctcgga cttggtccgt agacttggct gcgcggggg gcgggccta    5820 ttctcattgc cggagcctct cgggagtagg agcaggagga gcccgacccc ctcgcggccg    5880
taggttttct gcaggcatgc gcgggcctcg gcccaaccct gcgataatgc gaggaagata    5940
cggagtggct gccgggcgcg gaggcagggt ctcaacggat gactggccct gtgattgggt    6000
ggccctggga gcttgcggtt ctgcctccaa cattccgatc ccgcctcctt gccttactcc    6060
gtccccggag cggggatcac ctcaacttga ctgtggtccc ccagccctcc aagaaatgcc    6120
cataaaccaa ggaggagagg gtaaaaaata gaagaataca tggtagggag gaattccaaa    6180
aatgattacc cattaaaagg caggctggaa ggccttcctg gttttaagat ggatccccca    6240
```

```
aaatgaaggg ttgtgagttt agtttctctc ctaaaatgaa tgtatgccca ccagagcaga    6300
catcttccac gtggagaagc tgcagctctg gaaagagggt ttaagatgct aggatgaggc    6360
aggcccagtc ctcctccaga aaataagaca ggccacagga gggcagagtg gagtggaaat    6420
acccctaagt tggaaccaag aattgcaggc atatgggatg taagatgttc tttcctatat    6480
atggtttcca aagggtgccc ctatgatcca ttgtccccac tgcccacaaa tggctgacaa    6540
atatttattg ggcacctact atgtgccagg cactgtgtag gtgctgaaaa gtggccaagg    6600 gccaccccg ctgatgactc cttgcattcc ctcccctcac aacaaagaac tccactgtgg    6660
ggatgaagcg cttcttctag ccactgctat cgctatttaa gaaccctaaa tctgtcaccc    6720
ataataaagc tgatttgaag tgttaaaaaa aaaaaaaaaa aa    6762

<210> SEQ ID NO 34
<211> LENGTH: 200
<212> TYPE: DNA
<213> ORGANISM: Artificial Sequence
<220> FEATURE:
<223> OTHER INFORMATION: CMV promoter

<400> SEQUENCE: 34
atcgatgtta ataattaaca tatatgttaa tcattaacta tatagttaat tattaaccgc    60
tatgttaatg attaacacta gttaggcgtg tacggtggga ggcctatata agcagagctc    120
gtttagtgaa ccgtcagatc gcctggagac gccatccacg ctgttttgac ctccatagaa    180
gacaccggga ccgatccagc    200

<210> SEQ ID NO 35
<211> LENGTH: 9
<212> TYPE: DNA
<213> ORGANISM: Artificial Sequence
<220> FEATURE:
<223> OTHER INFORMATION: Kozak sequence

<400> SEQUENCE: 35 gccgccacc    9
```

METHODS AND COMPOSITIONS FOR REDUCING THE IMMUNOGENICITY OF CHIMERIC NOTCH RECEPTORS

CROSS-REFERENCE TO RELATED APPLICATIONS

This application claims priority to U.S. Provisional Patent Application Ser. No. 62/603,993, filed Jun. 19, 2017, and U.S. Provisional Patent Application Ser. No. 62/556,765, filed Sep. 11, 2017, both of which are hereby incorporated by reference in their entirety.

TECHNICAL FIELD

The present invention relates to molecular biology, and particularly to methods and compositions for reducing the immunogenicity of certain receptors useful for controlling selective gene expression in cells of the monocyte/macrophage lineage, and applications thereof.

BACKGROUND

An important problem which limits the development of gene therapy in humans is the regulation of therapeutic gene expression, such that gene expression or the vehicle used to realize expression, does not give rise to enhanced immunogenicity resulting in host rejection. One way to realize gene expression is described in U.S. Pat. No. 9,670,281, and Roybal et al., Cell, Feb. 11, 2016. There is described activation of gene expression using chimeric Notch receptors.

Notch receptors are single pass transmembrane proteins that mediate cell-cell contact signaling and play a central role in development and other aspects of cell-to-cell communication between two contacting cells, in which one contacting cell has the Notch receptor, and the other contacting cell is a cell that exhibits a ligand on its surface which binds to the corresponding Notch receptor. The engagement of native Notch and Delta, it's native ligand, leads to two-step proteolysis of the Notch receptor that ultimately causes the release of the intracellular portion of the receptor from the membrane into the cytoplasm, where it moves to the nucleus. There the released domain alters cell behavior by functioning as a transcriptional regulator. Notch receptors are involved in and are required for a variety of cellular functions during development and are critical for the function of numerous cell-types across species.

Described in U.S. Pat. No. 9,670,281 are chimeric Notch receptors which show that the Notch expressing cell can have one or more different binding moieties on the cell surface, for example, scFVs, nanobodies, single chain T-cell receptors, to name a few, that recognize a ligand associated with a cell ultimately causing the release of the intracellular, transcriptional regulatory portion of the receptor from the membrane into the cytoplasm resulting in transcriptional regulation. Engineered cells bearing chimeric Notch receptors that encounter their specific target antigen will then be cleaved such that their cytosolic fragment is free to translocate into the cell nucleus to regulate the transcription of any open reading frame (ORF) under the control of a synthetic promoter. The ORF expressed could be a cytokine to locally induce and recruit immune activity to the location of target antigen detection. Further, the ORF expressed could be a chimeric antigen T-cell receptor (CAR-T) that targets a separate, distinct target antigen for target cell killing, only after the priming target antigen detected by the chimeric Notch receptor has been detected. This enables highly-specific combinatorial antigen pattern recognition to allow greater discrimination between diseased or cancerous cells and healthy cells. This could greatly enable the application of engineered CAR-T cells to safely target a wider range of tumors with less side-effects on healthy tissue.

To date, the transcriptional machinery used in chimeric Notch constructs has been GAL4-VP16. Since the DNA-binding fragment, GAL4, is of yeast origin, and VP16, a highly acidic portion of the herpes simplex virus protein, GAL4-VP16 is highly immunogenic, and thus limits the use of chimeric Notch receptors for treating human disease.

Another major obstacle in the efficacy of many immunotherapy-based approaches for solid tumors, including cell therapy, is delivery of drugs or activation of immune cells in the solid tumor. Cells of the monocyte/macrophage lineage make up a major component of immune cells that infiltrate into solid tumors (Long et al., Oncoimmunology 2:e26860, 2013 doi:10.4161/onci26860). Because these cell types are actively recruited and retained in the solid tumor they could be an important cell type for the delivery of gene therapy.

The genetic engineering of macrophages with clinically approved vectors such has HIV-1-based lentivirus has been difficult due to the inhibition of HIV-1 infection in macrophages. Hrecka et al. ("Vpx relieves the inhibition of HIV-1 infection of macrophages mediated by the SAMHD1 protein," Nature 474(7353):658-661, 2011) demonstrated that the addition of the viron associated Vpx accessory proteins found in HIV-2 and simian immunodeficiency viruses relieves the inhibition of HIV-1 infection of macrophages through the degradation of a macrophage restriction factor SAMHD1. Subsequently, it has been demonstrated by the monocyte-derived macrophages can be efficiently transduced with Vpx+ lentivirus encoding for the production cytokines from macrophages aimed at modulating the tumor microenvironment (Moyes et al., Human Gene Therapy 28(2):200-215, 2017).

SUMMARY OF THE INVENTION

The present invention relates to methods and compositions for reducing the immunogenicity of chimeric Notch receptors. The Notch receptors described herein can be genetically engineered in cells of the monocyte/macrophage lineage.

Another embodiment of the invention relates to methods and compositions for reducing the immunogenicity of chimeric Notch receptors by humanizing transcription factors useful for controlling gene expression delivered to tissues by chimeric Notch receptors.

In yet another embodiment of the invention are methods and compositions for reducing the immunogenicity of chimeric Notch receptors by humanizing transcription factors used to express genes in cells that contain the chimeric Notch receptors wherein such transcription factors comprise a transcription factor from the family of Hepatocyte Nuclear Factor transcription factors.

The invention also relates to the use of the DNA binding domains (DBD) of HNF1 transcription factors, such as HNF1 alpha and vHNF1 beta, for generating chimeric transcription factors with reduced immunogenicity, useful for delivery of transgenes with chimeric Notch receptors to tissues preferably not expressing endogenous HNF1 or vHNF1. US Patent Application No. 200301096678.

A further embodiment of the invention is a human HNF1 DNA binding domain that is used in conjunction with a human transcriptional activator (TAD) or repressor domain, and optionally a human regulatory domain.

A further embodiment of the invention is a human HNF1 DNA binding domain that is used in conjunction with a human transcriptional activator domain (TAD) derived from the WWTR1 (TAZ) protein.

A further embodiment of the invention is a human HNF1 DNA binding domain that is used in conjunction with a human transcriptional activator domain (TAD) derived from the CREB3(LZIP) protein.

A further embodiment of the invention is a human HNF1 DNA binding domain that is used in conjunction with a human transcriptional activator domain (TAD) derived from the NF-κB system factor, p65 (RelA).

The present invention also relates to nucleic acid molecules and proteins useful for regulating the expression of genes in eukaryotic cells and organisms using chimeric Notch receptors having low immunogenicity.

The present invention further provides low immunogenicity chimeric Notch receptor polypeptides, nucleic acids comprising nucleotide sequences encoding the chimeric Notch receptor polypeptides, and host cells genetically modified with the nucleic acids wherein the low immunogenicity is realized by using transcription factor comprising a human HNF1 DNA binding domain in conjunction with a human transcriptional activator domain (TAD) derived from the NF-κB system factor, p65 (RelA).

In one specific embodiment of the invention, the humanized chimeric notch receptor is comprised of the following sequences, 5' to 3':

Human CD8a signal peptide 1-22 (NP_001139345 amino acids 1-22, (MALPVTALLLPLALLLHAARPS) (SEQ ID NO: 1))—directs protein expression to the cell surface.

Myc-tag (EQKLISEEDL) (SEQ ID NO: 2)—peptide tag for antibody labelling of surface-expressed synthetic receptor. A Myc antibody: Cell Signaling Techology, Myc-Tag (9B11) Mouse mAb (Alexa Fluor® 647 Conjugate; Catalogue No. 2233.

Anti-Human B cell (CD19) Antibody, clone FMC63.

Human Notch 3 core (gi|134244285|NP_000426.2 amino acids 1374-1738) comprising three LNR domains, the transmembrane domain, and a short cytosolic fragment including the native Nuclear Localization Sequence (NLS) of human Notch3.

GS flexible Linker (GSAAAGGSGGSGGS) (SEQ ID NO: 3).

Human HNF1alpha (gi|807201167|NP_001293108.1 amino acids 1-283) comprising the dimerization and DNA-Binding Domain (DBD) of *homo sapiens* hepatocyte nuclear factor 1-alpha isoform 1.

GS flexible Linker (GGGSGGGS) (SEQ ID NO: 4).

Human Rel-A (p65) (gi|223468676|NP_068810.3 amino acids 1-551) comprising the transactivation domain of transcription factor p65 isoform 1 [*Homo sapiens*].

Also provided herein is a method of treating disease, including cancer, in a subject (e.g., a human) that includes administering to the subject a mammalian cell comprising a humanized chimeric Notch receptor. In some embodiments, the mammalian cell can be a monocyte/macrophage cell.

Other features and advantages of the invention will be apparent from the following Detailed Description of the Invention, and from the claims. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
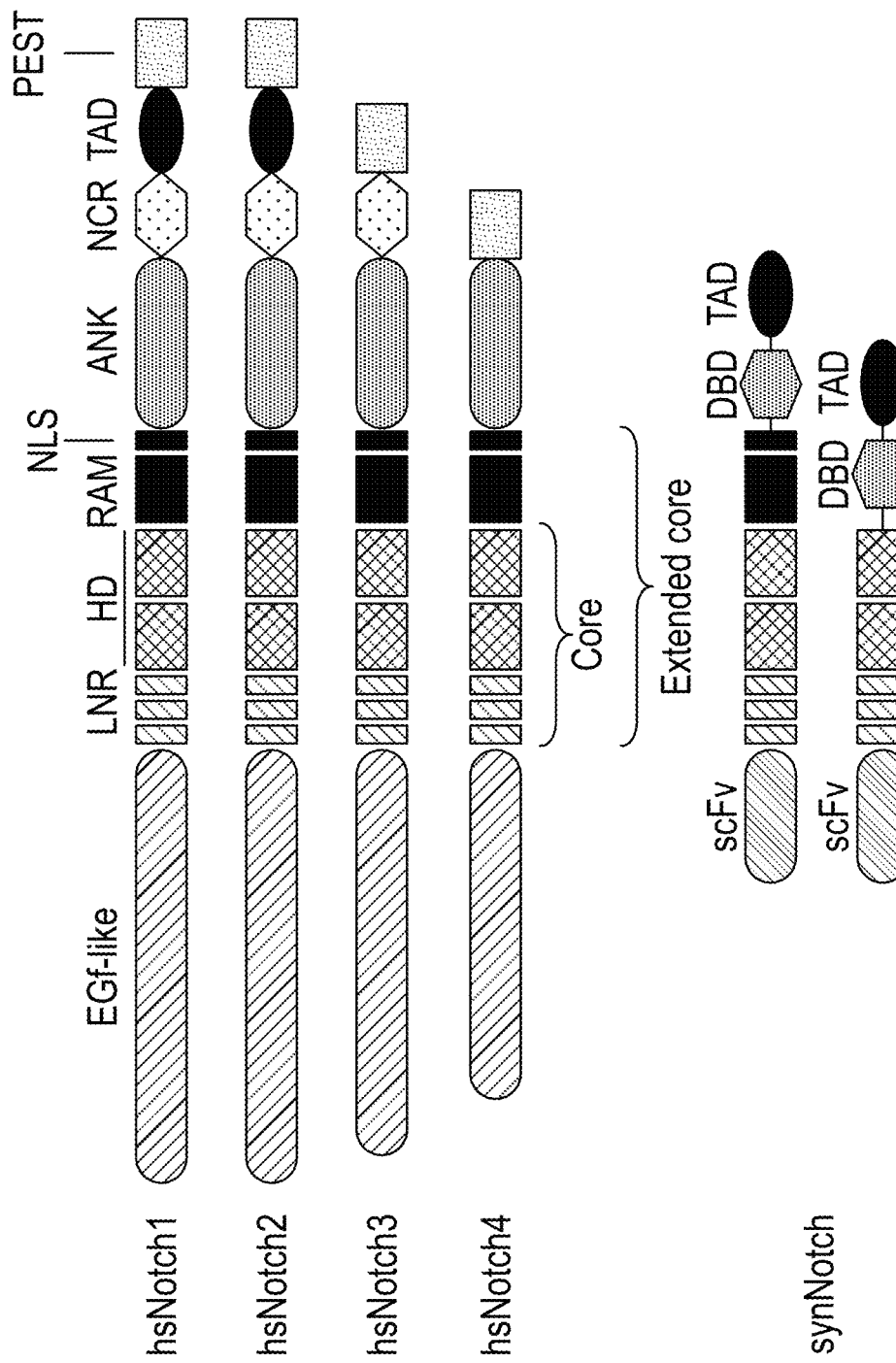
FIG. 1. Schematic of synthetic Notch receptor and the constituent domains comprising it.

Incorporation by reference: All publications mentioned herein, including patents, patent application publications, and scientific papers, are incorporated by reference in their entirety.

DETAILED DESCRIPTION OF THE INVENTION

Definitions

"Chimeric Notch polypeptide" also referred to as "Chimeric Notch receptor polypeptide," or "chimeric Notch" or "synNotch" is described in U.S. Pat. No. 9,670,281, and comprises, from N-terminal to C-terminal and in covalent linkage: a) an extracellular domain comprising a first member of a specific binding pair; b) wherein the Notch receptor polypeptide has a length of from 50 amino acids to 1000 amino acids, and comprises one or more ligand-inducible proteolytic cleavage sites; and c) an intracellular domain, wherein the first member of the specific binding pair is heterologous to the Notch receptor polypeptide, and wherein binding of the first member of the specific binding pair to a second member of the specific binding pair induces cleavage of the Notch receptor polypeptide at the one or more ligand-inducible proteolytic cleavage sites, thereby releasing the intracellular domain. In some cases, the Notch receptor polypeptide has a length of from 300 amino acids to 400 amino acids.

Further, the "chimeric Notch receptor polypeptide" comprises a linker interposed between the extracellular domain and the Notch receptor polypeptide. In some cases, the intracellular domain is a transcriptional activator. In some cases, the intracellular domain is a transcriptional repressor. In some cases, the first member of the specific binding pair comprises an antibody-based recognition scaffold. In some cases, the first member of the specific binding pair comprises an antibody. In some cases, where the first member of the specific binding pair is an antibody, the antibody specifically binds a tumor-specific antigen, a disease-associated antigen, or an extracellular matrix component. In some cases, where the first member of the specific binding pair is an antibody, the antibody specifically binds a cell surface antigen, a soluble antigen, or an antigen immobilized on an insoluble substrate. In some cases, where the first member of the specific binding pair is an antibody, the antibody is a single-chain Fv. In some cases, the first member of the specific binding pair is a nanobody, a single-domain antibody, a diabody, a triabody, or a minibody. In some cases, the first member of the specific binding pair is a non-antibody-based recognition scaffold. In some cases, where the first member of the specific binding pair is a non-antibody-based recognition scaffold, the non-antibody-based recognition scaffold is an avimer, a DARPin, an adnectin, an avimer, an affibody, an anticalin, or an affilin. In some cases, the first member of the specific binding pair is an antigen. In some cases, where the first member of the specific binding pair is an antigen, the antigen is an endogenous antigen. In some cases, where the first member of the specific binding pair is an antigen, the antigen is an exogenous antigen. In some cases, the first member of the specific binding pair is a ligand for a receptor. In some cases, the first member of the specific binding pair is a receptor. In some cases, the first member of the specific binding pair is a cellular adhesion molecule (e.g., all or a portion of an extracellular region of a cellular adhesion molecule).

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The phrase "extracellular side of the plasma membrane" when used to describe the location of a polypeptide means that the polypeptide includes at least one transmembrane domain that traverses the plasma membrane and at least one domain (e.g., at least one antigen-binding domain) that is located in the extracellular space.

"GFP" or green fluorescent protein (GFP), is a commonly used reporter of gene expression. Arun et al., *J. Pharmacol. Toxicol. Methods* 51(1):1-23, 2005.

By "HNF1 binding site" is intended any specific binding site for any of the known forms of HNF. HNF1 (also called LF-B1 or HNF1alpha) is a 628 aa long protein DNA binding protein that has been implicated as a major determinant of hepatocyte-specific transcription of several genes (Frain, *Cell* 59, 145-157, 1990).

In some embodiments, the DNA binding domain of human origin is a DNA-binding domain of a HNF1 transcription factor (e.g., any of the HNF1 transcription factors described herein or known in the art) and the transactivation domain is a human RelA protein or a portion thereof.

In some embodiments, the amino acid sequence of HNF1alpha is NCBI Nos. NP_001293108.1, NP_000536.5, or XP_005253988.1. In some embodiments, the amino acid sequence of the transcriptional regulator of the humanized chimeric Notch receptor comprises hepatocyte nuclear factor 1-alpha isoform 1 (NP_001293108.1), hepatocyte nuclear factor 1-alpha isoform 1 (NP_000536.5), or hepatocyte nuclear factor 1-alpha isoform X1 (XP_005253988.1), or a portion thereof. In some embodiments, the amino acid sequence of the transcriptional regulator of the humanized Notch receptor comprises all or a portion of SEQ ID NO: 5, SEQ ID NO: 6, or SEQ ID NO: 7.

As used herein, a "portion" of a polypeptide or protein refers at least 10 amino acids of the reference sequence, e.g., 10 to 200, 25 to 300, 50 to 400, 100 to 500, 200 to 600, 300 to 700, 400 to 800, 500 to 900, or 600 to 1000 or more amino acids of the reference sequence. In some embodiments, the portion of a polypeptide or protein is functional. In some embodiments, the transcriptional regulator is or comprises the dimerization and DNA-Binding Domain (DBD) of hepatocyte nuclear factor 1-alpha isoform 1 (NP_001293108.1), hepatocyte nuclear factor 1-alpha isoform 1 (NP_000536.5), or hepatocyte nuclear factor 1-alpha isoform X1 (XP_005253988.1). In some embodiments, the amino acid sequence of the transcriptional regulator of the humanized Notch receptor is amino acids is or comprises the dimerization and DNA-Binding Domain (DBD) of SEQ ID NO: 5, SEQ ID NO: 6, or SEQ ID NO:7. In some embodiments, the amino acid sequence of the transcriptional regulator of the humanized Notch receptor is or comprises amino acids 1-283 of SEQ ID NO: 5.

```
Human hepatocyte nuclear factor 1-alpha isoform 1
NP_001293108.1
                                        (SEQ ID NO: 5)
MVSKLSQLQTELLAALLESGLSKEALIQALGEPGPYLLAGEGPLDKGES

CGGGRGELAELPNGLGETRGSEDETDDDGEDFTPPILKELENLSPEEAA

HQKAVVETLLQEDPWRVAKMVKSYLQQHNIPQREVVDTTGLNQSHLSQH

LNKGTPMKTQKRAALYTWYVRKQREVAQQFTHAGQGGLIEEPTGDELPT

KKGRRNRFKWGPASQQILFQAYERQKNPSKEERETLVEECNRAECIQRG

VSPSQAQGLGSNLVTEVRVYNWFANRRKEEAFRHKLAMDTYSGPPPGPG

PGPALPAHSSPGLPPPALSPSKVHGVRYGQPATSETAEVPSSSGGPLVT

VSTPLHQVSPTGLEPSHSLLSTEAKLVSAAGGPLPPVSTLTALHSLEQT

SPGLNQQPQNLIMASLPGVMTIGPGEPASLGPTFTNTGASTLVIGLAST
```

QAQSVPVINSMGSSLTTLQPVQFSQPLHPSYQQPLMPPVQSHVTQSPFM

ATMAQLQSPHALYSHKPEVAQYTHTGLLPQTMLITDTTNLSALASLTPT

KQEAALLPQVFTSDTEASSESGLHTPASQATTLHVPSQDPAGIQHLQPA

HRLSASPTVSSSSLVLYQSSDSSNGQSHLLPSNHSVIETFISTQMASSS

Q

Human hepatocyte nuclear factor 1-alpha isoform 2
NP_000536.5
(SEQ ID NO: 6)
MVSKLSQLQTELLAALLESGLSKEALIQALGEPGPYLLAGEGPLDKGES

CGGGRGELAELPNGLGETRGSEDETDDDGEDFTPPILKELENLSPEEA

HQKAVVETLLQEDPWRVAKMVKSYLQQHNIPQREVVDTTGLNQSHLSQH

LNKGTPMKTQKRAALYTWYVRKQREVAQQFTHAGQGGLIEEPTGDELPT

KKGRRNRFKWGPASQQILFQAYERQKNPSKEERETLVEECNRAECIQRG

VSPSQAQGLGSNLVTEVRVYNWFANRRKEEAFRHKLAMDTYSGPPPGPG

PGPALPAHSSPGLPPPALSPSKVHGVRYGQPATSETAEVPSSSGGPLVT

VSTPLHQVSPTGLEPSHSLLSTEAKLVSAAGGPLPPVSTLTALHSLEQT

SPGLNQQPQNLIMASLPGVMTIGPGEPASLGPTFTNTGASTLVIGLAST

QAQSVPVINSMGSSLTTLQPVQFSQPLHPSYQQPLMPPVQSHVTQSPFM

ATMAQLQSPHALYSHKPEVAQYTHTGLLPQTMLITDTTNLSALASLTPT

KQVFTSDTEASSESGLHTPASQATTLHVPSQDPAGIQHLQPAHRLSASP

TVSSSSLVLYQSSDSSNGQSHLLPSNHSVIETFISTQMASSSQ

Human hepatocyte nuclear factor 1-alpha isoform
X1 (predicted) XP_005253988.1
(SEQ ID NO: 7)
MVSKLSQLQTELLAALLESGLSKEALIQALGEPGPYLLAGEGPLDKGES

CGGGRGELAELPNGLGETRGSEDETDDDGEDFTPPILKELENLSPEEA

HQKAVVETLLQEDPWRVAKMVKSYLQQHNIPQREVVDTTGLNQSHLSQH

LNKGTPMKTQKRAALYTWYVRKQREVAQQFTHAGQGGLIEEPTGDELPT

KKGRRNRFKWGPASQQILFQAYERQKNPSKEERETLVEECNRAECIQRG

VSPSQAQGLGSNLVTEVRVYNWFANRRKEEAFRHKLAMDTYSGPPPGPG

PGPALPAHSSPGLPPPALSPSKVHGVRYGQPATSETAEVPSSSGGPLVT

VSTPLHQVSPTGLEPSHSLLSTEAKLVSAAGGPLPPVSTLTALHSLEQT

SPGLNQQPQNLIMASLPGVMTIGPGEPASLGPTFTNTGASTLVIGLAST

QAQSVPVINSMGSSLTTLQPVQFSQPLHPSYQQPLMPPVQSHVTQSPFM

ATMAQLQSPHALYSHKPEVAQYTHTGLLPQTMLITDTTNLSALASLTPT

KQVRSRPAGPPLACDRAPHPHIPRAQEAALLPQVFTSDTEASSESGLHT

PASQATTLHVPSQDPASIQHLQPAHRLSASPTVSSSSLVLYQSSDSSNG

QSHLLPSNHSVIETFISTQMASSSQ

In some embodiments, the amino acid sequence of HNF1alpha or the portion thereof, as described herein, is at least 80% identical to a corresponding amino acid sequence in SEQ ID NO: 5, SEQ ID NO: 6, or SEQ ID NO: 7. In some embodiments, the amino acid sequence of HNF1alpha or portion thereof is 80%, 81%, 82%, 83%, 84%, 85%, 86%, 87%, 88%, 89%, 90%, 91%, 92%, 93%, 94%, 95%, 96%, 97%, 98%, or 99% identical to a corresponding amino acid sequence in SEQ ID NO: 5, SEQ ID NO: 6, or SEQ ID NO: 7. In some embodiments, the amino acid sequence of HNF1alpha or the portion thereof, as described herein, can vary from the corresponding amino acid sequence in SEQ ID NO: 5, SEQ ID NO: 6, or SEQ ID NO: 7 by 1 amino acid, 2 amino acids, 3 amino acids, 4 amino acids, 5 amino acids, 6 amino acids, 7 amino acids, 8 amino acids, 9 amino acids, or 10 or more amino acids.

In some embodiments, the mRNA sequence of HFN1alpha is NCBI No. NM_001306179.1, NM_00545.6, or XM_005253931.3. In some embodiments, the mRNA sequence of HFN1alpha is SEQ ID NO: 8, SEQ ID NO: 9, or SEQ ID NO: 10.

Human HNF1 homeobox A (HNF1A), transcript variant 1, mRNA NM_001306179.1
(SEQ ID NO: 8)
GGGGCCCTGATTCACGGGCCGCTGGGGCCAGGGTTGGGGGTTGGGGGTGCCCACAGGGCTTGGCTAGTGGGGT

TTTGGGGGGGCAGTGGGTGCAAGGAGTTTGGTTTGTGTCTGCCGGCCGGCAGGCAAACGCAACCCACGCGGTG

GGGGAGGCGGCTAGCGTGGTGGACCCGGGCCGCGTGGCCCTGTGGCAGCCGAGCCATGGTTTCTAAACTGAGC

CAGCTGCAGACGGAGCTCCTGGCGGCCCTGCTCGAGTCAGGGCTGAGCAAAGAGGCACTGATCCAGGCACTGG

GTGAGCCGGGCCCTACCTCCTGGCTGGAGAAGGCCCCCTGGACAAGGGGGAGTCCTGCGGCGGCGGTCGAGG

GGAGCTGGCTGAGCTGCCCAATGGGCTGGGGGAGACTCGGGGCTCCGAGGACGAGACGGACGACGATGGGGAA

GACTTCACGCCACCCATCCTCAAAGAGCTGGAGAACCTCAGCCCTGAGGAGGCGGCCCACCAGAAAGCCGTGG

TGGAGACCCTTCTGCAGGAGGACCCGTGGCGTGTGGCGAAGATGGTCAAGTCCTACCTGCAGCAGCACAACAT

CCCACAGCGGGAGGTGGTCGATACCACTGGCCTCAACCAGTCCCACCTGTCCCAACACCTCAACAAGGGCACT

CCCATGAAGACGCAGAAGCGGGCCGCCCTGTACACCTGGTACGTCCGCAAGCAGCGAGAGGTGGCGCAGCAGT

TCACCCATGCAGGGCAGGGAGGGCTGATTGAAGAGCCCACAGGTGATGAGCTACCAACCAAGAAGGGGCGGAG

GAACCGTTTCAAGTGGGGCCCAGCATCCCAGCAGATCCTGTTCCAGGCCTATGAGAGGCAGAAGAACCCTAGC

AAGGAGGAGCGAGAGACGCTAGTGGAGGAGTGCAATAGGGCGGAATGCATCCAGAGAGGGGTGTCCCCATCAC

AGGCACAGGGGCTGGGCTCCAACCTCGTCACGGAGGTGCGTGTCTACAACTGGTTTGCCAACCGGCGCAAAGA

-continued

```
AGAAGCCTTCCGGCACAAGCTGGCCATGGACACGTACAGCGGGCCCCCCCCAGGGCCAGGCCCGGGACCTGCG
CTGCCCGCTCACAGCTCCCCTGGCCTGCCTCCACCTGCCCTCTCCCCCAGTAAGGTCCACGGTGTGCGCTATG
GACAGCCTGCGACCAGTGAGACTGCAGAAGTACCCTCAAGCAGCGGCGGTCCCTTAGTGACAGTGTCTACACC
CCTCCACCAAGTGTCCCCCACGGGCCTGGAGCCCAGCCACAGCCTGCTGAGTACAGAAGCCAAGCTGGTCTCA
GCAGCTGGGGGCCCCCTCCCCCCTGTCAGCACCCTGACAGCACTGCACAGCTTGGAGCAGACATCCCCAGGCC
TCAACCAGCAGCCCCAGAACCTCATCATGGCCTCACTTCCTGGGGTCATGACCATCGGGCCTGGTGAGCCTGC
CTCCCTGGGTCCTACGTTCACCAACACAGGTGCCTCCACCCTGGTCATCGGCCTGGCCTCCACGCAGGCACAG
AGTGTGCCGGTCATCAACAGCATGGGCAGCAGCCTGACCACCCTGCAGCCCGTCCAGTTCTCCCAGCCGCTGC
ACCCCTCCTACCAGCAGCCGCTCATGCCACCTGTGCAGAGCCATGTGACCCAGAGCCCCTTCATGGCCACCAT
GGCTCAGCTGCAGAGCCCCCACGCCCTCTACAGCCACAAGCCCGAGGTGGCCCAGTACACCCACACGGGCCTG
CTCCCGCAGACTATGCTCATCACCGACACCACCAACCTGAGCGCCCTGGCCAGCCTCACGCCCACCAAGCAGG
AGGCTGCTCTGCTCCCCCAGGTCTTCACCTCAGACACTGAGGCCTCCAGTGAGTCCGGGCTTCACACGCCGGC
ATCTCAGGCCACCACCCTCCACGTCCCCAGCCAGGACCCTGCCGGCATCCAGCACCTGCAGCCGGCCCACCGG
CTCAGCGCCAGCCCCACAGTGCCTCCAGCAGCCTGGTGCTGTACCAGAGCTCAGACTCCAGCAATGGCCAGA
GCCACCTGCTGCCATCCAACCACAGCGTCATCGAGACCTTCATCTCCACCCAGATGGCCTCTTCCTCCCAGTA
ACCACGGCACCTGGGCCCTGGGGCCTGTACTGCCTGCTTGGGGGGTGATGAGGGCAGCAGCCAGCCCTGCCTG
GAGGACCTGAGCCTGCCGAGCAACCGTGGCCCTTCCTGGACAGCTGTGCCTCGCTCCCCACTCTGCTCTGATG
CATCAGAAAGGGAGGGCTCTGAGGCGCCCCAACCCGTGGAGGCTGCTCGGGGTGCACAGGAGGGGTCGTGGA
GAGCTAGGAGCAAAGCCTGTTCATGGCAGATGTAGGAGGGACTGTCGCTGCTTCGTGGGATACAGTCTTCTTA
CTTGGAACTGAAGGGGGCGGCCTATGACTTGGGCACCCCCAGCCTGGGCCTATGGAGAGCCCTGGGACCGCTA
CACCACTCTGGCAGCCACACTTCTCAGGACACAGGCCTGTGTAGCTGTGACCTGCTGAGCTCTGAGAGGCCCT
GGATCAGCGTGGCCTTGTTCTGTCACCAATGTACCCACCGGGCCACTCCTTCCTGCCCCAACTCCTTCCAGCT
AGTGACCCACATGCCATTTGTACTGACCCCATCACCTACTCACACAGGCATTTCCTGGGTGGCTACTCTGTGC
CAGAGCCTGGGGCTCTAACGCCTGAGCCCAGGGAGGCCGAAGCTAACAGGGAAGGCAGGCAGGGCTCTCCTGG
CTTCCCATCCCCAGCGATTCCCTCTCCCAGGCCCCATGACCTCCAGCTTTCCTGTATTTGTTCCCAAGAGCAT
CATGCCTCTGAGGCCAGCCTGGCCTCCTGCCTCTACTGGGAAGGCTACTTCGGGGCTGGGAAGTCGTCCTTAC
TCCTGTGGGAGCCTCGCAACCCGTGCCAAGTCCAGGTCCTGGTGGGGCAGCTCCTCTGTCTCGAGCGCCCTGC
AGACCCTGCCCTTGTTTGGGGCAGGAGTAGCTGAGCTCACAAGGCAGCAAGGCCCGAGCAGCTGAGCAGGGCC
GGGGAACTGGCCAAGCTGAGGTGCCCAGGAGAAGAAAGAGGTGACCCCAGGGCACAGGAGCTACCTGTGTGGA
CAGGACTAACACTCAGAAGCCTGGGGGCCTGGCTGGCTGAGGGCAGTTCGCAGCCACCCTGAGGAGTCTGAGG
TCCTGAGCACTGCCAGGAGGGACAAAGGAGCCTGTGAACCCAGGACAAGCATGGTCCCACATCCCTGGGCCTG
CTGCTGAGAACCTGGCCTTCAGTGTACCGCGTCTACCCTGGGATTCAGGAAAAGGCCTGGGGTGACCCGGCAC
CCCCTGCAGCTTGTAGCCAGCCGGGGCGAGTGGCACGTTTATTTAACTTTTAGTAAAGTCAAGGAGAAATGCG
GTGGAAA
```

Human HNF1 homeobox A (HNF1A), transcript variant 2, mRNA NM_000545.6
(SEQ ID NO: 9)

```
GGGGCCCTGATTCACGGGCCGCTGGGGCCAGGGTTGGGGGTTGGGGGTGCCCACAGGGCTTGGCTAGTGGGGT
TTTGGGGGGGCAGTGGGTGCAAGGAGTTTGGTTTGTGTCTGCCGGCCGGCAGGCAAACGCAACCCACGCGGTG
GGGGAGGCGGCTAGCGTGGTGGACCCGGGCCGCGTGGCCCTGTGGCAGCCGAGCCATGGTTTCTAAACTGAGC
CAGCTGCAGACGGAGCTCCTGGCGGCCCTGCTCGAGTCAGGGCTGAGCAAAGAGGCACTGATCCAGGCACTGG
GTGAGCCGGGGCCCTACCTCCTGGCTGGAGAAGGCCCCCTGGACAAGGGGGAGTCCTGCGGCGGCGGTCGAGG
```

-continued

```
GGAGCTGGCTGAGCTGCCCAATGGGCTGGGGGAGACTCGGGGCTCCGAGGACGAGACGGACGACGATGGGGAA

GACTTCACGCCACCCATCCTCAAAGAGCTGGAGAACCTCAGCCCTGAGGAGGCGGCCCACCAGAAAGCCGTGG

TGGAGACCCTTCTGCAGGAGGACCCGTGGCGTGTGGCGAAGATGGTCAAGTCCTACCTGCAGCAGCACAACAT

CCCACAGCGGGAGGTGGTCGATACCACTGGCCTCAACCAGTCCCACCTGTCCCAACACCTCAACAAGGGCACT

CCCATGAAGACGCAGAAGCGGGCCGCCCTGTACACCTGGTACGTCCGCAAGCAGCGAGAGGTGGCGCAGCAGT

TCACCCATGCAGGGCAGGGAGGGCTGATTGAAGAGCCCACAGGTGATGAGCTACCAACCAAGAAGGGGCGGAG

GAACCGTTTCAAGTGGGGCCCAGCATCCCAGCAGATCCTGTTCCAGGCCTATGAGAGGCAGAAGAACCCTAGC

AAGGAGGAGCGAGAGACGCTAGTGGAGGAGTGCAATAGGGCGGAATGCATCCAGAGAGGGGTGTCCCCATCAC

AGGCACAGGGGCTGGGCTCCAACCTCGTCACGGAGGTGCGTGTCTACAACTGGTTTGCCAACCGGCGCAAAGA

AGAAGCCTTCCGGCACAAGCTGGCCATGGACACGTACAGCGGGCCCCCCCCAGGGCCAGGCCCGGGACCTGCG

CTGCCCGCTCACAGCTCCCCTGGCCTGCCTCCACCTGCCCTCTCCCCCAGTAAGGTCCACGGTGTGCGCTATG

GACAGCCTGCGACCAGTGAGACTGCAGAAGTACCCTCAAGCAGCGGCGGTCCCTTAGTGACAGTGTCTACACC

CCTCCACCAAGTGTCCCCCACGGGCCTGGAGCCCAGCCACAGCCTGCTGAGTACAGAAGCCAAGCTGGTCTCA

GCAGCTGGGGGCCCCCTCCCCCCTGTCAGCACCCTGACAGCACTGCACAGCTTGGAGCAGACATCCCCAGGCC

TCAACCAGCAGCCCCAGAACCTCATCATGGCCTCACTTCCTGGGGTCATGACCATCGGGCCTGGTGAGCCTGC

CTCCCTGGGTCCTACGTTCACCAACACAGGTGCCTCCACCCTGGTCATCGGCCTGGCCTCCACGCAGGCACAG

AGTGTGCCGGTCATCAACAGCATGGGCAGCAGCCTGACCACCCTGCAGCCCGTCCAGTTCTCCCAGCCGCTGC

ACCCCTCCTACCAGCAGCCGCTCATGCCACCTGTGCAGAGCCATGTGACCCAGAGCCCCTTCATGGCCACCAT

GGCTCAGCTGCAGAGCCCCACGCCCTCTACAGCCACAAGCCCGAGGTGGCCCAGTACACCCACACGGGCCTG

CTCCCGCAGACTATGCTCATCACCGACACCACCAACCTGAGCGCCCTGGCCAGCCTCACGCCCACCAAGCAGG

TCTTCACCTCAGACACTGAGGCCTCCAGTGAGTCCGGGCTTCACACGCCGGCATCTCAGGCCACCACCCTCCA

CGTCCCCAGCCAGGACCCTGCCGGCATCCAGCACCTGCAGCCGGCCCACCGGCTCAGCGCCAGCCCCACAGTG

TCCTCCAGCAGCCTGGTGCTGTACCAGAGCTCAGACTCCAGCAATGGCCAGAGCCACCTGCTGCCATCCAACC

ACAGCGTCATCGAGACCTTCATCTCCACCCAGATGGCCTCTTCCTCCCAGTAACCACGGCACCTGGGCCCTGG

GGCCTGTACTGCCTGCTTGGGGGGTGATGAGGGCAGCAGCCAGCCCTGCCTGGAGGACCTGAGCCTGCCGAGC

AACCGTGGCCCTTCCTGGACAGCTGTGCCTCGCTCCCCACTCTGCTCTGATGCATCAGAAAGGGAGGGCTCTG

AGGCGCCCCAACCCGTGGAGGCTGCTCGGGGTGCACAGGAGGGGGTCGTGGAGAGCTAGGAGCAAAGCCTGTT

CATGGCAGATGTAGGAGGGACTGTCGCTGCTTCGTGGGATACAGTCTTCTTACTTGGAACTGAAGGGGGCGGC

CTATGACTTGGGCACCCCCAGCCTGGGCCTATGGAGAGCCCTGGGACCGCTACACCACTCTGGCAGCCACACT

TCTCAGGACACAGGCCTGTGTAGCTGTGACCTGCTGAGCTCTGAGAGGCCCTGGATCAGCGTGGCCTTGTTCT

GTCACCAATGTACCCACCGGGCCACTCCTTCCTGCCCCAACTCCTTCCAGCTAGTGACCCACATGCCATTTGT

ACTGACCCCATCACCTACTCACACAGGCATTTCCTGGGTGGCTACTCTGTGCCAGAGCCTGGGGCTCTAACGC

CTGAGCCCAGGGAGGCCGAAGCTAACAGGGAAGGCAGGCAGGGCTCTCCTGGCTTCCCATCCCCAGCGATTCC

CTCTCCCAGGCCCCATGACCTCCAGCTTTCCTGTATTTGTTCCCAAGAGCATCATGCCTCTGAGGCCAGCCTG

GCCTCCTGCCTCTACTGGGAAGGCTACTTCGGGGCTGGGAAGTCGTCCTTACTCCTGTGGGAGCCTCGCAACC

CGTGCCAAGTCCAGGTCCTGGTGGGGCAGCTCCTCTGTCTCGAGCGCCCTGCAGACCCTGCCCTTGTTTGGGG

CAGGAGTAGCTGAGCTCACAAGGCAGCAAGGCCCGAGCAGCTGAGCAGGGCCGGGGAACTGGCCAAGCTGAGG

TGCCCAGGAGAAGAAAGAGGTGACCCCAGGGCACAGGAGCTACCTGTGTGGACAGGACTAACACTCAGAAGCC

TGGGGGCCTGGCTGGCTGAGGGCAGTTCGCAGCCACCCTGAGGAGTCTGAGGTCCTGAGCACTGCCAGGAGGG
```

-continued

```
ACAAAGGAGCCTGTGAACCCAGGACAAGCATGGTCCCACATCCCTGGGCCTGCTGCTGAGAACCTGGCCTTCA

GTGTACCGCGTCTACCCTGGGATTCAGGAAAAGGCCTGGGGTGACCCGGCACCCCCTGCAGCTTGTAGCCAGC

CGGGGCGAGTGGCACGTTTATTTAACTTTTAGTAAAGTCAAGGAGAAATGCGGTGGAAA
```

Human HNF1 homeobox A (HNF1A), transcript variant X1, mRNA
XM_005253931.3

(SEQ ID NO: 10)
```
ATAAATATGAACCTTGGAGAATTTCCCCAGCTCCAATGTAAACAGAACAGGCAGGGGCCCTGATTCACGGGCC

GCTGGGGCCAGGGTTGGGGGTTGGGGGTGCCCACAGGGCTTGGCTAGTGGGGTTTTGGGGGGGCAGTGGGTGC

AAGGAGTTTGGTTTGTGTCTGCCGGCCGGCAGGCAAACGCAACCCACGCGGTGGGGGAGGCGGCTAGCGTGGT

GGACCCGGGCCGCGTGGCCCTGTGGCAGCCGAGCCATGGTTTCTAAACTGAGCCAGCTGCAGACGGAGCTCCT

GGCGGCCCTGCTCGAGTCAGGGCTGAGCAAAGAGGCACTGATCCAGGCACTGGGTGAGCCGGGGCCCTACCTC

CTGGCTGGAGAAGGCCCCCTGGACAAGGGGGAGTCCTGCGGCGGCGGTCGAGGGGAGCTGGCTGAGCTGCCCA

ATGGGCTGGGGGAGACTCGGGGCTCCGAGGACGAGACGGACGACGATGGGGAAGACTTCACGCCACCCATCCT

CAAAGAGCTGGAGAACCTCAGCCCTGAGGAGGCGGCCCACCAGAAAGCCGTGGTGGAGACCCTTCTGCAGGAG

GACCCGTGGCGTGTGGCGAAGATGGTCAAGTCCTACCTGCAGCAGCACAACATCCCACAGCGGGAGGTGGTCG

ATACCACTGGCCTCAACCAGTCCCACCTGTCCCAACACCTCAACAAGGGCACTCCCATGAAGACGCAGAAGCG

GGCCGCCCTGTACACCTGGTACGTCCGCAAGCAGCGAGAGGTGGCGCAGCAGTTCACCCATGCAGGGCAGGGA

GGGCTGATTGAAGAGCCCACAGGTGATGAGCTACCAACCAAGAAGGGCGGAGGAACCGTTTCAAGTGGGGCC

CAGCATCCCAGCAGATCCTGTTCCAGGCCTATGAGAGGCAGAAGAACCCTAGCAAGGAGGAGCGAGAGACGCT

AGTGGAGGAGTGCAATAGGGCGGAATGCATCCAGAGAGGGGTGTCCCCATCACAGGCACAGGGGCTGGGCTCC

AACCTCGTCACGGAGGTGCGTGTCTACAACTGGTTTGCCAACCGGCGCAAAGAAGAAGCCTTCCGGCACAAGC

TGGCCATGGACACGTACAGCGGGCCCCCCCCAGGGCCAGGCCCGGGACCTGCGCTGCCCGCTCACAGCTCCCC

TGGCCTGCCTCCACCTGCCCTCTCCCCCAGTAAGGTCCACGGTGTGCGCTATGGACAGCCTGCGACCAGTGAG

ACTGCAGAAGTACCCTCAAGCAGCGGCGGTCCCTTAGTGACAGTGTCTACACCCCTCCACCAAGTGTCCCCCA

CGGGCCTGGAGCCCAGCCACAGCCTGCTGAGTACAGAAGCCAAGCTGGTCTCAGCAGCTGGGGGCCCCCTCCC

CCCTGTCAGCACCCTGACAGCACTGCACAGCTTGGAGCAGACATCCCCAGGCCTCAACCAGCAGCCCCAGAAC

CTCATCATGGCCTCACTTCCTGGGGTCATGACCATCGGGCCTGGTGAGCCTGCCTCCCTGGGTCCTACGTTCA

CCAACACAGGTGCCTCCACCCTGGTCATCGGCCTGGCCTCCACGCAGGCACAGAGTGTGCCGGTCATCAACAG

CATGGGCAGCAGCCTGACCACCCTGCAGCCCGTCCAGTTCTCCCAGCCGCTGCACCCCTCCTACCAGCAGCCG

CTCATGCCACCTGTGCAGAGCCATGTGACCCAGAGCCCCTTCATGGCCACCATGGCTCAGCTGCAGAGCCCCC

ACGCCCTCTACAGCCACAAGCCCGAGGTGGCCCAGTACACCCACACGGGCCTGCTCCCGCAGACTATGCTCAT

CACCGACACCACCAACCTGAGCGCCCTGGCCAGCCTCACGCCCACCAAGCAGGTAAGGTCCAGGCCTGCTGGC

CCTCCCTTGGCCTGTGACAGAGCCCCTCACCCCCACATCCCCCGGGCTCAGGAGGCTGCTCTGCTCCCCCAGG

TCTTCACCTCAGACACTGAGGCCTCCAGTGAGTCCGGGCTTCACACGCCGGCATCTCAGGCCACCACCCTCCA

CGTCCCCAGCCAGGACCCTGCCAGCATCCAGCACCTGCAGCCGGCCCACCGGCTCAGCGCCAGCCCCACAGTG

TCCTCCAGCAGCCTGGTGCTGTACCAGAGCTCAGACTCCAGCAATGGCCAGAGCCACCTGCTGCCATCCAACC

ACAGCGTCATCGAGACCTTCATCTCCACCCAGATGGCCTCTTCCTCCCAGTAACCACGGCACCTGGGCCCTGG

GGCCTGTACTGCCTGCTTGGGGGGTGATGAGGGCAGCAGCCAGCCCTGCCTGGAGGACCTGAGCCTGCCGAGC

AACCGTGGCCCTTCCTGGACAGCTGTGCCTCGCTCCCCACTCTGCTCTGATGCATCAGAAAGGGAGGGCTCTG

AGGCGCCCCAACCCGTGGAGGCTGCTCGGGGTGCACAGGAGGGGTCGTGGAGAGCTAGGAGCAAAGCCTGTT

CATGGCAGATGTAGGAGGGACTGTCGCTGCTTCGTGGGATACAGTCTTCTTACTTGGAACTGAAGGGGGCGGC

CTATGACTTGGGCACCCCCAGCCTGGGCCTATGGAGAGCCCTGGGACCGCTACACCACTCTGGCAGCCACACT
```

```
TCTCAGGACACAGGCCTGTGTAGCTGTGACCTGCTGAGCTCTGAGAGGCCCTGGATCAGCGTGGCCTTGTTCT

GTCACCAATGTACCCACCGGGCCACTCCTTCCTGCCCCAACTCCTTCCAGCTAGTGACCCACATGCCATTTGT

ACTGACCCCATCACCTACTCACACAGGCATTTCCTGGGTGGCTACTCTGTGCCAGAGCCTGGGGCTCTAACGC

CTGAGCCCAGGGAGGCCGAAGCTAACAGGGAAGGCAGGCAGGGCTCTCCTGGCTTCCCATCCCCAGCGATTCC

CTCTCCCAGGCCCCATGACCTCCAGCTTTCCTGTATTTGTTCCCAAGAGCATCATGCCTCTGAGGCCAGCCTG

GCCTCCTGCCTCTACTGGGAAGGCTACTTCGGGGCTGGGAAGTCGTCCTTACTCCTGTGGGAGCCTCGCAACC

CGTGCCAAGTCCAGGTCCTGGTGGGGCAGCTCCTCTGTCTCGAGCGCCCTGCAGACCCTGCCCTTGTTTGGGG

CAGGAGTAGCTGAGCTCACAAGGCAGCAAGGCCCGAGCAGCTGAGCAGGGCCGGGGAACTGGCCAAGCTGAGG

TGCCCAGGAGAAGAAAGAGGTGACCCCAGGGCACAGGAGCTACCTGTGTGGACAGGACTAACACTCAGAAGCC

TGGGGGCCTGGCTGGCTGAGGGCAGTTCGCAGCCACCCTGAGGAGTCTGAGGTCCTGAGCACTGCCAGGAGGG

ACAAAGGAGCCTGTGAACCCAGGACAAGCATGGTCCCACATCCCTGGGCCTGCTGCTGAGAACCTGGCCTTCA

GTGTACCGCGTCTACCCTGGGATTCAGGAAAAGGCCTGGGGTGACCCGGCACCCCCTGCAGCTTGTAGCCAGC

CGGGGCGAGTGGCACGTTTATTTAACTTTTAGTAAAGTCAAGGAGAAATGCGGTGGAAA
```

In some embodiments, the HNF1alpha binds to the inverted palindrome 5-GTTAATNATTAAC-3 (SEQ ID NO: 11).

In some embodiments, the nucleic acid sequence encoding HNF1alpha, as described herein, is at least 80% identical to the sequence of SEQ ID NO: 8, SEQ ID NO: 9, or SEQ ID NO: 10. In some embodiments, the nucleic acid sequence encoding HNF1alpha is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 8, SEQ ID NO: 9, or SEQ ID NO: 10. In some embodiments, the nucleic acid nucleotide sequence encoding HNF1alpha, as described herein, can vary from the sequence of SEQ ID NO: 8, SEQ ID NO: 9, or SEQ ID NO: 10 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

In some embodiments, the amino acid sequence of Rel-A (p65) is NCBI No. NP_068810.3, NP_001138610.1, NP_001230913.1, NP_001230914.1, XP_011543508.1, or XP_011543509.1. In some embodiments, the amino acid sequence of Rel-A (p65) is or comprises all or a portion of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of the transactivation domain of the humanized chimeric Notch receptor comprises all or a portion of transcription factor p65 isoform 1 (NP_068810.3), transcription factor p65 isoform 2 (NP_001138610.1), transcription factor p65 isoform 3 (NP_001230913.1), transcription factor p65 isoform 4 (NP_001230914.1), transcription factor p65 isoform X1 (XP_011543508.1), or transcription factor p65 isoform X2 (XP_011543509.1). In some embodiments, the amino acid sequence of the transactivation domain of the humanized Notch receptor comprises all or a portion of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of the transactivation domain of the humanized Notch receptor is or comprises amino acids 1-551 of SEQ ID NO: 12.

```
Human transcription factor p65 isoform 1 NP_068810.3
                                                   (SEQ ID NO: 12)
MDELFPLIFPAEPAQASGPYVEIIEQPKQRGMRFRYKCEGRSAGSIPGERSTDT

TKTHPTIKINGYTGPGTVRISLVTKDPPHRPHPHELVGKDCRDGFYEAELCPDR

CIHSFQNLGIQCVKKRDLEQAISQRIQTNNNPFQVPIEEQRGDYDLNAVRLCFQ

VTVRDPSGRPLRLPPVLSHPIFDNRAPNTAELKTCRVNRNSGSCLGGDEIFLLC

DKVQKEDIEVYFTGPGWEARGSFSQADVHRQVAIVFRTPPYADPSLQAPVRVSM

QLRRPSDRELSEPMEFQYLPDTDDRHRIEEKRKRTYETFKSIMKKSPFSGPTDP

RPPPRRIAVPSRSSASVPKPAPQPYPFTSSLSTINYDEFPTMVFPSGQISQASA

LAPAPPQVLPQAPAPAPAPAMVSALAQAPAPVPVLAPGPPQAVAPPAPKPTQAG

EGTLSEALLQLQFDDEDLGALLGNSTDPAVFTDLASVDNSEFQQLLNQGIPVAP

HTTEPMLMEYPEAITRLVTGAQRPPDPAPAPLGAPGLPNGLLSGDEDFSSIADM

DFSALLSQISS
```

Human transcription factor p65 isoform 2 NP_001138610.1
(SEQ ID NO: 13)
MDELFPLIFPAEPAQASGPYVEIIEQPKQRGMRFRYKCEGRSAGSIPGERSTDT

TKTHPTIKINGYTGPGTVRISLVTKDPPHRPHPHELVGKDCRDGFYEAELCPDR

CIHSFQNLGIQCVKKRDLEQAISQRIQTNNNPFQEEQRGDYDLNAVRLCFQVTV

RDPSGRPLRLPPVLSHPIFDNRAPNTAELKTCRVNRNSGSCLGGDEIFLLCDKV

QKEDIEVYFTGPGWEARGSFSQADVHRQVAIVFRTPPYADPSLQAPVRVSMQLR

RPSDRELSEPMEFQYLPDTDDRHRIEEKRKRTYETFKSIMKKSPFSGPTDPRPP

PRRIAVPSRSSASVPKPAPQPYPFTSSLSTINYDEFPTMVFPSGQISQASALAP

APPQVLPQAPAPAPAPAMVSALAQAPAPVPVLAPGPPQAVAPPAPKPTQAGEGT

LSEALLQLQFDDEDLGALLGNSTDPAVFTDLASVDNSEFQQLLNQGIPVAPHTT

EPMLMEYPEAITRLVTGAQRPPDPAPAPLGAPGLPNGLLSGDEDFSSIADMDFS

ALLSQISS

Human transcription factor p65 isoform 3 NP_001230913.1
(SEQ ID NO: 14)
MDELFPLIFPAEPAQASGPYVEIIEQPKQRGMRFRYKCEGRSAGSIPGERSTDT

TKTHPTIKINGYTGPGTVRISLVTKDPPHRPHPHELVGKDCRDGFYEAELCPDR

CIHSFQNLGIQCVKKRDLEQAISQRIQTNNNPFQVPIEEQRGDYDLNAVRLCFQ

VTVRDPSGRPLRLPPVLSHPIFDNRAPNTAELKTCRVNRNSGSCLGGDEIFLLC

DKVQKEDIEVYFTGPGWEARGSFSQADVHRQVAIVFRTPPYADPSLQAPVRVSM

QLRRPSDRELSEPMEFQYLPDTDDRHRIEEKRKRTYETFKSIMKKSPFSGPTDP

RPPPRRIAVPSRSSASVPKPAPGPPQAVAPPAPKPTQAGEGTLSEALLQLQFDD

EDLGALLGNSTDPAVFTDLASVDNSEFQQLLNQGIPVAPHTTEPMLMEYPEAIT

RLVTGAQRPPDPAPAPLGAPGLPNGLLSGDEDFSSIADMDFSALLSQISS

Human transcription factor p65 isoform 4 NP_001230914.1
(SEQ ID NO: 15)
MDELFPLIFPAEPAQASGPYVEIIEQPKQRGMRFRYKCEGRSAGSIPGERSTDT

TKTHPTIKINGYTGPGTVRISLVTKDPPHRPHPHELVGKDCRDGFYEAELCPDR

CIHSFQNLGIQCVKKRDLEQAISQRIQTNNNPFQVPIEEQRGDYDLNAVRLCFQ

VTVRDPSGRPLRLPPVLSHPIFDNRAPNTAELKTCRVNRNSGSCLGGDEIFLLC

DKVQKEDIEVYFTGPGWEARGSFSQADVHRQVAIVFRTPPYADPSLQAPVRVSM

QLRRPSDRELSEPMEFQYLPDTDDRHRIEEKRKRTYETFKSIMKKSPFSGPTDP

RPPPRRIAVPSRSSASVPKPAPQPYPFTSSLSTINYDEFPTMVFPSGQISQASA

LAPAPPQVLPQAPAPAPAPAMVSALAQRPPDPAPAPLGAPGLPNGLLSGDEDFS

SIADMDFSALLSQISS

Human transcription factor p65 isoform X1 XP_011543508.1
(SEQ ID NO: 16)
MDELFPLIFPAEPAQASGPYVEIIEQPKQRGMRFRYKCEGRSAGSIPGERSTDT

TKTHPTIKINGYTGPGTVRISLVTKDPPHRPHPHELVGKDCRDGFYEAELCPDR

CIHSFQNLGIQCVKKRDLEQAISQRIQTNNNPFQVPIEEQRGDYDLNAVRLCFQ

VTVRDPSGRPLRLPPVLSHPIFDNRAPNTAELKTCRVNRNSGSCLGGDEIFLLC

DKVQKDDRHRIEEKRKRTYETFKSIMKKSPFSGPTDPRPPPRRIAVPSRSSASV

PKPAPQPYPFTSSLSTINYDEFPTMVFPSGQISQASALAPAPPQVLPQAPAPAP

APAMVSALAQAPAPVPVLAPGPPQAVAPPAPKPTQAGEGTLSEALLQLQFDDED

-continued

LGALLGNSTDPAVFTDLASVDNSEFQQLLNQGIPVAPHTTEPMLMEYPEAITRL

VTGAQRPPDPAPAPLGAPGLPNGLLSGDEDFSSIADMDFSALLSQISS

Human transcription factor p65 isoform X2 XP_011543509.1
(SEQ ID NO: 17)
MDELFPLIFPAEPAQASGPYVEIIEQPKQRGMRFRYKCEGRSAGSIPGERSTDT

TKTHPTIKINGYTGPGTVRISLVTKDPPHRPHPHELVGKDCRDGFYEAELCPDR

CIHSFQNLGIQCVKKRDLEQAISQRIQTNNNPFQVPIEEQRGDYDLNAVRLCFQ

VTVRDPSGRPLRLPPVLSHPIFDNHDRHRIEEKRKRTYETFKSIMKKSPFSGPT

DPRPPPRRIAVPSRSSASVPKPAPQPYPFTSSLSTINYDEFPTMVFPSGQISQA

SALAPAPPQVLPQAPAPAPAPAMVSALAQAPAPVPVLAPGPPQAVAPPAPKPTQ

AGEGTLSEALLQLQFDDEDLGALLGNSTDPAVFTDLASVDNSEFQQLLNQGIPV

APHTTEPMLMEYPEAITRLVTGAQRPPDPAPAPLGAPGLPNGLLSGDEDFSSIA

DMDFSALLSQISS

In some embodiments, the amino acid sequence of Rel-A (p65), as described herein, is at least 80% identical to the amino acid sequence of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of Rel-A (p65) is 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 12, SEQ ID NO: 13, SEQ ID NO: 14, SEQ ID NO: 15, SEQ ID NO: 16, or SEQ ID NO: 17. In some embodiments, the amino acid sequence of Rel-A (p65), as described herein, can vary from the amino acid sequence of SEQ ID NO: 12, SEQ ID NO: 13, SEQ ID NO: 14, SEQ ID NO: 15, SEQ ID NO: 16, or SEQ ID NO: 17 by 1 amino acid, 2 amino acids, 3 amino acids, 4 amino acids, 5 amino acids, 6 amino acids, 7 amino acids, 8 amino acids, 9 amino acids, or 10 or more amino acids.

In some embodiments, the nucleic acid sequence encoding Rel-A (p65) is provided by NCBI No. NM_021975.3, NM_001145138.1, NM_001243984.1, NM_001243985.1, XM_011545206.1, or XM_011545207.1. In some embodiments, the nucleic acid sequence encoding Rel-A (p65) is or comprises SEQ ID NO: 18, SEQ ID NO: 19, SEQ ID NO: 20, SEQ ID NO: 21, SEQ ID NO: 22, or SEQ ID NO: 23.

Human RELA proto-oncogene, NF-kB subunit (RELA), transcript
variant 1, mRNA NM_021975.3
(SEQ ID NO: 18)
AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG

GCTTCTATGAGGCTGAGCTCTGCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGTTCCTATAGAAGAGCAGCGTGGGGACT

ACGACCTGAATGCTGTGCGGCTCTGCTTCCAGGTGACAGTGCGGGACCCATCAG

GCAGGCCCCTCCGCCTGCCGCCTGTCCTTTCTCATCCCATCTTTGACAATCGTG

CCCCCAACACTGCCGAGCTCAAGATCTGCCGAGTGAACCGAAACTCTGGCAGCT

GCCTCGGTGGGATGAGATCTTCCTACTGTGTGACAAGGTGCAGAAAGAGGACA

TTGAGGTGTATTTCACGGGACCAGGCTGGGAGGCCCGAGGCTCCTTTTCGCAAG

CTGATGTGCACCGACAAGTGGCCATTGTGTTCCGGACCCCTCCCTACGCAGACC

CCAGCCTGCAGGCTCCTGTGCGTGTCTCCATGCAGCTGCGGCGGCCTTCCGACC

-continued
```
GGGAGCTCAGTGAGCCCATGGAATTCCAGTACCTGCCAGATACAGACGATCGTC

ACCGGATTGAGGAGAAACGTAAAAGGACATATGAGACCTTCAAGAGCATCATGA

AGAAGAGTCCTTTCAGCGGACCCACCGACCCCCGGCCTCCACCTCGACGCATTG

CTGTGCCTTCCCGCAGCTCAGCTTCTGTCCCCAAGCCAGCACCCCAGCCCTATC

CCTTTACGTCATCCCTGAGCACCATCAACTATGATGAGTTTCCCACCATGGTGT

TTCCTTCTGGGCAGATCAGCCAGGCCTCGGCCTTGGCCCCGGCCCCTCCCCAAG

TCCTGCCCCAGGCTCCAGCCCCTGCCCCTGCTCCAGCCATGGTATCAGCTCTGG

CCCAGGCCCCAGCCCCTGTCCCAGTCCTAGCCCCAGGCCCTCCTCAGGCTGTGG

CCCCACCTGCCCCCAAGCCCACCCAGGCTGGGGAAGGAACGCTGTCAGAGGCCC

TGCTGCAGCTGCAGTTTGATGATGAAGACCTGGGGGCCTTGCTTGGCAACAGCA

CAGACCCAGCTGTGTTCACAGACCTGGCATCCGTCGACAACTCCGAGTTTCAGC

AGCTGCTGAACCAGGGCATACCTGTGGCCCCCCACACAACTGAGCCCATGCTGA

TGGAGTACCCTGAGGCTATAACTCGCCTAGTGACAGGGGCCCAGAGGCCCCCCG

ACCCAGCTCCTGCTCCACTGGGGGCCCCGGGGCTCCCCAATGGCCTCCTTTCAG

GAGATGAAGACTTCTCCTCCATTGCGGACATGGACTTCTCAGCCCTGCTGAGTC

AGATCAGCTCCTAAGGGGGTGACGCCTGCCCTCCCCAGAGCACTGGGTTGCAGG

GGATTGAAGCCCTCCAAAAGCACTTACGGATTCTGGTGGGGTGTGTTCCAACTG

CCCCCAACTTTGTGGATGTCTTCCTTGGAGGGGGGAGCCATATTTTATTCTTTT

ATTGTCAGTATCTGTATCTCTCTCTTTTTGGAGGTGCTTAAGCAGAAGCATT

AACTTCTCTGGAAAGGGGGGAGCTGGGGAAACTCAAACTTTTCCCCTGTCCTGA

TGGTCAGCTCCCTTCTCTGTAGGGAACTCTGGGGTCCCCCATCCCCATCCTCCA

GCTTCTGGTACTCTCCTAGAGACAGAAGCAGGCTGGAGGTAAGGCCTTTGAGCC

CACAAAGCCTTATCAAGTGTCTTCCATCATGGATTCATTACAGCTTAATCAAAA

TAACGCCCCAGATACCAGCCCCTGTATGGCACTGGCATTGTCCCTGTGCCTAAC

ACCAGCGTTTGAGGGGCTGGCCTTCCTGCCCTACAGAGGTCTCTGCCGGCTCTT

TCCTTGCTCAACCATGGCTGAAGGAAACCAGTGCAACAGCACTGGCTCTCTCCA

GGATCCAGAAGGGGTTTGGTCTGGGACTTCCTTGCTCTCCCTCTTCTCAAGTGC

CTTAATAGTAGGGTAAGTTGTTAAGAGTGGGGGAGAGCAGGCTGGCAGCTCTCC

AGTCAGGAGGCATAGTTTTTACTGAACAATCAAAGCACTTGGACTCTTGCTCTT

TCTACTCTGAACTAATAAATCTGTTGCCAAGCTGGCTAGAAAAAAAAAAAAAAA

AAA
```

Human RELA proto-oncogene, NF-kB subunit (RELA), transcript
variant 2, mRNA NM_001145138.1

(SEQ ID NO: 19)
```
AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG
```

-continued
```
GCTTCTATGAGGCTGAGCTCTGCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGAAGAGCAGCGTGGGGACTACGACCTGA

ATGCTGTGCGGCTCTGCTTCCAGGTGACAGTGCGGGACCCATCAGGCAGGCCCC

TCCGCCTGCCGCCTGTCCTTTCTCATCCCATCTTTGACAATCGTGCCCCCAACA

CTGCCGAGCTCAAGATCTGCCGAGTGAACCGAAACTCTGGCAGCTGCCTCGGTG

GGGATGAGATCTTCCTACTGTGTGACAAGGTGCAGAAAGAGGACATTGAGGTGT

ATTTCACGGGACCAGGCTGGGAGGCCCGAGGCTCCTTTTCGCAAGCTGATGTGC

ACCGACAAGTGGCCATTGTGTTCCGGACCCCTCCCTACGCAGACCCCAGCCTGC

AGGCTCCTGTGCGTGTCTCCATGCAGCTGCGGCGGCCTTCCGACCGGGAGCTCA

GTGAGCCCATGGAATTCCAGTACCTGCCAGATACAGACGATCGTCACCGGATTG

AGGAGAAACGTAAAAGGACATATGAGACCTTCAAGAGCATCATGAAGAAGAGTC

CTTTCAGCGGACCCACCGACCCCCGGCCTCCACCTCGACGCATTGCTGTGCCTT

CCCGCAGCTCAGCTTCTGTCCCCAAGCCAGCACCCCAGCCCTATCCCTTTACGT

CATCCCTGAGCACCATCAACTATGATGAGTTTCCCACCATGGTGTTTCCTTCTG

GGCAGATCAGCCAGGCCTCGGCCTTGGCCCCGGCCCCTCCCCAAGTCCTGCCCC

AGGCTCCAGCCCCTGCCCCTGCTCCAGCCATGGTATCAGCTCTGGCCCAGGCCC

CAGCCCCTGTCCCAGTCCTAGCCCCAGGCCCTCCTCAGGCTGTGGCCCCACCTG

CCCCCAAGCCCACCCAGGCTGGGAAGGAACGCTGTCAGAGGCCCTGCTGCAGC

TGCAGTTTGATGATGAAGACCTGGGGGCCTTGCTTGGCAACAGCACAGACCCAG

CTGTGTTCACAGACCTGGCATCCGTCGACAACTCCGAGTTTCAGCAGCTGCTGA

ACCAGGGCATACCTGTGGCCCCCCACACAACTGAGCCCATGCTGATGGAGTACC

CTGAGGCTATAACTCGCCTAGTGACAGGGGCCCAGAGGCCCCCCGACCCAGCTC

CTGCTCCACTGGGGGCCCCGGGGCTCCCCAATGGCCTCCTTTCAGGAGATGAAG

ACTTCTCCTCCATTGCGGACATGGACTTCTCAGCCCTGCTGAGTCAGATCAGCT

CCTAAGGGGGTGACGCCTGCCCTCCCCAGAGCACTGGGTTGCAGGGGATTGAAG

CCCTCCAAAAGCACTTACGGATTCTGGTGGGGTGTGTTCCAACTGCCCCCAACT

TTGTGGATGTCTTCCTTGGAGGGGGGAGCCATATTTTATTCTTTTATTGTCAGT

ATCTGTATCTCTCTCTTTTTGGAGGTGCTTAAGCAGAAGCATTAACTTCTCT

GGAAAGGGGGGAGCTGGGGAAACTCAAACTTTTCCCCTGTCCTGATGGTCAGCT

CCCTTCTCTGTAGGGAACTCTGGGGTCCCCCATCCCCATCCTCCAGCTTCTGGT

ACTCTCCTAGAGACAGAAGCAGGCTGGAGGTAAGGCCTTTGAGCCCACAAAGCC

TTATCAAGTGTCTTCCATCATGGATTCATTACAGCTTAATCAAAATAACGCCCC

AGATACCAGCCCCTGTATGGCACTGGCATTGTCCCTGTGCCTAACACCAGCGTT

TGAGGGGCTGGCCTTCCTGCCCTACAGAGGTCTCTGCCGGCTCTTTCCTTGCTC

AACCATGGCTGAAGGAAACCAGTGCAACAGCACTGGCTCTCTCCAGGATCCAGA

AGGGGTTTGGTCTGGGACTTCCTTGCTCTCCCTCTTCTCAAGTGCCTTAATAGT

AGGGTAAGTTGTTAAGAGTGGGGGAGAGCAGGCTGGCAGCTCTCCAGTCAGGAG

GCATAGTTTTTACTGAACAATCAAAGCACTTGGACTCTTGCTCTTTCTACTCTG

AACTAATAAATCTGTTGCCAAGCTGGCTAGAAAAAAAAAAAAAAAAAAA
```

-continued

Human RELA proto-oncogene, NF-kB subunit (RELA), transcript
variant 3, mRNA NM_001243984.1

(SEQ ID NO: 20)

AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG

GCTTCTATGAGGCTGAGCTCTGCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGTTCCTATAGAAGAGCAGCGTGGGGACT

ACGACCTGAATGCTGTGCGGCTCTGCTTCCAGGTGACAGTGCGGGACCCATCAG

GCAGGCCCCTCCGCCTGCCGCCTGTCCTTTCTCATCCCATCTTTGACAATCGTG

CCCCCAACACTGCCGAGCTCAAGATCTGCCGAGTGAACCGAAACTCTGGCAGCT

GCCTCGGTGGGGATGAGATCTTCCTACTGTGTGACAAGGTGCAGAAAGAGGACA

TTGAGGTGTATTTCACGGGACCAGGCTGGGAGGCCCGAGGCTCCTTTTCGCAAG

CTGATGTGCACCGACAAGTGGCCATTGTGTTCCGGACCCCTCCCTACGCAGACC

CCAGCCTGCAGGCTCCTGTGCGTGTCTCCATGCAGCTGCGGCGGCCTTCCGACC

GGGAGCTCAGTGAGCCCATGGAATTCCAGTACCTGCCAGATACAGACGATCGTC

ACCGGATTGAGGAGAAACGTAAAAGGACATATGAGACCTTCAAGAGCATCATGA

AGAAGAGTCCTTTCAGCGGACCCACCGACCCCCGGCCTCCACCTCGACGCATTG

CTGTGCCTTCCCGCAGCTCAGCTTCTGTCCCCAAGCCAGCCCCAGGCCCTCCTC

AGGCTGTGGCCCCACCTGCCCCCAAGCCCACCCAGGCTGGGGAAGGAACGCTGT

CAGAGGCCCTGCTGCAGCTGCAGTTTGATGATGAAGACCTGGGGGCCTTGCTTG

GCAACAGCACAGACCCAGCTGTGTTCACAGACCTGGCATCCGTCGACAACTCCG

AGTTTCAGCAGCTGCTGAACCAGGGCATACCTGTGGCCCCCCACACAACTGAGC

CCATGCTGATGGAGTACCCTGAGGCTATAACTCGCCTAGTGACAGGGGCCCAGA

GGCCCCCCGACCCAGCTCCTGCTCCACTGGGGGCCCCGGGGCTCCCCAATGGCC

TCCTTTCAGGAGATGAAGACTTCTCCTCCATTGCGGACATGGACTTCTCAGCCC

TGCTGAGTCAGATCAGCTCCTAAGGGGGTGACGCCTGCCCTCCCCAGAGCACTG

GGTTGCAGGGGATTGAAGCCCTCCAAAAGCACTTACGGATTCTGGTGGGGTGTG

TTCCAACTGCCCCCAACTTTGTGGATGTCTTCCTTGGAGGGGGAGCCATATTT

TATTCTTTTATTGTCAGTATCTGTATCTCTCTCTTTTTGGAGGTGCTTAAGC

AGAAGCATTAACTTCTCTGGAAAGGGGGAGCTGGGGAAACTCAAACTTTTCCC

CTGTCCTGATGGTCAGCTCCCTTCTCTGTAGGGAACTCTGGGGTCCCCCATCCC

CATCCTCCAGCTTCTGGTACTCTCCTAGAGACAGAAGCAGGCTGGAGGTAAGGC

CTTTGAGCCCACAAAGCCTTATCAAGTGTCTTCCATCATGGATTCATTACAGCT

TAATCAAAATAACGCCCCAGATACCAGCCCCTGTATGGCACTGGCATTGTCCCT

GTGCCTAACACCAGCGTTTGAGGGGCTGGCCTTCCTGCCCTACAGAGGTCTCTG

-continued

```
CCGGCTCTTTCCTTGCTCAACCATGGCTGAAGGAAACCAGTGCAACAGCACTGG

CTCTCTCCAGGATCCAGAAGGGGTTTGGTCTGGGACTTCCTTGCTCTCCCTCTT

CTCAAGTGCCTTAATAGTAGGGTAAGTTGTTAAGAGTGGGGGAGAGCAGGCTGG

CAGCTCTCCAGTCAGGAGGCATAGTTTTTACTGAACAATCAAAGCACTTGGACT

CTTGCTCTTTCTACTCTGAACTAATAAATCTGTTGCCAAGCTGGCTAGAAAAAA

AAAAAAAAAAA
```

Human RELA proto-oncogene, NF-kB subunit (RELA), transcript
variant 4, mRNA NM_001243985.1

(SEQ ID NO: 21)

```
AGCGCGCAGGCGCGGCCGGATTCCGGGCAGTGACGCGACGGCGGGCCGCGCGGC

GCATTTCCGCCTCTGGCGAATGGCTCGTCTGTAGTGCACGCCGCGGGCCCAGCT

GCGACCCCGGCCCCGCCCCGGGACCCCGGCCATGGACGAACTGTTCCCCCTCA

TCTTCCCGGCAGAGCCAGCCCAGGCCTCTGGCCCCTATGTGGAGATCATTGAGC

AGCCCAAGCAGCGGGGCATGCGCTTCCGCTACAAGTGCGAGGGGCGCTCCGCGG

GCAGCATCCCAGGCGAGAGGAGCACAGATACCACCAAGACCCACCCCACCATCA

AGATCAATGGCTACACAGGACCAGGGACAGTGCGCATCTCCCTGGTCACCAAGG

ACCCTCCTCACCGGCCTCACCCCCACGAGCTTGTAGGAAAGGACTGCCGGGATG

GCTTCTATGAGGCTGAGCTCTGCCCGGACCGCTGCATCCACAGTTTCCAGAACC

TGGGAATCCAGTGTGTGAAGAAGCGGGACCTGGAGCAGGCTATCAGTCAGCGCA

TCCAGACCAACAACAACCCCTTCCAAGTTCCTATAGAAGAGCAGCGTGGGGACT

ACGACCTGAATGCTGTGCGGCTCTGCTTCCAGGTGACAGTGCGGGACCCATCAG

GCAGGCCCCTCCGCCTGCCGCCTGTCCTTTCTCATCCCATCTTTGACAATCGTG

CCCCCAACACTGCCGAGCTCAAGATCTGCCGAGTGAACCGAAACTCTGGCAGCT

GCCTCGGTGGGATGAGATCTTCCTACTGTGTGACAAGGTGCAGAAAGAGGACA

TTGAGGTGTATTTCACGGGACCAGGCTGGGAGGCCCGAGGCTCCTTTTCGCAAG

CTGATGTGCACCGACAAGTGGCCATTGTGTTCCGGACCCCTCCCTACGCAGACC

CCAGCCTGCAGGCTCCTGTGCGTGTCTCCATGCAGCTGCGGCGGCCTTCCGACC

GGGAGCTCAGTGAGCCCATGGAATTCCAGTACCTGCCAGATACAGACGATCGTC

ACCGGATTGAGGAGAAACGTAAAAGGACATATGAGACCTTCAAGAGCATCATGA

AGAAGAGTCCTTTCAGCGGACCCACCGACCCCCGGCCTCCACCTCGACGCATTG

CTGTGCCTTCCCGCAGCTCAGCTTCTGTCCCCAAGCCAGCACCCCAGCCCTATC

CCTTTACGTCATCCCTGAGCACCATCAACTATGATGAGTTTCCCACCATGGTGT

TTCCTTCTGGGCAGATCAGCCAGGCCTCGGCCTTGGCCCCGGCCCCTCCCCAAG

TCCTGCCCCAGGCTCCAGCCCCTGCCCCTGCTCCAGCCATGGTATCAGCTCTGG

CCCAGAGGCCCCCCGACCCAGCTCCTGCTCCACTGGGGGCCCCGGGGCTCCCCA

ATGGCCTCCTTTCAGGAGATGAAGACTTCTCCTCCATTGCGGACATGGACTTCT

CAGCCCTGCTGAGTCAGATCAGCTCCTAAGGGGGTGACGCCTGCCCTCCCCAGA

GCACTGGGTTGCAGGGGATTGAAGCCCTCCAAAAGCACTTACGGATTCTGGTGG

GGTGTGTTCCAACTGCCCCCAACTTTGTGGATGTCTTCCTTGGAGGGGGGAGCC

ATATTTTATTCTTTTATTGTCAGTATCTGTATCTCTCTCTTTTTGGAGGTGC

TTAAGCAGAAGCATTAACTTCTCTGGAAAGGGGGAGCTGGGGAAACTCAAACT

TTTCCCCTGTCCTGATGGTCAGCTCCCTTCTCTGTAGGGAACTCTGGGGTCCCC
```

-continued

```
CATCCCCATCCTCCAGCTTCTGGTACTCTCCTAGAGACAGAAGCAGGCTGGAGG

TAAGGCCTTTGAGCCCACAAAGCCTTATCAAGTGTCTTCCATCATGGATTCATT

ACAGCTTAATCAAAATAACGCCCCAGATACCAGCCCCTGTATGGCACTGGCATT

GTCCCTGTGCCTAACACCAGCGTTTGAGGGGCTGGCCTTCCTGCCCTACAGAGG

TCTCTGCCGGCTCTTTCCTTGCTCAACCATGGCTGAAGGAAACCAGTGCAACAG

CACTGGCTCTCTCCAGGATCCAGAAGGGGTTTGGTCTGGGACTTCCTTGCTCTC

CCTCTTCTCAAGTGCCTTAATAGTAGGGTAAGTTGTTAAGAGTGGGGGAGAGCA

GGCTGGCAGCTCTCCAGTCAGGAGGCATAGTTTTTACTGAACAATCAAAGCACT

TGGACTCTTGCTCTTTCTACTCTGAACTAATAAATCTGTTGCCAAGCTGGCTAG

AAAAAAAAAAAAAAAAAA
```

Human RELA proto-oncogene, NF-kB subunit (RELA), transcript variant X1, mRNA XM_011545206.1

(SEQ ID NO: 22)

```
ATTCCGGGCAGTGACGCGACGGCGGGCCGCGCGGCGCATTTCCGCCTCTGGCGA

ATGGCTCGTCTGTAGTGCACGCCGCGGGCCCAGCTGCGACCCCGGCCCCGCCCC

CGGGACCCCGGCCATGGACGAACTGTTCCCCCTCATCTTCCCGGCAGAGCCAGC

CCAGGCCTCTGGCCCCTATGTGGAGATCATTGAGCAGCCCAAGCAGCGGGGCAT

GCGCTTCCGCTACAAGTGCGAGGGGCGCTCCGCGGGCAGCATCCCAGGCGAGAG

GAGCACAGATACCACCAAGACCCACCCCACCATCAAGATCAATGGCTACACAGG

ACCAGGGACAGTGCGCATCTCCCTGGTCACCAAGGACCCTCCTCACCGGCCTCA

CCCCCACGAGCTTGTAGGAAAGGACTGCCGGGATGGCTTCTATGAGGCTGAGCT

CTGCCCGGACCGCTGCATCCACAGTTTCCAGAACCTGGGAATCCAGTGTGTGAA

GAAGCGGGACCTGGAGCAGGCTATCAGTCAGCGCATCCAGACCAACAACAACCC

CTTCCAAGTTCCTATAGAAGAGCAGCGTGGGGACTACGACCTGAATGCTGTGCG

GCTCTGCTTCCAGGTGACAGTGCGGGACCCATCAGGCAGGCCCCTCCGCCTGCC

GCCTGTCCTTTCTCATCCCATCTTTGACAATCGTGCCCCCAACACTGCCGAGCT

CAAGATCTGCCGAGTGAACCGAAACTCTGGCAGCTGCCTCGGTGGGGATGAGAT

CTTCCTACTGTGTGACAAGGTGCAGAAAGACGATCGTCACCGGATTGAGGAGAA

ACGTAAAAGGACATATGAGACCTTCAAGAGCATCATGAAGAAGAGTCCTTTCAG

CGGACCCACCGACCCCCGGCCTCCACCTCGACGCATTGCTGTGCCTTCCCGCAG

CTCAGCTTCTGTCCCCAAGCCAGCACCCCAGCCCTATCCCTTTACGTCATCCCT

GAGCACCATCAACTATGATGAGTTTCCCACCATGGTGTTCCTTCTGGGCAGAT

CAGCCAGGCCTCGGCCTTGGCCCCGGCCCCTCCCCAAGTCCTGCCCCAGGCTCC

AGCCCCTGCCCCTGCTCCAGCCATGGTATCAGCTCTGGCCCAGGCCCCAGCCCC

TGTCCCAGTCCTAGCCCCAGGCCCTCCTCAGGCTGTGGCCCCACCTGCCCCCAA

GCCCACCCAGGCTGGGGAAGGAACGCTGTCAGAGGCCCTGCTGCAGCTGCAGTT

TGATGATGAAGACCTGGGGGCCTTGCTTGGCAACAGCACAGACCCAGCTGTGTT

CACAGACCTGGCATCCGTCGACAACTCCGAGTTTCAGCAGCTGCTGAACCAGGG

CATACCTGTGGCCCCCCACACAACTGAGCCCATGCTGATGGAGTACCCTGAGGC

TATAACTCGCCTAGTGACAGGGGCCCAGAGGCCCCCCGACCCAGCTCCTGCTCC

ACTGGGGGCCCCGGGGCTCCCCAATGGCCTCCTTTCAGGAGATGAAGACTTCTC

CTCCATTGCGGACATGGACTTCTCAGCCCTGCTGAGTCAGATCAGCTCCTAAGG
```

-continued

```
GGGTGACGCCTGCCCTCCCCAGAGCACTGGGTTGCAGGGGATTGAAGCCCTCCA

AAAGCACTTACGGATTCTGGTGGGGTGTGTTCCAACTGCCCCCAACTTTGTGGA

TGTCTTCCTTGGAGGGGGGAGCCATATTTTATTCTTTTATTGTCAGTATCTGTA

TCTCTCTCTCTTTTTGGAGGTGCTTAAGCAGAAGCATTAACTTCTCTGGAAAGG

GGGGAGCTGGGGAAACTCAAACTTTTCCCCTGTCCTGATGGTCAGCTCCCTTCT

CTGTAGGGAACTCTGGGGTCCCCCATCCCCATCCTCCAGCTTCTGGTACTCTCC

TAGAGACAGAAGCAGGCTGGAGGTAAGGCCTTTGAGCCCACAAAGCCTTATCAA

GTGTCTTCCATCATGGATTCATTACAGCTTAATCAAAATAACGCCCCAGATACC

AGCCCCTGTATGGCACTGGCATTGTCCCTGTGCCTAACACCAGCGTTTGAGGGG

CTGGCCTTCCTGCCCTACAGAGGTCTCTGCCGGCTCTTTCCTTGCTCAACCATG

GCTGAAGGAAACCAGTGCAACAGCACTGGCTCTCTCCAGGATCCAGAAGGGGTT

TGGTCTGGGACTTCCTTGCTCTCCCTCTTCTCAAGTGCCTTAATAGTAGGGTAA

GTTGTTAAGAGTGGGGGAGAGCAGGCTGGCAGCTCTCCAGTCAGGAGGCATAGT

TTTTACTGAACAATCAAAGCACTTGGACTCTTGCTCTTTCTACTCTGAACTAAT

AAATCTGTTGCCAAGCTGG

Human RELA proto-oncogene, NF-kB subunit (RELA), transcript
variant X2, mRNA XM_011545207.1
                                                (SEQ ID NO: 23)
ATTCCGGGCAGTGACGCGACGGCGGGCCGCGCGGCGCATTTCCGCCTCTGGCGA

ATGGCTCGTCTGTAGTGCACGCCGCGGGCCCAGCTGCGACCCCGGCCCCGCCCC

CGGGACCCCGGCCATGGACGAACTGTTCCCCCTCATCTTCCCGGCAGAGCCAGC

CCAGGCCTCTGGCCCCTATGTGGAGATCATTGAGCAGCCCAAGCAGCGGGGCAT

GCGCTTCCGCTACAAGTGCGAGGGGCGCTCCGCGGGCAGCATCCCAGGCGAGAG

GAGCACAGATACCACCAAGACCCACCCCACCATCAAGATCAATGGCTACACAGG

ACCAGGGACAGTGCGCATCTCCCTGGTCACCAAGGACCCTCCTCACCGGCCTCA

CCCCCACGAGCTTGTAGGAAAGGACTGCCGGGATGGCTTCTATGAGGCTGAGCT

CTGCCCGGACCGCTGCATCCACAGTTTCCAGAACCTGGGAATCCAGTGTGTGAA

GAAGCGGGACCTGGAGCAGGCTATCAGTCAGCGCATCCAGACCAACAACAACCC

CTTCCAAGTTCCTATAGAAGAGCAGCGTGGGGACTACGACCTGAATGCTGTGCG

GCTCTGCTTCCAGGTGACAGTGCGGGACCCATCAGGCAGGCCCCTCCGCCTGCC

GCCTGTCCTTTCTCATCCCATCTTTGACAATACGATCGTCACCGGATTGAGGA

GAAACGTAAAAGGACATATGAGACCTTCAAGAGCATCATGAAGAAGAGTCCTTT

CAGCGGACCCACCGACCCCCGGCCTCCACCTCGACGCATTGCTGTGCCTTCCCG

CAGCTCAGCTTCTGTCCCCAAGCCAGCACCCCAGCCCTATCCCTTTACGTCATC

CCTGAGCACCATCAACTATGATGAGTTTCCCACCATGGTGTTTCCTTCTGGGCA

GATCAGCCAGGCCTCGGCCTTGGCCCCGGCCCCTCCCCAAGTCCTGCCCCAGGC

TCCAGCCCCTGCCCCTGCTCCAGCCATGGTATCAGCTCTGGCCCAGGCCCCAGC

CCCTGTCCCAGTCCTAGCCCCAGGCCCTCCTCAGGCTGTGGCCCCACCTGCCCC

CAAGCCCACCCAGGCTGGGGAAGGAACGCTGTCAGAGGCCCTGCTGCAGCTGCA

GTTTGATGATGAAGACCTGGGGGCCTTGCTTGGCAACAGCACAGACCCAGCTGT

GTTCACAGACCTGGCATCCGTCGACAACTCCGAGTTTCAGCAGCTGCTGAACCA

GGGCATACCTGTGGCCCCCCACACAACTGAGCCCATGCTGATGGAGTACCCTGA
```

-continued

```
GGCTATAACTCGCCTAGTGACAGGGGCCCAGAGGCCCCCGACCCAGCTCCTGC

TCCACTGGGGGCCCCGGGGCTCCCCAATGGCCTCCTTTCAGGAGATGAAGACTT

CTCCTCCATTGCGGACATGGACTTCTCAGCCCTGCTGAGTCAGATCAGCTCCTA

AGGGGGTGACGCCTGCCCTCCCCAGAGCACTGGGTTGCAGGGGATTGAAGCCCT

CCAAAAGCACTTACGGATTCTGGTGGGGTGTGTTCCAACTGCCCCCAACTTTGT

GGATGTCTTCCTTGGAGGGGGGAGCCATATTTTATTCTTTTATTGTCAGTATCT

GTATCTCTCTCTTTTTGGAGGTGCTTAAGCAGAAGCATTAACTTCTCTGGAA

AGGGGGGAGCTGGGGAAACTCAAACTTTTCCCCTGTCCTGATGGTCAGCTCCCT

TCTCTGTAGGGAACTCTGGGGTCCCCCATCCCCATCCTCCAGCTTCTGGTACTC

TCCTAGAGACAGAAGCAGGCTGGAGGTAAGGCCTTTGAGCCCACAAAGCCTTAT

CAAGTGTCTTCCATCATGGATTCATTACAGCTTAATCAAAATAACGCCCCAGAT

ACCAGCCCCTGTATGGCACTGGCATTGTCCCTGTGCCTAACACCAGCGTTTGAG

GGGCTGGCCTTCCTGCCCTACAGAGGTCTCTGCCGGCTCTTTCCTTGCTCAACC

ATGGCTGAAGGAAACCAGTGCAACAGCACTGGCTCTCTCCAGGATCCAGAAGGG

GTTTGGTCTGGGACTTCCTTGCTCTCCCTCTTCTCAAGTGCCTTAATAGTAGGG

TAAGTTGTTAAGAGTGGGGGAGAGCAGGCTGGCAGCTCTCCAGTCAGGAGGCAT

AGTTTTTACTGAACAATCAAAGCACTTGGACTCTTGCTCTTTCTACTCTGAACT

AATAAATCTGTTGCCAAGCTGG
```

In some embodiments, the nucleic acid sequence encoding Rel-A (p65), as described herein, is at least 80% identical to the sequence of SEQ ID NO: 18, SEQ ID NO: 19, SEQ ID NO: 20. SEQ ID NO: 21, SEQ ID NO: 22, or SEQ ID NO: 23. In some embodiments, the nucleic acid sequence encoding Rel-A (p65) is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 18, SEQ ID NO: 19, SEQ ID NO: 20, SEQ ID NO: 21, SEQ ID NO: 22, or SEQ ID NO: 23. In some embodiments, the nucleic acid encoding Rel-A (p65), as described herein, can vary from the sequence of SEQ ID NO: 18, SEQ ID NO: 19, SEQ ID NO: 20, SEQ ID NO: 21, SEQ ID NO: 22, or SEQ ID NO: 23 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

"Linkers" are short amino acid sequences created in nature to separate multiple domains in a single protein, and, generally, can be classified into three groups: flexible, rigid and cleavable. Chen, X., et al., 2013, Adv. Drug Deliv. Rev., 65, 1357-1369. Linkers can be natural or synthetic. A number of linkers are employed to realize the subject invention including "flexible linkers." The latter are rich in glycine. Klein et al., Protein Engineering, Design & Selection Vol. 27, No. 10, pp. 325-330, 2014; Priyanka et al., Protein Sci., 2013 February; 22(2): 153-167.

In some embodiments, the linker is a synthetic linker. A synthetic linker can have a length of from about 10 amino acids to about 200 amino acids, e.g., from 10 to 25 amino acids, from 25 to 50 amino acids, from 50 to 75 amino acids, from 75 to 100 amino acids, from 100 to 125 amino acids, from 125 to 150 amino acids, from 150 to 175 amino acids, or from 175 to 200 amino acids. A synthetic linker can have a length of from 10 to 30 amino acids, e.g., 10, 11, 12, 13, 14, 15, 16, 17, 18, 19, 20, 21, 22, 23, 24, 25, 26, 27, 28, 29, or 30 amino acids. A synthetic linker can have a length of from 30 to 50 amino acids, e.g., from 30 to 35 amino acids, from 35 to 40 amino acids, from 40 to 45 amino acids, or from 45 to 50 amino acids.

In some embodiments, the linker is a flexible linker. In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) sequences, e.g., 1, 2, 3, 4, 5, 6, 7, 8, 9, or 10 or more GGGS sequences. In some embodiments, the linker has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker has one or more Gly-Gly-Ser-Gly (GGSG) sequences, e.g., 1, 2, 3, 4, 5, 6, 7, 8, 9, or 10 or more GGSG sequences. In some embodiments, the linker is GSAAAGGSGGSGGS (SEQ ID NO: 3). In some embodiments, the linker is GGGSGGGS (SEQ ID NO: 4).

"Native or natural Notch" is meant to encompass all known forms of Notch receptors. In humans, 4 forms of Notch are known. Joanna Pancewicz: BMC Cancer 11(1): 502 November 2011. The human Notch family includes four receptors and five ligands.

In some embodiments, the chimeric Notch receptor polypeptide contains all or a portion of human Notch1, Notch2, Notch3, or Notch4. In some embodiments, the chimeric Notch receptor polypeptide contains all or a portion of SEQ ID NO: 24, SEQ ID NO: 25, SEQ ID NO: 26, SEQ ID NO: 27, or SEQ ID NO: 28.

In some embodiments, a "portion" of Notch comprises the three LNR Domains, the transmembrane domain, and a short cytosolic fragment including the native Nuclear Localization Sequence (NLS) of Notch.

Human neurogenic locus notch homolog protein 1 preprotein NP_060087.3
(SEQ ID NO: 24)

MPPLLAPLLCLALLPALAARGPRCSQPGETCLNGGKCEAANGTEACVCGGAFVG

PRCQDPNPCLSTPCKNAGTCHVVDRRGVADYACSCALGFSGPLCLTPLDNACLT

NPCRNGGTCDLLTLTEYKCRCPPGWSGKSCQQADPCASNPCANGGQCLPFEASY

TCHCPPSFHGPTCRQDVNECGQKPGLCRHGGTCHNEVGSYRCVCRATHTGPNCE

RPYVPCSPSPCQNGGTCRPTGDVTHECACLPGFTGQNCEENIDDCPGNNCKNGG

ACVDGVNTYNCRCPPEWTGQYCTEDVDECQLMPNACQNGGTCHNTHGGYNCVCV

NGWTGEDCSENIDDCASAACFHGATCHDRVASFYCECPHGRTGLLCHLNDACIS

NPCNEGSNCDTNPVNGKATCTCPSGYTGPACSQDVDECSLGANPCEHAGKCINT

LGSFECQCLQGYTGPRCEIDVNECVSNPCQNDATCLDQTGEFQCTCMPGYEGVH

CEVNTDECASSPCLHNGRCLDKINEFQCECPTGFTGHLCQYDVDECASTPCKNG

AKCLDGPNTYTCVCTEGYTGTHCEVDIDECDPDPCHYGSCKDGVATFTCLCRPG

YTGHHCETNINECSSQPCRHGGTCQDRDNAYLCFCLKGTTGPNCEINLDDCASS

PCDSGTCLDKIDGYECACEPGYTGSMCNINIDECAGNPCHNGGTCEDGINGFTC

RCPEGYHDPTCLSEVNECNSNPCVHGACRDSLNGYKCDCDPGWSGTNCDINNNE

CESNPCVNGGTCKDMTSGYVCTCREGFSGPNCQTNINECASNPCLNQGTCIDDV

AGYKCNCLLPYTGATCEVVLAPCAPSPCRNGGECRQSEDYESFSCVCPTGWQGQ

TCEVDINECVLSPCRHGASCQNTHGGYRCHCQAGYSGRNCETDIDDCRPNPCHN

GGSCTDGINTAFCDCLPGFRGTFCEEDINECASDPCRNGANCTDCVDSYTCTCP

AGFSGIHCENNTPDCTESSCFNGGTCVDGINSFTCLCPPGFTGSYCQHDVNECD

SQPCLHGGTCQDGCGSYRCTCPQGYTGPNCQNLVHWCDSSPCKNGGKCWQTHTQ

YRCECPSGWTGLYCDVPSVSCEVAAQRQGVDVARLCQHGGLCVDAGNTHHCRCQ

AGYTGSYCEDLVDECSPSPCQNGATCTDYLGGYSCKCVAGYHGVNCSEEIDECL

SHPCQNGGTCLDLPNTYKCSCPRGTQGVHCEINVDDCNPPVDPVSRSPKCFNNG

TCVDQVGGYSCTCPPGFVGERCEGDVNECLSNPCDARGTQNCVQRVNDFHCECR

AGHTGRRCESVINGCKGKPCKNGGTCAVASNTARGFTCKCPAGFEGATCENDAR

TCGSLRCLNGGTCISGPRSPTCLCLGPFTGPECQFPASSPCLGGNPCYNQGTCE

PTSESPFYRCLCPAKFNGLLCHILDYSFGGGAGRDIPPPLIEEACELPECQEDA

GNKVCSLQCNNHACGWDGGDCSLNFNDPWKNCTQSLQCWKYFSDGHCDSQCNSA

GCLFDGFDCQRAEGQCNPLYDQYCKDHFSDGHCDQGCNSAECEWDGLDCAEHVP

ERLAAGTLVVVVLMPPEQLRNSSFHFLRELSRVLHTNVVFKRDAHGQQMIFPYY

GREEELRKHPIKRAAEGWAAPDALLGQVKASLLPGGSEGGRRRRELDPMDVRGS

IVYLEIDNRQCVQASSQCFQSATDVAAFLGALASLGSLNIPYKIEAVQSETVEP

PPPAQLHFMYVAAAAFVLLFFVGCGVLLSRKRRRQHGQLWFPEGFKVSEASKKK

RREPLGEDSVGLKPLKNASDGALMDDNQNEWGDEDLETKKFRFEEPVVLPDLDD

QTDHRQWTQQHLDAADLRMSAMAPTPPQGEVDADCMDVNVRGPDGFTPLMIASC

SGGGLETGNSEEEEDAPAVISDFIYQGASLHNQTDRTGETALHLAARYSRSDAA

KRLLEASADANIQDNMGRTPLHAAVSADAQGVFQILIRNRATDLDARMHDGTTP

LILAARLAVEGMLEDLINSHADVNAVDDLGKSALHWAAAVNNVDAAVVLLKNGA

NKDMQNNREETPLFLAAREGSYETAKVLLDHFANRDITDHMDRLPRDIAQERMH

HDIVRLLDEYNLVRSPQLHGAPLGGTPTLSPPLCSPNGYLGSLKPGVQGKKVRK

-continued

PSSKGLACGSKEAKDLKARRKKSQDGKGCLLDSSGMLSPVDSLESPHGYLSDVA

SPPLLPSPFQQSPSVPLNHLPGMPDTHLGTGHLNVAAKPEMAALGGGGRLAFET

GPPRLSHLPVASGTSTVLGSSSGGALNFTVGGSTSLNGQCEWLSRLQSGMVPNQ

YNPLRGSVAPGPLSTQAPSLQHGMVGPLHSSLAASALSQMMSYQGLPSTRLATQ

PHLVQTQQVQPQNLQMQQQNLQPANIQQQQSLQPPPPPPQPHLGVSSAASGHLG

RSFLSGEPSQADVQPLGPSSLAVHTILPQESPALPTSLPSSLVPPVTAAQFLTP

PSQHSYSSPVDNTPSHQLQVPEHPFLTPSPESPDQWSSSSPHSNVSDWSEGVSS

PPTSMQSQIARIPEAFK

Human neurogenic locus notch homolog protein 2 isoform 1 preprotein
NP_077719.2
                                                          SEQ ID NO: 25)
MPALRPALLWALLALWLCCAAPAHALQCRDGYEPCVNEGMCVTYHNGTGYCKCP

EGFLGEYCQHRDPCEKNRCQNGGTCVAQAMLGKATCRCASGFTGEDCQYSTSHP

CFVSRPCLNGGTCHMLSRDTYECTCQVGFTGKECQWTDACLSHPCANGSTCTTV

ANQFSCKCLTGFTGQKCETDVNECDIPGHCQHGGTCLNLPGSYQCQCPQGFTGQ

YCDSLYVPCAPSPCVNGGTCRQTGDFTFECNCLPGFEGSTCERNIDDCPNHRCQ

NGGVCVDGVNTYNCRCPPQWTGQFCTEDVDECLLQPNACQNGGTCANRNGGYGC

VCVNGWSGDDCSENIDDCAFASCTPGSTCIDRVASFSCMCPEGKAGLLCHLDDA

CISNPCHKGALCDTNPLNGQYTCTCPQGYKGADCTEDVDECAMANSNPCEHAGK

CVNTDGAFHCECLKGYAGPRCEMDINECHSDPCQNDATCLDKTGGFTCLCMPGF

KGVHCELEINECQSNPCVNNGQCVDKVNRFQCLCPPGFTGPVCQIDIDDCSSTP

CLNGAKCIDHPNGYECQCATGFTGVLCEENIDNCDPDPCHHGQCQDGIDSYTCI

CNPGYMGATCSDQIDECYSSPCLNDGRCIDLVNGYQCNCQPGTSGVNCEINFDD

CASNPCIHGTCMDGINRYSCVCSPGFTGQRCNIDIDECASNPCRKGATCINGVN

GFRCTCPEGPHHPSCYSQVNECLSNPCIHGNCTGGLSGYKCLCDAGWVGINCEV

DKNECLSNPCQNGGTCDNLVNGYRCTCKKGFKGYNCQVNIDECASNPCLNQGTC

FDDISGYTCHCVLPYTGKNCQTVLAPCSPNPCENAAVCKESPNFESYTCLCAPG

WQGQRCTIDIDECISKPCMNHGLCHNTQGSYMCECPPGFSGMDCEEDIDDCLAN

PCQNGGSCMDGVNTFSCLCLPGFTGDKCQTDMNECLSEPCKNGGTCSDYVNSYT

CKCQAGFDGVHCENNINECTESSCFNGGTCVDGINSFSCLCPVGFTGSFCLHEI

NECSSHPCLNEGTCVDGLGTYRCSCPLGYTGKNCQTLVNLCSRSPCKNKGTCVQ

KKAESQCLCPSGWAGAYCDVPNVSCDIAASRRGVLVEHLCQHSGVCINAGNTHY

CQCPLGYTGSYCEEQLDECASNPCQHGATCSDFTGGYRCECVPGYQGVNCEYEV

DECQNQPCQNGGTCIDLVNHFKCSCPPGTRGLLCEENIDDCARGPHCLNGGQCM

DRTGGYSCRCLPGFAGERCEGDINECLSNPCSSEGSLDCIQLTNDYLCVCRSAF

TGRHCETFVDVCPQMPCLNGGTCAVASNMPDGFTCRCPPGFSGARCQSSCGQVK

CRKGEQCVHTASGPRCFCPSPRDCESGCASSPCQHGGSCHPQRQPPYYSCQCAP

PFSGSRCELYTAPPSTPPATCLSQYCADKARDGVCDEACNSHACQWDGGDCSLI

MENPWANCSSPLPCWDYINNQCDELCNTVECLFDNFECQGNSKTCKYDKYCADH

FKDNHCDQGCNSEECGWDGLDCAADQPENLAEGTLVIVVLMPPEQLLQDARSFL

RALGTLLHTNLRIKRDSQGELMVYPYYGEKSAAMKKQRMTRRSLPGEQEQEVAG

SKVFLEIDNRQCVQDSDHCFKNTDAAAALLASHAIQGTLSYPLVSVVSESLTPE

-continued

```
RTQLLYLLAVAVVIILFIILLGVIMAKRKRKHGSLWLPEGFTLRRDASNHKRRE

PVGQDAVGLKNLSVQVSEANLTGTGTSEHWVDDEGPQPKKVKAEDEALLSEEDD

PIDRRPWTQQHLEAADIRRTPSLALTPPQAEQEVDVLDVNVRGPDGCTPLMLAS

LRGGSSDLSDEDEDAEDSSANIITDLVYQGASLQAQTDRTGEMALHLAARYSRA

DAAKRLLDAGADANAQDNMGRCPLHAAVAADAQGVFQILIRNRVTDLDARMNDG

TTPLILAARLAVEGMVAELINCQADVNAVDDHGKSALHWAAAVNNVEATLLLLK

NGANRDMQDNKEETPLFLAAREGSYEAAKILLDHFANRDITDHMDRLPRDVARD

RMHHDIVRLLDEYNVTPSPPGTVLTSALSPVTCGPNRSFLSLKHTPMGKKSRRP

SAKSTMPTSLPNLAKEAKDAKGSRRKKSLSEKVQLSESSVTLSPVDSLESPHTY

VSDTTSSPMITSPGILQASPNPMLATAAPPAPVHAQHALSFSNLHEMQPLAHGA

STVLPSVSQLLSHHHIVSPGSGSAGSLSRLHPVPVPADWMNRMEVNETQYNEMF

GMVLAPAEGTHPGIAPQSRPPEGKHITTPREPLPPIVTFQLIPKGSIAQPAGAP

QPQSTCPPAVAGPLPTMYQIPEMARLPSVAFPTAMMPQQDGQVAQTILPAYHPF

PASVGKYPTPPSQHSYASSNAAERTPSHSGHLQGEHPYLTPSPESPDQWSSSSP

HSASDWSDVTTSPTPGGAGGGQRGPGTHMSEPPHNNMQVYA

Human neurogenic locus notch homolog protein 2 isoform 2 precursor
NP_001186930.1
                                                    (SEQ ID NO: 26)
MPALRPALLWALLALWLCCAAPAHALQCRDGYEPCVNEGMCVTYHNGTGYCKCP

EGFLGEYCQHRDPCEKNRCQNGGTCVAQAMLGKATCRCASGFTGEDCQYSTSHP

CFVSRPCLNGGTCHMLSRDTYECTCQVGFTGKECQWIDACLSHPCANGSTCTTV

ANQFSCKCLTGFTGQKCETDVNECDIPGHCQHGGTCLNLPGSYQCQCPQGFTGQ

YCDSLYVPCAPSPCVNGGTCRQTGDFTFECNCLPGFEGSTCERNIDDCPNHRCQ

NGGVCVDGVNTYNCRCPPQWTGQFCTEDVDECLLQPNACQNGGTCANRNGGYGC

VCVNGWSGDDCSENIDDCAFASCTPGSTCIDRVASFSCMCPEGKAGLLCHLDDA

CISNPCHKGALCDTNPLNGQYTCTCPQGYKGADCTEDVDECAMANSNPCEHAGK

CVNTDGAFHCECLKGYAGPRCEMDINECHSDPCQNDATCLDKTGGFTCLCMPGF

KGVHCELEINECQSNPCVNNGQCVDKVNRFQCLCPPGFTGPVCQIDIDDCSSTP

CLNGAKCIDHPNGYECQCATGFTGVLCEENIDNCDPDPCHHGQCQDGIDSYTCI

CNPGYMGATCSDQIDECYSSPCLNDGRCIDLVNGYQCNCQPGTSGVNCEINFDD

CASNPCIHGTCMDGINRYSCVCSPGFTGQRCNIDIDECASNPCRKGATCINGVN

GFRCTCPEGPHHPSCYSQVNECLSNPCIHGNCTGGLSGYKCLCDAGWVGINCEV

DKNECLSNPCQNGGTCDNLVNGYRCTCKKGFKGYNCQVNIDECASNPCLNQGTC

FDDISGYTCHCVLPYTGKNCQTVLAPCSPNPCENAAVCKESPNFESYTCLCAPG

WQGQRCTIDIDECISKPCMNHGLCHNTQGSYMCECPPGFSGMDCEEDIDDCLAN

PCQNGGSCMDGVNTFSCLCLPGFTGDKCQTDMNECLSEPCKNGGTCSDYVNSYT

CKCQAGFDGVHCENNINECTESSCFNGGTCVDGINSFSCLCPVGFTGSFCLHEI

NECSSHPCLNEGTCVDGLGTYRCSCPLGYTGKNCQTLVNLCSRSPCKNKGTCVQ

KKAESQCLCPSGWAGAYCDVPNVSCDIAASRRGVLVEHLCQHSGVCINAGNTHY

CQCPLGYTGSYCEEQLDECASNPCQHGATCSDFTGGYRCECVPGYQGVNCEYEV

DECQNQPCQNGGTCIDLVNHFKCSCPPGTRGMKSSLSIFHPGHCLKL
```

-continued

Human neurogenic locus notch homolog protein 3 precursor NP_000426.2
(SEQ ID NO: 27)

```
MGPGARGRRRRRRPMSPPPPPPPVRALPLLLLLAGPGAAAPPCLDGSPCANGGR
CTQLPSREAACLCPPGWVGERCQLEDPCHSGPCAGRGVCQSSVVAGTARFSCRC
PRGFRGPDCSLPDPCLSSPCAHGARCSVGPDGRFLCSCPPGYQGRSCRSDVDEC
RVGEPCRHGGTCLNTPGSFRCQCPAGYTGPLCENPAVPCAPSPCRNGGTCRQSG
DLTYDCACLPGFEGQNCEVNVDDCPGHRCLNGGTCVDGVNTYNCQCPPEWTGQF
CTEDVDECQLQPNACHNGGTCFNTLGGHSCVCVNGWTGESCSQNIDDCATAVCF
HGATCHDRVASFYCACPMGKTGLLCHLDDACVSNPCHEDATCDTNPVNGRATCT
CPPGFTGGACDQDVDECSTGANPCEHLGRCVNTQGSFLCQCGRGYTGPRCETDV
NECLSGPCRNQATCLDRTGQFTCTCMAGFTGTYCEVDIDECQSSPCVNGGVCKD
RVNGFSCTCPSGFSGSTCQLDVDECASTPCRNGAKCVDQPDGYECRCAEGFEGT
LCDRNVDDCSPDPCHHGRCVDGIASFSCACAPGYTGTRCESQVDECRSQPCRHG
GKCLDLVDKYLCRCPSGTTGVNCEVNIDDCASNPCTFGVCRDGINRYDCVCQPG
FTGPLCNVEINECASSPCGEGGSCVDGENGFRCLCPPGSLPPLCLPPSHPCAHE
PCSHGTCYDAPGGFRCVCEPGWSGPRCSQSLARDACESQPCRAGGTCSSDGMGF
HCTCPPGVQGRQCELLSPCIPNPCEHGGRCESAPGQLPVCSCPQGWQGPRCQQD
VDECAGPAPCGPHGTCTNLAGSFSCTCHGGYTGPSCDQDINDCDPNPCLNGGSC
QDGVGSFSCSCLPGFAGPRCARDVDECLSNPCGPGTCTDHVASFTCTCPPGYGG
FHCEQDLPDCSPSSCFNGGTCVDGVNSFSCLCRPGYTGAHCQHEADPCLSRPCL
HGGVCSAAHPGFRCTCLESFTGPQCQTLVDWCSRQPCQNGGRCVQTGAYCLCPP
GWSGRLCDIRSLPCREAAAQTGVRLEQLCQAGGQCVDEDSSHYCVCPEGRTGSH
CEQEVDPCLAQPCQHGGTCRGYMGGYMCECLPGYNGDNCEDDVDECASQPCQHG
GSCIDLVARYLCSCPPGTLGVLCEINEDDCGPGPPLDSGPRCLHNGTCVDLVGG
FRCTCPPGYTGLRCEADINECRSGACHAAHTRDCLQDPGGGFRCLCHAGFSGPR
CQTVLSPCESQPCQHGGQCRPSPGPGGGLTFTCHCAQPFWGPRCERVARSCREL
QCPVGVPCQQTPRGPRCACPPGLSGPSCRSFPGSPPGASNASCAAAPCLHGGSC
RPAPLAPFFRCACAQGWTGPRCEAPAAAPEVSEEPRCPRAACQAKRGDQRCDRE
CNSPGCGWDGGDCSLSVGDPWRQCEALQCWRLFNNSRCDPACSSPACLYDNFDC
HAGGRERTCNPVYEKYCADHFADGRCDQGCNTEECGWDGLDCASEVPALLARGV
LVLTVLLPPEELLRSSADFLQRLSAILRTSLRFRLDAHGQAMVFPYHRPSPGSE
PRARRELAPEVTGSVVMLEIDNRLCLQSPENDHCFPDAQSAADYLGALSAVERL
DFPYPLRDVRGEPLEPPEPSVPLLPLLVAGAVLLLVILVLGVMVARRKREHSTL
WFPEGFSLHKDVASGHKGRREPVGQDALGMKNMAKGESLMGEVATDWMDTECPE
AKRLKVEEPGMGAEEAVDCRQWTQHHLVAADIRVAPAMALTPPQGDADADGMDV
NVRGPDGFTPLMLASFCGGALEPMPTEEDEADDTSASIISDLTCQGAQLGARTD
RTGETALHLAARYARADAAKRLLDAGADTNAQDHSGRTPLHTAVTADAQGVFQI
LIRNRSTDLDARMADGSTALILAARLAVEGMVEELIASHADVNAVDELGKSALH
WAAAVNNVEATLALLKNGANKDMQDSKEETPLFLAAREGSYEAAKLLLDHFANR
EITDHLDRLPRDVAQERLHQDIVRLLDQPSGPRSPPGPHGLGPLLCPPGAFLPG
LKAAQSGSKKSRRPPGKAGLGPQGPRGRGKKLTLACPGPLADSSVTLSPVDSLD
```

-continued

SPRPFGGPPASPGGFPLEGPYAAATATAVSLAQLGGPGRAGLGRQPPGGCVLSL

GLLNPVAVPLDWARLPPPAPPGPSFLLPLAPGPQLLNPGTPVSPQERPPPYLAV

PGHGEEYPAAGAHSSPPKARFLRVPSEHPYLTPSPESPEHWASPSPPSLSDWSE

STPSPATATGAMATTTGALPAQPLPLSVPSSLAQAQTQLGPQPEVTPKRQVLA

Human neurogenic locus notch homolog protein 4 preprotein NP_004548.3
(SEQ ID NO: 28)

MQPPSLLLLLLLLLLLCVSVVRPRGLLCGSFPEPCANGGTCLSLSLGQGTCQCA

PGFLGETCQFPDPCQNAQLCQNGGSCQALLPAPLGLPSSPSPLTPSFLCTCLPG

FTGERCQAKLEDPCPPSFCSKRGRCHIQASGRPQCSCMPGWTGEQCQLRDFCSA

NPCVNGGVCLATYPQIQCHCPPGFEGHACERDVNECFQDPGPCPKGTSCHNTLG

SFQCLCPVGQEGPRCELRAGPCPPRGCSNGGTCQLMPEKDSTFHLCLCPPGFTG

PDCEVNPDNCVSHQCQNGGTCQDGLDTYTCLCPETWTGWDCSEDVDECETQGPP

HCRNGGTCQNSAGSFHCVCVSGWGGTSCEENLDDCIAATCAPGSTCIDRVGSFS

CLCPPGRTGLLCHLEDMCLSQPCHGDAQCSTNPLTGSTLCLCQPGYSGPTCHQD

LDECLMAQQGPSPCEHGGSCLNTPGSFNCLCPPGYTGSRCEADHNECLSQPCHP

GSTCLDLLATFHCLCPPGLEGQLCEVETNECASAPCLNHADCHDLLNGFQCTCL

PGFSGTRCEEDIDECRSSPCANGGQCQDQPGAFHCKCLPGFEGPRCQTEVDECL

SDPCPVGASCLDLPGAFFCLCPSGFTGQLCEVPLCAPNLCQPKQTCKDQKDKAN

CLCPDGSPGCAPPEDNCTCHHGHCQRSSCVCDVGWTGPECEAELGGCISAPCAH

GGTCYPQPSGYNCTCPTGYTGPTCSEEMTACHSGPCLNGGSCNPSPGGYYCTCP

PSHTGPQCQTSTDYCVSAPCFNGGTCVNRPGTFSCLCAMGFQGPRCEGKLRPSC

ADSPCRNRATCQDSPQGPRCLCPTGYTGGSCQTLMDLCAQKPCPRNSHCLQTGP

SFHCLCLQGWTGPLCNLPLSSCQKAALSQGIDVSSLCHNGGLCVDSGPSYFCHC

PPGFQGSLCQDHVNPCESRPCQNGATCMAQPSGYLCQCAPGYDGQNCSKELDAC

QSQPCHNHGTCTPKPGGFHCACPPGFVGLRCEGDVDECLDQPCHPTGTAACHSL

ANAFYCQCLPGHTGQWCEVEIDPCHSQPCFHGGTCEATAGSPLGFTCHCPKGFE

GPTCSHRAPSCGFHHCHHGGLCLPSPKPGFPPRCACLSGYGGPDCLTPPAPKGC

GPPSPCLYNGSCSETTGLGGPGFRCSCPHSSPGPRCQKPGAKGCEGRSGDGACD

AGCSGPGGNWDGGDCSLGVPDPWKGCPSHSRCWLLFRDGQCHPQCDSEECLFDG

YDCETPPACTPAYDQYCHDHFHNGHCEKGCNTAECGWDGGDCRPEDGDPEWGPS

LALLVVLSPPALDQQLFALARVLSLTLRVGLWVRKDRDGRDMVYPYPGARAEEK

LGGIRDPTYQERAAPQTQPLGKETDSLSAGFVVVMGVDLSRCGPDHPASRCPWD

PGLLLRFLAAMAAVGALEPLLPGPLLAVHPHAGTAPPANQLPWPVLCSPVAGVI

LLALGALLVLQLIRRRREHGALWLPPGFTRRPRTQSAPHRRRPPLGEDSTGLK

ALKPKAEVDEDGVVMCSGPEEGEEVGQAEETGPPSTCQLWSLSGGCGALPQAAM

LIPPQESEMEAPDLDTRGPDGVTPLMSAVCCGEVQSGTFQGAWLGCPEPWEPLL

DGGACPQAHTVGTGETPLHLAARFSRPTAARRLLEAGANPNQPDRAGRTPLHAA

VAADAREVCQLLLRSRQTAVDARTEDGTTPLMLAARLAVEDLVEELIAAQADVG

ARDKWGKTALHWAAAVNNARAARSLLQAGADKDAQDNREQTPLFLAAREGAVEV

AQLLLGLGAARELRDQAGLAPADVAHQRNHWDLLTLLEGAGPPEARHKATPGRE

AGPFPRARTVSVSVPPHGGGALPRCRTLSAGAGPRGGGACLQARTWSVDLAARG

GGAYSHCRSLSGVGAGGGPTPRGRRFSAGMRGPRPNPAIMRGRYGVAAGRGGRV

-continued

```
STDDWPCDWVALGACGSASNIPIPPPCLTPSPERGSPQLDCGPPALQEMPINQG

GEGKK
```

In some embodiments, the Notch core of the chimeric Notch receptor polypeptide contains a portion of SEQ ID NO: 24, SEQ ID NO: 25, SEQ ID NO: 26, SEQ ID NO: 27, or SEQ ID NO: 28. In some embodiments, the chimeric Notch receptor polypeptide contains 50 to 1000 amino acids of SEQ ID NO: 24, SEQ ID NO: 25, SEQ ID NO: 26, SEQ ID NO: 27, or SEQ ID NO: 28. In some embodiments, the chimeric Notch receptor polypeptide contains 50 to 900 amino acids, 100 to 800 amino acids, 200 to 700 amino acids, 300 to 600 amino acids, 400 to 500 amino acids of SEQ ID NO: 24, SEQ ID NO: 25, SEQ ID NO: 26, SEQ ID NO: 27, or SEQ ID NO: 28. In some embodiments, the chimeric Notch receptor polypeptide contains amino acids 1374 to 1734 of SEQ ID NO: 27.

In some embodiments, the amino acid sequence of Notch, as described herein, is at least 80% identical to a corresponding amino acid sequence in SEQ ID NO: 24, SEQ ID NO: 25, SEQ ID NO: 26, SEQ ID NO: 27, or SEQ ID NO: 28. In some embodiments, the amino acid sequence of Notch is 80%, 81%, 82%, 83%, 84%, 85%, 86%, 87%, 88%, 89%, 90%, 91%, 92%, 93%, 94%, 95%, 96%, 97%, 98%, or 99% identical to a corresponding amino acid sequence in SEQ ID NO: 24, SEQ ID NO: 25, SEQ ID NO: 26, SEQ ID NO: 27, or SEQ ID NO: 28. In some embodiments, the amino acid sequence of Notch, as described herein, can vary from the amino acid sequence of SEQ ID NO: 24, SEQ ID NO: 25, SEQ ID NO: 26, SEQ ID NO: 27, or SEQ ID NO: 28 by 1 to 50 amino acids, e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 amino acids.

In some embodiments, the mRNA sequence of Notch, as described herein, is SEQ ID NO: 29, SEQ ID NO: 30, SEQ ID NO: 31, SEQ ID NO: 32, or SEQ ID NO: 33.

```
Human notch 1 (NOTCH1) mRNA NM_017617.4
                                                   (SEQ ID NO: 29)
ATGCCGCCGCTCCTGGCGCCCCTGCTCTGCCTGGCGCTGCTGCCCGCGCTCGCC

GCACGAGGCCCGCGATGCTCCCAGCCCGGTGAGACCTGCCTGAATGGCGGGAAG

TGTGAAGCGGCCAATGGCACGGAGGCCTGCGTCTGTGGCGGGGCCTTCGTGGGC

CCGCGATGCCAGGACCCCAACCCGTGCCTCAGCACCCCCTGCAAGAACGCCGGG

ACATGCCACGTGGTGGACCGCAGAGGCGTGGCAGACTATGCCTGCAGCTGTGCC

CTGGGCTTCTCTGGGCCCCTCTGCCTGACACCCCTGGACAATGCCTGCCTCACC

AACCCCTGCCGCAACGGGGGCACCTGCGACCTGCTCACGCTGACGGAGTACAAG

TGCCGCTGCCCGCCCGGCTGGTCAGGGAAATCGTGCCAGCAGGCTGACCCGTGC

GCCTCCAACCCCTGCGCCAACGGTGGCCAGTGCCTGCCCTTCGAGGCCTCCTAC

ATCTGCCACTGCCCACCCAGCTTCCATGGCCCCACCTGCCGGCAGGATGTCAAC

GAGTGTGGCCAGAAGCCCGGGCTTTGCCGCCACGGAGGCACCTGCCACAACGAG

GTCGGCTCCTACCGCTGCGTCTGCCGCGCCACCCACACTGGCCCCAACTGCGAG

CGGCCCTACGTGCCCTGCAGCCCCTCGCCCTGCCAGAACGGGGGCACCTGCCGC

CCCACGGGCGACGTCACCCACGAGTGTGCCTGCCTGCCAGGCTTCACCGGCCAG

AACTGTGAGGAAAATATCGACGATTGTCCAGGAAACAACTGCAAGAACGGGGGT

GCCTGTGTGGACGGCGTGAACACCTACAACTGCCGCTGCCCGCCAGAGTGGACA

GGTCAGTACTGTACCGAGGATGTGGACGAGTGCCAGCTGATGCCAAATGCCTGC

CAGAACGGCGGGACCTGCCACAACACCCACGGTGGCTACAACTGCGTGTGTGTC

AACGGCTGGACTGGTGAGGACTGCAGCGAGAACATTGATGACTGTGCCAGCGCC

GCCTGCTTCCACGGCGCCACCTGCCATGACCGTGTGGCCTCCTTCTACTGCGAG

TGTCCCCATGGCCGCACAGGTCTGCTGTGCCACCTCAACGACGCATGCATCAGC

AACCCCTGTAACGAGGGCTCCAACTGCGACACCAACCCTGTCAATGGCAAGGCC

ATCTGCACCTGCCCCTCGGGGTACACGGGCCCGGCCTGCAGCCAGGACGTGGAT

GAGTGCTCGCTGGGTGCCAACCCCTGCGAGCATGCGGGCAAGTGCATCAACACG

CTGGGCTCCTTCGAGTGCCAGTGTCTGCAGGGCTACACGGGCCCCCGATGCGAG
```

-continued

```
ATCGACGTCAACGAGTGCGTCTCGAACCCGTGCCAGAACGACGCCACCTGCCTG

GACCAGATTGGGGAGTTCCAGTGCATCTGCATGCCCGGCTACGAGGGTGTGCAC

TGCGAGGTCAACACAGACGAGTGTGCCAGCAGCCCCTGCCTGCACAATGGCCGC

TGCCTGGACAAGATCAATGAGTTCCAGTGCGAGTGCCCCACGGGCTTCACTGGG

CATCTGTGCCAGTACGATGTGGACGAGTGTGCCAGCACCCCTGCAAGAATGGT

GCCAAGTGCCTGGACGGACCCAACACTTACACCTGTGTGTGCACGGAAGGGTAC

ACGGGGACGCACTGCGAGGTGGACATCGATGAGTGCGACCCCGACCCCTGCCAC

TACGGCTCCTGCAAGGACGGCGTCGCCACCTTCACCTGCCTCTGCCGCCCAGGC

TACACGGGCCACCACTGCGAGACCAACATCAACGAGTGCTCCAGCCAGCCCTGC

CGCCACGGGGGCACCTGCCAGGACCGCGACAACGCCTACCTCTGCTTCTGCCTG

AAGGGGACCACAGGACCCAACTGCGAGATCAACCTGGATGACTGTGCCAGCAGC

CCCTGCGACTCGGGCACCTGTCTGGACAAGATCGATGGCTACGAGTGTGCCTGT

GAGCCGGGCTACACAGGGAGCATGTGTAACATCAACATCGATGAGTGTGCGGGC

AACCCCTGCCACAACGGGGGCACCTGCGAGGACGGCATCAATGGCTTCACCTGC

CGCTGCCCCGAGGGCTACCACGACCCCACCTGCCTGTCTGAGGTCAATGAGTGC

AACAGCAACCCCTGCGTCCACGGGGCCTGCCGGGACAGCCTCAACGGGTACAAG

TGCGACTGTGACCCTGGGTGGAGTGGGACCAACTGTGACATCAACAACAATGAG

TGTGAATCCAACCCTTGTGTCAACGGCGGCACCTGCAAAGACATGACCAGTGGC

TACGTGTGCACCTGCCGGGAGGGCTTCAGCGGTCCCAACTGCCAGACCAACATC

AACGAGTGTGCGTCCAACCCATGTCTGAACCAGGGCACGTGTATTGACGACGTT

GCCGGGTACAAGTGCAACTGCCTGCTGCCCTACACAGGTGCCACGTGTGAGGTG

GTGCTGGCCCCGTGTGCCCCCAGCCCCTGCAGAAACGGCGGGGAGTGCAGGCAA

TCCGAGGACTATGAGAGCTTCTCCTGTGTCTGCCCCACGGGCTGGCAAGGGCAG

ACCTGTGAGGTCGACATCAACGAGTGCGTTCTGAGCCCGTGCCGGCACGGCGCA

TCCTGCCAGAACACCCACGGCGGCTACCGCTGCCACTGCCAGGCCGGCTACAGT

GGGCGCAACTGCGAGACCGACATCGACGACTGCCGGCCCAACCCGTGTCACAAC

GGGGGCTCCTGCACAGACGGCATCAACACGGCCTTCTGCGACTGCCTGCCCGGC

TTCCGGGGCACTTTCTGTGAGGAGGACATCAACGAGTGTGCCAGTGACCCCTGC

CGCAACGGGGCCAACTGCACGGACTGCGTGGACAGCTACACGTGCACCTGCCCC

GCAGGCTTCAGCGGGATCCACTGTGAGAACAACACGCCTGACTGCACAGAGAGC

TCCTGCTTCAACGGTGGCACCTGCGTGGACGGCATCAACTCGTTCACCTGCCTG

TGTCCACCCGGCTTCACGGGCAGCTACTGCCAGCACGATGTCAATGAGTGCGAC

TCACAGCCCTGCCTGCATGGCGGCACCTGTCAGGACGGCTGCGGCTCCTACAGG

TGCACCTGCCCCCAGGGCTACACTGGCCCCAACTGCCAGAACCTTGTGCACTGG

TGTGACTCCTCGCCCTGCAAGAACGGCGGCAAATGCTGGCAGACCCACACCCAG

TACCGCTGCGAGTGCCCCAGCGGCTGGACCGGCCTTTACTGCGACGTGCCCAGC

GTGTCCTGTGAGGTGGCTGCGCAGCGACAAGGTGTTGACGTTGCCCGCCTGTGC

CAGCATGGAGGGCTCTGTGTGGACGCGGGCAACACGCACCACTGCCGCTGCCAG

GCGGGCTACACAGGCAGCTACTGTGAGGACCTGGTGGACGAGTGCTCACCCAGC

CCCTGCCAGAACGGGGCCACCTGCACGGACTACCTGGGCGGCTACTCCTGCAAG

TGCGTGGCCGGCTACCACGGGGTGAACTGCTCTGAGGAGATCGACGAGTGCCTC
```

-continued

```
TCCCACCCCTGCCAGAACGGGGGCACCTGCCTCGACCTCCCCAACACCTACAAG

TGCTCCTGCCCACGGGGCACTCAGGGTGTGCACTGTGAGATCAACGTGGACGAC

TGCAATCCCCCCGTTGACCCCGTGTCCCGGAGCCCCAAGTGCTTTAACAACGGC

ACCTGCGTGGACCAGGTGGGCGGCTACAGCTGCACCTGCCCGCCGGGCTTCGTG

GGTGAGCGCTGTGAGGGGATGTCAACGAGTGCCTGTCCAATCCCTGCGACGCC

CGTGGCACCCAGAACTGCGTGCAGCGCGTCAATGACTTCCACTGCGAGTGCCGT

GCTGGTCACACCGGGCGCCGCTGCGAGTCCGTCATCAATGGCTGCAAAGGCAAG

CCCTGCAAGAATGGGGGCACCTGCGCCGTGGCCTCCAACACCGCCCGCGGGTTC

ATCTGCAAGTGCCCTGCGGGCTTCGAGGGCGCCACGTGTGAGAATGACGCTCGT

ACCTGCGGCAGCCTGCGCTGCCTCAACGGCGGCACATGCATCTCCGGCCCGCGC

AGCCCCACCTGCCTGTGCCTGGGCCCCTTCACGGGCCCCGAATGCCAGTTCCCG

GCCAGCAGCCCTGCCTGGGCGGCAACCCCTGCTACAACCAGGGGACCTGTGAG

CCCACATCCGAGAGCCCCTTCTACCGTTGCCTGTGCCCCGCCAAATTCAACGGG

CTCTTGTGCCACATCCTGGACTACAGCTTCGGGGGTGGGGCCGGGCGCGACATC

CCCCCGCCGCTGATCGAGGAGGCGTGCGAGCTGCCCGAGTGCCAGGAGGACGCG

GGCAACAAGGTCTGCAGCCTGCAGTGCAACAACCACGCGTGCGGCTGGGACGGC

GGTGACTGCTCCCTCAACTTCAATGACCCCTGGAAGAACTGCACGCAGTCTCTG

CAGTGCTGGAAGTACTTCAGTGACGGCCACTGTGACAGCCAGTGCAACTCAGCC

GGCTGCCTCTTCGACGGCTTTGACTGCCAGCGTGCGGAAGGCCAGTGCAACCCC

CTGTACGACCAGTACTGCAAGGACCACTTCAGCGACGGGCACTGCGACCAGGGC

TGCAACAGCGCGGAGTGCGAGTGGGACGGGCTGGACTGTGCGGAGCATGTACCC

GAGAGGCTGGCGGCCGGCACGCTGGTGGTGGTGGTGCTGATGCCGCCGGAGCAG

CTGCGCAACAGCTCCTTCCACTTCCTGCGGGAGCTCAGCCGCGTGCTGCACACC

AACGTGGTCTTCAAGCGTGACGCACACGGCCAGCAGATGATCTTCCCCTACTAC

GGCCGCGAGGAGGAGCTGCGCAAGCACCCCATCAAGCGTGCCGCCGAGGGCTGG

GCCGCACCTGACGCCCTGCTGGGCCAGGTGAAGGCCTCGCTGCTCCCTGGTGGC

AGCGAGGGTGGGCGGCGGCGGAGGGAGCTGGACCCCATGGACGTCCGCGGCTCC

ATCGTCTACCTGGAGATTGACAACCGGCAGTGTGTGCAGGCCTCCTCGCAGTGC

TTCCAGAGTGCCACCGACGTGGCCGCATTCCTGGGAGCGCTCGCCTCGCTGGGC

AGCCTCAACATCCCCTACAAGATCGAGGCCGTGCAGAGTGAGACCGTGGAGCCG

CCCCCGCCGGCGCAGCTGCACTTCATGTACGTGGCGGCGGCCGCCTTTGTGCTT

CTGTTCTTCGTGGGCTGCGGGGTGCTGCTGTCCCGCAAGCGCCGGCGGCAGCAT

GGCCAGCTCTGGTTCCCTGAGGGCTTCAAAGTGTCTGAGGCCAGCAAGAAGAAG

CGGCGGGAGCCCCTCGGCGAGGACTCCGTGGGCCTCAAGCCCCTGAAGAACGCT

TCAGACGGTGCCCTCATGGACGACAACCAGAATGAGTGGGGGGACGAGGACCTG

GAGACCAAGAAGTTCCGGTTCGAGGAGCCCGTGGTTCTGCCTGACCTGGACGAC

CAGACAGACCACCGGCAGTGGACTCAGCAGCACCTGGATGCCGCTGACCTGCGC

ATGTCTGCCATGGCCCCACACCGCCCCAGGGTGAGGTTGACGCCGACTGCATG

GACGTCAATGTCCGCGGGCCTGATGGCTTCACCCCGCTCATGATCGCCTCCTGC

AGCGGGGCGGCCTGGAGACGGGCAACAGCGAGGAAGAGGAGGACGCGCCGGCC
```

-continued

```
GTCATCTCCGACTTCATCTACCAGGGCGCCAGCCTGCACAACCAGACAGACCGC
ACGGGCGAGACCGCCTTGCACCTGGCCGCCCGCTACTCACGCTCTGATGCCGCC
AAGCGCCTGCTGGAGGCCAGCGCAGATGCCAACATCCAGGACAACATGGGCCGC
ACCCCGCTGCATGCGGCTGTGTCTGCCGACGCACAAGGTGTCTTCCAGATCCTG
ATCCGGAACCGAGCCACAGACCTGGATGCCCGCATGCATGATGGCACGACGCCA
CTGATCCTGGCTGCCCGCCTGGCCGTGGAGGGCATGCTGGAGGACCTCATCAAC
TCACACGCCGACGTCAACGCCGTAGATGACCTGGGCAAGTCCGCCCTGCACTGG
GCCGCCGCCGTGAACAATGTGGATGCCGCAGTTGTGCTCCTGAAGAACGGGGCT
AACAAAGATATGCAGAACAACAGGGAGGAGACACCCCTGTTTCTGGCCGCCCGG
GAGGGCAGCTACGAGACCGCCAAGGTGCTGCTGGACCACTTTGCCAACCGGGAC
ATCACGGATCATATGGACCGCCTGCCGCGCGACATCGCACAGGAGCGCATGCAT
CACGACATCGTGAGGCTGCTGGACGAGTACAACCTGGTGCGCAGCCCGCAGCTG
CACGGAGCCCCGCTGGGGGGCACGCCCACCCTGTCGCCCCCGCTCTGCTCGCCC
AACGGCTACCTGGGCAGCCTCAAGCCCGGCGTGCAGGGCAAGAAGGTCCGCAAG
CCCAGCAGCAAAGGCCTGGCCTGTGGAAGCAAGGAGGCCAAGGACCTCAAGGCA
CGGAGGAAGAAGTCCCAGGACGGCAAGGGCTGCCTGCTGGACAGCTCCGGCATG
CTCTCGCCCGTGGACTCCCTGGAGTCACCCCATGGCTACCTGTCAGACGTGGCC
TCGCCGCCACTGCTGCCCTCCCCGTTCCAGCAGTCTCCGTCCGTGCCCCTCAAC
CACCTGCCTGGGATGCCCGACACCCACCTGGGCATCGGGCACCTGAACGTGGCG
GCCAAGCCCGAGATGGCGGCGCTGGGTGGGGCGGCCGGCTGGCCTTTGAGACT
GGCCCACCTCGTCTCTCCCACCTGCCTGTGGCCTCTGGCACCAGCACCGTCCTG
GGCTCCAGCAGCGGAGGGGCCCTGAATTTCACTGTGGGCGGGTCCACCAGTTTG
AATGGTCAATGCGAGTGGCTGTCCCGGCTGCAGAGCGGCATGGTGCCGAACCAA
TACAACCCTCTGCGGGGAGTGTGGCACCAGGCCCCCTGAGCACACAGGCCCCC
TCCCTGCAGCATGGCATGGTAGGCCCGCTGCACAGTAGCCTTGCTGCCAGCGCC
CTGTCCCAGATGATGAGCTACCAGGGCCTGCCCAGCACCCGGCTGGCCACCCAG
CCTCACCTGGTGCAGACCCAGCAGGTGCAGCCACAAAACTTACAGATGCAGCAG
CAGAACCTGCAGCCAGCAAACATCCAGCAGCAGCAAAGCCTGCAGCCGCCACCA
CCACCACCACAGCCGCACCTTGGCGTGAGCTCAGCAGCCAGCGGCCACCTGGGC
CGGAGCTTCCTGAGTGGAGAGCCGAGCCAGGCAGACGTGCAGCCACTGGGCCCC
AGCAGCTGGCGGTGCACACTATTCTGCCCCAGGAGAGCCCCGCCCTGCCCACG
TCGCTGCCATCCTCGCTGGTCCCACCCGTGACCGCAGCCCAGTTCCTGACGCCC
CCCTCGCAGCACAGCTACTCCTCGCCTGTGGACAACACCCCCAGCCACCAGCTA
CAGGTGCCTGAGCACCCCTTCCTCACCCCGTCCCCTGAGTCCCCTGACCAGTGG
TCCAGCTCGTCCCCGCATTCCAACGTCTCCGACTGGTCCGAGGGCGTCTCCAGC
CCTCCCACCAGCATGCAGTCCCAGATCGCCCGCATTCCGGAGGCCTTCAAGTAA
ACGGCGCGCCCCACGAGACCCCGGCTTCCTTTCCCAAGCCTTCGGGCGTCTGTG
TGCGCTCTGTGGATGCCAGGGCCGACCAGAGGAGCCTTTTTAAAACACATGTTT
TTATACAAAATAAGAACGAGGATTTTAATTTTTTTTAGTATTTATTTATGTACT
TTTTATTTTACACAGAAACACTGCCTTTTTATTTATATGTACTGTTTTATCTGGC
CCCAGGTAGAAACTTTTATCTATTCTGAGAAAACAAGCAAGTTCTGAGAGCCAG
```

-continued

```
GGTTTTCCTACGTAGGATGAAAAGATTCTTCTGTGTTTATAAAATATAAACAAA

GATTCATGATTTATAAATGCCATTTATTTATTGATTCCTTTTTTCAAAATCCAA

AAAGAAATGATGTTGGAGAAGGGAAGTTGAACGAGCATAGTCCAAAAAGCTCCT

GGGGCGTCCAGGCCGCGCCCTTTCCCCGACGCCCACCCAACCCCAAGCCAGCCC

GGCCGCTCCACCAGCATCACCTGCCTGTTAGGAGAAGCTGCATCCAGAGGCAAA

CGGAGGCAAAGCTGGCTCACCTTCCGCACGCGGATTAATTTGCATCTGAAATAG

GAAACAAGTGAAAGCATATGGGTTAGATGTTGCCATGTGTTTTAGATGGTTTCT

TGCAAGCATGCTTGTGAAAATGTGTTCTCGGAGTGTGTATGCCAAGAGTGCACC

CATGGTACCAATCATGAATCTTTGTTTCAGGTTCAGTATTATGTAGTTGTTCGT

TGGTTATACAAGTTCTTGGTCCCTCCAGAACCACCCCGGCCCCCTGCCCGTTCT

TGAAATGTAGGCATCATGCATGTCAAACATGAGATGTGTGGACTGTGGCACTTG

CCTGGGTCACACACGGAGGCATCCTACCCTTTTCTGGGGAAAGACACTGCCTGG

GCTGACCCCGGTGGCGGCCCCAGCACCTCAGCCTGCACAGTGTCCCCCAGGTTC

CGAAGAAGATGCTCCAGCAACACAGCCTGGGCCCCAGCTCGCGGGACCCGACCC

CCCGTGGGCTCCCGTGTTTTGTAGGAGACTTGCCAGAGCCGGGCACATTGAGCT

GTGCAACGCCGTGGGCTGCGTCCTTTGGTCCTGTCCCCGCAGCCCTGGCAGGGG

GCATGCGGTCGGGCAGGGGCTGGAGGGAGGCGGGGCTGCCCTTGGGCCACCCC

TCCTAGTTTGGGAGGAGCAGATTTTTGCAATACCAAGTATAGCCTATGGCAGAA

AAAATGTCTGTAAATATGTTTTTAAAGGTGGATTTTGTTTAAAAAATCTTAATG

AATGAGTCTGTTGTGTGTCATGCCAGTGAGGGACGTCAGACTTGGCTCAGCTCG

GGGAGCCTTAGCCGCCCATGCACTGGGGACGCTCCGCTGCCGTGCCGCCTGCAC

TCCTCAGGGCAGCCTCCCCCGGCTCTACGGGGCCGCGTGGTGCCATCCCCAGG

GGGCATGACCAGATGCGTCCCAAGATGTTGATTTTTACTGTGTTTTATAAAATA

GAGTGTAGTTTACAGAAAAAGACTTTAAAAGTGATCTACATGAGGAACTGTAGA

TGATGTATTTTTTTCATCTTTTTTGTTAACTGATTTGCAATAAAAATGATACTG

ATGGTGATCTGGCTTCAAAAAAAAAAAAAAAAA
```

Human notch 2 (NOTCH2), transcript variant 1, mRNA NM_024408.3
(SEQ ID NO: 30)

```
GCTTGCGGTGGGAGGAGGCGGCTGAGGCGGAAGGACACACGAGGCTGCTTCGTT

GCACACCCGAGAAAGTTTCAGCCAAACTTCGGGCGGCGGCTGAGGCGGCGGCCG

AGGAGCGGCGGACTCGGGGCGCGGGGAGTCGAGGCATTTGCGCCTGGGCTTCGG

AGCGTAGCGCCAGGGCCTGAGCCTTTGAAGCAGGAGGAGGGGAGGAGAGAGTGG

GGCTCCTCTATCGGGACCCCCTCCCCATGTGGATCTGCCCAGGCGGCGGCGGCG

GCGGCGGAGGAGGAGGCGACCGAGAAGATGCCCGCCCTGCGCCCCGCTCTGCTG

TGGGCGCTGCTGGCGCTCTGGCTGTGCTGCGCGGCCCCCGCGCATGCATTGCAG

TGTCGAGATGGCTATGAACCCTGTGTAAATGAAGGAATGTGTGTTACCTACCAC

AATGGCACAGGATACTGCAAATGTCCAGAAGGCTTCTTGGGGGAATATTGTCAA

CATCGAGACCCCTGTGAGAAGAACCGCTGCCAGAATGGTGGGACTTGTGTGGCC

CAGGCCATGCTGGGGAAAGCCACGTGCCGATGTGCCTCAGGGTTTACAGGAGAG

GACTGCCAGTACTCAACATCTCATCCATGCTTTGTGTCTCGACCCTGCCTGAAT

GGCGGCACATGCCATATGCTCAGCCGGGATACCTATGAGTGCACCTGTCAAGTC
```

-continued

```
GGGTTTACAGGTAAGGAGTGCCAATGGACGGATGCCTGCCTGTCTCATCCCTGT

GCAAATGGAAGTACCTGTACCACTGTGGCCAACCAGTTCTCCTGCAAATGCCTC

ACAGGCTTCACAGGGCAGAAATGTGAGACTGATGTCAATGAGTGTGACATTCCA

GGACACTGCCAGCATGGTGGCACCTGCCTCAACCTGCCTGGTTCCTACCAGTGC

CAGTGCCCTCAGGGCTTCACAGGCCAGTACTGTGACAGCCTGTATGTGCCCTGT

GCACCCTCACCTTGTGTCAATGGAGGCACCTGTCGGCAGACTGGTGACTTCACT

TTTGAGTGCAACTGCCTTCCAGGTTTTGAAGGGAGCACCTGTGAGAGGAATATT

GATGACTGCCCTAACCACAGGTGTCAGAATGGAGGGGTTTGTGTGGATGGGGTC

AACACTTACAACTGCCGCTGTCCCCCACAATGGACAGGACAGTTCTGCACAGAG

GATGTGGATGAATGCCTGCTGCAGCCCAATGCCTGTCAAAATGGGGCACCTGT

GCCAACCGCAATGGAGGCTATGGCTGTGTATGTGTCAACGGCTGGAGTGGAGAT

GACTGCAGTGAGAACATTGATGATTGTGCCTTCGCCTCCTGTACTCCAGGCTCC

ACCTGCATCGACCGTGTGGCCTCCTTCTCTTGCATGTGCCCAGAGGGGAAGGCA

GGTCTCCTGTGTCATCTGGATGATGCATGCATCAGCAATCCTTGCCACAAGGGG

GCACTGTGTGACACCAACCCCCTAAATGGGCAATATATTTGCACCTGCCCACAA

GGCTACAAAGGGGCTGACTGCACAGAAGATGTGGATGAATGTGCCATGGCCAAT

AGCAATCCTTGTGAGCATGCAGGAAAATGTGTGAACACGGATGGCGCCTTCCAC

TGTGAGTGTCTGAAGGGTTATGCAGGACCTCGTTGTGAGATGGACATCAATGAG

TGCCATTCAGACCCCTGCCAGAATGATGCTACCTGTCTGGATAAGATTGGAGGC

TTCACATGTCTGTGCATGCCAGGTTTCAAAGGTGTGCATTGTGAATTAGAAATA

AATGAATGTCAGAGCAACCCTTGTGTGAACAATGGGCAGTGTGTGGATAAAGTC

AATCGTTTCCAGTGCCTGTGTCCTCCTGGTTTCACTGGGCCAGTTTGCCAGATT

GATATTGATGACTGTTCCAGTACTCCGTGTCTGAATGGGGCAAAGTGTATCGAT

CACCCGAATGGCTATGAATGCCAGTGTGCCACAGGTTTCACTGGTGTGTTGTGT

GAGGAGAACATTGACAACTGTGACCCCGATCCTTGCCACCATGGTCAGTGTCAG

GATGGTATTGATTCCTACACCTGCATCTGCAATCCCGGGTACATGGGCGCCATC

TGCAGTGACCAGATTGATGAATGTTACAGCAGCCCTTGCCTGAACGATGGTCGC

TGCATTGACCTGGTCAATGGCTACCAGTGCAACTGCCAGCCAGGCACGTCAGGG

GTTAATTGTGAAATTAATTTTGATGACTGTGCAAGTAACCCTTGTATCCATGGA

ATCTGTATGGATGGCATTAATCGCTACAGTTGTGTCTGCTCACCAGGATTCACA

GGGCAGAGATGTAACATTGACATTGATGAGTGTGCCTCCAATCCCTGTCGCAAG

GGTGCAACATGTATCAACGGTGTGAATGGTTTCCGCTGTATATGCCCCGAGGGA

CCCCATCACCCCAGCTGCTACTCACAGGTGAACGAATGCCTGAGCAATCCCTGC

ATCCATGGAAACTGTACTGGAGGTCTCAGTGGATATAAGTGTCTCTGTGATGCA

GGCTGGGTTGGCATCAACTGTGAAGTGGACAAAAATGAATGCCTTTCGAATCCA

TGCCAGAATGGAGGAACTTGTGACAATCTGGTGAATGGATACAGGTGTACTTGC

AAGAAGGGCTTTAAAGGCTATAACTGCCAGGTGAATATTGATGAATGTGCCTCA

AATCCATGCCTGAACCAAGGAACCTGCTTTGATGACATAAGTGGCTACACTTGC

CACTGTGTGCTGCCATACACAGGCAAGAATTGTCAGACAGTATTGGCTCCCTGT

TCCCCAAACCCTTGTGAGAATGCTGCTGTTTGCAAAGAGTCACCAAATTTTGAG

AGTTATACTTGCTTGTGTGCTCCTGGCTGGCAAGGTCAGCGGTGTACCATTGAC
```

-continued

```
ATTGACGAGTGTATCTCCAAGCCCTGCATGAACCATGGTCTCTGCCATAACACC

CAGGGCAGCTACATGTGTGAATGTCCACCAGGCTTCAGTGGTATGGACTGTGAG

GAGGACATTGATGACTGCCTTGCCAATCCTTGCCAGAATGGAGGTTCCTGTATG

GATGGAGTGAATACTTTCTCCTGCCTCTGCCTTCCGGGTTTCACTGGGGATAAG

TGCCAGACAGACATGAATGAGTGTCTGAGTGAACCCTGTAAGAATGGAGGGACC

TGCTCTGACTACGTCAACAGTTACACTTGCAAGTGCCAGGCAGGATTTGATGGA

GTCCATTGTGAGAACAACATCAATGAGTGCACTGAGAGCTCCTGTTTCAATGGT

GGCACATGTGTTGATGGGATTAACTCCTTCTCTTGCTTGTGCCCTGTGGGTTTC

ACTGGATCCTTCTGCCTCCATGAGATCAATGAATGCAGCTCTCATCCATGCCTG

AATGAGGGAACGTGTGTTGATGGCCTGGGTACCTACCGCTGCAGCTGCCCCCTG

GGCTACACTGGGAAAAACTGTCAGACCCTGGTGAATCTCTGCAGTCGGTCTCCA

TGTAAAAACAAAGGTACTTGCGTTCAGAAAAAAGCAGAGTCCCAGTGCCTATGT

CCATCTGGATGGGCTGGTGCCTATTGTGACGTGCCCAATGTCTCTTGTGACATA

GCAGCCTCCAGGAGAGGTGTGCTTGTTGAACACTTGTGCCAGCACTCAGGTGTC

TGCATCAATGCTGGCAACACGCATTACTGTCAGTGCCCCCTGGGCTATACTGGG

AGCTACTGTGAGGAGCAACTCGATGAGTGTGCGTCCAACCCCTGCCAGCACGGG

GCAACATGCAGTGACTTCATTGGTGGATACAGATGCGAGTGTGTCCCAGGCTAT

CAGGGTGTCAACTGTGAGTATGAAGTGGATGAGTGCCAGAATCAGCCCTGCCAG

AATGGAGGCACCTGTATTGACCTTGTGAACCATTTCAAGTGCTCTTGCCCACCA

GGCACTCGGGGCCTACTCTGTGAAGAGAACATTGATGACTGTGCCCGGGGTCCC

CATTGCCTTAATGGTGGTCAGTGCATGGATAGGATTGGAGGCTACAGTTGTCGC

TGCTTGCCTGGCTTTGCTGGGGAGCGTTGTGAGGGAGACATCAACGAGTGCCTC

TCCAACCCCTGCAGCTCTGAGGGCAGCCTGGACTGTATACAGCTCACCAATGAC

TACCTGTGTGTTTGCCGTAGTGCCTTTACTGGCCGGCACTGTGAAACCTTCGTC

GATGTGTGTCCCCAGATGCCCTGCCTGAATGGAGGGACTTGTGCTGTGGCCAGT

AACATGCCTGATGGTTTCATTTGCCGTTGTCCCCCGGGATTTTCCGGGGCAAGG

TGCCAGAGCAGCTGTGGACAAGTGAAATGTAGGAAGGGGAGCAGTGTGTGCAC

ACCGCCTCTGGACCCCGCTGCTTCTGCCCCAGTCCCCGGGACTGCGAGTCAGGC

TGTGCCAGTAGCCCCTGCCAGCACGGGGGCAGCTGCCACCCTCAGCGCCAGCCT

CCTTATTACTCCTGCCAGTGTGCCCCACCATTCTCGGGTAGCCGCTGTGAACTC

TACACGGCACCCCCAGCACCCCTCCTGCCACCTGTCTGAGCCAGTATTGTGCC

GACAAAGCTCGGGATGGCGTCTGTGATGAGGCCTGCAACAGCCATGCCTGCCAG

TGGGATGGGGGTGACTGTTCTCTCACCATGGAGAACCCCTGGGCCAACTGCTCC

TCCCCACTTCCCTGCTGGGATTATATCAACAACCAGTGTGATGAGCTGTGCAAC

ACGGTCGAGTGCCTGTTTGACAACTTTGAATGCCAGGGGAACAGCAAGACATGC

AAGTATGACAAATACTGTGCAGACCACTTCAAAGACAACCACTGTGACCAGGGG

TGCAACAGTGAGGAGTGTGGTTGGGATGGGCTGGACTGTGCTGCTGACCAACCT

GAGAACCTGGCAGAAGGTACCCTGGTTATTGTGGTATTGATGCCACCTGAACAA

CTGCTCCAGGATGCTCGCAGCTTCTTGCGGGCACTGGGTACCCTGCTCCACACC

AACCTGCGCATTAAGCGGGACTCCCAGGGGGAACTCATGGTGTACCCCTATTAT
```

-continued

```
GGTGAGAAGTCAGCTGCTATGAAGAAACAGAGGATGACACGCAGATCCCTTCCT

GGTGAACAAGAACAGGAGGTGGCTGGCTCTAAAGTCTTTCTGGAAATTGACAAC

CGCCAGTGTGTTCAAGACTCAGACCACTGCTTCAAGAACACGGATGCAGCAGCA

GCTCTCCTGGCCTCTCACGCCATACAGGGGACCCTGTCATACCCTCTTGTGTCT

GTCGTCAGTGAATCCCTGACTCCAGAACGCACTCAGCTCCTCTATCTCCTTGCT

GTTGCTGTTGTCATCATTCTGTTTATTATTCTGCTGGGGGTAATCATGGCAAAA

CGAAAGCGTAAGCATGGCTCTCTCTGGCTGCCTGAAGGTTTCACTCTTCGCCGA

GATGCAAGCAATCACAAGCGTCGTGAGCCAGTGGGACAGGATGCTGTGGGGCTG

AAAAATCTCTCAGTGCAAGTCTCAGAAGCTAACCTAATTGGTACTGGAACAAGT

GAACACTGGGTCGATGATGAAGGGCCCCAGCCAAAGAAAGTAAAGGCTGAAGAT

GAGGCCTTACTCTCAGAAGAAGATGACCCCATTGATCGACGGCCATGGACACAG

CAGCACCTTGAAGCTGCAGACATCCGTAGGACACCATCGCTGGCTCTCACCCCT

CCTCAGGCAGAGCAGGAGGTGGATGTGTTAGATGTGAATGTCCGTGGCCCAGAT

GGCTGCACCCCATTGATGTTGGCTTCTCTCCGAGGAGGCAGCTCAGATTTGAGT

GATGAAGATGAAGATGCAGAGGACTCTTCTGCTAACATCATCACAGACTTGGTC

TACCAGGGTGCCAGCCTCCAGGCCCAGACAGACCGGACTGGTGAGATGGCCCTG

CACCTTGCAGCCCGCTACTCACGGGCTGATGCTGCCAAGCGTCTCCTGGATGCA

GGTGCAGATGCCAATGCCCAGGACAACATGGGCCGCTGTCCACTCCATGCTGCA

GTGGCAGCTGATGCCCAAGGTGTCTTCCAGATTCTGATTCGCAACCGAGTAACT

GATCTAGATGCCAGGATGAATGATGGTACTACACCCCTGATCCTGGCTGCCCGC

CTGGCTGTGGAGGGAATGGTGGCAGAACTGATCAACTGCCAAGCGGATGTGAAT

GCAGTGGATGACCATGGAAAATCTGCTCTTCACTGGGCAGCTGCTGTCAATAAT

GTGGAGGCAACTCTTTTGTTGTTGAAAAATGGGGCCAACCGAGACATGCAGGAC

AACAAGGAAGAGACACCTCTGTTTCTTGCTGCCCGGGAGGGGAGCTATGAAGCA

GCCAAGATCCTGTTAGACCATTTTGCCAATCGAGACATCACAGACCATATGGAT

CGTCTTCCCCGGGATGTGGCTCGGGATCGCATGCACCATGACATTGTGCGCCTT

CTGGATGAATACAATGTGACCCCAAGCCCTCCAGGCACCGTGTTGACTTCTGCT

CTCTCACCTGTCATCTGTGGGCCCAACAGATCTTTCCTCAGCCTGAAGCACACC

CCAATGGGCAAGAAGTCTAGACGGCCCAGTGCCAAGAGTACCATGCCTACTAGC

CTCCCTAACCTTGCCAAGGAGGCAAAGGATGCCAAGGGTAGTAGGAGGAAGAAG

TCTCTGAGTGAGAAGGTCCAACTGTCTGAGAGTTCAGTAACTTTATCCCCTGTT

GATTCCCTAGAATCTCCTCACACGTATGTTTCCGACACCACATCCTCTCCAATG

ATTACATCCCCTGGGATCTTACAGGCCTCACCCAACCCTATGTTGGCCACTGCC

GCCCCTCCTGCCCCAGTCCATGCCCAGCATGCACTATCTTTTTCTAACCTTCAT

GAAATGCAGCCTTTGGCACATGGGGCCAGCACTGTGCTTCCCTCAGTGAGCCAG

TTGCTATCCCACCACCACATTGTGTCTCCAGGCAGTGGCAGTGCTGGAAGCTTG

AGTAGGCTCCATCCAGTCCCAGTCCCAGCAGATTGGATGAACCGCATGGAGGTG

AATGAGACCCAGTACAATGAGATGTTTGGTATGGTCCTGGCTCCAGCTGAGGGC

ACCCATCCTGGCATAGCTCCCCAGAGCAGGCACCTGAAGGGAAGCACATAACC

ACCCCTCGGGAGCCCTTGCCCCCCATTGTGACTTTCCAGCTCATCCCTAAAGGC

AGTATTGCCCAACCAGCGGGGGCTCCCCAGCCTCAGTCCACCTGCCCTCCAGCT
```

-continued

```
GTTGCGGGCCCCCTGCCCACCATGTACCAGATTCCAGAAATGGCCCGTTTGCCC

AGTGTGGCTTTCCCCACTGCCATGATGCCCCAGCAGGACGGGCAGGTAGCTCAG

ACCATTCTCCCAGCCTATCATCCTTTCCCAGCCTCTGTGGGCAAGTACCCCACA

CCCCCTTCACAGCACAGTTATGCTTCCTCAAATGCTGCTGAGCGAACACCCAGT

CACAGTGGTCACCTCCAGGGTGAGCATCCCTACCTGACACCATCCCCAGAGTCT

CCTGACCAGTGGTCAAGTTCATCACCCCACTCTGCTTCTGACTGGTCAGATGTG

ACCACCAGCCCTACCCCTGGGGGTGCTGGAGGAGGTCAGCGGGGACCTGGGACA

CACATGTCTGAGCCACCACACAACAACATGCAGGTTTATGCGTGAGAGAGTCCA

CCTCCAGTGTAGAGACATAACTGACTTTTGTAAATGCTGCTGAGGAACAAATGA

AGGTCATCCGGGAGAGAAATGAAGAAATCTCTGGAGCCAGCTTCTAGAGGTAGG

AAAGAGAAGATGTTCTTATTCAGATAATGCAAGAGAAGCAATTCGTCAGTTTCA

CTGGGTATCTGCAAGGCTTATTGATTATTCTAATCTAATAAGACAAGTTTGTGG

AAATGCAAGATGAATACAAGCCTTGGGTCCATGTTTACTCTCTTCTATTTGGAG

AATAAGATGGATGCTTATTGAAGCCCAGACATTCTTGCAGCTTGGACTGCATTT

TAAGCCCTGCAGGCTTCTGCCATATCCATGAAGAAGATTCTACACTAGCGTCCTG

TTGGGAATTATGCCCTGGAATTCTGCCTGAATTGACCTACGCATCTCCTCCTCC

TTGGACATTCTTTTGTCTTCATTTGGTGCTTTTGGTTTTGCACCTCTCCGTGAT

TGTAGCCCTACCAGCATGTTATAGGGCAAGACCTTTGTGCTTTTGATCATTCTG

GCCCATGAAAGCAACTTTGGTCTCCTTTCCCCTCCTGTCTTCCCGGTATCCCTT

GGAGTCTCACAAGGTTTACTTTGGTATGGTTCTCAGCACAAACCTTTCAAGTAT

GTTGTTTCTTTGGAAAATGGACATACTGTATTGTGTTCTCCTGCATATATCATT

CCTGGAGAGAGAAGGGGAGAAGAATACTTTTCTTCAACAAATTTTGGGGGCAGG

AGATCCCTTCAAGAGGCTGCACCTTAATTTTTCTTGTCTGTGTGCAGGTCTTCA

TATAAACTTTACCAGGAAGAAGGGTGTGAGTTTGTTGTTTTTCTGTGTATGGGC

CTGGTCAGTGTAAAGTTTTATCCTTGATAGTCTAGTTACTATGACCCTCCCCAC

TTTTTTAAAACCAGAAAAAGGTTTGGAATGTTGGAATGACCAAGAGACAAGTTA

ACTCGTGCAAGAGCCAGTTACCCACCCACAGGTCCCCCTACTTCCTGCCAAGCA

TTCCATTGACTGCCTGTATGGAACACATTTGTCCCAGATCTGAGCATTCTAGGC

CTGTTTCACTCACTCACCCAGCATATGAAACTAGTCTTAACTGTTGAGCCTTTC

CTTTCATATCCACAGAAGACACTGTCTCAAATGTTGTACCCTTGCCATTTAGGA

CTGAACTTTCCTTAGCCCAAGGGACCCAGTGACAGTTGTCTTCCGTTTGTCAGA

TGATCAGTCTCTACTGATTATCTTGCTGCTTAAAGGCCTGCTCACCAATCTTTC

TTTCACACCGTGTGGTCCGTGTTACTGGTATACCCAGTATGTTCTCACTGAAGA

CATGGACTTTATATGTTCAAGTGCAGGAATTGGAAAGTTGGACTTGTTTTCTAT

GATCCAAAACAGCCCTATAAGAAGGTTGGAAAAGGAGGAACTATATAGCAGCCT

TTGCTATTTTCTGCTACCATTTCTTTTCCTCTGAAGCGGCCATGACATTCCCTT

TGGCAACTAACGTAGAAACTCAACAGAACATTTTCCTTTCCTAGAGTCACCTTT

TAGATGATAATGGACAACTATAGACTTGCTCATTGTTCAGACTGATTGCCCCTC

ACCTGAATCCACTCTCTGTATTCATGCTCTTGGCAATTTCTTTGACTTTCTTTT

AAGGGCAGAAGCATTTTAGTTAATTGTAGATAAAGAATAGTTTTCTTCCTCTTC
```

-continued

```
TCCTTGGGCCAGTTAATAATTGGTCCATGGCTACACTGCAACTTCCGTCCAGTG

CTGTGATGCCCATGACACCTGCAAAATAAGTTCTGCCTGGGCATTTTGTAGATA

TTAACAGGTGAATTCCCGACTCTTTTGGTTTGAATGACAGTTCTCATTCCTTCT

ATGGCTGCAAGTATGCATCAGTGCTTCCCACTTACCTGATTTGTCTGTCGGTGG

CCCCATATGGAAACCCTGCGTGTCTGTTGGCATAATAGTTTACAAATGGTTTTT

TCAGTCCTATCCAAATTTATTGAACCAACAAAAATAATTACTTCTGCCCTGAGA

TAAGCAGATTAAGTTTGTTCATTCTCTGCTTTATTCTCTCCATGTGGCAACATT

CTGTCAGCCTCTTTCATAGTGTGCAAACATTTTATCATTCTAAATGGTGACTCT

CTGCCCTTGGACCCATTTATTATTCACAGATGGGGAGAACCTATCTGCATGGAC

CTCTGTGGACCACAGCGTACCTGCCCCTTTCTGCCCTCCTGCTCCAGCCCCACT

TCTGAAAGTATCAGCTACTGATCCAGCCACTGGATATTTTATATCCTCCCTTTT

CCTTAAGCACAATGTCAGACCAAATTGCTTGTTTCTTTTTCTTGGACTACTTTA

ATTTGGATCCTTTGGGTTTGGAGAAAGGGAATGTGAAAGCTGTCATTACAGACA

ACAGGTTTCAGTGATGAGGAGGACAACACTGCCTTTCAAACTTTTTACTGATCT

CTTAGATTTTAAGAACTCTTGAATTGTGTGGTATCTAATAAAAGGGAAGGTAAG

ATGGATAATCACTTTCTCATTTGGGTTCTGAATTGGAGACTCAGTTTTTATGAG

ACACATCTTTTATGCCATGTATAGATCCTCCCCTGCTATTTTTGGTTTATTTTT

ATTGTTATAAATGCTTTCTTTCTTTGACTCCTCTTCTGCCTGCCTTTGGGGATA

GGTTTTTTTGTTTGTTTATTTGCTTCCTCTGTTTTGTTTTAAGCATCATTTTCT

TATGTGAGGTGGGGAAGGGAAAGGTATGAGGGAAAGAGAGTCTGAGAATTAAAA

TATTTTAGTATAAGCAATTGGCTGTGATGCTCAAATCCATTGCATCCTCTTATT

GAATTTGCCAATTTGTAATTTTTGCATAATAAAGAACCAAAGGTGTAATGTTTT

GTTGAGAGGTGGTTTAGGGATTTTGGCCCTAACCAATACATTGAATGTATGATG

ACTATTTGGGAGGACACATTTATGTACCCAGAGGCCCCCACTAATAAGTGGTAC

TATGGTTACTTCCTTGTGTACATTTCTCTTAAAAGTGATATTATATCTGTTTGT

ATGAGAAACCCAGTAACCAATAAAATGACCGCATATTCCTGACTAAACGTAGTA

AGGAAAATGCACACTTTGTTTTTACTTTTCCGTTTCATTCTAAAGGTAGTTAAG

ATGAAATTTATATGAAAGCATTTTTATCACAAAATAAAAAGGTTTGCCAAGCT

CAGTGGTGTTGTATTTTTTATTTTCCAATACTGCATCCATGGCCTGGCAGTGTT

ACCTCATGATGTCATAATTTGCTGAGAGAGCAAATTTTCTTTTCTTTCTGAATC

CCACAAAGCCTAGCACCAAACTTCTTTTTTTCTTCCTTTAATTAGATCATAAAT

AAATGATCCTGGGGAAAAAGCATCTGTCAAATAGGAAACATCACAAAACTGAGC

ACTCTTCTGTGCACTAGCCATAGCTGGTGACAAACAGATGGTTGCTCAGGGACA

AGGTGCCTTCCAATGGAAATGCGAAGTAGTTGCTATAGCAAGAATTGGGAACTG

GGATATAAGTCATAATATTAATTATGCTGTTATGTAAATGATTGGTTTGTAACA

TTCCTTAAGTGAAATTTGTGTAGAACTTAATATACAGGATTATAAAATAATATT

TTGTGTATAAATTTGTTATAAGTTCACATTCATACATTTATTTATAAAGTCAGT

GAGATATTTGACATGAAAAAAAAAAA

Human notch 2 (NOTCH2), transcript variant 2, mRNA NM_001200001.1
                                                  (SEQ ID NO: 31)
GCTTGCGGTGGGAGGAGGCGGCTGAGGCGGAAGGACACACGAGGCTGCTTCGTT

GCACACCCGAGAAAGTTTCAGCCAAACTTCGGGCGGCGGCTGAGGCGGCGGCCG
```

-continued

```
AGGAGCGGCGGACTCGGGGCGCGGGGAGTCGAGGCATTTGCGCCTGGGCTTCGG

AGCGTAGCGCCAGGGCCTGAGCCTTTGAAGCAGGAGGAGGGGAGGAGAGAGTGG

GGCTCCTCTATCGGGACCCCCTCCCCATGTGGATCTGCCCAGGCGGCGGCGGCG

GCGGCGGAGGAGGAGGCGACCGAGAAGATGCCCGCCCTGCGCCCCGCTCTGCTG

TGGGCGCTGCTGGCGCTCTGGCTGTGCTGCGCGGCCCCCGCGCATGCATTGCAG

TGTCGAGATGGCTATGAACCCTGTGTAAATGAAGGAATGTGTGTTACCTACCAC

AATGGCACAGGATACTGCAAATGTCCAGAAGGCTTCTTGGGGGAATATTGTCAA

CATCGAGACCCCTGTGAGAAGAACCGCTGCCAGAATGGTGGGACTTGTGTGGCC

CAGGCCATGCTGGGGAAAGCCACGTGCCGATGTGCCTCAGGGTTTACAGGAGAG

GACTGCCAGTACTCAACATCTCATCCATGCTTTGTGTCTCGACCCTGCCTGAAT

GGCGGCACATGCCATATGCTCAGCCGGGATACCTATGAGTGCACCTGTCAAGTC

GGGTTTACAGGTAAGGAGTGCCAATGGACGGATGCCTGCCTGTCTCATCCCTGT

GCAAATGGAAGTACCTGTACCACTGTGGCCAACCAGTTCTCCTGCAAATGCCTC

ACAGGCTTCACAGGGCAGAAATGTGAGACTGATGTCAATGAGTGTGACATTCCA

GGACACTGCCAGCATGGTGGCACCTGCCTCAACCTGCCTGGTTCCTACCAGTGC

CAGTGCCCTCAGGGCTTCACAGGCCAGTACTGTGACAGCCTGTATGTGCCCTGT

GCACCCTCACCTTGTGTCAATGGAGGCACCTGTCGGCAGACTGGTGACTTCACT

TTTGAGTGCAACTGCCTTCCAGGTTTTGAAGGGAGCACCTGTGAGAGGAATATT

GATGACTGCCCTAACCACAGGTGTCAGAATGGAGGGGTTTGTGTGGATGGGGTC

AACACTTACAACTGCCGCTGTCCCCCACAATGGACAGGACAGTTCTGCACAGAG

GATGTGGATGAATGCCTGCTGCAGCCCAATGCCTGTCAAAATGGGGGCACCTGT

GCCAACCGCAATGGAGGCTATGGCTGTGTATGTGTCAACGGCTGGAGTGGAGAT

GACTGCAGTGAGAACATTGATGATTGTGCCTTCGCCTCCTGTACTCCAGGCTCC

ACCTGCATCGACCGTGTGGCCTCCTTCTCTTGCATGTGCCCAGAGGGGAAGGCA

GGTCTCCTGTGTCATCTGGATGATGCATGCATCAGCAATCCTTGCCACAAGGGG

GCACTGTGTGACACCAACCCCCTAAATGGGCAATATATTTGCACCTGCCCACAA

GGCTACAAAGGGGCTGACTGCACAGAAGATGTGGATGAATGTGCCATGGCCAAT

AGCAATCCTTGTGAGCATGCAGGAAAATGTGTGAACACGGATGGCGCCTTCCAC

TGTGAGTGTCTGAAGGGTTATGCAGGACCTCGTTGTGAGATGGACATCAATGAG

TGCCATTCAGACCCCTGCCAGAATGATGCTACCTGTCTGGATAAGATTGGAGGC

TTCACATGTCTGTGCATGCCAGGTTTCAAAGGTGTGCATTGTGAATTAGAAATA

AATGAATGTCAGAGCAACCCTTGTGTGAACAATGGGCAGTGTGTGGATAAAGTC

AATCGTTTCCAGTGCCTGTGTCCTCCTGGTTTCACTGGGCCAGTTTGCCAGATT

GATATTGATGACTGTTCCAGTACTCCGTGTCTGAATGGGGCAAAGTGTATCGAT

CACCCGAATGGCTATGAATGCCAGTGTGCCACAGGTTTCACTGGTGTGTTGTGT

GAGGAGAACATTGACAACTGTGACCCCGATCCTTGCCACCATGGTCAGTGTCAG

GATGGTATTGATTCCTACACCTGCATCTGCAATCCCGGGTACATGGGCGCCATC

TGCAGTGACCAGATTGATGAATGTTACAGCAGCCCTTGCCTGAACGATGGTCGC

TGCATTGACCTGGTCAATGGCTACCAGTGCAACTGCCAGCCAGGCACGTCAGGG

GTTAATTGTGAAATTAATTTTGATGACTGTGCAAGTAACCCTTGTATCCATGGA
```

-continued
```
ATCTGTATGGATGGCATTAATCGCTACAGTTGTGTCTGCTCACCAGGATTCACA

GGGCAGAGATGTAACATTGACATTGATGAGTGTGCCTCCAATCCCTGTCGCAAG

GGTGCAACATGTATCAACGGTGTGAATGGTTTCCGCTGTATATGCCCCGAGGGA

CCCCATCACCCCAGCTGCTACTCACAGGTGAACGAATGCCTGAGCAATCCCTGC

ATCCATGGAAACTGTACTGGAGGTCTCAGTGGATATAAGTGTCTCTGTGATGCA

GGCTGGGTTGGCATCAACTGTGAAGTGGACAAAAATGAATGCCTTTCGAATCCA

TGCCAGAATGGAGGAACTTGTGACAATCTGGTGAATGGATACAGGTGTACTTGC

AAGAAGGGCTTTAAAGGCTATAACTGCCAGGTGAATATTGATGAATGTGCCTCA

AATCCATGCCTGAACCAAGGAACCTGCTTTGATGACATAAGTGGCTACACTTGC

CACTGTGTGCTGCCATACACAGGCAAGAATTGTCAGACAGTATTGGCTCCCTGT

TCCCCAAACCCTTGTGAGAATGCTGCTGTTTGCAAAGAGTCACCAAATTTTGAG

AGTTATACTTGCTTGTGTGCTCCTGGCTGGCAAGGTCAGCGGTGTACCATTGAC

ATTGACGAGTGTATCTCCAAGCCCTGCATGAACCATGGTCTCTGCCATAACACC

CAGGGCAGCTACATGTGTGAATGTCCACCAGGCTTCAGTGGTATGGACTGTGAG

GAGGACATTGATGACTGCCTTGCCAATCCTTGCCAGAATGGAGGTTCCTGTATG

GATGGAGTGAATACTTTCTCCTGCCTCTGCCTTCCGGGTTTCACTGGGGATAAG

TGCCAGACAGACATGAATGAGTGTCTGAGTGAACCCTGTAAGAATGGAGGGACC

TGCTCTGACTACGTCAACAGTTACACTTGCAAGTGCCAGGCAGGATTTGATGGA

GTCCATTGTGAGAACAACATCAATGAGTGCACTGAGAGCTCCTGTTTCAATGGT

GGCACATGTGTTGATGGGATTAACTCCTTCTCTTGCTTGTGCCCTGTGGGTTTC

ACTGGATCCTTCTGCCTCCATGAGATCAATGAATGCAGCTCTCATCCATGCCTG

AATGAGGGAACGTGTGTTGATGGCCTGGGTACCTACCGCTGCAGCTGCCCCCTG

GGCTACACTGGGAAAAACTGTCAGACCCTGGTGAATCTCTGCAGTCGGTCTCCA

TGTAAAAACAAAGGTACTTGCGTTCAGAAAAAAGCAGAGTCCCAGTGCCTATGT

CCATCTGGATGGGCTGGTGCCTATTGTGACGTGCCCAATGTCTCTTGTGACATA

GCAGCCTCCAGGAGAGGTGTGCTTGTTGAACACTTGTGCCAGCACTCAGGTGTC

TGCATCAATGCTGGCAACACGCATTACTGTCAGTGCCCCCTGGGCTATACTGGG

AGCTACTGTGAGGAGCAACTCGATGAGTGTGCGTCCAACCCCTGCCAGCACGGG

GCAACATGCAGTGACTTCATTGGTGGATACAGATGCGAGTGTGTCCCAGGCTAT

CAGGGTGTCAACTGTGAGTATGAAGTGGATGAGTGCCAGAATCAGCCCTGCCAG

AATGGAGGCACCTGTATTGACCTTGTGAACCATTTCAAGTGCTCTTGCCCACCA

GGCACTCGGGGTATGAAATCATCCTTATCCATTTTCCATCCAGGGCATTGTCTT

AAGTTATAAATCCATTCTTAGTGTTCAGGGGATTTTATAAAATTAAAGATAGGA

AGACTAGCTTCATTCCAAGCATTTAGTTCTACATCCTAGTAATTCAAGCCATTT

TATTCTCCCATCTCTTGCTAGCTCTGATGTTGTGGTTTATGTTGTCAGTTTTAT

CTGGTTGTTTGGCATCTTGATATTCCATGAAACACAGAATATGGAAGGGATACA

ACATTAGCATAACATTAAAAAATTAGCCTGGTCAGTAAGATTTCTTGTTGCTTC

ACAGAAAAGCAACTAATGGCCTCTAAAATAAACAATTTACATTTAAAAAAAAAA

AAAAAA
```

-continued

Human notch 3 (NOTCH3), mRNA NM_000435.2

(SEQ ID NO: 32)

GCGGCGCGGAGGCTGGCCCGGGACGCGCCCGGAGCCCAGGGAAGGAGGGAGGAG

GGGAGGGTCGCGGCCGGCCGCCATGGGGCCGGGGGCCCGTGGCCGCCGCCGCCG

CCGTCGCCCGATGTCGCCGCCACCGCCACCGCCACCCGTGCGGGCGCTGCCCCT

GCTGCTGCTGCTAGCGGGGCCGGGGGCTGCAGCCCCCCCTTGCCTGGACGGAAG

CCCGTGTGCAAATGGAGGTCGTTGCACCCAGCTGCCCTCCCGGGAGGCTGCCTG

CCTGTGCCCGCCTGGCTGGGTGGGTGAGCGGTGTCAGCTGGAGGACCCCTGTCA

CTCAGGCCCCTGTGCTGGCCGTGGTGTCTGCCAGAGTTCAGTGGTGGCTGGCAC

CGCCCGATTCTCATGCCGGTGCCCCGTGGCTTCCGAGGCCCTGACTGCTCCCT

GCCAGATCCCTGCCTCAGCAGCCCTTGTGCCCACGGTGCCCGCTGCTCAGTGGG

GCCCGATGGACGCTTCCTCTGCTCCTGCCCACCTGGCTACCAGGGCCGCAGCTG

CCGAAGCGACGTGGATGAGTGCCGGGTGGGTGAGCCCTGCCGCCATGGTGGCAC

CTGCCTCAACACACCTGGCTCCTTCCGCTGCCAGTGTCCAGCTGGCTACACAGG

GCCACTATGTGAGAACCCCGCGGTGCCCTGTGCACCCTCACCATGCCGTAACGG

GGGCACCTGCAGGCAGAGTGGCGACCTCACTTACGACTGTGCCTGTCTTCCTGG

GTTTGAGGGTCAGAATTGTGAAGTGAACGTGGACGACTGTCCAGGACACCGATG

TCTCAATGGGGGACATGCGTGGATGGCGTCAACACCTATAACTGCCAGTGCCC

TCCTGAGTGGACAGGCCAGTTCTGCACGGAGGACGTGGATGAGTGTCAGCTGCA

GCCCAACGCCTGCCACAATGGGGGTACCTGCTTCAACACGCTGGGTGGCCACAG

CTGCGTGTGTGTCAATGGCTGGACAGGCGAGAGCTGCAGTCAGAATATCGATGA

CTGTGCCACAGCCGTGTGCTTCCATGGGGCCACCTGCCATGACCGCGTGGCTTC

TTTCTACTGTGCCTGCCCCATGGGCAAGACTGGCCTCCTGTGTCACCTGGATGA

CGCCTGTGTCAGCAACCCCTGCCACGAGGATGCTATCTGTGACACAAATCCGGT

GAACGGCCGGGCCATTTGCACCTGTCCTCCCGGCTTCACGGGTGGGGCATGTGA

CCAGGATGTGGACGAGTGCTCTATCGGCGCCAACCCCTGCGAGCACTTGGGCAG

GTGCGTGAACACGCAGGGCTCCTTCCTGTGCCAGTGCGGTCGTGGCTACACTGG

ACCTCGCTGTGAGACCGATGTCAACGAGTGTCTGTCGGGCCCTGCCGAAACCA

GGCCACGTGCCTCGACCGCATAGGCCAGTTCACCTGTATCTGTATGGCAGGCTT

CACAGGAACCTATTGCGAGGTGGACATTGACGAGTGTCAGAGTAGCCCCTGTGT

CAACGGTGGGGTCTGCAAGGACCGAGTCAATGGCTTCAGCTGCACCTGCCCCTC

GGGCTTCAGCGGCTCCACGTGTCAGCTGGACGTGGACGAATGCGCCAGCACGCC

CTGCAGGAATGGCGCCAAATGCGTGGACCAGCCCGATGGCTACGAGTGCCGCTG

TGCCGAGGGCTTTGAGGGCACGCTGTGTGATCGCAACGTGGACGACTGCTCCCC

TGACCCATGCCACCATGGTCGCTGCGTGGATGGCATCGCCAGCTTCTCATGTGC

CTGTGCTCCTGGCTACACGGGCACACGCTGCGAGAGCCAGGTGGACGAATGCCG

CAGCCAGCCCTGCCGCCATGGCGGCAAATGCCTAGACCTGGTGGACAAGTACCT

CTGCCGCTGCCCTTCTGGGACCACAGGTGTGAACTGCGAAGTGAACATTGACGA

CTGTGCCAGCAACCCCTGCACCTTTGGAGTCTGCCGTGATGGCATCAACCGCTA

CGACTGTGTCTGCCAACCTGGCTTCACAGGGCCCCTTTGTAACGTGGAGATCAA

TGAGTGTGCTTCCAGCCCATGCGGCGAGGGAGGTTCCTGTGTGGATGGGGAAAA

-continued

```
TGGCTTCCGCTGCCTCTGCCCGCCTGGCTCCTTGCCCCCACTCTGCCTCCCCCC
GAGCCATCCCTGTGCCCATGAGCCCTGCAGTCACGGCATCTGCTATGATGCACC
TGGCGGGTTCCGCTGTGTGTGTGAGCCTGGCTGGAGTGGCCCCGCTGCAGCCA
GAGCCTGGCCCGAGACGCCTGTGAGTCCCAGCCGTGCAGGGCCGGTGGGACATG
CAGCAGCGATGGAATGGGTTTCCACTGCACCTGCCCGCCTGGTGTCCAGGGACG
TCAGTGTGAACTCCTCTCCCCCTGCACCCCGAACCCCTGTGAGCATGGGGGCCG
CTGCGAGTCTGCCCCTGGCCAGCTGCCTGTCTGCTCCTGCCCCCAGGGCTGGCA
AGGCCCACGATGCCAGCAGGATGTGGACGAGTGTGCTGGCCCCGCACCCTGTGG
CCCTCATGGTATCTGCACCAACCTGGCAGGGAGTTTCAGCTGCACCTGCCATGG
AGGGTACACTGGCCCTTCCTGCGATCAGGACATCAATGACTGTGACCCCAACCC
ATGCCTGAACGGTGGCTCGTGCCAAGACGGCGTGGGCTCCTTTTCCTGCTCCTG
CCTCCCTGGTTTCGCCGGCCCACGATGCGCCCGCGATGTGGATGAGTGCCTGAG
CAACCCCTGCGGCCCGGGCACCTGTACCGACCACGTGGCCTCCTTCACCTGCAC
CTGCCCGCCAGGCTACGGAGGCTTCCACTGCGAACAGGACCTGCCCGACTGCAG
CCCCAGCTCCTGCTTCAATGGCGGGACCTGTGTGGACGGCGTGAACTCGTTCAG
CTGCCTGTGCCGTCCCGGCTACACAGGAGCCCACTGCCAACATGAGGCAGACCC
CTGCCTCTCGCGGCCCTGCCTACACGGGGCGTCTGCAGCGCCGCCCACCCTGG
CTTCCGCTGCACCTGCCTCGAGAGCTTCACGGGCCCGCAGTGCCAGACGCTGGT
GGATTGGTGCAGCCGCCAGCCTTGTCAAAACGGGGGTCGCTGCGTCCAGACTGG
GGCCTATTGCCTTTGTCCCCCTGGATGGAGCGGACGCCTCTGTGACATCCGAAG
CTTGCCCTGCAGGGAGGCCGCAGCCCAGATCGGGGTGCGGCTGGAGCAGCTGTG
TCAGGCGGGTGGGCAGTGTGTGGATGAAGACAGCTCCCACTACTGCGTGTGCCC
AGAGGGCCGTACTGGTAGCCACTGTGAGCAGGAGGTGGACCCCTGCTTGGCCCA
GCCCTGCCAGCATGGGGGGACCTGCCGTGGCTATATGGGGGGCTACATGTGTGA
GTGTCTTCCTGGCTACAATGGTGATAACTGTGAGGACGACGTGGACGAGTGTGC
CTCCCAGCCCTGCCAGCACGGGGGTTCATGCATTGACCTCGTGGCCCGCTATCT
CTGCTCCTGTCCCCAGGAACGCTGGGGGTGCTCTGCGAGATTAATGAGGATGA
CTGCGGCCCAGGCCCACCGCTGGACTCAGGGCCCCGGTGCCTACACAATGGCAC
CTGCGTGGACCTGGTGGGTGGTTTCCGCTGCACCTGTCCCCCAGGATACACTGG
TTTGCGCTGCGAGGCAGACATCAATGAGTGTCGCTCAGGTGCCTGCCACGCGGC
ACACACCCGGGACTGCCTGCAGGACCCAGGCGGAGGTTTCCGTTGCCTTTGTCA
TGCTGGCTTCTCAGGTCCTCGCTGTCAGACTGTCCTGTCTCCCTGCGAGTCCCA
GCCATGCCAGCATGGAGGCCAGTGCCGTCCTAGCCCGGGTCCTGGGGGTGGGCT
GACCTTCACCTGTCACTGTGCCCAGCCGTTCTGGGGTCCGCGTTGCGAGCGGGT
GGCGCGCTCCTGCCGGGAGCTGCAGTGCCCGGTGGGCGTCCCATGCCAGCAGAC
GCCCCGCGGGCCGCGCTGCGCCTGCCCCCCAGGGTTGTCGGGACCCTCCTGCCG
CAGCTTCCCGGGGTCGCCGCCGGGGGCCAGCAACGCCAGCTGCGCGGCCGCCCC
CTGTCTCCACGGGGGCTCCTGCCGCCCCGCGCCGCTCGCGCCCTTCTTCCGCTG
CGCTTGCGCGCAGGGCTGGACCGGGCCGCGCTGCGAGGCGCCCGCCGCGGCACC
CGAGGTCTCGGAGGAGCCGCGGTGCCCGCGCGCCGCCTGCCAGGCCAAGCGCGG
GGACCAGCGCTGCGACCGCGAGTGCAACAGCCCAGGCTGCGGCTGGGACGGCGG
```

-continued

```
CGACTGCTCGCTGAGCGTGGGCGACCCCTGGCGGCAATGCGAGGCGCTGCAGTG
CTGGCGCCTCTTCAACAACAGCCGCTGCGACCCCGCCTGCAGCTCGCCCGCCTG
CCTCTACGACAACTTCGACTGCCACGCCGGTGGCCGCGAGCGCACTTGCAACCC
GGTGTACGAGAAGTACTGCGCCGACCACTTTGCCGACGGCCGCTGCGACCAGGG
CTGCAACACGGAGGAGTGCGGCTGGGATGGGCTGGATTGTGCCAGCGAGGTGCC
GGCCCTGCTGGCCCGCGGCGTGCTGGTGCTCACAGTGCTGCTGCCGCCAGAGGA
GCTACTGCGTTCCAGCGCCGACTTTCTGCAGCGGCTCAGCGCCATCCTGCGCAC
CTCGCTGCGCTTCCGCCTGGACGCGCACGGCCAGGCCATGGTCTTCCCTTACCA
CCGGCCTAGTCCTGGCTCCGAACCCCGGGCCCGTCGGGAGCTGGCCCCCGAGGT
GATCGGCTCGGTAGTAATGCTGGAGATTGACAACCGGCTCTGCCTGCAGTCGCC
TGAGAATGATCACTGCTTCCCCGATGCCCAGAGCGCCGCTGACTACCTGGGAGC
GTTGTCAGCGGTGGAGCGCCTGGACTTCCCGTACCCACTGCGGGACGTGCGGGG
GGAGCCGCTGGAGCCTCCAGAACCCAGCGTCCCGCTGCTGCCACTGCTAGTGGC
GGGCGCTGTCTTGCTGCTGGTCATTCTCGTCCTGGGTGTCATGGTGGCCCGGCG
CAAGCGCGAGCACAGCACCCTCTGGTTCCCTGAGGGCTTCTCACTGCACAAGGA
CGTGGCCTCTGGTCACAAGGGCCGGCGGGAACCCGTGGGCCAGGACGCGCTGGG
CATGAAGAACATGGCCAAGGGTGAGAGCCTGATGGGGGAGGTGGCCACAGACTG
GATGGACACAGAGTGCCCAGAGGCCAAGCGGCTAAAGGTAGAGGAGCCAGGCAT
GGGGGCTGAGGAGGCTGTGGATTGCCGTCAGTGGACTCAACACCATCTGGTTGC
TGCTGACATCCGCGTGGCACCAGCCATGGCACTGACACCACCACAGGGCGACGC
AGATGCTGATGGCATGGATGTCAATGTGCGTGGCCCAGATGGCTTCACCCCGCT
AATGCTGGCTTCCTTCTGTGGGGGGGCTCTGGAGCCAATGCCAACTGAAGAGGA
TGAGGCAGATGACACATCAGCTAGCATCATCTCCGACCTGATCTGCCAGGGGGC
TCAGCTTGGGGCACGGACTGACCGTACTGGCGAGACTGCTTTGCACCTGGCTGC
CCGTTATGCCCGTGCTGATGCAGCCAAGCGGCTGCTGGATGCTGGGGCAGACAC
CAATGCCCAGGACCACTCAGGCCGCACTCCCCTGCACACAGCTGTCACAGCCGA
TGCCCAGGGTGTCTTCCAGATTCTCATCCGAAACCGCTCTACAGACTTGGATGC
CCGCATGGCAGATGGCTCAACGGCACTGATCCTGGCGGCCCGCCTGGCAGTAGA
GGGCATGGTGGAAGAGCTCATCGCCAGCCATGCTGATGTCAATGCTGTGGATGA
GCTTGGGAAATCAGCCTTACACTGGGCTGCGGCTGTGAACAACGTGGAAGCCAC
TTTGGCCCTGCTCAAAAATGGAGCCAATAAGGACATGCAGGATAGCAAGGAGGA
GACCCCCCTATTCCTGGCCGCCCGCGAGGGCAGCTATGAGGCTGCCAAGCTGCT
GTTGGACCACTTTGCCAACCGTGAGATCACCGACCACCTGGACAGGCTGCCGCG
GGACGTAGCCCAGGAGAGACTGCACCAGGACATCGTGCGCTTGCTGGATCAACC
CAGTGGGCCCCGCAGCCCCCCGGTCCCCACGGCCTGGGGCCTCTGCTCTGTCC
TCCAGGGGCCTTCCTCCCTGGCCTCAAAGCGGCACAGTCGGGGTCCAAGAAGAG
CAGGAGGCCCCCCGGGAAGGCGGGGCTGGGGCCGCAGGGGCCCCGGGGCGGGG
CAAGAAGCTGACGCTGGCCTGCCCGGGCCCCCTGGCTGACAGCTCGGTCACGCT
GTCGCCCGTGGACTCGCTGGACTCCCCGCGGCCTTTCGGTGGGCCCCCTGCTTC
CCCTGGTGGCTTCCCCCTTGAGGGGCCCTATGCAGCTGCCACTGCCACTGCAGT
```

-continued

```
GTCTCTGGCACAGCTTGGTGGCCCAGGCCGGGCGGGTCTAGGGCGCCAGCCCCC
TGGAGGATGTGTACTCAGCCTGGGCCTGCTGAACCCTGTGGCTGTGCCCCTCGA
TTGGGCCCGGCTGCCCCCACCTGCCCCTCCAGGCCCTCGTTCCTGCTGCCACT
GGCGCCGGGACCCCAGCTGCTCAACCCAGGGACCCCCGTCTCCCCGCAGGAGCG
GCCCCCGCCTTACCTGGCAGTCCCAGGACATGGCGAGGAGTACCCGGCGGCTGG
GGCACACAGCAGCCCCCAAAGGCCCGCTTCCTGCGGGTTCCCAGTGAGCACCC
TTACCTGACCCCATCCCCCGAATCCCTGAGCACTGGGCCAGCCCCTCACCTCC
CTCCCTCTCAGACTGGTCCGAATCCACGCCTAGCCCAGCCACTGCCACTGGGGC
CATGGCCACCACCACTGGGGCACTGCCTGCCCAGCCACTTCCCTTGTCTGTTCC
CAGCTCCCTTGCTCAGGCCCAGACCCAGCTGGGGCCCCAGCCGGAAGTTACCCC
CAAGAGGCAAGTGTTGGCCTGAGACGCTCGTCAGTTCTTAGATCTTGGGGGCCT
AAAGAGACCCCCGTCCTGCCTCCTTTCTTTCTCTGTCTCTTCCTTCCTTTTAGT
CTTTTTCATCCTCTTCTCTTTCCACCAACCCTCCTGCATCCTTGCCTTGCAGCG
TGACCGAGATAGGTCATCAGCCCAGGGCTTCAGTCTTCCTTTATTTATAATGGG
TGGGGGCTACCACCCACCCTCTCAGTCTTGTGAAGAGTCTGGGACCTCCTTCTT
CCCCACTTCTCTCTTCCCTCATTCCTTTCTCTCTCCTTCTGGCCTCTCATTTCC
TTACACTCTGACATGAATGAATTATTATTATTTTTATTTTTCTTTTTTTTTTA
CATTTTGTATAGAAACAAATTCATTTAAACAAACTTATTATTATTATTTTTTAC
AAAATATATATATGGAGATGCTCCCTCCCCCTGTGAACCCCCCAGTGCCCCCGT
GGGGCTGAGTCTGTGGGCCCATTCGGCCAAGCTGGATTCTGTGTACCTAGTACA
CAGGCATGACTGGGATCCCGTGTACCGAGTACACGACCCAGGTATGTACCAAGT
AGGCACCCTTGGGCGCACCCACTGGGGCCAGGGTCGGGGGAGTGTTGGGAGCC
TCCTCCCCACCCCACCTCCCTCACTTCACTGCATTCCAGATGGGACATGTTCCA
TAGCCTTGCTGGGGAAGGGCCCACTGCCAACTCCCTCTGCCCCAGCCCCACCCT
TGGCCATCTCCCTTTGGGAACTAGGGGGCTGCTGGTGGGAAATGGGAGCCAGGG
CAGATGTATGCATTCCTTTGTGTCCCTGTAAATGTGGGACTACAAGAAGAGGAG
CTGCCTGAGTGGTACTTTCTCTTCCTGGTAATCCTCTGGCCCAGCCTCATGGCA
GAATAGAGGTATTTTTAGGCTATTTTTGTAATATGGCTTCTGGTCAAAATCCCT
GTGTAGCTGAATTCCCAAGCCCTGCATTGTACAGCCCCCCACTCCCCTCACCAC
CTAATAAAGGAATAGTTAACACTCAAAAAAAAAAAAAAAAAA
Human notch 4 (NOTCH4) mRNA NM_004557.3
                                                (SEQ ID NO: 33)
AGACGTGAGGCTTGCAGCAGGCCGAGGAGGAAGAAGAGGGGCAGTGGGAGCAGA
GGAGGTGGCTCCTGCCCCAGTGAGAGCTCTGAGGGTCCCTGCCTGAAGAGGGAC
AGGGACCGGGGCTTGGAGAAGGGGCTGTGGAATGCAGCCCCCTTCACTGCTGCT
GCTGCTGCTGCTGCTGCTGCTATGTGTCTCAGTGGTCAGACCCAGAGGGCT
GCTGTGTGGGAGTTTCCCAGAACCCTGTGCCAATGGAGGCACCTGCCTGAGCCT
GTCTCTGGGACAAGGGACCTGCCAGTGTGCCCCTGGCTTCCTGGGTGAGACGTG
CCAGTTTCCTGACCCCTGCCAGAACGCCCAGCTCTGCCAAAATGGAGGCAGCTG
CCAAGCCCTGCTTCCCGCTCCCCTAGGGCTCCCCAGCTCTCCCTCTCCATTGAC
ACCCAGCTTCTTGTGCACTTGCCTCCCTGGCTTCACTGGTGAGAGATGCCAGGC
CAAGCTTGAAGACCCTTGTCCTCCCTCCTTCTGTTCCAAAAGGGGCCGCTGCCA
```

-continued

```
CATCCAGGCCTCGGGCCGCCCACAGTGCTCCTGCATGCCTGGATGGACAGGTGA

GCAGTGCCAGCTTCGGGACTTCTGTTCAGCCAACCCATGTGTTAATGGAGGGGT

GTGTCTGGCCACATACCCCCAGATCCAGTGCCACTGCCCACCGGGCTTCGAGGG

CCATGCCTGTGAACGTGATGTCAACGAGTGCTTCCAGGACCCAGGACCCTGCCC

CAAAGGCACCTCCTGCCATAACACCCTGGGCTCCTTCCAGTGCCTCTGCCCTGT

GGGGCAGGAGGGTCCACGTTGTGAGCTGCGGGCAGGACCCTGCCCTCCTAGGGG

CTGTTCGAATGGGGGCACCTGCCAGCTGATGCCAGAGAAAGACTCCACCTTTCA

CCTCTGCCTCTGTCCCCCAGGTTTCATAGGCCCAGACTGTGAGGTGAATCCAGA

CAACTGTGTCAGCCACCAGTGTCAGAATGGGGGCACTTGCCAGGATGGGCTGGA

CACCTACACCTGCCTCTGCCCAGAAACCTGGACAGGCTGGGACTGCTCCGAAGA

TGTGGATGAGTGTGAGACCCAGGGTCCCCCTCACTGCAGAAACGGGGGCACCTG

CCAGAACTCTGCTGGTAGCTTTCACTGCGTGTGTGAGTGGCTGGGGCGGCAC

AAGCTGTGAGGAGAACCTGGATGACTGTATTGCTGCCACCTGTGCCCCGGGATC

CACCTGCATTGACCGGGTGGGCTCTTTCTCCTGCCTCTGCCCACCTGGACGCAC

AGGACTCCTGTGCCACTTGGAAGACATGTGTCTGAGCCAGCCGTGCCATGGGA

TGCCCAATGCAGCACCAACCCCCTCACAGGCTCCACACTCTGCCTGTGTCAGCC

TGGCTATTCGGGCCCACCTGCCACCAGGACCTGGACGAGTGTCTGATGGCCCA

GCAAGGCCCAAGTCCCTGTGAACATGGCGGTTCCTGCCTCAACACTCCTGGCTC

CTTCAACTGCCTCTGTCCACCTGGCTACACAGGCTCCCGTTGTGAGGCTGATCA

CAATGAGTGCCTCTCCCAGCCCTGCCACCCAGGAAGCACCTGTCTGGACCTACT

TGCCACCTTCCACTGCCTCTGCCCGCCAGGCTTAGAAGGGCAGCTCTGTGAGGT

GGAGACCAACGAGTGTGCCTCAGCTCCCTGCCTGAACCACGCGGATTGCCATGA

CCTGCTCAACGGCTTCCAGTGCATCTGCCTGCCTGGATTCTCCGGCACCCGATG

TGAGGAGGATATCGATGAGTGCAGAAGCTCTCCCTGTGCCAATGGTGGGCAGTG

CCAGGACCAGCCTGGAGCCTTCCACTGCAAGTGTCTCCCAGGCTTTGAAGGGCC

ACGCTGTCAAACAGAGGTGGATGAGTGCCTGAGTGACCCATGTCCCGTTGGAGC

CAGCTGCCTTGATCTTCCAGGAGCCTTCTTTTGCCTCTGCCCCTCTGGTTTCAC

AGGCCAGCTCTGTGAGGTTCCCCTGTGTGCTCCCAACCTGTGCCAGCCCAAGCA

GATATGTAAGGACCAGAAAGACAAGGCCAACTGCCTCTGTCCTGATGGAAGCCC

TGGCTGTGCCCCACCTGAGGACAACTGCACCTGCCACCACGGGCACTGCCAGAG

ATCCTCATGTGTGTGTGACGTGGGTTGGACGGGGCCAGAGTGTGAGGCAGAGCT

AGGGGGCTGCATCTCTGCACCCTGTGCCCATGGGGGACCTGCTACCCCCAGCC

CTCTGGCTACAACTGCACCTGCCCTACAGGCTACACAGGACCCACCTGTAGTGA

GGAGATGACAGCTTGTCACTCAGGGCCATGTCTCAATGGCGGCTCCTGCAACCC

TAGCCCTGGAGGCTACTACTGCACCTGCCCTCCAAGCCACACAGGGCCCCAGTG

CCAAACCAGCACTGACTACTGTGTGTCTGCCCCGTGCTTCAATGGGGGTACCTG

TGTGAACAGGCCTGGCACCTTCTCCTGCCTCTGTGCCATGGGCTTCCAGGGCCC

GCGCTGTGAGGGAAAGCTCCGCCCCAGCTGTGCAGACAGCCCCTGTAGGAATAG

GGCAACCTGCCAGGACAGCCCTCAGGGTCCCCGCTGCCTCTGCCCCACTGGCTA

CACCGGAGGCAGCTGCCAGACTCTGATGGACTTATGTGCCCAGAAGCCCTGCCC
```

-continued

```
ACGCAATTCCCACTGCCTCCAGACTGGGCCTCCTTCCACTGCTTGTGCCTCCA
GGGATGGACCGGGCCTCTCTGCAACCTTCCACTGTCCTCCTGCCAGAAGGCTGC
ACTGAGCCAAGGCATAGACGTCTCTTCCCTTTGCCACAATGGAGGCCTCTGTGT
CGACAGCGGCCCCTCCTATTTCTGCCACTGCCCCCCTGGATTCCAAGGCAGCCT
GTGCCAGGATCACGTGAACCCATGTGAGTCCAGGCCTTGCCAGAACGGGGCCAC
CTGCATGGCCCAGCCCAGTGGGTATCTCTGCCAGTGTGCCCCAGGCTACGATGG
ACAGAACTGCTCAAAGGAACTCGATGCTTGTCAGTCCCAACCCTGTCACAACCA
TGGAACCTGTACTCCCAAACCTGGAGGATTCCACTGTGCCTGCCCTCCAGGCTT
TGTGGGGCTACGCTGTGAGGGAGACGTGGACGAGTGTCTGGACCAGCCCTGCCA
CCCCACAGGCACTGCAGCCTGCCACTCTCTGGCCAATGCCTTCTACTGCCAGTG
TCTGCCTGGACACACAGGCCAGTGGTGTGAGGTGGAGATAGACCCCTGCCACAG
CCAACCCTGCTTTCATGGAGGGACCTGTGAGGCCACAGCAGGATCACCCCTGGG
TTTCATCTGCCACTGCCCCAAGGGTTTTGAAGGCCCCACCTGCAGCCACAGGGC
CCCTTCCTGCGGCTTCCATCACTGCCACCACGGAGGCCTGTGTCTGCCCTCCCC
TAAGCCAGGCTTCCCACCACGCTGTGCCTGCCTCAGTGGCTATGGGGGTCCTGA
CTGCCTGACCCCACCAGCTCCTAAAGGCTGTGGCCCTCCCTCCCCATGCCTATA
CAATGGCAGCTGCTCAGAGACCACGGGCTTGGGGGGCCCAGGCTTTCGATGCTC
CTGCCCTCACAGCTCTCCAGGGCCCCGGTGTCAGAAACCCGGAGCCAAGGGGTG
TGAGGGCAGAAGTGGAGATGGGGCCTGCGATGCTGGCTGCAGTGGCCCGGGAGG
AAACTGGGATGGAGGGGACTGCTCTCTGGGAGTCCCAGACCCCTGGAAGGGCTG
CCCCTCCCACTCTCGGTGCTGGCTTCTCTTCCGGGACGGGCAGTGCCACCCACA
GTGTGACTCTGAAGAGTGTCTGTTTGATGGCTACGACTGTGAGACCCCTCCAGC
CTGCACTCCAGCCTATGACCAGTACTGCCATGATCACTTCCACAACGGGCACTG
TGAGAAAGGCTGCAACACTGCAGAGTGTGGCTGGGATGGAGGTGACTGCAGGCC
TGAAGATGGGGACCCAGAGTGGGGGCCCTCCCTGGCCCTGCTGGTGGTACTGAG
CCCCCCAGCCCTAGACCAGCAGCTGTTTGCCCTGGCCCGGGTGCTGTCCCTGAC
TCTGAGGGTAGGACTCTGGGTAAGGAAGGATCGTGATGGCAGGGACATGGTGTA
CCCCTATCCTGGGGCCCGGGCTGAAGAAAAGCTAGGAGGAACTCGGGACCCCAC
CTATCAGGAGAGAGCAGCCCCTCAAACGCAGCCCCTGGGCAAGGAGACCGACTC
CCTCAGTGCTGGGTTTGTGGTGGTCATGGGTGTGGATTTGTCCCGCTGTGGCCC
TGACCACCCGGCATCCCGCTGTCCCTGGGACCCTGGGCTTCTACTCCGCTTCCT
TGCTGCGATGGCTGCAGTGGGAGCCCTGGAGCCCCTGCTGCCTGGACCACTGCT
GGCTGTCCACCCTCATGCAGGGACCGCACCCCCTGCCAACCAGCTTCCCTGGCC
TGTGCTGTGCTCCCCAGTGGCCGGGGTGATTCTCCTGGCCCTAGGGGCTCTTCT
CGTCCTCCAGCTCATCCGGCGTCGACGCCGAGAGCATGGAGCTCTCTGGCTGCC
CCCTGGTTTCACTCGACGGCCTCGGACTCAGTCAGCTCCCCACCGACGCCGGCC
CCCACTAGGCGAGGACAGCATTGGTCTCAAGGCACTGAAGCCAAAGGCAGAAGT
TGATGAGGATGGAGTTGTGATGTGCTCAGGCCCTGAGGAGGGAGAGGAGGTGGG
CCAGGCTGAAGAAACAGGCCCACCCTCCACGTGCCAGCTCTGGTCTCTGAGTGG
TGGCTGTGGGGCGCTCCCTCAGGCAGCCATGCTAACTCCTCCCCAGGAATCTGA
GATGGAAGCCCCTGACCTGGACACCCGTGGACCTGATGGGGTGACACCCCTGAT
```

```
GTCAGCAGTTTGCTGTGGGAAGTACAGTCCGGGACCTTCCAAGGGGCATGGTT

GGGATGTCCTGAGCCCTGGGAACCTCTGCTGGATGGAGGGGCCTGTCCCCAGGC

TCACACCGTGGGCACTGGGGAGACCCCCCTGCACCTGGCTGCCCGATTCTCCCG

GCCAACCGCTGCCCGCCGCCTCCTTGAGGCTGGAGCCAACCCCAACCAGCCAGA

CCGGGCAGGGCGCACACCCCTTCATGCTGCTGTGGCTGCTGATGCTCGGGAGGT

CTGCCAGCTTCTGCTCCGTAGCAGACAAACTGCAGTGGACGCTCGCACAGAGGA

CGGGACCACACCCTTGATGCTGGCTGCCAGGCTGGCGGTGGAAGACCTGGTTGA

AGAACTGATTGCAGCCCAAGCAGACGTGGGGGCCAGAGATAAATGGGGGAAAAC

TGCGCTGCACTGGGCTGCTGCCGTGAACAACGCCCGAGCCGCCCGCTCGCTTCT

CCAGGCCGGAGCCGATAAAGATGCCCAGGACAACAGGGAGCAGACGCCGCTATT

CCTGGCGGCGCGGGAAGGAGCGGTGGAAGTAGCCCAGCTACTGCTGGGGCTGGG

GGCAGCCCGAGAGCTGCGGGACCAGGCTGGGCTAGCGCCGGCGGACGTCGCTCA

CCAACGTAACCACTGGGATCTGCTGACGCTGCTGGAAGGGGCTGGGCCACCAGA

GGCCCGTCACAAAGCCACGCCGGGCCGCGAGGCTGGGCCCTTCCCGCGCGCACG

GACGGTGTCAGTAAGCGTGCCCCCGCATGGGGCGGGGCTCTGCCGCGCTGCCG

GACGCTGTCAGCCGGAGCAGGCCCTCGTGGGGCGGAGCTTGTCTGCAGGCTCG

GACTTGGTCCGTAGACTTGGCTGCGCGGGGGGGCGGGCCTATTCTCATTGCCG

GAGCCTCTCGGGAGTAGGAGCAGGAGGAGGCCCGACCCCTCGCGGCCGTAGGTT

TTCTGCAGGCATGCGCGGGCCTCGGCCCAACCCTGCGATAATGCGAGGAAGATA

CGGAGTGGCTGCCGGGCGCGGAGGCAGGGTCTCAACGGATGACTGGCCCTGTGA

TTGGGTGGCCCTGGGAGCTTGCGGTTCTGCCTCCAACATTCCGATCCCGCCTCC

TTGCCTTACTCCGTCCCCGGAGCGGGGATCACCTCAACTTGACTGTGGTCCCCC

AGCCCTCCAAGAAATGCCCATAAACCAAGGAGGAGAGGGTAAAAAATAGAAGAA

TACATGGTAGGGAGGAATTCCAAAAATGATTACCCATTAAAAGGCAGGCTGGAA

GGCCTTCCTGGTTTTAAGATGGATCCCCCAAAATGAAGGGTTGTGAGTTTAGTT

TCTCTCCTAAAATGAATGTATGCCCACCAGAGCAGACATCTTCCACGTGGAGAA

GCTGCAGCTCTGGAAAGAGGGTTTAAGATGCTAGGATGAGGCAGGCCCAGTCCT

CCTCCAGAAAATAAGACAGGCCACAGGAGGGCAGAGTGGAGTGGAAATACCCCT

AAGTTGGAACCAAGAATTGCAGGCATATGGGATGTAAGATGTTCTTTCCTATAT

ATGGTTTCCAAAGGGTGCCCCTATGATCCATTGTCCCCACTGCCCACAAATGGC

TGACAAATATTTATTGGGCACCTACTATGTGCCAGGCACTGTGTAGGTGCTGAA

AAGTGGCCAAGGGCCACCCCCGCTGATGACTCCTTGCATTCCCTCCCCTCACAA

CAAAGAACTCCACTGTGGGGATGAAGCGCTTCTTCTAGCCACTGCTATCGCTAT

TTAAGAACCCTAAATCTGTCACCCATAATAAAGCTGATTTGAAGTGTTAAAAAA

AAAAAAAAAAA
```

In some embodiments, the nucleic acid sequence encoding Notch, as described herein, is at least 80% identical to the sequence of SEQ ID NO: 29, SEQ ID NO: 30, SEQ ID NO: 31. SEQ ID NO: 32, or SEQ ID NO: 33. In some embodiments, the nucleic acid sequence encoding Notch is 80%, 81%, 82%, 83%, 84%, 85%, 86%, 87%, 88%, 89%, 90%, 91%, 92%, 93%, 94%, 95%, 96%, 97%, 98%, or 99% identical to the sequence of SEQ ID NO: 29, SEQ ID NO: 30, SEQ ID NO: 31. SEQ ID NO: 32, or SEQ ID NO: 33. In some embodiments, the nucleic acid sequence of Notch, as described herein, can vary from the sequence of SEQ ID NO: 29, SEQ ID NO: 30, SEQ ID NO: 31. SEQ ID NO: 32, or SEQ ID NO: 33 by 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more nucleotides.

A "chimeric Notch receptor polypeptide" of the present disclosure comprises: a) an extracellular domain comprising a first member of a specific binding pair; b) a Notch receptor polypeptide, where the Notch receptor polypeptide has a length of from 50 amino acids to 1000 amino acids, and comprises one or more ligand-inducible proteolytic cleavage sites; and c) an intracellular domain Binding of the first member of the specific binding pair to a second member of the specific binding pair induces cleavage of the Notch receptor polypeptide at the one or more ligand-inducible proteolytic cleavage sites, thereby releasing the intracellular domain. Release of the intracellular domain modulates an activity of a cell that produces the chimeric Notch receptor polypeptide. The extracellular domain comprises a first member of a specific binding pair; the first member of a specific binding pair comprises an amino acid sequence that is heterologous to the Notch receptor polypeptide. The intracellular domain comprises an amino acid sequence that is heterologous to the Notch receptor polypeptide.

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein, including, without limitation, scFvs, or LBDs (Ligand Binding Domains) of growth factors. Additional examples of antigen-binding domains are known in the art.

As used herein, the term "antigen" refers generally to a binding partner specifically recognized by an antigen-binding domain described herein. Exemplary antigens include different classes of molecules, such as, but not limited to, polypeptides and peptide fragments thereof, small molecules, lipids, carbohydrates, and nucleic acids. Non-limiting examples of antigen or antigens that can be specifically bound by any of the antigen-binding domains are described herein. Additional examples of antigen or antigens that can be specifically bound by any of the antigen-binding domains are known in the art.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, nanobodies, bi-specific antibodies, multi-specific antibodies, and fusion proteins comprising an antigen-binding (also referred to herein as antigen binding) portion of an antibody and a non-antibody protein. Also encompassed by the term are Fab', Fv, F(ab').sub.2, and or other antibody fragments that retain specific binding to antigen, and monoclonal antibodies. A monoclonal antibody can be produced using hybridoma production technology, other production methods known to those skilled in the art can also be used (e.g., antibodies derived from antibody phage display libraries). An antibody can be monovalent or bivalent.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a complementarity-determining region (CDR) derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin. See, e.g., Cabilly et al., U.S. Pat. No. 4,816,567; Boss et al., U.S. Pat. No. 4,816,397; Neuberger, M. S. et al., WO 86/01533; Winter, U.S. Pat. No. 5,225,539; See also, Ladner et al., U.S. Pat. No. 4,946,778; Huston, U.S. Pat. No. 5,476,786; and Bird, R. E. et al., Science, 242: 423-426 (1988)), regarding single chain antibodies.

The term "nanobody" (Nb) refers to the smallest antigen binding fragment or single variable domain (V.sub.HH) derived from naturally occurring heavy chain antibody. They are derived from heavy chain only antibodies, seen in camelids. In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); domain antibodies (dAb; Holt et al., *Trends Biotechnol.* 21:484, 2003); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, Vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). Diabodies are described in EP 404,097; WO 93/11161; and Hollinger et al., *Proc. Natl. Acad. Sci. U.S.A.* 90:6444-6448, 1993.

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified to greater than 90%, greater than 95%, or greater than 98%, The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants, i.e., CAR variants are described, e.g., in PCT Application No. US2014/016527; Fedorov et al., *Sci Transl. Med.* 5(215):215ra172, 2013; Glienke et al., *Front. Pharmacol.* 6:21, 2015; Kakarla & Gottschalk, *Cancer J.* 20(2):151-155, 2014; Riddell et al., *Cancer J.* 20(2):141-144, 2014; Pegram et al., *Cancer J.* 20(2):127-33, 2014; Cheadle et al., *Immunol Rev.* 257(1):91-106, 2014; Barrett et al., *Ann. Rev. Med.* 65:333-347, 2014; Sadelain et al., *Cancer Discov.* 3(4):388-98, 2013; and Cartellieri et al., *J. Biomed. Biotechnol.* 956304, 2010; the disclosures of which are incorporated herein by reference in their entirety.

In the instant invention, transcription of a nucleotide sequence is activated by a transcriptional activator fusion protein composed of HNF1 DNA binding domain (e.g., a human HNF1 DNA-binding domain), which binds with high selectivity to selected DNA sequences, fused to different polypeptides responsible for the ligand-dependent activity of the transactivator and its transcriptional activity (e.g., a human RelA protein). The fusion proteins of the invention are useful for modulating the level of transcription of any target gene linked to the selected HNF1 DNA binding sites. The fusion proteins can be used to specifically activate transcription from genes controlled by HNF1 responsive promoters in tissues lacking endogenous HNF1 and vHNF1 proteins. The fusion proteins of the invention are composed primarily of human elements. Fully human proteins mitigate the risk of immune recognition of the transactivator. Repressors are also provided in similar fashion.

U.S. Pat. No. 9,670,281 describes various chimeric Notch receptors, how to construct them, and methods of using them. The examples described below which detail how to humanize chimeric Notch receptors to have low immunogenicity can employ the chimeric Notch receptors shown in U.S. Pat. No. 9,670,281, e.g., in cells of the monocyte/macrophage lineage.

Certain abbreviations are used throughout to describe the domains of the four human Notch proteins. These are: NEC: extracellular subunit; NTM: transmembrane subunit; EGF: epidermal growth factor; HD: heterodimerization domain; ICN: intracellular domain; LNR: cysteine-rich LNR repeats; TM: transmembrane domain; RAM: RAM domain; NLS: nuclear localizing signals; ANK: ankyrin repeat domain; NCR: cysteine response region; TAD: transactivation domain; PEST: region rich in proline (P), glutamine (E), serine (S) and threonine (T) residues.

Methods

Besides the use for gene therapy, ligand-dependent transcription factors incorporating a humanized DBD of the invention can be used to modulate expression of genes that are contained in recombinant viral vectors and that might interfere with the growth of the viruses in the packaging cell lines during the production processes. These recombinant viruses might be derivatives of Adenoviruses, Retroviruses, Lentiviruses, Herpesviruses, Adeno-associated viruses and other viruses which are familiar to those skilled in the art. Another use would be to provide large scale production of a toxic protein of interest using cultured cells in vitro that do not contain endogenous HNF1/vHNF1 and which have been modified to contain a nucleic acid encoding the transactivator carrying the DBD of the invention in a form suitable for expression of the transactivator in the cells and a gene encoding the protein of interest operatively linked to, for example, an HNF1-dependent promoter.

To induce or repress transcription in vivo the ligand may be administered to the body, or a tissue of interest (e.g. by injection). The body to be treated may be that of an animal, particularly a mammal, which may be human or non-human, such as rabbit, guinea pig, rat, mouse or other rodent, cat, dog, pig, sheep, goat, cattle or horse, or which is a bird, such as a chicken. Suitable routes of administration include oral, intraperitoneal, intramuscular, or i.v.

One convenient way of producing a polypeptide or fusion protein according to the present invention is to express nucleic acid encoding it, by use of nucleic acid in an expression system. Accordingly the present invention also provides in various aspects nucleic acid encoding the transcriptional activator or repressor of the invention, which may be used for production of the encoded protein.

Generally, whether encoding for a protein or component in accordance with the present invention, nucleic acid is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as encompassing reference to the RNA equivalent, with U substituted for T.

Nucleic acid sequences encoding a polypeptide or fusion protein in accordance with the present invention can be readily prepared by the skilled person using the information and references contained herein and techniques known in the art. Sambrook, et al., A Molecular Cloning, A Laboratory Manual, Cold Spring Harbor Laboratory Press (1989-2016), and Ausubel et al., Current Protocols in Molecular Biology, John Wiley and Sons, (1994-2016)). These techniques include (i) the use of the polymerase chain reaction (PCR) to amplify samples of such nucleic acid, e.g. from genomic sources, (ii) chemical synthesis, or (iii) preparing cDNA sequences. DNA encoding portions of full-length coding sequences (e.g. a DNA binding domain, or regulatory domain as the case may be) may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the relevant sequence may be made, e.g. using site directed mutagenesis, to lead to the expression of modified peptide or to take account of codon preference in the host cells used to express the nucleic acid.

In order to obtain expression of the nucleic acid sequences, the sequences may be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of $E.\ coli$, yeast, and eukaryotic cells such as COS or CHO cells.

Thus, the present invention also encompasses a method of making a polypeptide or fusion protein as disclosed, the method including expression from nucleic acid encoding the product (generally nucleic acid according to the invention). This may conveniently be achieved by growing a host cell in culture, containing such a vector, under appropriate conditions which cause or allow expression of the polypeptide. Polypeptides may also be expressed in in vitro systems.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is $E.\ coli$.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular cloning: a Laboratory Manual: 4th edition, Green and Sambrook et al., 2012, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al., Eds., John Wiley & Sons, 2016.

For use in mammalian cells, a recombinant expression vector's control functions may be provided by viral genetic material. Exemplary promoters include those derived from polyoma, Adenovirus 2, cytomegalovirus and SV40.

A regulatory sequences of a recombinant expression vector used in the present invention may direct expression of a polypeptide or fusion protein preferentially in a particular cell type, i.e., tissue-specific regulatory elements can be used. In one embodiment, the recombinant expression vector of the invention is a plasmid. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in Ausubel, et al. (supra). The genome of a virus such as adenovirus can be manipulated such that it encodes and expresses a transactivator or repressor protein but is inactivated in terms of its ability to replicate in a normal lytic viral life cycle.

Thus, a further aspect of the present invention provides a host cell containing heterologous nucleic acid as disclosed herein.

Still further, a recombinant expression vector can be designed to allow homologous recombination between the nucleic acid encoding the transactivator or repressor and a target gene in a host cell. Such homologous recombination vectors can be used to create homologous recombinant animals that express a fusion protein of the invention.

Examples of mammalian cell lines which may be used include CHO dhfr-cells (Urlaub and Chasin, *Proc. Natl. Acad. Sci. U.S.A.* 77:4216-4220, 1980), 293 cells (Graham et al., *J. Gen. Virol.* 36:59, 1977) and myeloma cells like SP2 or NS0 (*Meth. Enzymol.* 73(B):3-46, 2016). In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, muscle cells, neuronal cells and skin epithelium and airway epithelium. Additionally, for transgenic or homologous recombinant animals, embryonic stem cells and fertilized oocytes can be modified to contain nucleic acid encoding a transactivator or repressor fusion protein.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All four human Notch proteins (Notch 1-4) were tested for their ability of their core LNR, HD and transmembrane domains to selectively release a GAL4-VP16 transcription factor fused C-terminal to their intracellular portion in response to an N-terminal extracellular CD19 ScFv fusion binding to its cognate antigen. Human Notch2 and Notch3 released functional quantities of the transcription factor upon antigen binding. Human Notch1 released small amounts of transcription factor in response to antigen-binding, while human Notch 4 released no detectable amount of transcription factor. Human Notch3 showed the best functional release of transcription factor in response to antigen-binding, and was used for a number of designs.

We further improved the minimal LIN12-HD-transmembrane "core" Notch2 and Notch3 domains to include an extra, short (~60aa) intracellular domain that includes the natural Notch Nuclear Localization Sequence (NLS) to improve nuclear import upon self-cleavage and release of the transcription factor domain.

In order to minimize immunogenicity of the chimeric Notch receptor, a series of synthetic humanized transcription factors were designed and built from (1) a minimized human DNA-Binding Domain (DBD) and (2) a minimized, strong Transactivation Domain (TAD). The reason for creating an unnatural but humanized chimera is to eliminate unwanted endogenous cofactor interactions between the chimeric Notch receptor-released humanized transcription factor and the natural binding partners that a full-length human transcription factor would interact with. This is to improve the robustness and predictability of the chimeric antigen receptor induced transcriptional response in cellular applications utilizing a humanized antigen receptor.

A comprehensive screen of human transcription factors was undertaken in order to find natural DNA-Binding Domains to satisfy several criteria: (1) that the DNA Binding Domain belonged to a transcription factor that is generally not naturally expressed in the target host-cell-type. In the present embodiment we sought DNA-binding domains absent from any hematopoietic lineage, including especially lymphoid and T-cell lineages; and (2) that the DNA Binding Domain bound to its target DNA sequence with high affinities, with a dissociation constant at or lower than 10 nM.

The DNA-Binding Domains were first tested for their ability to bind to multisite synthetic promoters by expressing the DNA-binding domain fused to a natural transactivation domain to verify that it could upregulate GFP driven by the synthetic multisite promoter. This verifies that the designed cognate promoter—DNA-Binding Domain pair were correct.

The verified DNA-Binding Domains were then tested as fusions to synNotch along with a strong transactivation domain and assayed for their ability to upregulate the cognate-multisite-promoter driving GFP upon stimulation by external antigen and release to the nucleus.

Examples of human DNA-binding domains tested with this strategy were those taken from human CRX (Furukawa, Takahisa, Eric M. Morrow, and Constance L. Cepko. "Crx, a novel otx-like homeobox gene, shows photoreceptor-specific expression and regulates photoreceptor differentiation." Cell 91.4 (1997):531-541, //doi.org/10.1016/S0092-8674(00)80439-0), POU1F1 (Jacobson, Eric M., et al. "Structure of Pit-1 POU domain bound to DNA as a dimer: unexpected arrangement and flexibility." Genes & Development 11.2 (1997): 198-212, doi:10.1101/gad.11.2.198), HNF1A, EGR1 (Thiel, Gerald, and Giuseppe Cibelli. "Regulation of life and death by the zinc finger transcription factor Egr-1." Journal of cellular physiology 193.3 (2002): 287-292, DOI: 10.1002/jcp.10178) ZBTB18 (Najafabadi, Hamed S., et al. "C2H2 zinc finger proteins greatly expand the human regulatory lexicon." (Nature biotechnology 33.5 (2015): 555-562. doi:10.1038/nbt.3128), and ZNF528 (Najafabadi, Hamed S., et al. "C2H2 zinc finger proteins greatly expand the human regulatory lexicon." Nature biotechnology 33.5 (2015): 555-562, doi:10.1038/nbt.3128). All DNA-binding domains were able to induce strong GFP expression under control of their cognate promoters when expressed as soluble transcription factors. However, only the DNA-binding domains of HNF1A and EGR1 were able to induce detectable expression of GFP under their cognate promoter when expressed and released from a chimeric Notch fusion construct. Only a small fraction of the expressed chimeric Notch protein will self-cleave on response to stimulation by antigen-binding, so the effective concentration of the liberated, nuclear-imported transcription factor will be much lower than compared to a directly expressed transcription factor. Thus, a chimeric Notch-released transcription factor must exhibit extremely strong binding to its cognate promoter in order to be functional.

Human Transactivation Domains were screened for activity in the context of chimeric Notch designs by expressing them as fusions to a Gal4 DNA Binding Domain and measuring relative levels of GFP expression under control of a cognate Gal4 multisite promoter. These were also compared against the GFP expression levels induced by the non-human VP64 transactivation domain.

Examples of human transactivation domains screened in this manner include RelA (p65) (Wang, Weixin, et al. "The nuclear factor-κB RelA transcription factor is constitutively activated in human pancreatic adenocarcinoma cells." Clinical Cancer Research 5.1 (1999): 119-127), YAP (Lian, Ian, et al. "The role of YAP transcription coactivator in regulating stem cell self-renewal and differentiation." Genes & development 24.11 (2010): 1106-1118, doi:10.1101/gad.1903310), WWTR1(TAZ) (Hong, Jeong-Ho, et al.

"TAZ, a transcriptional modulator of mesenchymal stem cell differentiation." Science 309.5737 (2005): 1074-1078, doi: 10.1126/science.1110955), CREB3(LZIP) (Omori, Yoshihiro, et al. "CREB-H: a novel mammalian transcription factor belonging to the CREB/ATF family and functioning via the box-B element with a liver-specific expression." Nucleic acids research 29.10 (2001): 2154-2162, doi: //doi.org/10.1093/nar/29.10.2154), and MyoD (Weintraub, Harold, and Robert Davis. "The myoD gene family: nodal point during specification of the muscle cell lineage." Science 251.4995 (1991): 761, doi: 10.1126/science.1846704). Of these, the transactivation domains of RelA(p65), WWTR1(TAZ), and CREB3(LZIP) showed activity in chimeric Notch. The activity of the transactivation domain of RelA(p65) was measured to be the strongest in inducing GFP expression.

Combining the best performing human Notch domain, the best performing DNA-binding domain, and the best-performing Transactivation domain results in the Notch3-HNF1a-p65 design for a chimeric, humanized Notch receptor.

Applications of humanized chimeric Notch receptor are numerous. Such can, for example, deliver CARs or t-cell receptors to treat disease. U.S. Pat. No. 9,670,281.

Reference to nucleotide or protein sequences below, generally refer to sequences in the National Center for Biotechnology Information (NCBI) (ncbi.nlm.niv.gov). Nucleotide sequences are all 5' to 3.'

Example 1. Construction of Chimeric Notch with Notch3, DNA Binding Domain of HNF1alpha and p65 Transactivation Domain The following sequences were ordered as double-stranded synthetic DNA fragments (IDT gBlocks) or single-stranded long-oligonucleotides (IDT ultramers) which were made double-stranded by annealing with a short 3' reverse-complement oligo and second-strand synthesis by Phusion polymerase (Thermo Scientific™ Phusion™ High-Fidelity DNA Polymerase; Catalogue No. F534S).

Four synthetic dsDNA pieces were ordered from Integrated DNA Technologies (IDT) containing:
1. Human CD8a signal peptide 1-22 (NP_001139345 amino acids 1-22, (MALPVTALLLPLALLL-HAARPS) (SEQ ID NO: 1)), Myc-tag (EQKLI-SEEDL) (SEQ ID NO: 2), Anti-Human B cell (CD19) Antibody, clone FMC63.
2. Human Notch3 core (gi|134244285|NP_000426.2 amino acids 1374-1734).
3. GS flexible Linker (GSAAAGGSGGSGGS) (SEQ ID NO: 3), Human HNF1alpha (gi|807201167|NP_001293108.1 amino acids 1-283), GS flexible Linker (GGGSGGGS) (SEQ ID NO: 4).
4. Human Rel-A (p65) (gi|223468676|NP_068810.3 amino acids 1-551) plus stop codon.

These were designed to incorporate 20 nt of homology with 5' and 3' neighboring fragments for in-vitro recombination by the In-fusion cloning system (Clontech). All fragments were assembled by the In-fusion into the MluI/NotI cut vector backbone of self-inactivating lentivirus vector pHR-SIN: SFFV (Addgene; Catalogue No. 79121.

A second reporter construct was constructed by assembling three synthetic dsDNA fragments:
1. a 4× repeated palindromic DNA binding sequence for the HNF1a DNA-binding domain dimer, immediately followed by a minimal CMV promoter (SEQ ID NO: 34)
atcgatGTTAATaATTAACatatatGTTAATcATTAACtatataGTTAAT tATTAACcgctatGTTAATgATTAACactagttaggcgtgtacggtggga ggcctatataagcagagctcgttagtgaaccgtcagatcgcctggagac gccatccacgctgttttgacctccatagaagacaccgggaccgatccagc 2. A Kozak sequence (GCCGCCACC) (SEQ ID NO: 35) and coding sequence for EGFP.
3. An EF1α promoter sequence
4. A Kozak sequence (GCCGCCACC) (SEQ ID NO: 35) and coding sequence for mCherry.

These fragments were designed to incorporate an additional 20-25 nt of homology with 5' and 3' neighboring fragments for in-vitro recombination by the In-fusion cloning system (Clontech). All fragments were assembled by the In-fusion reaction into the MluI/NotI cut vector backbone of self-inactivating lentivirus vector pHR-SIN: SFFV.

The lentiviral construct was then co-transfected into 293T cells together with the viral packaging plasmids pCMVdR8.91 and pMD2.G using the transfection reagent FuGENE HD (Roche). Amphotropic VSV-G pseudotyped lentiviral particles in the supernatant were collected 48 hours later.

Viral particles from both synnotch and reporter constructs were used to transduce simultaneously either Jurkat cells or primary CD4+/CD8+ pan-T cells from human donors. An extended description of lentiviral protocols can be found in Morsut et al. Cell. 2016 Feb. 11; 164(4): 780-91.

Transduced Jurkat cells were tested for expression 2 days post-transduction, transduced human primary pan-T cells were tested for expression 7 days post-transduction. Expression of the synnotch construct was tested by labelling the expressed cell-surface Myc-tag marker with alexa-647-conjugated anti-myc antibody (Cell Signaling Techology, Myc-Tag (9B11) Mouse mAb (Alexa Fluor® 647 Conjugate; Catalogue No. 2233).

Expression of the cognate reporter construct for the synnotch was tested by observing the constitutive mCherry expression produced from the reporter vector. Double-positive cells were sorted for further assays.

Cells expressing both synnotch constructs and its reporter were assayed for synnotch activity by stimulating the cells for 24 hours with magnetic beads coated with anti-Myc-tag antibodies (obtained from Thermofisher Scientific, Catalog number: 88842) or magnetic beads coated with anti-HA-tag antibodies as a negative control (obtained from Pierce™ Anti-HA Magnetic Beads, catalog number 88836). The mean fluorescence intensity of the reporter's EGFP expression in response to the antibody-binding stimulation was measured for the stimulated cells vs that of the negative-control stimulated cells.

Cells expressing both synnotch constructs and its reporter were additionally assayed for synnotch activity by stimulating the cells for 24 hours by coincubating with a Raji cell line expressing high-levels of CD19 antigen (American Type Culture Collection (ATCC) CCL-86™ (Raji)) as well as coincubating with cell lines negative for cell-surface CD19. The mean fluorescence intensity of the cotransduced reporter's9 EGFP expression in response to the cell-bound-antigen stimulation was measured for the stimulated cells vs that of the negative-control stimulated cells.

Example 2. Construction of Chimeric Notch with Notch3, DNA Binding Domain of EGR1 and p65 Transactivation Domain Vector construction was similar to that of Example 1 with the exception that the synthetic DNA fragment containing the DNA-binding domain of human HNF1a was substituted for the following containing the human EGR1 DNA-binding domain:

GS flexible Linker (GSAAAGGSGGSGGS) (SEQ ID NO: 3), Human EGR1 (genbank NP_001955 amino acids 333-423), GS flexible Linker (GGGSGGGS) (SEQ ID NO: 4)

The reporter construct contained a cognate 4× binding site a 5× repeated DNA binding sequence for the EGR1 DNA-binding domain dimer, immediately followed by a minimal CMV promoter:

(SEQ ID NO: 34)
acccgggggacagcagagatccagtttatcgatGCGTGGGCGataGCGG

GGGCGtatGCGTGGGCGattGCGGGGGCGttaGCGTGGGCGactagttag gcgtgtacggtgggaggcctatataagcagagctcgtttagtgaaccgtc agatcgcctggagacgccatccacgctgttttgacctccatagaagacac cgggaccgatccagc

Example 3. Construction of Above Examples with WWTR1 (TAZ) Transactivation Domain Vector construction was identical to that of Example 1&2 with the exception that the synthetic DNA fragment containing the transactivation domain of human RelA(p65) was replaced by the following containing the transactivation domain of human WWTR1:

Human WWTR1(TAZ) (Genpept NP_056287.1 amino acids 165-395) plus stop codon.

Example 4. Construction of Above Examples with CREB3(LZIP) Transactivation Domain Vector construction was identical to that of Example 1 & 2 with the exception that the synthetic DNA fragment containing the transactivation domain of human RelA(p65) was replaced by the following containing the transactivation domain of human CREB3(LZIP):

Human CREB3(LZIP) (Genpept NP_006359.3 amino acids 1-95) plus stop codon.

Example 5. Construction of the Above Examples Using the Human Notch 2 Domain Vector construction was identical to that of Examples above with the exception that the synthetic DNA fragment containing the minimized human notch3 lin12-HD-NLS domains were replaced by the following fragment containing the minimized LIN12-HD-NLS domains of human notch2:Human Notch2 core (gi|24041035|NP_077719.2) amino acids 1413-1780.

Example 6. Transduction of Monocyte-Derived Macrophages with a Chimeric Notch Made from Notch3, the DNA Binding Domain of HNF1alpha, and the p65 Transactivation Domain Mouse Notch 1 and human Notch 3 proteins were both tested for the ability of their core LNR, HD and transmembrane domains to selectively release a transcription factor, Gal4-VP64 for the mouse Notch protein or HNF1a-p65 for the human Notch protein, which was fused C-terminal to the intracellular portion of the protein, in response to the binding of the N-terminal extracellular CD19 scFv fusion portion of each protein to its cognate antigen in human monocyte-derived macrophages. The human Notch chimeric protein was constructed as described herein. The mouse Notch chimeric protein was constructed as described in U.S. Pat. No. 9,670,281.

Lentiviral constructs were co-transfected into 293T cells together with the viral packaging plasmids pCMV-dR8.91 and pMD2.G as well as the pVpx plasmid using the transfection reagent FuGENE HD (Roche). Amphotropic VSV-G pseudotyped lentiviral particles in the supernatant were collected 48 hours later. Jurkat cells were infected with different dilutions of viral supernatant and 7 days post infection and VCNs were determined by using the dd PCR.

Human macrophages were derived from monocytes isolated from freshly isolated (within 8 hours) healthy adult human blood (AllCells Inc.). CD14+ monocyte cells were enriched from blood utilizing RosetteSep negative selection (STEMCELL Technologies, RosetteSep™ Human Monocyte Enrichment Cocktail, Catalogue No. 15028). CD14+ cells were differentiated into macrophages as previously described (Hrecka et al., *Nature* 2011). Briefly, CD14% cells were placed in 24 well plates at a density of $3 \times 10^5$ cells/mL in 1 mL of media. Media was comprised of Dulbecco's Modified Eagle Media supplemented with 10% heat inactived foetal bovine serum, 2 mM L-glutamine, 100 u/ml Penicillin-G, 100 ug/mL streptomycin, 10 ng/mL macrophage-colony stimulating factor (M-CSF, Miltenyi Biotec) from day 0 to 2 than at 20 ng/mL from day 2 onwards.

Viral particles from both synNotch and reporter constructs were used to simultaneously to transduce monocyte-derived macrophage cells from human donors 4 days following isolation. Cells were transduced across a range of multiplicity of infections (0.1 to 1) with either the human Notch3, DNA binding domain of HNF1α and p65 transactivation domain (hNotch3/HNF1a/p65) or the mouse Notch 1, DNA binding domain of Gal4 and VP64 transactivation domain (mNotch1/Gal4/VP64). An extended description of lentiviral protocols can be found in Morsut L, et al. *Cell*. 2016 Feb. 11; 164(4):780-91.

Transduced human primary myeloid cells were tested for expression 7 days post-transduction by flow cytometry. Expression of the synNotch construct in myeloid cells was tested by labelling the myeloid cells with an PE-Cy7 anti-CD14+ antibody (BD Biosciences, PE-Cy™7 Mouse Anti-Human CD14 Antibody (Clone M5E2 (RUO)), Catalogue No. 557907) as well as the cell-surface expressed Myc-tag marker with an alexa-647-conjugated anti-my antibody (Cell Signaling Techology, Myc-Tag (9B11) Mouse mAb (Alexa Fluor® 647 Conjugate; Catalogue No. 2233).

Expression of the cognate reporter construct for the synNotch was tested by measuring the constitutive mCherry expression produced from the reporter vector by flow cytometry.

Cells were assayed for synNotch activity by stimulating the cells for 24 hours by co-culturing with a Daudi cell line expressing high-levels of CD19 antigen (American Type Culture Collection (ATCC) CCL-213™ cells (Daudi cells)) as well as cell lines negative for cell-surface CD19.

The fluorescence intensity of the cotransduced reporter's EGFP expression in response to the cell-bound-antigen stimulation was measured for these CD14+ monocyte-derived macrophages when stimulated with antigen positive CD19+ cells versus that of the negative-control stimulated cells.

Overall, in monocyte-derived macrophages, the chimeric humanized Notch receptor, human Notch3-HNF1a-p65, induced unregulated expression of the reporter construct.

Figure 2:
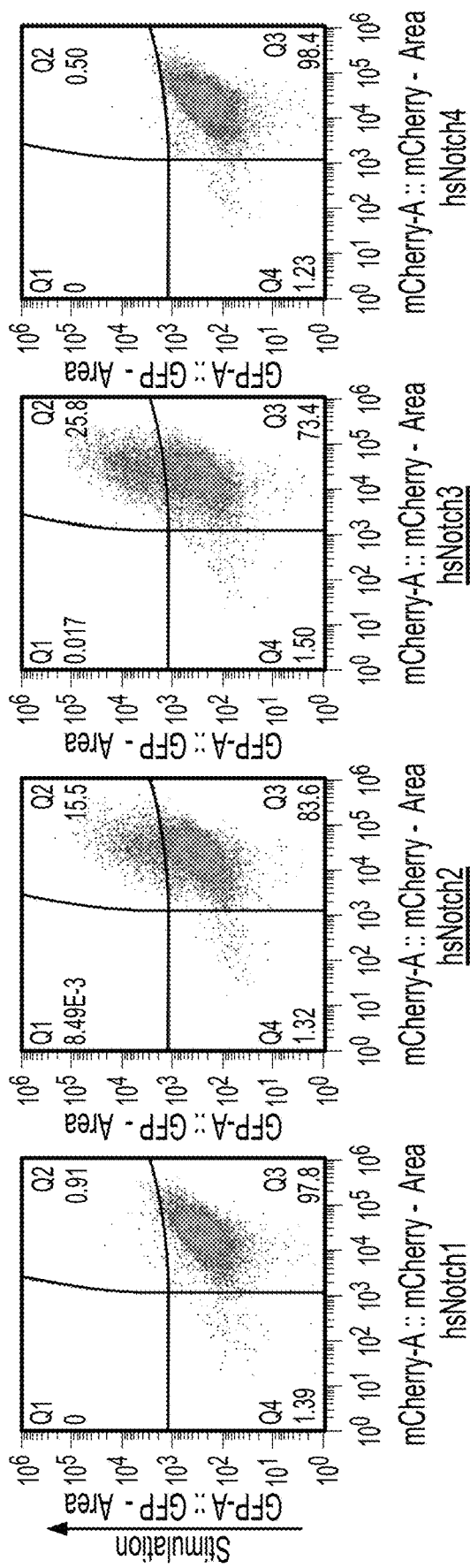
FIG. 2. Experimental data showing the relative performance of the four human Notch homologs in releasing GAL4-vp64 upon stimulation by an external myc-tag binding antigen to myc-bearing beads. hsNotch2 and hsNotch3 are the only homologs showing strong activity.
Figure 3A:
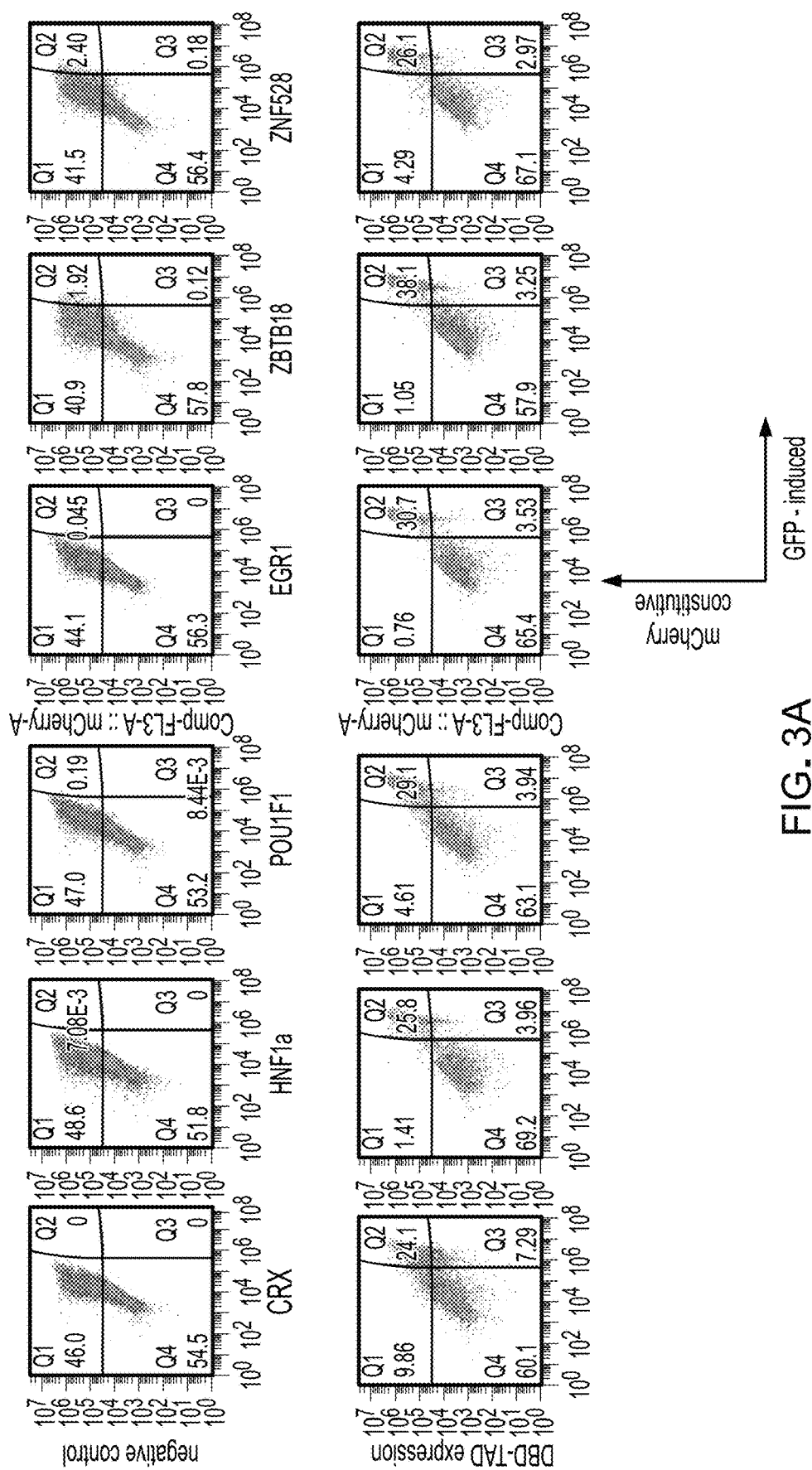
FIG. 3A. Experimental data showing the functional behavior of human DNA-binding domains fused to p65 transactivation domain upregulating GFP expression.
Figure 3B:
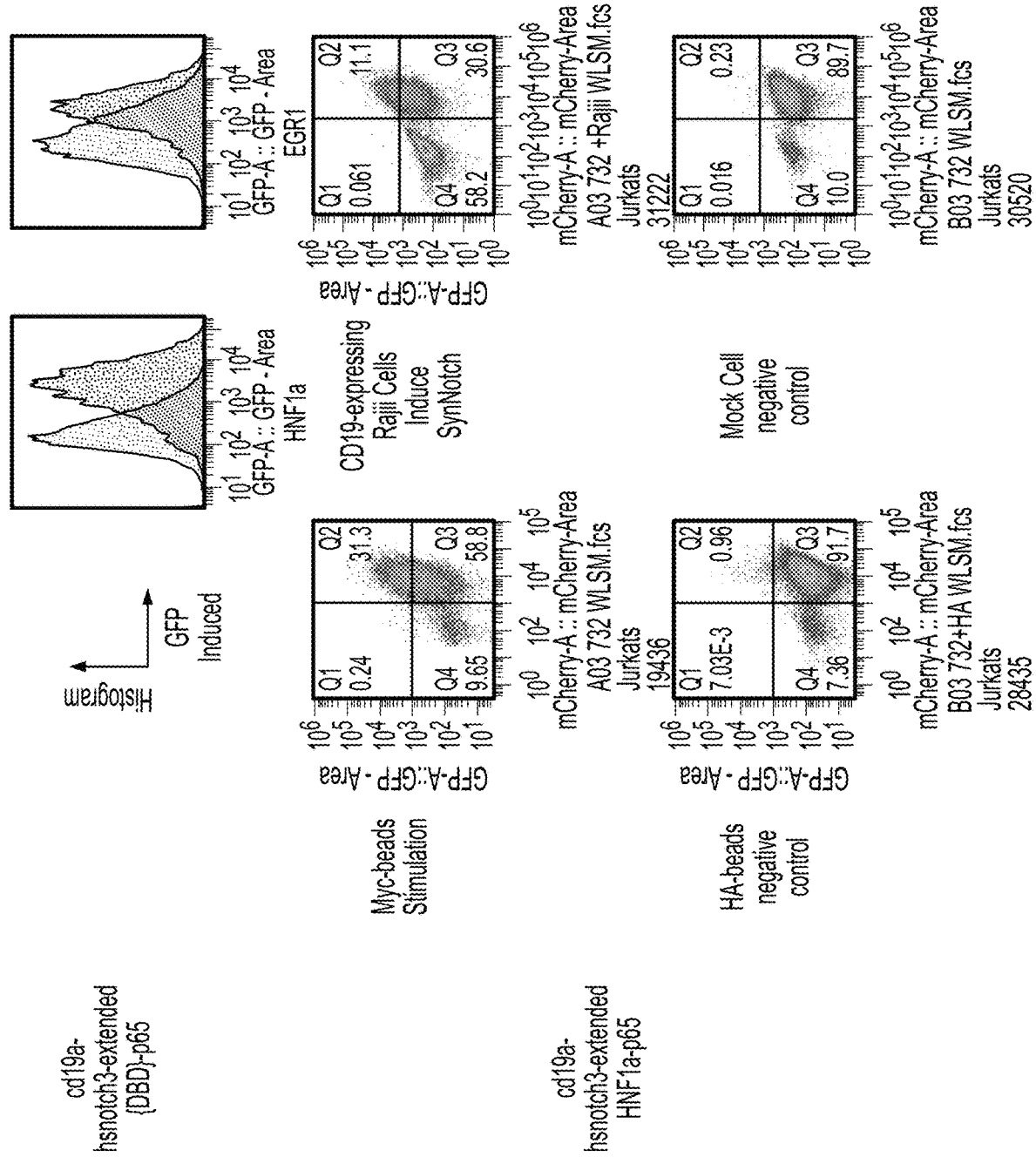
FIG. 3B. Experimental data showing the functional behavior of two working synthetic Notch human DNA-binding domains with p65 transactivation domains upregulating GFP expression.
Figure 4:
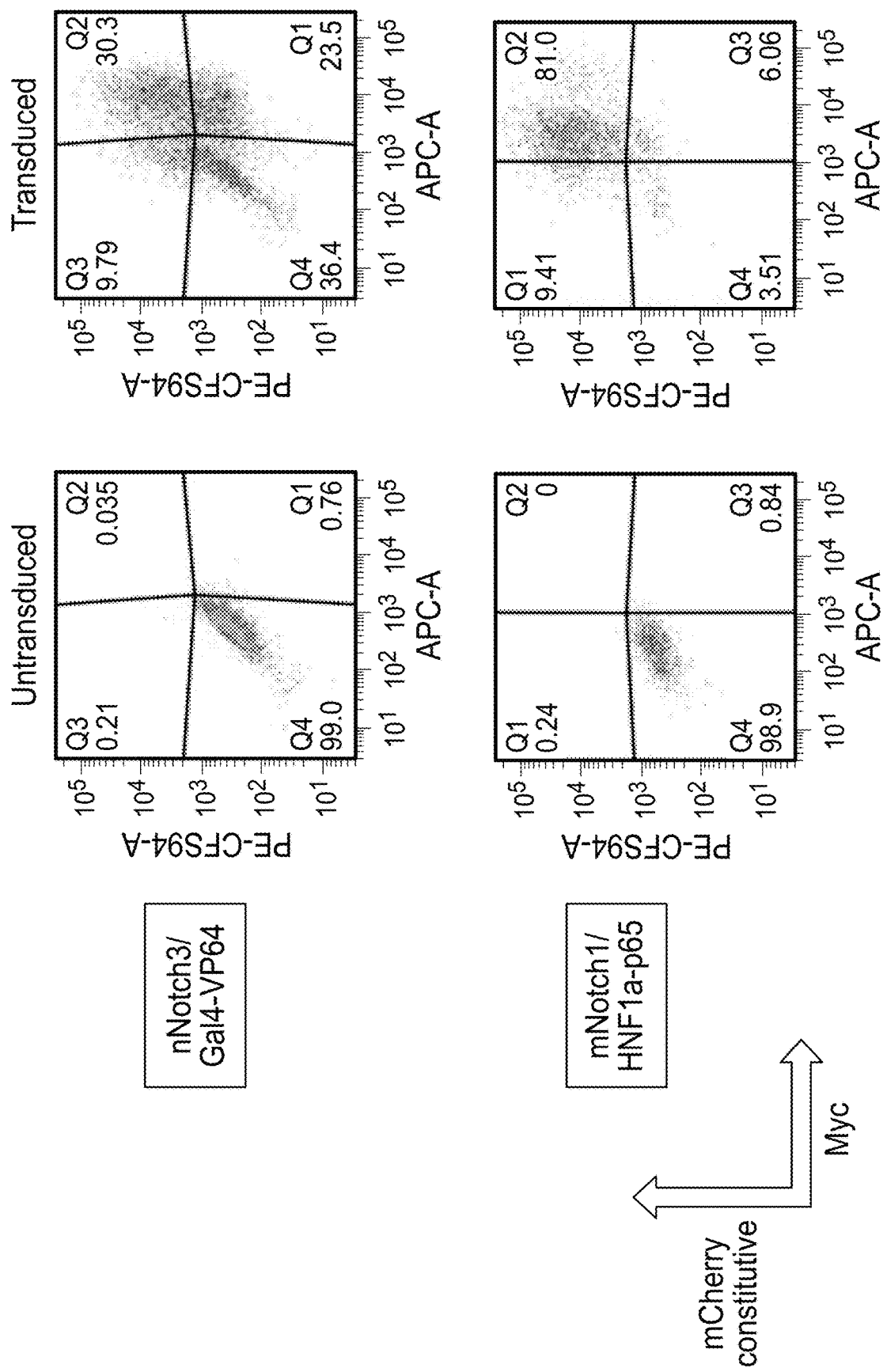
FIG. 4. Experimental data showing the expression of chimeric notch receptors in human monocyte-derived macrophage cells. Experimental data showing the percent transduction of mouse Notch 1 protein/Gal4 and VP64 transcription factors (top) and human Notch 3 protein/HNF1a and p65 transcription factors (bottom) relative to untransduced monocyte-derived macrophages (right).
Figure 5A:
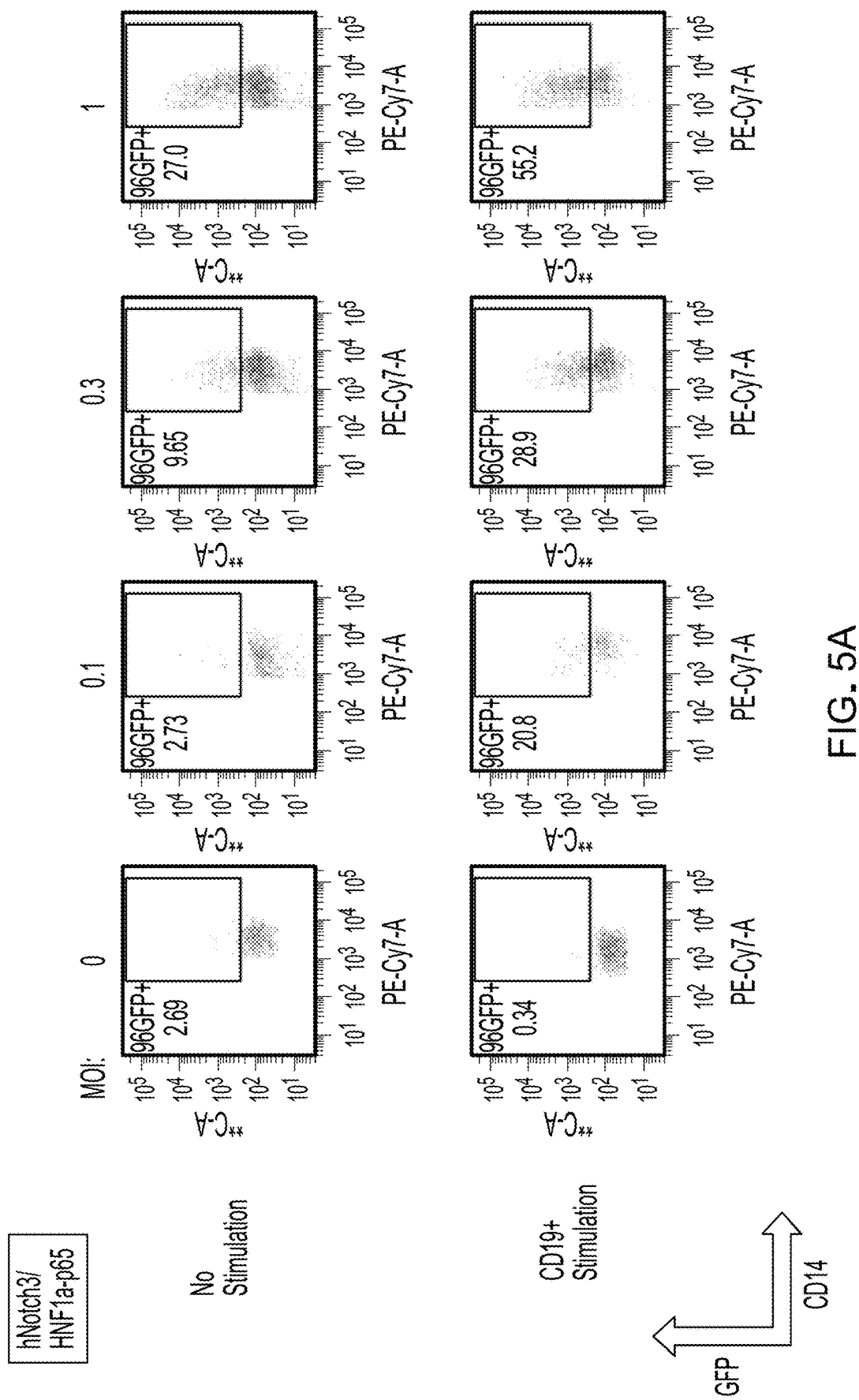
FIG. 5A. Experimental data showing the functional behavior of human Notch 3 and human DNA-binding domains fused to p65 transactivation domain upregulating GFP expression in human monocyte-derived macrophages.
Figure 5B:
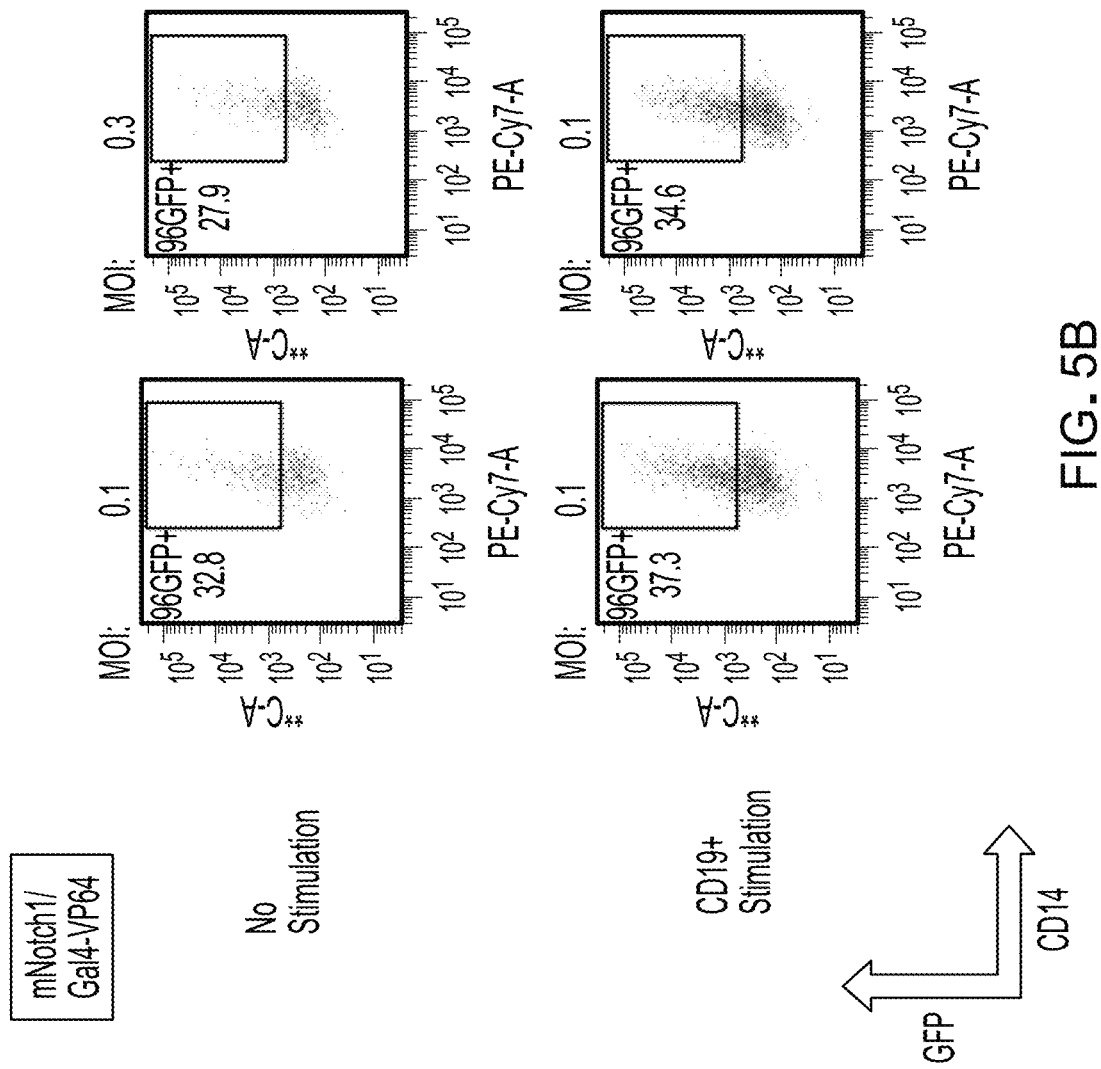
FIG. 5B. Experimental data showing the functional behavior of mouse Notch 1 and non-human Gal4 binding domains fused to VP64 transactivation upregulating GFP expression in human myeloid cells.

The Notch, DNA-binding domain, and transactivation domain components of the protein were functional in macrophages. The chimeric mouse Notch receptor, Notch1-Gal4-VP64, did not induce the selective expression of GFP in response to an N-terminal extracellular CD19 scFv fusion binding to its cognate antigen compared to a negative control without any CD19 expression. See, FIGS. 2, 3A, 3B, 4, 5A, and 5B.

What is claimed is:

1. A nucleic acid comprising a nucleotide sequence encoding a chimeric Notch polypeptide comprising, from N-terminal to C-terminal and in covalent linkage: a) an extracellular domain comprising a binding agent that specifically binds to an antigen; b) a Notch 2 or Notch 3 core region; c) one or more proteolytic cleavage sites; and d) an intracellular domain comprising a transcriptional regulator, wherein binding of the binding agent to the antigen induces cleavage of the Notch polypeptide at the one or more proteolytic cleavage sites, thereby releasing the intracellular domain and the transcriptional regulator;
   wherein the transcriptional regulator comprises a DNA binding domain of human origin and a transactivation domain of human origin;
   wherein the transactivation domain is selected from the group consisting of RelA (p65), YAP, WWTR1 (TAZ), and CREB3 (LZIP); and
   wherein the Notch 2 or Notch 3 core region comprises a human Lin12 LNR.

2. A nucleic acid as described in claim 1, wherein said binding agent comprises an antibody.

3. A nucleic acid as described in claim 2, wherein said antibody is selected from the group consisting of scFv, bispecific antibody, nanobody, or bite.

4. A nucleic acid as described in claim 3, wherein said transcriptional regulator is a transcriptional activator.

5. A recombinant vector comprising the nucleic acid of claim 4.

6. A nucleic acid as described in claim 1, wherein said transcriptional regulator is from the Hepatocyte Nuclear Factor (HNF) transcriptional regulator family.

7. A nucleic acid as described in claim 6, wherein said transcriptional regulator is HNF1 alpha or HNF1 beta.

8. A recombinant vector comprising the nucleic acid of claim 6.

9. A recombinant vector comprising the nucleic acid of claim 1.

10. A host cell transformed with the nucleic acid of claim 1.

11. The host cell of claim 10, wherein the cell is a macrophage.

12. The host cell of claim 11, wherein the macrophage is derived from monocytes.

13. A method of making a chimeric Notch polypeptide comprising a transcriptional regulator wherein said transcriptional regulator comprises a DNA binding domain of human origin, and wherein said method comprises culturing a host cell of claim 10.

14. A nucleic acid as described in claim 1, wherein the Notch 2 or Notch 3 core region further comprises a Nuclear Localization Signal (NLS).

15. A recombinant vector comprising the nucleic acid of claim 14.

* * * * *

UNITED STATES PATENT AND TRADEMARK OFFICE
CERTIFICATE OF CORRECTION

| | |
|---|---|
| PATENT NO. | : 11,325,957 B2 |
| APPLICATION NO. | : 16/010805 |
| DATED | : May 10, 2022 |
| INVENTOR(S) | : Amy Gilbert et al. |

It is certified that error appears in the above-identified patent and that said Letters Patent is hereby corrected as shown below:

In the Specification

Column 1, Line 13, insert the following paragraph and paragraph heading:
--STATEMENT REGARDING SEQUENCE LISTING
The Sequence Listing associated with this application is provided in text format in lieu of paper copy, and is hereby incorporated by reference into the specification. The name of the text file containing the Sequence Listing is "431590066001SequenceListing.txt" The text file is 218 kilobytes, was created on June 20, 2018, and was submitted electronically via EFS–Web.--

Signed and Sealed this
Fourteenth Day of May, 2024

Katherine Kelly Vidal
*Director of the United States Patent and Trademark Office*